United States Patent
Osakada et al.

(10) Patent No.: US 8,273,738 B2
(45) Date of Patent: Sep. 25, 2012

(54) IMIDAZOLE DERIVATIVES

(75) Inventors: Naoto Osakada, Sunto-gun (JP);
Mariko Osakada, Sunto-gun (JP);
Takashi Sawada, Sunto-gun (JP);
Satoshi Kaneko, Sunto-gun (JP);
Atsuko Mizutani, Sunto-gun (JP);
Noriaki Uesaka, Sunto-gun (JP);
Yoshisuke Nakasato, Susono (JP);
Keishi Katayama, Mishima (JP);
Masamori Sugawara, Sunto-gun (JP);
Yushi Kitamura, Sakai (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 270 days.

(21) Appl. No.: 12/440,237

(22) PCT Filed: Sep. 5, 2007

(86) PCT No.: PCT/JP2007/067261
§ 371 (c)(1),
(2), (4) Date: Nov. 10, 2009

(87) PCT Pub. No.: WO2008/029825
PCT Pub. Date: Mar. 13, 2008

(65) Prior Publication Data
US 2010/0152178 A1  Jun. 17, 2010

(30) Foreign Application Priority Data
Sep. 5, 2006 (JP) ................................. 2006-239907

(51) Int. Cl.
*A61K 31/535* (2006.01)
*A61K 31/4965* (2006.01)
(52) U.S. Cl. .............. 514/230.8; 514/235.8; 514/255.05
(58) Field of Classification Search .................. None
See application file for complete search history.

(56) References Cited

U.S. PATENT DOCUMENTS

| | | |
|---|---|---|
| 5,028,618 A | 7/1991 | Seele et al. |
| 5,039,691 A | 8/1991 | Spagnuolo et al. |
| 5,210,211 A | 5/1993 | Hodges et al. |
| 5,276,048 A | 1/1994 | Hodges et al. |
| 5,332,831 A | 7/1994 | Dowle et al. |
| 5,498,722 A | 3/1996 | Ross et al. |
| 5,587,390 A | 12/1996 | Salimbeni et al. |
| 5,817,678 A | 10/1998 | Kim et al. |
| 5,932,590 A | 8/1999 | Ciccarone et al. |
| 6,358,956 B1 | 3/2002 | Hartman et al. |
| 6,653,304 B2 | 11/2003 | Leftheris et al. |
| 7,135,493 B2 | 11/2006 | Urano et al. |
| 7,214,802 B2 | 5/2007 | Cogan et al. |
| 7,244,747 B2 | 7/2007 | Kenda et al. |
| 7,361,678 B2 | 4/2008 | Mjalli et al. |
| 7,407,968 B2 | 8/2008 | Pagé et al. |
| 7,414,061 B2 | 8/2008 | Buettelmann et al. |
| 7,423,052 B2 | 9/2008 | Chan et al. |
| 7,425,642 B2 | 9/2008 | Watanabe et al. |
| 7,514,458 B2 | 4/2009 | Cogan et al. |
| 2002/0119972 A1 | 8/2002 | Leftheris et al. |
| 2003/0100769 A1 | 5/2003 | Imoto et al. |
| 2004/0082542 A1 | 4/2004 | Mjalli et al. |
| 2004/0215014 A1 | 10/2004 | Chan et al. |
| 2004/0229889 A1 | 11/2004 | Urano et al. |
| 2004/0259917 A1 | 12/2004 | Cosford et al. |
| 2005/0137241 A1 | 6/2005 | Kenda et al. |
| 2005/0159470 A1 | 7/2005 | Bressi et al. |
| 2006/0009472 A1 | 1/2006 | Wang et al. |
| 2006/0079519 A1 | 4/2006 | Cogan et al. |
| 2006/0194779 A1 | 8/2006 | Lange et al. |
| 2006/0194857 A1 | 8/2006 | Watanabe et al. |
| 2007/0021386 A1 | 1/2007 | Mjalli et al. |
| 2007/0021405 A1 | 1/2007 | Abouabdellah et al. |
| 2007/0072853 A1 | 3/2007 | Liu et al. |
| 2007/0105893 A1 | 5/2007 | Page et al. |
| 2007/0142371 A1 | 6/2007 | Cogan et al. |
| 2007/0161654 A1 | 7/2007 | Buettelmann et al. |
| 2007/0197619 A1 | 8/2007 | Zelle et al. |
| 2007/0213347 A1 | 9/2007 | Mjalli et al. |
| 2007/0281937 A1 | 12/2007 | Zelle et al. |
| 2008/0081832 A1 | 4/2008 | Kenda et al. |
| 2008/0103139 A1 | 5/2008 | Ishizuka et al. |
| 2008/0242716 A1 | 10/2008 | Zelle et al. |
| 2008/0306275 A1 | 12/2008 | Watanabe et al. |
| 2008/0312435 A1 | 12/2008 | Saito et al. |

FOREIGN PATENT DOCUMENTS

| | | |
|---|---|---|
| CA | 2114178 | 7/1994 |
| CN | 1764648 | 4/2006 |
| CN | 1990473 | 7/2007 |
| EP | 608858 | 8/1994 |
| JP | 2006-182668 | 7/2006 |
| WO | WO-95/22543 | 8/1995 |
| WO | WO-2004/048341 | 6/2004 |

(Continued)

OTHER PUBLICATIONS

Anderson (Chem and Biol 10:787-797, 2003).*

(Continued)

*Primary Examiner* — Craig Ricci
(74) *Attorney, Agent, or Firm* — Edwards Wildman Palmer LLP; David G. Conlin; Mark D. Russett

(57) ABSTRACT

A CB2 receptor modulator comprising an imidazole derivative represented by the general formula (I):

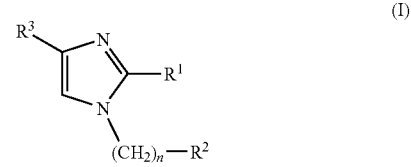

[wherein, $R^1$ represents optionally substituted lower alkyl or the like; $R^2$ represents optionally substituted cycloalkyl or the like; $R^3$ represents optionally substituted aryl or the like; and n represents an integer of 0 to 3] or a pharmaceutically acceptable salt thereof as an active ingredient, and the like are provided.

2 Claims, No Drawings

FOREIGN PATENT DOCUMENTS

| WO | WO-2005/030761 | | 4/2005 |
|----|----------------|---|--------|
| WO | WO-2005/047281 | | 5/2005 |
| WO | WO-2006/002236 | | 1/2006 |
| WO | WO-2006/087355 | | 8/2006 |
| WO | WO 2006/087355 | * | 8/2006 |
| WO | WO-2007/014054 | | 2/2007 |
| WO | WO-2007/076709 | | 7/2007 |

OTHER PUBLICATIONS

Thiel (Nature Biotechnol 2:513-519, 2004).*

Yang et al (Bioorg Med Chem Lett 21:182-185, 2011).*

Horiuchi et al., "Evidence against in Vivo Presence of 2-(2-Furoyl)-4(5)-(2-furanyl)-1*H*-imidazole, a Major Fluorescent Advanced End Product Generated by Nonenzymatic Glycosylation", The Journal of Biological Chemistry, vol. 263, No. 35, pp. 18821-18826 (1988).

Lipshutz et al., "An approach to the Cyclopeptide Alkaloids (Phencyclopeptines) via Heterocyclic Diamide/Dipeptide Equivalents. Preparation and N-Alkylation Studies of 2,4(5)-Disubstituted Imidazoles", J. Org. Chem. vol. 48, No. 21, pp. 3745-3750 (1983).

Sircar et al., "Nonpeptide Angiotensin II Receptor Antagonists. 2. Design, Synthesis, and Structure-Activity Relationships of 2-Alkyl-4-(1*H*-pyrrol-1-y1)-1*H*-imidazole Derivatives: Profile of 2-Propyl-1-[[2'-(1*H*-tetrazol-5-yl)-[1,1'-biphenyl]-4-yl]-methyl]-4-[2-(trifluoroacetyl)-1*H*-pyrrol-1-yl]-1*H*-imidazole-5-carboxylic Acid (Cl-996)", J. Med. Chem. vol. 36, No. 16, pp. 2253-2265 (1993).

Lee et al., "Solid-Phase Synthesis of *N*-Alkyl-*N*;(β-keto)amides and 1,2,4,5-Tetrasubstituted Imidazoles Using a Traceless Cleavage Strategy", Organic Letters, vol. 2, No. 3, pp. 323-326 (2000).

Harmat et al., "4-Diazinyl- and 4-Pyridinylimidazoles: Potent Angiotensin II Antagonists. A Study of Their Activity and Computational Characterization", J. Med. Chem., vol. 38, No. 15, pp. 2925-2937 (1995).

International Search Report dated Oct. 16, 2007, for PCT Application No. PCT/JP2007/067261.

Written Opinion dated Oct. 16, 2007, for PCT Application No. PCT/JP2007/067261.

Hertzog, D.L., Expert Opin. Ther. Patents (2004) 14(10):1435-1452.

* cited by examiner

IMIDAZOLE DERIVATIVES

CROSS-REFERENCE TO RELATED APPLICATIONS

This application is the national stage application pursuant to 35 U.S.C. §371 of PCT application PCT/JP2007/067261, filed Sep. 5, 2007, which claims priority to Japanese patent application No. 2006-239907, filed Sep. 5, 2006. The contents of these applications are incorporated herein by reference in their entirety.

TECHNICAL FIELD

The present invention relates to a cannabinoid type 2 (CB2) receptor modulator comprising an imidazole derivative or a pharmaceutically acceptable salt thereof as an active ingredient, and a novel imidazole derivative or a pharmaceutically acceptable salt thereof which has an effect to modulate a CB2 receptor and is useful as a therapeutic and/or preventive agent for a pain or the like.

BACKGROUND ART

Cannabinoids are substances isolated as biologically active components of marijuana, and have an antiemetic effect, an intraocular pressure lowering effect, an anticonvulsant effect, an analgesic effect, an orexigenic effect, a bronchodilator effect, an anti-asthmatic effect, an anti-inflammatory effect, an anti-anxiety effect, a sedative effect, a psychotropic effect and the like.

It is known that there are two subtypes of cannabinoid receptors, type 1 (CB1) receptors [Nature, vol. 346, p. 561 (1990)] and type 2 (CB2) receptors.

The CB1 receptors are distributed predominantly in the central nervous system such as brain, and it has been considered that the central effects of cannabinoids such as sedative effect and psychotropic effect are mediated by CB1 receptors. Further, because it has also been confirmed that the CB1 receptors are distributed in tissues which participate in the nociceptive signal transduction such as the dorsal horn of the spinal cord and the dorsal root ganglion neuron (DRG) [Neuroscience, vol. 92, p. 1171 (1999); Molecular and cellular neurosciences, vol. 15, p. 510 (2000)], it has been considered that the analgesic effects of cannabinoids are mediated by CB1 receptors.

On the other hand, it has been confirmed that the CB2 receptors are distributed in the spleen, lymph nodes, and also white blood cells, B cells, T cells, macrophages, mast cells and the like. Because the CB2 receptors are abundantly distributed mainly in tissues and cells of the immune system including hematopoietic cells, it has been considered that the anti-asthmatic effect and anti-inflammatory effect of cannabinoids are mediated by CB2 receptors [Nature, vol. 365, p. 61 (1993); British Journal of Pharmacology, vol. 139, p. 775 (2003)]. In addition, it has been reported that CB2 receptor-selective agonists show a peripheral analgesic effect [Pain, vol. 93, p. 239 (2001); Proceedings of the National Academy of Science of the United States of America, vol. 102, p. 3093 (2005)] and a central analgesic effect [European Journal of Neuroscience, vol. 17, p. 2750 (2003); European Journal of Neuroscience, vol. 22, p. 371 (2005); European Journal of Neuroscience, vol. 23, p. 1530 (2006)], and it has been revealed that the analgesic effects of cannabinoids are also mediated by CB2 receptors. Further, as CB2 receptor-mediated effects, an antipruritic effect (WO2002/065997, WO2003/035109, WO2003/070277, WO2006/046778), an inhibitory effect on osteoclast proliferation and activity [Proceedings of the National Academy of Science of the United States of America, vol. 103, p. 696 (2006)] and the like have also been reported recently.

As described above, as the elucidation of the function of cannabinoid receptors has been progressing, among the modulators of cannabinoid receptor functions, a medicament which does not have effects mediated by the CB1 receptors, that is, central effects such as sedative effect and psychotropic effect have been expected as an excellent medicament without side effects specific to cannabinoids. That is, a CB2 receptor-selective modulator has been expected to be useful as a therapeutic and/or preventive agent for various diseases associated with CB2 receptors without side effects specific to cannabinoids. In particular, CB2-selective agonists have been expected as, for example, therapeutic and/or preventive agents for pains (such as neuropathic pain, trigeminal neuralgia, diabetic pain, postherpetic neuralgia, neuropathic low back pain, HIV-related pain, fibromyalgia, cancer pain, inflammatory pain, acute pain, chronic pain, postoperative pain, acute pain after tooth extraction, chronic musculoskeletal pain, noxious pain, psychogenic pain, and menstrual pain), migraine, pruritus, inflammation, allergies, immunodeficiency, autoimmune diseases, chronic rheumatoid arthritis, osteoarthritis, inflammatory bowel disease, irritable bowel syndrome, multiple sclerosis, asthma (such as airway inflammatory cell infiltration, airway hyperresponsiveness, bronchoconstriction, and mucus hypersecretion), chronic obstructive lung disease, emphysema, pulmonary fibrosis, coughing, allergic rhinitis, dermatitis, atopic dermatitis, arteriosclerosis, glaucoma, anorexia, osteoporosis, and the like.

As the CB2 receptor modulator, for example, a large number of compounds such as indole derivatives, benzimidazole derivatives, sulfonamide derivatives, thiazine derivatives, pyrimidine derivatives, imine derivatives, and pyridone derivatives (see, for example, Non-patent document 1, Patent documents 1, 2, and 3, etc.). Further, imidazole derivatives having a carbamoyl group at the 4-position are also known (see Patent document 4).

On the other hand, as for imidazole derivatives having aryl or a heteroaromatic group at the 4-position, for example, as compounds having lower alkyl substituted with an aliphatic heterocyclic group at the 1-position, compounds represented by the following formulae (A), (B), and (C) (see Patent documents 5, 6, and 7), and the like are known, and as compounds having lower alkyl at the 2-position, for example, a compound represented by the following formula (D) (see Patent document 8), and the like are known. Further, compounds having lower alkyl substituted with an aliphatic heterocyclic group at the 1-position (see, for example, Patent documents 9 and 10, etc.), compounds having lower alkyl substituted with aryl at the 2-position (see, for example, Patent documents 11, 12, and 13, etc.), and the like are also known. Further, a large number of imidazole derivatives are known (see, for example, Patent documents 3, 14, 15, 16, 17, 18, 19, 20 and 21, etc.).

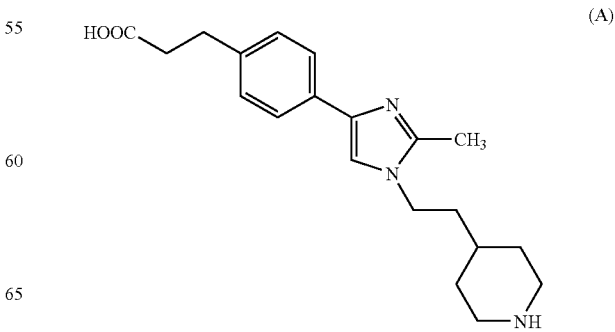

(A)

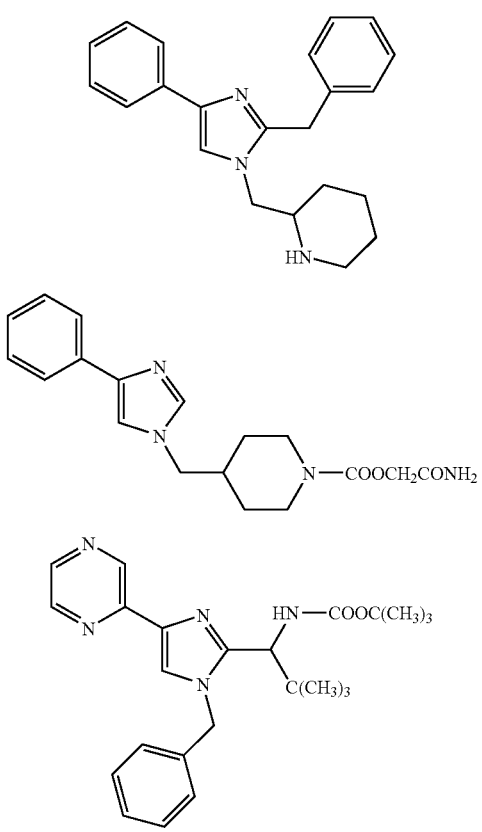

Patent document 1: WO 2004/035548
Patent document 2: WO 2006/051704
Patent document 3: WO 2006/046778
Patent document 4: WO 01/58869
Patent document 5: Japanese Published Unexamined Patent Application No. 2851/1995
Patent document 6: WO 03/002559
Patent document 7: WO 2005/090347
Patent document 8: WO 2006/002236
Patent document 9: WO 2005/054188
Patent document 10: WO 2005/065681
Patent document 11: WO 2005/087229
Patent document 12: WO 2005/087748
Patent document 13: WO 2005/086836
Patent document 14: Japanese Published Unexamined Patent Application No. 302643/2001
Patent document 15: WO 03/053922
Patent document 16: WO 00/051611
Patent document 17: U.S. Pat. No. 5,039,691
Patent document 18: U.S. Pat. No. 5,817,678
Patent document 19: WO 03/075921
Patent document 20: WO 99/28314
Patent document 21: U.S. Pat. No. 5,028,618
Non-patent document 1: "Expert Opin. Ther. Patents.", 2004, vol. 14, p. 1435

DISCLOSURE OF THE INVENTION

Problems to be Solved by the Invention

An object of the present invention is to provide a CB2 receptor modulator, a CB2 receptor agonist and the like which comprise an imidazole derivative or a pharmaceutically acceptable salt thereof as an active ingredient. Another object of the invention is to provide a novel imidazole derivative or a pharmaceutically acceptable salt thereof which has an effect to modulate a CB2 receptor and is useful as, for example, a CB2 receptor agonist, a therapeutic and/or preventive agent for a pain, or the like.

Means for Solving the Problems

The present invention relates to the following (1) to (27).
(1) A cannabinoid type 2 (CB2) receptor modulator comprising an imidazole derivative represented by the general formula (I) or a pharmaceutically acceptable salt thereof as an active ingredient:

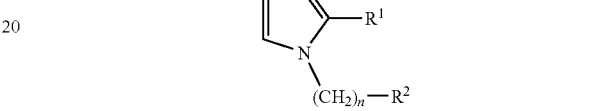

[wherein $R^1$ represents optionally substituted lower alkyl, optionally substituted aralkyl, optionally substituted cycloalkyl, optionally substituted lower alkenyl, an optionally substituted aliphatic heterocyclic group, or an optionally substituted heteroaromatic group;
$R^2$ represents optionally substituted cycloalkyl, an optionally substituted aliphatic heterocyclic group, optionally substituted aryl, or an optionally substituted heteroaromatic group;
$R^3$ represents optionally substituted aryl, an optionally substituted condensed aromatic hydrocarbon group, an optionally substituted heteroaromatic group, or optionally substituted vinyl; and
n represents an integer of 0 to 3].
(2) The modulator according to (1), wherein the modulator is an agonist.
(3) An imidazole derivative represented by the general formula (IA) or a pharmaceutically acceptable salt thereof:

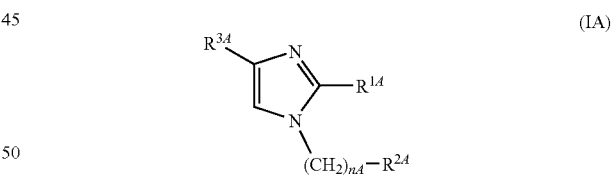

[wherein $R^{1A}$ represents lower alkyl which may have 1 to 3 substituents selected from the group consisting of halogen, hydroxy, and lower alkoxy, or lower alkenyl which may have 1 to 3 substituents selected from the group consisting of halogen, hydroxy, and lower alkoxy;
$R^{2A}$ represents cycloalkyl which may have 1 to 3 substituents selected from the group consisting of cyano, halogen, hydroxy, lower alkoxy, lower alkyl, oxo, lower alkoxycarbonyl, and aralkyl, or an aliphatic heterocyclic group which may have 1 to 3 substituents selected from the group consisting of cyano, halogen, hydroxy, lower alkoxy, lower alkyl, oxo, lower alkoxycarbonyl, and aralkyl;
$R^{3A}$ represents aryl which may have 1 to 5 substituents selected from the following substituent group A, a heteroaromatic group which may have 1 to 4 substituents selected from the following substituent group A, a condensed aromatic hydrocarbon group which may have 1 to 3 substituents selected from the following substituent group A and oxo, an aliphatic heterocyclic group which may have 1 to 3 substituents selected from the following substituent group A and oxo, or vinyl which may have 1 to 3 substituents selected from the following substituent group A;

nA represents an integer of 1 to 3;

the substituent group A refers to a group consisting of (i) halogen, (ii) nitro, (iii) cyano, (iv) —$OR^4$ (wherein $R^4$ represents a hydrogen atom, lower alkyl which may be substituted with the following substituent B, cycloalkyl which may be substituted with the following substituent D, aralkyl which may be substituted with the following substituent C, aryl which may be substituted with the following substituent C, a heteroaromatic group which may be substituted with the following substituent C, an aliphatic heterocyclic group which may be substituted with the following substituent D, lower alkanoyl which may be substituted with the following substituent B, or aroyl which may be substituted with the following substituent C), (v) —$COR^6$ [wherein $R^6$ represents a hydrogen atom, lower alkyl which may be substituted with the following substituent B, cycloalkyl which may be substituted with the following substituent D, aralkyl which may be substituted with the following substituent C, aryl which may be substituted with the following substituent C, a heteroaromatic group which may be substituted with the following substituent C, or an aliphatic heterocyclic group which may be substituted with the following substituent D], (vi) —$NR^7R^8$ [wherein $R^7$ and $R^8$ may be the same or different, and each represents a hydrogen atom, hydroxy, lower alkoxy which may be substituted with the following substituent B, amino, lower alkylamino which may be substituted with the following substituent B, lower alkyl which may be substituted with the following substituent B, lower alkenyl which may be substituted with the following substituent B, cycloalkyl which may be substituted with the following substituent D, aralkyl which may be substituted with the following substituent C, aryl which may be substituted with the following substituent C, a heteroaromatic group which may be substituted with the following substituent C, an aliphatic heterocyclic group which may be substituted with the following substituent D, lower alkoxycarbonyl which may be substituted with the following substituent B, lower alkanoyl which may be substituted with the following substituent B, cycloalkylcarbonyl which may be substituted with the following substituent D, aralkylcarbonyl which may be substituted with the following substituent C, aroyl which may be substituted with the following substituent C, lower alkylsulfonyl which may be substituted with the following substituent B, cycloalkylsulfonyl which may be substituted with the following substituent D, aralkylsulfonyl which may be substituted with the following substituent C, arylsulfonyl which may be substituted with the following substituent C, lower alkylsulfamoyl which may be substituted with the following substituent B, di-lower alkylsulfamoyl which may be substituted with the following substituent B, carbamoyl, lower alkylcarbamoyl which may be substituted with the following substituent B, or di-lower alkylcarbamoyl which may be substituted with the following substituent B, or $R^7$ and $R^8$ are combined together with the adjacent nitrogen atom thereto and represent a nitrogen-containing heterocyclic group which may be substituted with the following substituent C], (vii) —$C(=W)NR^9R^{10}$ [wherein W represents an oxygen atom or a sulfur atom, $R^9$ and $R^{10}$ may be the same or different, and each represents a hydrogen atom, hydroxy, lower alkoxy which may be substituted with the following substituent B, amino, lower alkylamino which may be substituted with the following substituent B, lower alkyl which may be substituted with the following substituent B, lower alkenyl which may be substituted with the following substituent B, lower alkanoyl which may be substituted with the following substituent B, cycloalkyl which may be substituted with the following substituent D, aralkyl which may be substituted with the following substituent C, aryl which may be substituted with the following substituent C, a heteroaromatic group which may be substituted with the following substituent C, or an aliphatic heterocyclic group which may be substituted with the following substituent D, or $R^9$ and $R^{10}$ are combined together with the adjacent nitrogen atom thereto and represent a nitrogen-containing heterocyclic group which may be substituted with the following substituent C], (viii) lower alkyl which may be substituted with the following substituent B, (ix) an aliphatic heterocyclic group which may be substituted with the following substituent D, (x) aralkyl which may be substituted with the following substituent C, (xi) aryl which may be substituted with the following substituent C, (xii) a heteroaromatic group which may be substituted with the following substituent C, (xiii) cycloalkyl which may be substituted with the following substituent D, (xiv) lower alkylsulfanyl which may be substituted with the following substituent B, (xv) lower alkylsulfinyl which may be substituted with the following substituent B, (xvi) lower alkylsulfonyl which may be substituted with the following substituent B, (xvii) lower alkylsulfamoyl which may be substituted with the following substituent B, (xviii) di-lower alkylsulfamoyl which may be substituted with the following substituent B, (xix)—$C(=C(CN)_2)R^{13}$ (wherein $R^{13}$ represents lower alkyl), and (xx)—$C(=NOR^{14})R^{15}$ (wherein $R^{14}$ represents a hydrogen atom or lower alkyl, and $R^{15}$ represents lower alkyl);

the substituent B refers to 1 to 3 substituents selected from the group consisting of cyano; lower alkylsulfonyl; lower alkylsulfinyl; lower alkylsulfanyl; halogen; hydroxy; lower alkoxy; aralkyloxy; —$NR^{11}R^{12}$ (wherein $R^{11}$ and $R^{12}$ may be the same or different, and each represents a hydrogen atom, lower alkyl, aralkyl, aryl, lower alkanoyl, lower alkoxycarbonyl, aroyl, lower alkylsulfonyl, or arylsulfonyl); a heteroaromatic group which may have 1 to 3 substituents selected from the group consisting of halogen, hydroxy, lower alkoxy, and lower alkyl; an aliphatic heterocyclic group which may have 1 to 3 substituents selected from the group consisting of halogen, oxo, hydroxy, lower alkoxy, and lower alkyl; and cycloalkyl which may have 1 to 3 substituents selected from the group consisting of halogen, oxo, hydroxy, lower alkoxy, and lower alkyl;

the substituent C refers to 1 to 3 substituents selected from the group consisting of cyano; lower alkylsulfonyl; lower alkylsulfinyl; lower alkylsulfanyl; halogen; hydroxy; lower alkoxy; aralkyloxy; —$NR^{11}R^{12}$ (wherein $R^{11}$ and $R^{12}$ have the same definitions as described above, respectively); a heteroaromatic group which may have 1 to 3 substituents selected from the group consisting of halogen, hydroxy, lower alkoxy, and lower alkyl; an aliphatic heterocyclic group which may have 1 to 3 substituents selected from the group consisting of halogen, oxo, hydroxy, lower alkoxy, and lower alkyl; aryl which may be substituted with 1 to 3 substituents selected from the group consisting of halogen, hydroxy, lower alkoxy, and lower alkyl; lower alkyl which may be substituted with 1 to 3 substituents selected from the group consisting of halogen, hydroxy, and lower alkoxy; and cycloalkyl which may have 1 to 3 substituents selected from the group consisting of halogen, oxo, hydroxy, lower alkoxy, and lower alkyl; and the substituent D refers to 1 to 3 substituents selected from the group consisting of oxo; cyano; lower alkylsulfonyl; lower alkylsulfinyl; lower alkylsulfanyl; halogen; hydroxy; lower alkoxy; aralkyloxy; —NR$^{11}$R$^{12}$ (wherein R$^{11}$ and R$^{12}$ have the same definitions as described above, respectively); a heteroaromatic group which may have 1 to 3 substituents selected from the group consisting of halogen, hydroxy, lower alkoxy, and lower alkyl; an aliphatic heterocyclic group which may have 1 to 3 substituents selected from the group consisting of halogen, oxo, hydroxy, lower alkoxy, and lower alkyl; aryl which may be substituted with 1 to 3 substituents selected from the group consisting of halogen, hydroxy, lower alkoxy, and lower alkyl; lower alkyl which may be substituted with 1 to 3 substituents selected from the group consisting of halogen, hydroxy, and lower alkoxy; and cycloalkyl which may have 1 to 3 substituents selected from the group consisting of halogen, oxo, hydroxy, lower alkoxy, and lower alkyl].

(4) The imidazole derivative or the pharmaceutically acceptable salt thereof according to (3), wherein R$^{1A}$ is lower alkyl which may have 1 to 3 substituents selected from the group consisting of halogen, hydroxy, and lower alkoxy.

(5) The imidazole derivative or the pharmaceutically acceptable salt thereof according to (3), wherein R$^{1A}$ is lower alkyl.

(6) The imidazole derivative or the pharmaceutically acceptable salt thereof according to (3), wherein R$^{1A}$ is tert-butyl.

(7) The imidazole derivative or the pharmaceutically acceptable salt thereof according to any one of (3) to (6), wherein R$^{2A}$ is cycloalkyl which may have 1 to 3 substituents selected from the group consisting of cyano, halogen, hydroxy, lower alkoxy, lower alkyl, oxo, lower alkoxycarbonyl, and aralkyl.

(8) The imidazole derivative or the pharmaceutically acceptable salt thereof according to any one of (3) to (6), wherein R$^{2A}$ is an aliphatic heterocyclic group which may have 1 to 3 substituents selected from the group consisting of cyano, halogen, hydroxy, lower alkoxy, lower alkyl, oxo, lower alkoxycarbonyl, and aralkyl.

(9) The imidazole derivative or the pharmaceutically acceptable salt thereof according to (8), wherein the aliphatic heterocyclic group is an oxygen-containing aliphatic heterocyclic group.

(10) The imidazole derivative or the pharmaceutically acceptable salt thereof according to (8), wherein the aliphatic heterocyclic group is an aliphatic heterocyclic group represented by the following formula (X):

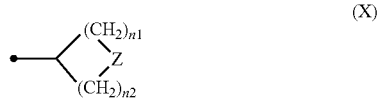

(wherein Z represents an oxygen atom or a sulfur atom, n1 and n2 independently represent an integer of 0 to 3).

(11) The imidazole derivative or the pharmaceutically acceptable salt thereof according to any one of (3) to (6), wherein R$^{2A}$ is cyclohexyl which may have 1 to 3 substituents selected from the group consisting of cyano, halogen, hydroxy, lower alkoxy, lower alkyl, oxo, lower alkoxycarbonyl, and aralkyl, or 4-tetrahydropyranyl which may have 1 to 3 substituents selected from the group consisting of cyano, halogen, hydroxy, lower alkoxy, lower alkyl, oxo, lower alkoxycarbonyl, and aralkyl.

(12) The imidazole derivative or the pharmaceutically acceptable salt thereof according to any one of (3) to (11), wherein R$^{3A}$ is aryl which has 1 to 5 substituents selected from the substituent group A.

(13) The imidazole derivative or the pharmaceutically acceptable salt thereof according to any one of (3) to (11), wherein R$^{3A}$ is a heteroaromatic group which may have 1 to 5 substituents selected from the substituent group A.

(14) The imidazole derivative or the pharmaceutically acceptable salt thereof according to any one of (3) to (11), wherein R$^{3A}$ is vinyl which has 1 to 3 substituents selected from the substituent group A.

(15) The imidazole derivative or the pharmaceutically acceptable salt thereof according to any one of (3) to (14), wherein the substituent group A is a group consisting of cyano, —COR$^6$ (wherein R$^6$ has the same definition as described above), —NR$^7$R$^8$ (wherein R$^7$ and R$^8$ have the same definitions as described above, respectively), and —C(=O)NR$^9$R$^{10}$ (wherein R$^9$ and R$^{10}$ have the same definitions as described above, respectively).

(16) The imidazole derivative or the pharmaceutically acceptable salt thereof according to any one of (3) to (14), wherein the substituent group A is a group consisting of —NR$^7$R$^8$ (wherein R$^7$ and R$^8$ have the same definitions as described above, respectively) and —C(=O)NR$^9$R$^{10}$ (wherein R$^9$ and R$^{10}$ have the same definitions as described above, respectively).

(17) The imidazole derivative or the pharmaceutically acceptable salt thereof according to any one of (3) to (16), wherein n is 1.

(18) A pharmaceutical composition comprising the imidazole derivative or the pharmaceutically acceptable salt thereof described in any one of (3) to (17) as an active ingredient.

(19) A CB2 receptor modulator comprising the imidazole derivative or the pharmaceutically acceptable salt thereof described in any one of (3) to (17) as an active ingredient.

(20) The modulator according to (19), wherein the modulator is an agonist.

(21) A therapeutic and/or preventive agent for a pain comprising the imidazole derivative or the pharmaceutically acceptable salt thereof described in any one of (3) to (17) as an active ingredient.

(22) A method for modulating a CB2 receptor characterized by administering the imidazole derivative or the pharmaceutically acceptable salt thereof described in any one of (3) to (17).

(23) The method according to (22), wherein the modulation method is agonization method.

(24) A method for treating and/or preventing a pain characterized by administering the imidazole derivative or the pharmaceutically acceptable salt thereof described in any one of (3) to (17).

(25) Use of the imidazole derivative or the pharmaceutically acceptable salt thereof described in any one of (3) to (17) for the manufacture of a CB2 receptor modulator.

(26) The use according to (25), wherein the modulator is an agonist.

(27) Use of the imidazole derivative or the pharmaceutically acceptable salt thereof described in any one of (3) to (17) for the manufacture of a therapeutic and/or preventive agent for a pain.

Effect of the Invention

According to the present invention, a CB2 receptor modulator (such as a CB2 receptor agonist) and the like comprising an imidazole derivative or a pharmaceutically acceptable salt thereof as an active ingredient are provided. Further, a novel imidazole derivative or a pharmaceutically acceptable salt thereof which has an effect to modulate a CB2 receptor and is useful as, for example, a CB2 receptor agonist, a therapeutic and/or preventive agent for a pain, or the like is provided.

BEST MODE FOR CARRYING OUT THE INVENTION

Hereinafter, the compound represented by the general formula (I) is referred to as Compound (I). The compounds having the other formula numbers are referred to in the same manner.

The definitions of the respective groups in the general formulae (I) and (IA) are as follows.

Examples of the lower alkyl and the lower alkyl moieties of the lower alkoxy, the lower alkylamino, the lower alkanoyl, the lower alkoxycarbonyl, the lower alkylsulfonyl, the lower alkylsulfinyl, the lower alkylsulfanyl, the lower alkylsulfamoyl, the di-lower alkylsulfamoyl, the lower alkylcarbamoyl, and the di-lower alkylcarbamoyl include linear or branched alkyl having 1 to 10 carbon atoms. More specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, and the like. The two lower alkyl moieties of the di-lower alkylsulfamoyl and the di-lower alkylcarbamoyl may be the same or different from each other.

Examples of the lower alkenyl include linear or branched alkenyl having 2 to 10 carbon atoms. More specific examples thereof include vinyl, allyl, 1-propenyl, butenyl, pentenyl, hexenyl, heptenyl, octenyl, nonenyl, decenyl, and the like.

Examples of the cycloalkyl and the cycloalkyl moieties of the cycloalkylcarbonyl and the cycloalkylsulfonyl include cycloalkyl having 3 to 8 carbon atoms. More specific examples thereof include cyclopropyl, cyclobutyl, cyclopentyl, cyclohexyl, cycloheptyl, cyclooctyl, and the like.

Examples of the aralkyl and the aralkyl moieties of the aralkylcarbonyl, the aralkylsulfonyl, and the aralkyloxy include aralkyl having 7 to 16 carbon atoms. More specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl, and the like.

Examples of the aryl and the aryl moieties of the aroyl and the arylsulfonyl include aryl having 6 to 14 carbon atoms. More specific examples thereof include phenyl, naphthyl, azulenyl, anthryl, and the like.

Examples of the condensed aromatic hydrocarbon group include a hydrocarbon group formed by condensation of the above-mentioned aryl having 8 to 12 carbon atoms with cycloalkyl and the like. More specific examples thereof include indenyl, indanyl, dihydronaphthalenyl, tetrahydronaphthalenyl, dihydroazulenyl, tetrahydroazulenyl, benzocyclobutenyl, benzocycloheptenyl, benzocyclooctanyl, and the like.

Examples of the aliphatic heterocyclic group include a 5- or 6-membered monocyclic aliphatic heterocyclic group which contains at least one atom selected from a nitrogen atom, an oxygen atom, and a sulfur atom, a bicyclic or tricyclic condensed aliphatic heterocyclic group in which 3- to 8-membered rings are fused and contains at least one atom selected from a nitrogen atom, an oxygen atom, and a sulfur atom, and the like. More specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, tetrahydrothiophenyl, tetrahydro-2H-thiopyranyl, 1-oxo-tetrahydrothiophenyl, 1,1-dioxo-tetrahydrothiophenyl, 1-oxo-tetrahydro-2H-thiopyranyl, 1,1-dioxo-tetrahydro-2H-thiopyranyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, oxetanyl, [1,4]dioxepanyl, 7,8-dihydro-5H-pyrido[4,3-d]pyrimidinyl, 1,2-dihydropyridyl, and the like.

Examples of the oxygen-containing aliphatic heterocyclic group include an aliphatic heterocyclic group containing an oxygen atom among the above-mentioned aliphatic heterocyclic groups. More specific examples thereof include oxiranyl, tetrahydrofuranyl, tetrahydro-2H-pyranyl, 5,6-dihydro-2H-pyranyl, oxazolidinyl, morpholino, morpholinyl, 2H-oxazolyl, dihydrobenzofuranyl, dihydrobenzoxazolyl, benzodioxolinyl, dihydro-2H-chromanyl, dihydro-1H-chromanyl, dihydrobenzodioxanyl, oxetanyl, [1,4]dioxepanyl, and the like.

Examples of the heteroaromatic group include a 5- or 6-membered monocyclic heteroaromatic group which contains at least one atom selected from a nitrogen atom, an oxygen atom, and a sulfur atom, a bicyclic or tricyclic condensed heteroaromatic group in which 3- to 8-membered rings are fused and contains at least one atom selected from a nitrogen atom, an oxygen atom, and a sulfur atom and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, dihydropyridopyrimidinyl, 7,8-dihydropyrido-5H-pyrimidinyl, pyridopyrazinyl, dihydropyridopyrazinyl, and the like.

Examples of the nitrogen-containing heterocyclic group formed together with the adjacent nitrogen atom thereto include a 5- or 6-membered monocyclic heterocyclic group which contains at least one nitrogen atom (the monocyclic heterocyclic group may further contain another nitrogen atom, an oxygen atom, or a sulfur atom), a bicyclic or tricyclic condensed heterocyclic group in which 3- to 8-membered rings are fused and contains at least one nitrogen atom (the condensed heterocyclic group may further contain another nitrogen atom, an oxygen atom, or a sulfur atom), and the like. More specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl, and the like.

The halogen refers to each atom of fluorine, chlorine, bromine, and iodine.

Examples of the substituents for the optionally substituted lower alkyl and the optionally substituted lower alkenyl, which may be the same or different and in number of 1 to a substitutable number, preferably in number of 1 to 3, include (1) halogen, (2) nitro, (3) cyano, (4) —$OR^a$ (wherein $R^a$ represents a hydrogen atom, $C_{1-10}$ alkyl which may be substituted with the following substituent P, $C_{3-8}$ cycloalkyl which may be substituted with the following substituent R, $C_{7-16}$ aralkyl which may be substituted with the following substituent Q, $C_{6-14}$ aryl which may be substituted with the following substituent Q, a heteroaromatic group which may be substituted with the following substituent Q, an aliphatic heterocyclic group which may be substituted with the following substituent R, $C_{2-11}$ alkanoyl which may be substituted with the following substituent P, or $C_{7-15}$ aroyl which may be substituted with the following substituent Q), (5) —$COR^b$ [wherein $R^b$ represents a hydrogen atom, $C_{1-10}$ alkyl which may be substituted with the following substituent P, $C_{3-8}$ cycloalkyl which may be substituted with the following substituent R, $C_{7-16}$ aralkyl which may be substituted with the following substituent Q, $C_{6-14}$ aryl which may be substituted with the following substituent Q, a heteroaromatic group which may be substituted with the following substituent Q, an aliphatic heterocyclic group which may be substituted with the following substituent R, hydroxy, $C_{1-10}$ alkoxy which may be substituted with the following substituent P, $C_{3-8}$ cycloalkyloxy which may be substituted with the following substituent R, $C_{7-16}$ aralkyloxy which may be substituted with the following substituent Q, or $C_{6-14}$ aryloxy which may be substituted with the following substituent Q], (6) —$NR^cR^d$ [wherein $R^c$ and $R^d$ may be the same or different, and each represents a hydrogen atom, hydroxy, $C_{1-10}$ alkoxy which may be substituted with the following substituent P, amino, $C_{1-10}$ alkylamino which may be substituted with the following substituent P, di-$C_{1-10}$ alkylamino which may be substituted with the following substituent P, $C_{1-10}$ alkyl which may be substituted with the following substituent P, $C_{2-10}$ alkenyl which may be substituted with the following substituent P, $C_{3-8}$ cycloalkyl which may be substituted with the following substituent R, $C_{7-16}$ aralkyl which may be substituted with the following substituent Q, $C_{6-14}$ aryl which may be substituted with the following substituent Q, a heteroaromatic group which may be substituted with the following substituent Q, an aliphatic heterocyclic group which may be substituted with the following substituent R, $C_{2-11}$ alkanoyl which may be substituted with the following substituent P, $C_{4-9}$ cycloalkylcarbonyl which may be substituted with the following substituent R, $C_{8-17}$ aralkylcarbonyl which may be substituted with the following substituent Q, $C_{7-15}$ aroyl which may be substituted with the following substituent Q, $C_{1-10}$ alkoxycarbonyl which may be substituted with the following substituent P, $C_{1-10}$ alkylsulfonyl which may be substituted with the following substituent P, $C_{3-8}$ cycloalkylsulfonyl which may be substituted with the following substituent R, $C_{7-16}$ aralkylsulfonyl which may be substituted with the following substituent Q, $C_{6-14}$ arylsulfonyl which may be substituted with the following substituent Q, $C_{1-10}$ alkylsulfamoyl which may be substituted with the following substituent P, di-$C_{1-10}$ alkylsulfamoyl which may be substituted with the following substituent P, carbamoyl, $C_{1-10}$ alkylcarbamoyl which may be substituted with the following substituent P, di-$C_{1-10}$ alkylcarbamoyl which may be substituted with the following substituent P, or $R^c$ and $R^d$ are combined together with the adjacent nitrogen atom thereto and represent a nitrogen-containing heterocyclic group which may be substituted with the following substituent R], (7) —$C(=V)NR^eR^f$ [wherein V represents an oxygen atom or a sulfur atom, $R^e$ and $R^f$ may be the same or different, and each represents a hydrogen atom, hydroxy, $C_{1-10}$ alkoxy which may be substituted with the following substituent P, amino, $C_{1-10}$ alkylamino which may be substituted with the following substituent P, di-$C_{1-10}$ alkylamino which may be substituted with the following substituent P, $C_{1-10}$ alkyl which may be substituted with the following substituent P, $C_{2-10}$ alkenyl which may be substituted with the following substituent P, $C_{3-8}$ cycloalkyl which may be substituted with the following substituent R, $C_{7-16}$ aralkyl which may be substituted with the following substituent Q, $C_{6-14}$ aryl which may be substituted with the following substituent Q, a heteroaromatic group which may be substituted with the following substituent Q, an aliphatic heterocyclic group which may be substituted with the following substituent R, or $R^e$ and $R^f$ are combined together with the adjacent nitrogen atom thereto and represent a nitrogen-containing heterocyclic group which may be substituted with the following substituent R], (8) an aliphatic heterocyclic group which may be substituted with the following substituent R, (9) a heteroaromatic group which may be substituted with the following substituent Q, (10) —$S(=O)_{mg}R^g$ (wherein mg represents an integer of 0 to 2, $R^g$ represents a hydrogen atom, $C_{1-10}$ alkyl which may be substituted with the following substituent P, or $C_{6-14}$ aryl which may be substituted with the following substituent Q), (11) $C_{1-10}$ lower alkylsulfamoyl which may be substituted with the following substituent P, (12) di-$C_{1-10}$ lower alkylsulfamoyl which may be substituted with the following substituent P, and the like.

Here, the substituent P refers to 1 to 3 substituents selected from the group consisting of halogen; hydroxy; $C_{1-10}$ alkoxy which may have 1 to 3 substituents selected from the group consisting of halogen, hydroxy, and $C_{1-10}$ alkoxy; $C_{7-16}$ aralkyloxy; —$NR^hR^i$ (wherein $R^h$ and $R^i$ may be the same or different, and each represents a hydrogen atom, $C_{1-10}$ alkyl, $C_{7-16}$ aralkyl, $C_{6-14}$ aryl, $C_{2-11}$ alkanoyl, $C_{7-15}$ aroyl, $C_{1-10}$ alkylsulfonyl, or $C_{6-14}$ arylsulfonyl); a heteroaromatic group which may have 1 to 3 substituents selected from the group consisting of halogen, hydroxy, $C_{1-10}$ alkoxy, and $C_{1-10}$ alkyl; an aliphatic heterocyclic group which may have 1 to 3 substituents selected from the group consisting of halogen, oxo, hydroxy, $C_{1-10}$ alkoxy, and $C_{1-10}$ alkyl; $C_{3-8}$ cycloalkyl; sulfanyl; and $C_{1-10}$ alkylsulfanyl.

The substituent Q refers to 1 to 3 substituents selected from the group consisting of halogen; hydroxy; $C_{1-10}$ alkoxy; $C_{7-16}$ aralkyloxy; —$NR^hR^i$ (wherein $R^h$ and $R^i$ have the same definitions as described above, respectively); a heteroaromatic group which may have 1 to 3 substituents selected from the group consisting of halogen, hydroxy, $C_{1-10}$ alkoxy, and $C_{1-10}$ alkyl; an aliphatic heterocyclic group which may have 1 to 3 substituents selected from the group consisting of halogen, oxo, hydroxy, $C_{1-10}$ alkoxy, and $C_{1-10}$ alkyl; $C_{3-8}$ cycloalkyl; $C_{6-14}$ aryl which may be substituted with 1 to 3 substituents selected from the group consisting of halogen, hydroxy, $C_{1-10}$ alkoxy, and $C_{1-10}$ alkyl; $C_{1-10}$ alkyl which may be substituted with 1 to 3 substituents selected from the group consisting of halogen, hydroxy, and $C_{1-10}$ alkoxy; sulfanyl; and $C_{1-10}$ alkylsulfanyl.

The substituent R refers to 1 to 3 substituents selected from the group consisting of oxo; halogen; hydroxy; $C_{1-10}$ alkoxy; $C_{7-16}$ aralkyloxy; —$NR^hR^i$ (wherein $R^h$ and $R^i$ have the same definitions as described above, respectively); a heteroaromatic group which may have 1 to 3 substituents selected from the group consisting of halogen, hydroxy, $C_{1-10}$ alkoxy, and $C_{1-10}$ alkyl; an aliphatic heterocyclic group which may have 1 to 3 substituents selected from the group consisting of halogen, oxo, hydroxy, $C_{1-10}$ to alkoxy, and $C_{1-10}$ alkyl; $C_{3-8}$ cycloalkyl; $C_{6-14}$ aryl which may be substituted with 1 to 3 substituents selected from the group consisting of halogen, hydroxy, $C_{1-10}$ alkoxy, and $C_{1-10}$ alkyl; $C_{1-10}$ alkyl which may be substituted with 1 to 3 substituents selected from the group consisting of halogen, hydroxy, and $C_{1-10}$ alkoxy; sulfanyl; and $C_{1-10}$ alkylsulfanyl.

Examples of the substituents for the optionally substituted vinyl, the optionally substituted aryl, the optionally substituted aralkyl, and the optionally substituted heteroaromatic group, which may be the same or different and in number of 1 to a substitutable number, preferably in number of 1 to 3, include (1) halogen, (2) nitro, (3) cyano, (4) —$OR^a$ (wherein $R^a$ has the same definition as described above), (5) —$COR^b$ (wherein $R^b$ has the same definition as described above), (6) —$NR^cR^d$ (wherein $R^c$ and $R^d$ have the same definitions as described above, respectively), (7) —$C(=V)NR^eR^f$ (wherein V, $R^e$, and $R^f$ have the same definitions as described above, respectively), (8) $C_{1-10}$ alkyl which may be substituted with the above-mentioned substituent P, (9) an aliphatic heterocyclic group which may be substituted with the above-mentioned substituent R, (10) $C_{7-16}$ aralkyl which may be substituted with the above-mentioned substituent Q, (11) $C_{6-14}$ aryl which may be substituted with the above-mentioned substituent Q, (12) a heteroaromatic group which may be substituted with the above-mentioned substituent Q, (13) —$S(=O)_{mg}R^g$ (wherein mg and $R^g$ have the same definitions as described above, respectively), (14) $C_{2-10}$ alkenyl which may be substituted with the above-mentioned substituent P, (15) $C_{1-10}$ alkylsulfamoyl which may be substituted with the above-mentioned substituent P, (16) di-$C_{1-10}$ alkylsulfamoyl which may be substituted with the above-mentioned substituent P, (17) —$C(=C(CN)_2)R^x$ (wherein $R^x$ represents $C_{1-10}$ alkyl which may be substituted with the above-mentioned substituent P), (18) —$C(=NOR^y)R^z$ (wherein $R^y$ represents a hydrogen atom or $C_{1-10}$ alkyl and $R^z$ represents $C_{1-10}$ alkyl), and the like.

Examples of the substituents for the optionally substituted cycloalkyl, the optionally substituted condensed aromatic hydrocarbon group, and the optionally substituted aliphatic heterocyclic group, which may be the same or different and in number of 1 to a substitutable number, preferably in number of 1 to 3, include (1) halogen, (2) nitro, (3) cyano, (4) oxo, (5) —$OR^a$ (wherein $R^a$ has the same definition as described above), (6) —$COR^b$ (wherein $R^b$ has the same definition as described above), (7) —$NR^cR^d$ (wherein $R^c$ and $R^d$ have the same definitions as described above, respectively), (8) —$C(=V)NR^eR^f$ (wherein V, $R^e$, and $R^f$ have the same definitions as described above, respectively), (9) $C_{1-10}$ alkyl which may be substituted with the above-mentioned substituent P, (10) an aliphatic heterocyclic group which may be substituted with the above-mentioned substituent R, (11) $C_{7-16}$ aralkyl which may be substituted with the above-mentioned substituent Q, (12) $C_{6-14}$ aryl which may be substituted with the above-mentioned substituent Q, (13) a heteroaromatic group which may be substituted with the above-mentioned substituent Q, (14) —$S(=O)_{mg}R^g$ (wherein mg and $R^g$ have the same definitions as described above), (15) $C_{1-10}$ alkylsulfamoyl which may be substituted with the above-mentioned substituent P, (16) di-$C_{1-10}$ alkylsulfamoyl which may be substituted with the above-mentioned substituent P, and the like.

Examples of the $C_{1-10}$ alkyl and the $C_{1-10}$ alkyl moieties of the $C_{2-11}$ alkanoyl, the $C_{1-10}$ alkoxy, the $C_{1-10}$ alkoxycarbonyl, the $C_{1-10}$ alkylamino, the di-$C_{1-10}$ alkylamino, the $C_{1-10}$ alkylsulfonyl, the $C_{1-10}$ alkylsulfamoyl, the di-$C_{1-10}$ alkylsulfamoyl, the $C_{1-10}$ alkylcarbamoyl, the di-$C_{1-10}$ alkylcarbamoyl, and the $C_{1-10}$ alkylsulfanyl illustrated in the definitions of the substituents described above include the groups illustrated for the lower alkyl described above, and the two $C_{1-10}$ alkyl moieties of the di-$C_{1-10}$ alkylamino, the di-$C_{1-10}$ alkylsulfamoyl, and the di-$C_{1-10}$ alkylcarbamoyl may be the same or different from each other. Examples of the $C_{3-8}$ cycloalkyl and the $C_{3-8}$ cycloalkyl moieties of the $C_{3-8}$ cycloalkyloxy, the $C_{4-9}$ cycloalkylcarbonyl, and the $C_{3-8}$ cycloalkylsulfonyl include the groups illustrated for the cycloalkyl described above. Examples of the $C_{6-14}$ aryl and the $C_{6-14}$ aryl moieties of the $C_{7-15}$ aroyl, the $C_{6-14}$ aryloxy, and the $C_{6-14}$ arylsulfonyl include the groups illustrated for the aryl described above. Examples of the $C_{2-10}$ alkenyl, the heteroaromatic group, the aliphatic heterocyclic group, the nitrogen-containing heterocyclic group formed together with the adjacent nitrogen atom, and the halogen include the groups illustrated for the lower alkenyl described above, the heteroaromatic group described above, the aliphatic heterocyclic group described above, the nitrogen-containing heterocyclic group formed together with the adjacent nitrogen atom described above, and the halogen described above, respectively. Examples of the $C_{7-16}$ aralkyl and the aralkyl moieties of the $C_{7-16}$ aralkyloxy, the $C_{8-17}$ aralkylcarbonyl, and the $C_{7-16}$ aralkylsulfonyl include the groups illustrated for the aralkyl described above.

The respective groups of Compound (I) are as follows.

As $R^1$, for example, alkyl which may have 1 to 3 substituents selected from the group consisting of halogen, hydroxy, and $C_{1-10}$ alkoxy is preferred, and $C_{1-10}$ alkyl and the like are more preferred. More specifically, for example, methyl, ethyl, propyl, 2-propyl, butyl, 2-butyl, tert-butyl, pentyl, 2-pentyl, 3-pentyl, 1,1-dimethylpropyl, hexyl, 2-hexyl, 3-hexyl, 3-methyl-3-pentyl, 2-methyl-2-pentyl, 3-methyl-3-hexyl, 2-methyl-2-hexyl, 3-ethyl-3-hexyl, and the like are preferred, and $C_{1-10}$ alkyl groups having a quaternary carbon such as tert-butyl, 1,1-dimethylpropyl, 3-methyl-3-pentyl, 2-methyl-2-pentyl, 3-methyl-3-hexyl, 2-methyl-2-hexyl, and 3-ethyl-3-hexyl are preferred, and tert-butyl, 1,1-dimethylpropyl, and the like are more preferred, and tert-butyl and the like are further more preferred.

As $R^2$, for example, cycloalkyl, an aliphatic heterocyclic group, and the like are preferred. As the cycloalkyl, for example, cyclopentyl, cyclohexyl, cycloheptyl, and the like are preferred, and cyclohexyl and the like are more preferred. As the aliphatic heterocyclic group, for example, tetrahydrofuranyl, tetrahydrothiophenyl, tetrahydro-2H-pyranyl, tetrahydro-2H-thiopyranyl, morpholinyl, thiomorpholinyl, 5,6-dihydro-2H-pyranyl, [1,4]dioxepanyl, and the like are preferred, and tetrahydro-2H-pyranyl and the like are more preferred. Such cycloalkyl and aliphatic heterocyclic group may have 1 to 3 substituents, and as the substituents, for example, cyano, halogen, hydroxy, $C_{1-10}$ alkoxy, $C_{1-10}$ alkyl, oxo, and the like are preferred, and specifically, for example, cyano, a fluorine atom, a chlorine atom, an iodine atom, hydroxy, methoxy, ethoxy, propoxy, isopropoxy, methyl, ethyl, propyl, isopropyl, oxo, and the like are preferred, and cyano, a fluorine atom, a chlorine atom, an iodine atom, hydroxy, methoxy, methyl, oxo, and the like are more preferred.

As $R^3$, for example, optionally substituted aryl, an optionally substituted heteroaromatic group, and the like are preferred. As the substituent, for example, cyano, —$COR^6$ (wherein $R^6$ has the same definition as described above), —$NR^7R^8$ (wherein $R^7$ and $R^8$ have the same definitions as described above, respectively), —$C(=O)NR^9R^{10}$ (wherein $R^9$ and $R^{10}$ have the same definitions as described above, respectively), and the like are preferred, and —$NR^7R^8$ (wherein $R^7$ and $R^8$ have the same definitions as described above, respectively), —$C(=O)NR^9R^{10}$ (wherein $R^9$ and $R^{10}$ have the same definitions as described above, respectively), and the like are more preferred, and —$C(=O)NR^9R^{10}$ (wherein $R^9$ and $R^{10}$ have the same definitions as described above, respectively), and the like are further more preferred. Specifically, for example, optionally substituted phenyl, optionally substituted pyridyl, optionally substituted thienyl, optionally substituted oxazolyl, optionally substituted thiazolyl, optionally substituted pyrazinyl, optionally substituted pyrimidinyl, and the like are preferred, and as the substituents for these groups, for example, cyano, $C_{2-11}$ alkanoyl, aliphatic heterocyclic carbonyl, $C_{1-10}$ alkylamino, $C_{2-11}$ alkanoylamino, $C_{1-10}$ alkylcarbamoyl, di-$C_{1-10}$ alkylcarbamoyl, and the like are preferred, and these substituents may be further substituted with a substituent such as halogen, hydroxy, $C_{1-10}$ alkoxy, cyano, or a heteroaromatic group.

Preferably, n is for example, 1 or 2, and more preferably 1.

Examples of the pharmaceutically acceptable salt of Compound (I) include pharmaceutically acceptable acid addition salts, metal salts, ammonium salts, organic amine addition salts, amino acid addition salts, and the like. Examples of the pharmaceutically acceptable acid addition salts of Compound (I) include inorganic acid salts such as hydrochlorides, hydrobromides, nitrates, sulfates, and phosphates, organic acid salts such as acetates, oxalates, maleates, fumarates, citrates, benzoates, methanesulfonates, and the like. Examples of the pharmaceutically acceptable metal salts include alkali metal salts such as sodium salts and potassium salts, alkaline earth metal salts such as magnesium salts and calcium salts, aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

Hereinafter, production methods of Compound (I) will be described.

In the production methods described below, when a defined group changes under the conditions of the production methods or is not suitable for carrying out the production methods, it is possible to produce a desired compound using a method, which is commonly used in synthetic organic chemistry, for introducing and removing a protecting group [for example, the method described in Protective Groups in Organic Synthesis, third edition, T. W. Greene, John Wiley & Sons Inc. (1999), etc.] or the like. If necessary, the order of reaction steps such as introduction of a substituent can be changed.

Production Method 1

Compound (I) can be produced according to the following steps.

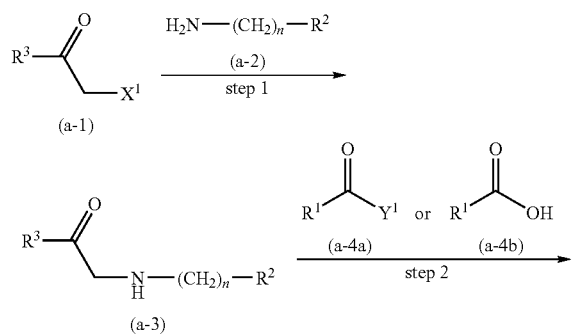

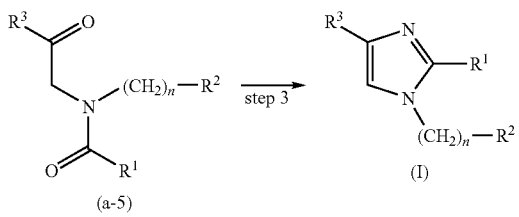

[In the formulae, $X^1$ represents a chlorine atom, a bromine atom, or an iodine atom, $Y^1$ represents a chlorine atom, a bromine atom or $OCOR^1$ (wherein $R^1$ has the same definition as described above), and $R^1$, $R^2$, $R^3$, and n have the same definitions as described above, respectively.]

Step 1

Compound (a-3) can be obtained by reacting Compound (a-1) with preferably 1 to 20 equivalents of Compound (a-2) without solvent or in a solvent, and if necessary, in the presence of preferably 1 to 10 equivalents of sodium iodide or potassium iodide, and/or if necessary, in the presence of preferably 1 to 10 equivalents of a base at a temperature between −10° C. and 150° C. for 5 minutes to 72 hours.

Compound (a-1) can be obtained as a commercially available product, or can also be obtained by performing a Still coupling reaction [for example, Bull. Chem. Soc. Jpn., vol. 60, p. 767 (1978), etc.] of a corresponding aryl derivative, heteroaromatic derivative, or vinyl derivative with tributyl(1-ethoxyvinyl)tin, or performing the Friedel-Crafts reaction [for example, Shin-Jikken Kagaku Koza, 4th Ed., vol. 14, p. 799, Maruzen (1977), etc.] thereof with a corresponding acyl halide or acid anhydride, and if necessary, an acetyl group of the resulting product is halogenated [for example, Shin-Jikken Kagaku Koza, 4th Ed., vol. 14, p. 345, Maruzen (1977), etc.]. Compound (a-2) can be obtained as a commercially available product, or can be obtained by a known method [for example, Shin-Jikken Kagaku Koza, 4th Ed., vol. 14, p. 1332, Maruzen (1978), etc.] or a modified method thereof.

Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, 1,8-diazabicyclo[5.4.0]-7-undecene (DBU), and the like. Examples of the solvent include methanol, ethanol, dichloromethane, chloroform, 1,2-dichloroethane, toluene, xylene, ethyl acetate, acetonitrile, diethyl ether, tetrahydrofuran (THF), 1,2-dimethoxyethane (DME), 1,4-dioxane, N,N-dimethylformamide (DMF), N,N-dimethylacetamide (DMA), N-methylpyrrolidone (NMP), dimethyl sulfoxide (DMSO), pyridine, water, and the like. These are used alone or as a mixture thereof.

Step 2

Compound (a-5) can be obtained by reacting Compound (a-3) with preferably 1 to 20 equivalents of Compound (a-4a) in a solvent, and if necessary, in the presence of preferably 1 to 20 equivalents of a base at a temperature between −10° C. and the boiling point of the solvent used for 5 minutes to 72 hours.

Compound (a-4a) can be obtained as a commercially available product, or by a known method [for example, Shin-Jikken Kagaku Koza, 4th Ed., vol. 14, pp. 1106 and 1120, Maruzen (1977), etc.] or a modified method thereof.

Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof.

Further, Compound (a-5) can also be obtained by reacting Compound (a-3) with preferably 1 to 20 equivalents of Compound (a-4b) in a solvent in the presence of preferably 1 to 20 equivalents of a suitable condensing agent, and if necessary, in the presence of preferably 1 to 20 equivalents of an additive at a temperature between −10° C. and the boiling point of the solvent used for 5 minutes to 72 hours.

Examples of the condensing agent include 1,3-dicyclohexanecarbodiimide (DCC), 1,3-diisopropylcarbodiimide, 1-(3-dimethylaminopropyl)-3-ethylcarbodiimide (EDC), EDC hydrochloride, and the like. Examples of the additive include 1-hydroxybenzotriazole monohydrate (HOBt.H$_2$O), 4-dimethylaminopyridine (DMAP), and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, pyridine, water, and the like. These are used alone or as a mixture thereof.

Step 3

Compound (I) can be obtained by reacting Compound (a-5) with preferably 1 equivalent to a large excess amount of ammonium acetate or ammonium trifluoroacetate without solvent or in a solvent at a temperature between room temperature and 200° C. for 5 minutes to 72 hours. Preferably, Compound (I) is obtained by treating Compound (a-5) in ammonium trifluoroacetate.

Examples of the solvent include acetic acid, propionic acid, acetonitrile, 1,4-dioxane, THF, diethyl ether, diisopropyl ether, benzene, toluene, xylene, DMF, NMP, DMSO, and the like. These are used alone or as a mixture thereof.

Production Method 2

Compound (I) can also be produced according to the following steps.

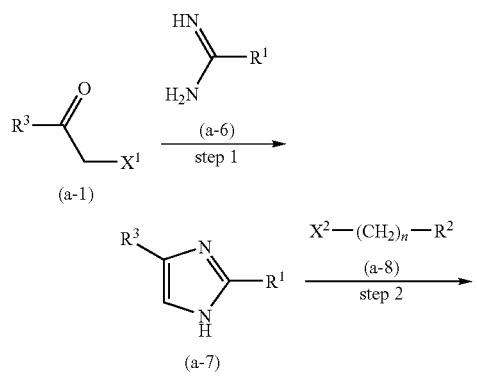

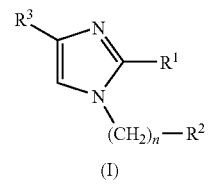

(In the formulae, X$^2$ represents a leaving group such as a chlorine atom, a bromine atom, an iodine atom, trifluoromethanesulfonyloxy, methanesulfonyloxy, benzenesulfonyloxy, p-toluenesulfonyloxy, and X$^1$, R$^1$, R$^2$, R$^3$, and n have the same definitions as described above, respectively.)

Step 1

Compound (a-7) can be obtained by reacting Compound (a-1) with preferably 1 to 20 equivalents of Compound (a-6) without solvent or in a solvent, and if necessary, in the presence of preferably 1 to 10 equivalents of sodium iodide or potassium iodide, and/or if necessary, in the presence of preferably 1 to 10 equivalents of a base at a temperature between −10° C. and 150° C. for 5 minutes to 72 hours.

Compound (a-6) can be obtained as a commercially available product, or by a known method [for example, Jikken Kagaku Koza, 5th Ed., vol. 14, p. 400, Maruzen (2005), etc.] or a modified method thereof.

Examples of the base include potassium carbonate, sodium carbonate, lithium hydroxide, potassium hydroxide, sodium hydroxide, sodium hydride, triethylamine, diisopropylethylamine, N-methylmorpholine, N-methylpiperidine, pyridine, DBU, and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof.

Step 2

Compound (I) can be obtained by reacting Compound (a-7) with preferably 1 to 20 equivalents of Compound (a-8) without solvent or in a solvent, and if necessary, in the presence of preferably 1 to 10 equivalents of sodium iodide or potassium iodide, and/or if necessary, in the presence of preferably 1 to 10 equivalents of a base at a temperature between −10° C. and 150° C. for 5 minutes to 72 hours.

Compound (a-8) can be obtained as a commercially available product, or by a known method [for example, Shin-Jikken Kagaku Koza, 4th Ed., vol. 14, pp. 361 and 1793, Maruzen (1978), etc.] or a modified method thereof. Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof.

Production Method 3

Compound (I) can also be produced according to the following steps.

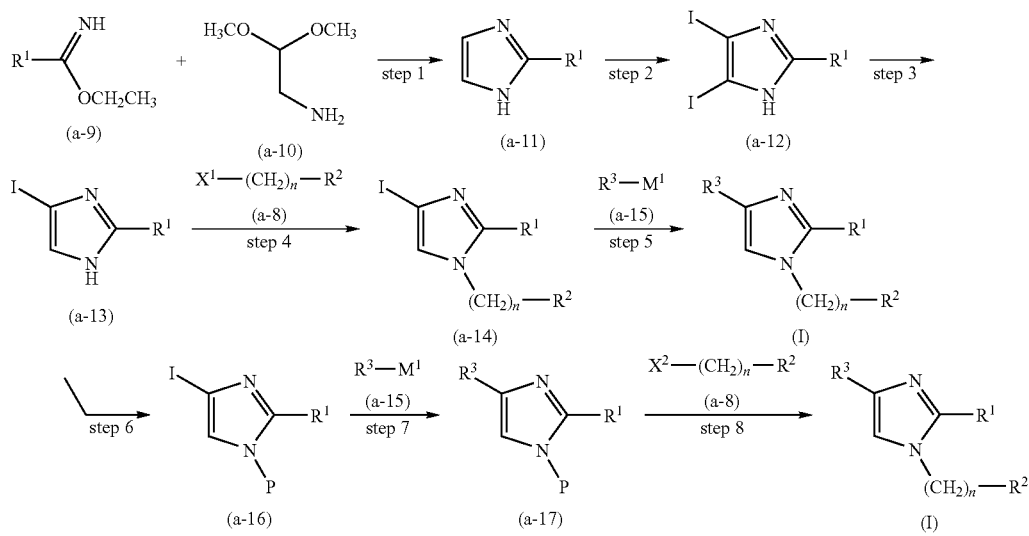

[In the formulae, $M^1$ represents B $(OR^{ma})$ $(OR^{mb})$ (wherein $R^{ma}$ and $R^{mb}$ may be the same or different, and each represents a hydrogen atom, $C_{1-6}$ alkyl, or $R^{ma}$ and $R^{mb}$ are combined and represent $C_{1-6}$ alkylene which may be substituted with methyl) or $SnR^{mc}R^{md}R^{me}$ (wherein $R^{mc}$, $R^{md}$ and $R^{me}$ may be the same or different, and each represents $C_{1-6}$ alkyl or phenyl), P represents a protecting group such as tert-butoxycarbonyl (Boc), benzyl, 3,4-dimethoxybenzyl, nitrobenzenesulfonyl, methoxymethyl, ethoxymethyl, benzyloxymethyl, tert-butyldimethylsilyl, and $X^2$, $R^1$, $R^2$, $R^3$, and n have the same definitions as described above, respectively.]

Step 1

Compound (a-11) can be obtained, for example, in the same manner as the method described in U.S. Pat. No. 5,039,691. That is, Compound (a-11) can be obtained by reacting Compound (a-9) with preferably 1 to 20 equivalents of Compound (a-10) without solvent or in a solvent at a temperature between –10° C. and 150° C. for 5 minutes to 72 hours.

Compound (a-9) can be obtained as a commercially available product, or by treating a corresponding nitrile compound with hydrogen chloride (J. Am. Chem. Soc., vol. 68, p. 2738 (1946), etc.). Further, Compound (a-10) can be obtained as a commercially available product.

Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof.

Step 2

Compound (a-12) can be obtained by reacting Compound (a-11) with preferably 1 to 20 equivalents of iodine in a solvent, and if necessary, in the presence of preferably 1 to 10 equivalents of a base at a temperature between –10° C. and the boiling point of the solvent used for 5 minutes to 72 hours.

Examples of the base include sodium hydrogen carbonate, potassium carbonate, sodium carbonate, lithium hydroxide, potassium hydroxide, sodium hydroxide, triethylamine, diisopropylethylamine, N-methylmorpholine, N-methylpiperidine, pyridine, DBU, and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof. It is preferred to use water and 1,4-dioxane in combination at a ratio of 1:1.

Step 3

Compound (a-13) can be obtained by treating Compound (a-12) in a solvent with preferably 1 to 20 equivalents of sodium sulfite at a temperature between –10° C. and the boiling point of the solvent used for 5 minutes to 96 hours.

Examples of the solvent include methanol, ethanol, propanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof. It is preferred to use water and ethanol in combination.

Step 4

Compound (a-14) can be obtained in the same manner as in step 2 of Production method 2, using Compound (a-13).

Step 5

Compound (I) can be obtained by reacting Compound (a-14) with preferably 1 to 10 equivalents of Compound (a-15) in a solvent in the presence of preferably 0.001 to 1 equivalent of a palladium catalyst, and if necessary, in the presence of preferably 0.1 to 10 equivalents of a base at a temperature between –10° C. and the boiling point of the solvent used for 5 minutes to 72 hours.

Compound (a-15) can be obtained as a commercially available product, or by a known method [for example, Jikken Kagaku Koza, 5th Ed., vol. 18, pp. 95 and 183, Maruzen (2004), etc.] or a modified method thereof.

Examples of the base include potassium acetate, sodium acetate, potassium carbonate, cesium carbonate, sodium carbonate, sodium hydrogen carbonate, sodium hydroxide, lithium hydroxide, potassium hydroxide, potassium phosphate, pyridine, triethylamine, N-methylmorpholine, N-methylpiperidine, diisopropylethylamine, DBU, and the like. Examples of the palladium catalyst include a compound in which phosphine ligands are coordinated to palladium atoms, and examples of the palladium source include palladium acetate, palladium trifluoroacetate, tris(dibenzylideneacetone)dipalladium, chloroform adduct thereof, and the like. Examples of the phosphine ligands include triphenylphosphine, 1,1'-bis(diphenylphosphino)ferrocene, o-tolylphosphine, and the like. Any of these compounds is preferably used in an amount of 1 to 10 equivalents to the palladium source described above. Incidentally, a commercially available reagent such as tetrakis(triphenylphosphine)palladium or the like can also be used. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These are used alone or as a mixture thereof. It is preferred to use a mixed solvent of water and 1,4-dioxane.

In the case where $R^3$ is optionally substituted vinyl, Compound (I) can also be obtained by reacting Compound (a-14) with a vinyl compound corresponding to $R^3$ in the presence of the same palladium catalyst and base as described above (Heck reaction).

Step 6

Compound (a-16) can be obtained, for example, according to the method for introducing a protecting group described in Protective Groups in Organic Synthesis, third edition, T. W. Greene, John Wiley & Sons Inc. (1999), etc. using Compound (a-13).

Step 7

Compound (a-17) can be obtained in the same manner as in the above-mentioned step 5, using Compound (a-16).

Step 8

Compound (I) can be obtained in the same manner as in Step described above after removing the protective group from Compound (a-17), according to, for example, the method described in Protective Groups in Organic Synthesis, third edition, T. W. Greene, John Wiley & Sons Inc. (1999), etc.

Production Method 4

Among Compounds (I), Compound (I-C) having lower alkoxycarbonyl, aralkyloxycarbonyl, or aryloxycarbonyl in $R^3$, Compound (I-D) having carboxy in $R^3$, Compound (I-E) having —CONR$^9$R$^{10}$ (wherein R$^9$ and R$^{10}$ have the same definitions as described above, respectively) in $R^3$, and Compound (I-F) having —CSNR$^9$R$^{10}$ (wherein R$^9$ and R$^{10}$ have the same definitions as described above, respectively) in $R^3$ can also be produced according to the following steps.

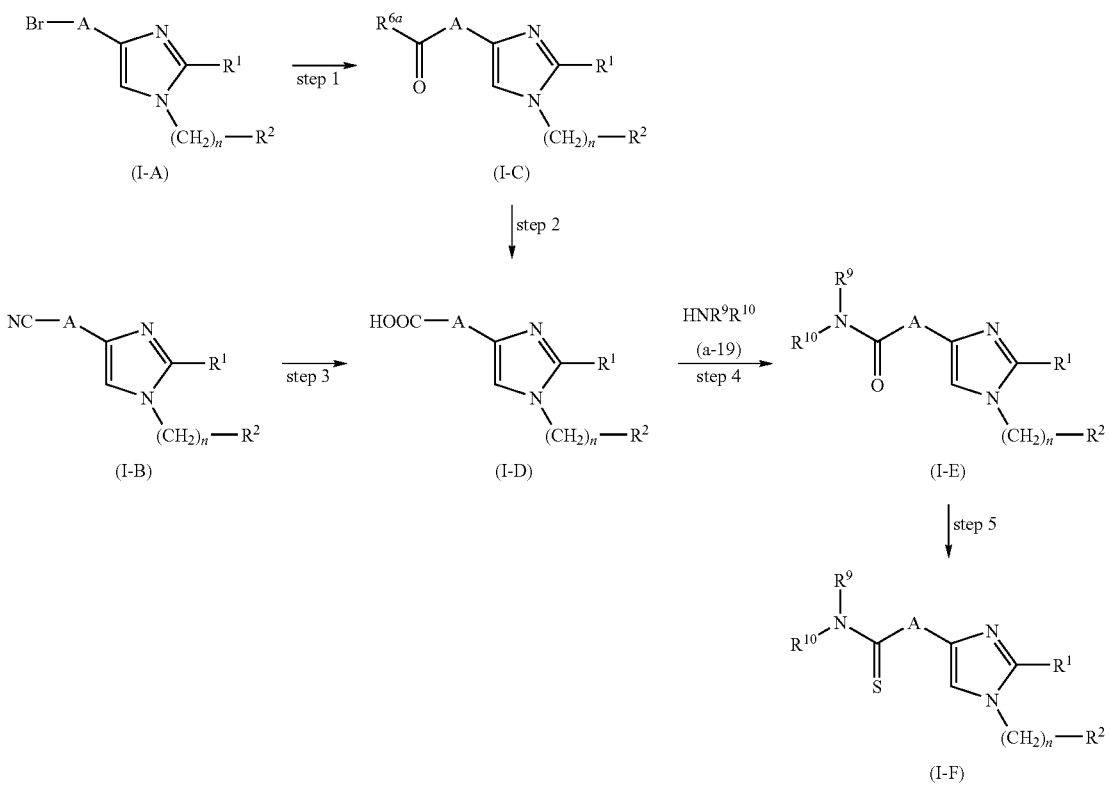

(In the formulae, A represents an aryl moiety, a condensed aromatic hydrocarbon moiety, a heteroaromatic moiety, or a vinyl moiety in the definition of $R^3$, COR$^{6a}$ represents a lower alkoxycarbonyl moiety, an aralkyloxycarbonyl moiety or an aryloxycarbonyl moiety as a substituent in the definition of $R^3$ described above, and $R^9$, $R^{10}$, $R^1$, $R^2$ and n have the same definitions as described above, respectively.)

Step 1

Compound (I-C) can be obtained by reacting Compound (I-A) obtained by the production methods 1 to 3 with preferably 1 equivalent to a large excess amount of R$^{6a}$H (wherein R$^{6a}$ has the same definition as described above) in a solvent in the presence of preferably 0.001 to 1 equivalent of a palladium catalyst and preferably 1 to 100 equivalents of a base under a carbon monoxide gas atmosphere at a temperature between −10° C. and the boiling point of the solvent used for 5 minutes to 72 hours.

Examples of the palladium catalyst include a compound in which phosphine ligands are coordinated to palladium atoms, and examples of the palladium source include palladium acetate, tris(dibenzylideneacetone)dipalladium, chloroform adduct thereof, and the like. Examples of the phosphine ligands include triphenylphosphine, 1,1'-bis(diphenylphosphino)ferrocene, o-tolylphosphine, 1,2-bis(diphenylphosphino)ethane, 1,3-bis(diphenylphosphino)propane, 1,4-bis(diphenylphosphino)butane, di-tert-butyldiphenylphosphine, and the like. Any of these compounds is preferably used in an amount of 1 to 10 equivalents to the palladium source described above. Incidentally, a commercially available reagent such as tetrakis(triphenylphosphine)palladium or 1,1'-bis(diphenylphosphinoferrocene)dichloropalladium/dichloromethane 1/1 adduct can also be used. It is preferred to use palladium acetate and 1,3-bis(diphenylphosphino)propane in combination at a ratio of 1:1. Examples of the base include potassium acetate, sodium acetate, potassium carbonate, cesium carbonate, sodium carbonate, sodium hydrogen carbonate, sodium hydroxide, lithium hydroxide, potassium hydroxide, potassium phosphate, pyridine, triethylamine, N-methylmorpholine, N-methylpiperidine, diisopropylethylamine, DBU, and the like. Examples of the solvent include dichloromethane, chloroform, 1,2-dichloroethane, toluene, xylene, ethyl acetate, acetonitrile, diethyl ether, THF, DME, 1,4-dioxane, DMF, DMA, NMP, pyridine, and the like. These are used alone or as a mixture thereof.

Step 2

Compound (I-D) can be obtained by treating Compound (I-C) in a solvent containing water in the presence of preferably 1 to 100 equivalents of a base at a temperature between −10° C. and the boiling point of the solvent used for 5 minutes to 72 hours.

Examples of the base include potassium carbonate, lithium hydroxide, potassium hydroxide, sodium hydroxide, sodium methoxide, and the like. Examples of the solvent include methanol, ethanol, dichloromethane, chloroform, 1,2-dichloroethane, toluene, xylene, acetonitrile, diethyl ether, THF, DME, 1,4-dioxane, DMF, DMA, NMP, DMSO, pyridine, water, and the like. A mixed solvent of these solvents and water are used.

Step 3

Compound (I-D) can also be obtained in the same manner as in the above-mentioned step 2, using Compound (I-B) obtained in Production methods 1 to 3.

Step 4

Compound (I-E) can also be obtained by reacting Compound (I-D) with preferably 1 to 20 equivalents of Compound (a-19) in a solvent in the presence of preferably 1 to 20 equivalents of a suitable condensing agent, and if necessary, in the presence of preferably 1 to 20 equivalents of an additive at a temperature between −10° C. and the boiling point of the solvent used for 5 minutes to 72 hours.

Compound (a-19) can be obtained as a commercially available product, or by a known method [for example, Shin-Jikken Kagaku Koza, 4th Ed., vol. 14, p. 1332, Maruzen (1978), etc.] or a modified method thereof.

Examples of the condensing agent include DCC, 1,3-diisopropylcarbodiimide, EDC, EDC hydrochloride, and the like. Examples of the additive include HOBt.H$_2$O, DMAP, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, water, and the like. These are used alone or as a mixture thereof.

Step 5

Compound (I-F) can be obtained by a known method [for example, Shin-Jikken Kagaku Koza, 4th Ed., vol. 14, p. 1827, Maruzen (1978), etc.] using Compound (I-E). That is, Compound (I-F) can be obtained by treating Compound (I-E) in a solvent, and if necessary, in the presence of preferably a catalytic amount to 20 equivalents of a base with preferably 1 to 20 equivalents of a sulfurizing agent such as Lawesson's reagent or diphosphorus pentasulfide at a temperature between 0° C. and the boiling point of the solvent used for 5 minutes to 72 hours.

Examples of the solvent include toluene, xylene, THF, DME, acetonitrile, dichloromethane, chloroform, pyridine, water, and the like. These are used alone or as a mixture thereof.

Production Method 5

Among Compounds (I), Compound (Ia) in which $R^3$ is vinyl having a substituent and the substituent is $COR^{6a}$ (wherein $R^{6a}$ has the same definition as described above), Compound (Ib) in which the substituent is COOH, Compound (Ic) in which the substituent is $CONR^9R^{10}$ (wherein $R^9$ and $R^{10}$ have the same definitions as described above, respectively), and Compound (Id) in which the substituent is $CSNR^9R^{10}$ (wherein $R^9$ and $R^{10}$ have the same definitions as described above, respectively), can also be produced according to the following steps.

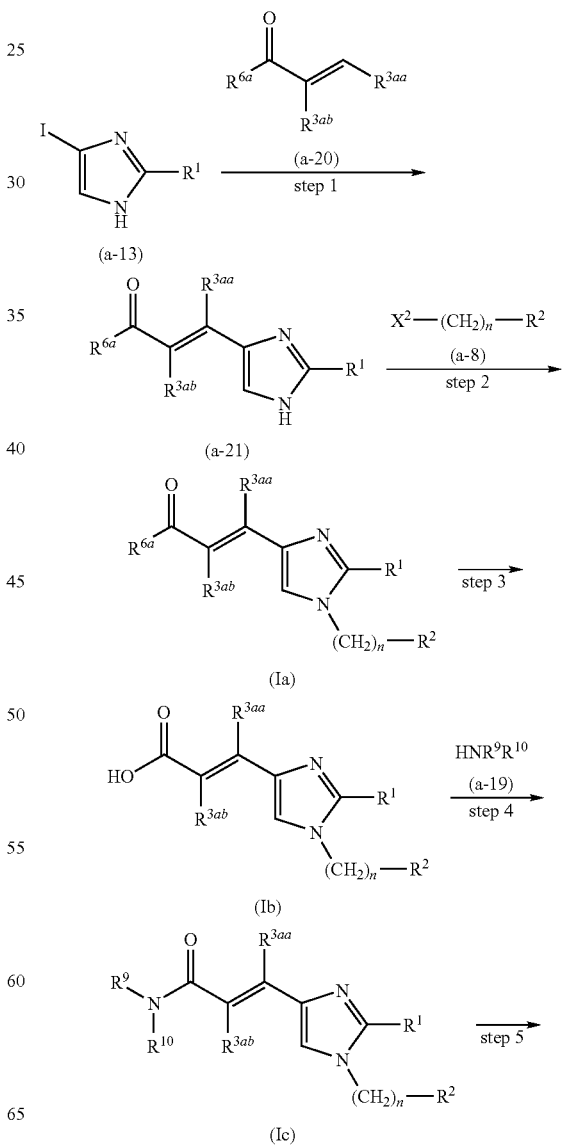

-continued

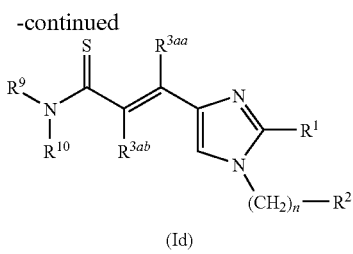

(Id)

[In the formulae, $R^{3aa}$ and $R^{3ab}$ represent a substituent bound to a vinyl moiety of the optionally substituted vinyl in the definition of $R^3$, and $R^1$, $R^2$, $R^{6a}$, $R^9$, $R^{10}$, n, and $X^2$ have the same definitions as described above, respectively.]

Step 1

Compound (a-21) can be obtained, for example, according to the method described in Jikken Kagaku Koza, 5th Ed., vol. 18, p. 381, Maruzen (2004), etc. That is, Compound (a-21) can be obtained by reacting Compound (a-13) obtained by the production method 3 with preferably 1 to 10 equivalents of Compound (a-20) in a solvent in the presence of preferably 0.001 to 1 equivalent of a palladium catalyst, and if necessary, in the presence of preferably 1 to 10 equivalents of a base at a temperature between −10° C. and the boiling point of the solvent used for 5 minutes to 72 hours.

Compound (a-20) can be obtained as a commercially available product, or by a known method [for example, Shin-Jikken Kagaku Koza, 4th Ed., vol. 14, p. 1017, Maruzen (1977), etc.] or a modified method thereof.

Examples of the palladium catalyst include a compound in which phosphine ligands are coordinated to palladium atoms, and examples of the palladium source include palladium acetate, palladium trifluoroacetate, tris(dibenzylideneacetone)dipalladium, chloroform adduct thereof, and the like. Examples of the phosphine ligands include triphenylphosphine, 1,1'-bis(diphenylphosphino)ferrocene, o-tolylphosphine, and the like. Any of these compounds is preferably used in an amount of 1 to 10 equivalents to the palladium source described above. Incidentally, a commercially available reagent such as tetrakis(triphenylphosphine)palladium can also be used. Examples of the base include potassium carbonate, sodium carbonate, sodium hydrogen carbonate, cesium carbonate, sodium hydroxide, lithium hydroxide, potassium hydroxide, pyridine, triethylamine, diisopropylethylamine, N-methylmorpholine, N-methylpiperidine, DBU, and the like. Examples of the solvent include dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, and the like. These are used alone or as a mixture thereof.

Step 2

Compound (Ia) can be obtained in the same manner as in step 2 of Production method 2, using Compound (a-21).

Step 3

Compound (Ib) can be obtained in the same manner as in step 2 of Production method 4, using Compound (Ia).

Step 4

Compound (Ic) can be obtained in the same manner as in step 4 of Production method 4, using Compound (Ib) and Compound (a-19).

Step 5

Compound (Id) can be obtained in the same manner as in step 5 of Production method 4, using Compound (Ic).

Production Method 6

Among Compounds (I), Compound (I-G) having $COR^{6b}$ (wherein $R^{6b}$ represents a group in the definition of $R^6$ described above except for a hydrogen atom) as a substituent in $R^3$, Compound (I-H) having $CH(OH)R^{6b}$ (wherein $R^{6b}$ has the same definition as described above, and $CH(OH)R^{6b}$ represents one of the groups defined as the substituent of $R^3$) as a substituent in $R^3$, and Compound (I-I) having $C(OH)R^{6b}R^{6c}$ (wherein $R^{6b}$ has the same definition as described above and $R^{6c}$ has the same definition as the $R^{6b}$ described above, and $C(OH)R^{6b}R^{6c}$ represents one of the groups defined as the substituent of $R^3$) in $R^3$ can also be produced according to the following steps.

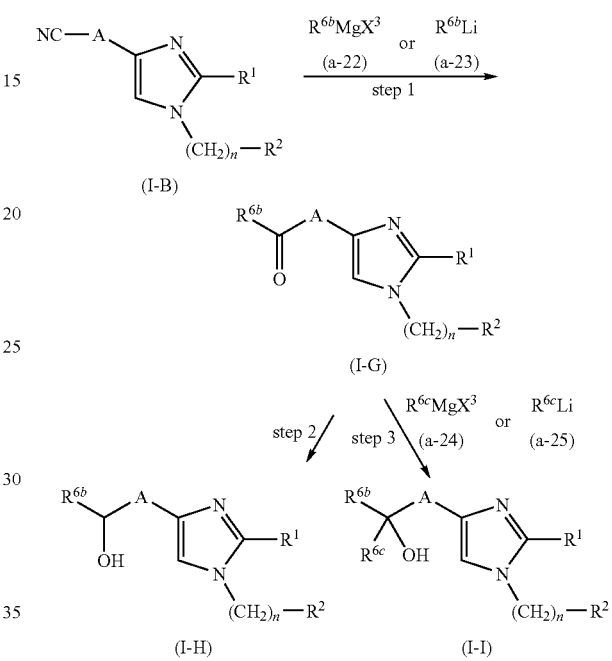

(In the formulae, $R^1$, $R^2$, $R^{6b}$, $R^{6c}$, n, and A have the same definitions as described above respectively, and $X^3$ represents a chlorine atom or a bromine atom.)

Step 1

Compound (I-G) can be obtained by reacting Compound (I-B) obtained by any of the production methods 1 to 3 and the like with preferably 1 to 20 equivalents of a Grignard reagent [Compound (a-22)] or an organic lithium reagent [Compound (a-23)] in a solvent at a temperature between −90° C. and the boiling point of the solvent used for 5 minutes to 72 hours, and then, hydrolyzing the resulting product, if necessary, in the presence of an excess amount of an acid.

Examples of the acid include hydrochloric acid, sulfuric acid, and the like. Examples of the solvent include benzene, toluene, xylene, diethyl ether, THF, DME, hexanedimethoxyethane, diisopropyl ether, 1,4-dioxane, hexane, and the like. These are used alone or as a mixture thereof.

The organic lithium reagent and the Grignard reagent can be obtained as commercially available products, or by a known method [for example, Shin-Jikken Kagaku Koza, 4th Ed., vol. 12, pp. 43 and 62, Maruzen (1976), etc.] or a modified method thereof.

Step 2

Compound (I-H) can be obtained by reducing a carbonyl group in $R^3$ of Compound (I-G) according to a known method [for example, Shin-Jikken Kagaku Koza, 4th Ed., vol. 14, p. 461, Maruzen (1978), etc.].

Step 3

Compound (I-I) can be obtained by reacting Compound (I-G) with preferably 1 to 20 equivalents of a Grignard reagent [Compound (a-24)] or an organic lithium reagent [Compound (a-25)] in the same manner as in Step 1 described above.

Production Method 7

Among Compounds (I), Compound (I-K) having $NR^7R^8$ (wherein $R^7$ and $R^8$ have the same definitions as described above, respectively) as a substituent in $R^3$ can also be produced according to the following steps.

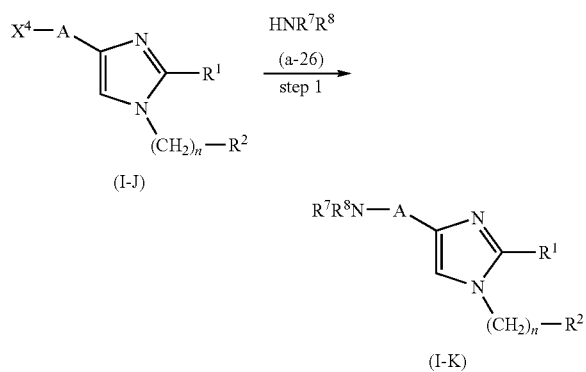

(In the formulae, $X^4$ represents a chlorine atom, a bromine atom, an iodine atome, or trifluoromethanesulfonyloxy, and $R^1, R^2, R^7, R^8$, n, and A have the same definitions as described above, respectively)

Step 1

Compound (I-K) can be obtained by reacting Compound (I-J) obtained by the production methods 1 to 3 and the like with preferably 1 to 10 equivalents of Compound (a-26) in a solvent in the presence of preferably 0.1 to 10 equivalents of a base and preferably 0.001 to 1 equivalent of a palladium catalyst, and if necessary, in the presence of preferably 0.001 to 1 equivalent of a phosphine compound at a temperature between −20° C. and the boiling point of the solvent used for 5 minutes to 72 hours.

Compound (a-26) can be obtained as a commercially available product, or by a known method [for example, Shin-Jikken Kagaku Koza, 4th Ed., vol. 14, p. 1332, Maruzen (1978), etc.] or a modified method thereof.

Examples of the base include potassium carbonate, cesium carbonate, potassium phosphate, potassium tert-butoxide, sodium tert-butoxide, and the like. Examples of the palladium catalyst include palladium acetate, palladium trifluoroacetate, tris(dibenzylideneacetone)dipalladium, chloroform adduct thereof, tetrakis(triphenylphosphine)palladium, [1,1'-bis(diphenylphosphino)ferrocene]dichloropalladium dichloromethane adduct (1:1), and the like. Examples of the phosphine compounds include 2,2'-bis(diphenylphosphino)-1,1'-binaphthyl, o-tolylphosphine, tributylphosphine, di-tert-butyldiphenylphosphine, 2-(di-tert-butylphosphino)biphenyl, 2-(dicyclohexylphosphino)biphenyl, and the like. Examples of the solvent include toluene, xylene, ethyl acetate, acetonitrile, diethyl ether, THF, DME, 1,4-dioxane, and the like. These are used alone or as a mixture thereof.

Production Method 8

Among Compounds (I), Compounds (I-M), (I-N), (I-O), (I-P), (I-Q), and (I-R) having $NH_2$, $NHR^{7a}$ (wherein $R^{7a}$ represents optionally substituted lower alkyl, optionally substituted cycloalkyl, or optionally substituted aralkyl in the definition of $R^7$ described above), $NR^{7a}{}_2$ (wherein $R^{7a}$ has the same definition as described above), $NHR^{7b}$ (wherein $R^{7b}$ represents optionally substituted lower alkanoyl, optionally substituted cycloalkylcarbonyl, optionally substituted aralkylcarbonyl, optionally substituted aroyl, optionally substituted lower alkoxycarbonyl, optionally substituted lower alkylsulfonyl, optionally substituted cycloalkylsulfonyl, optionally substituted aralkylsulfonyl, optionally substituted arylsulfonyl, optionally substituted lower alkylsulfamoyl, optionally substituted di-lower alkylsulfamoyl, optionally substituted lower alkylcarbamoyl, or optionally substituted di-lower alkylcarbamoyl in the definition of $R^7$ described above), $NR^{7b}{}_2$ (wherein $R^{7b}$ has the same definition as described above), and $NR^{7a}R^{7b}$ (wherein $R^{7a}$ and $R^{7b}$ have the same definitions as described above, respectively) as a substituent in $R^3$, can also be produced according to the following steps.

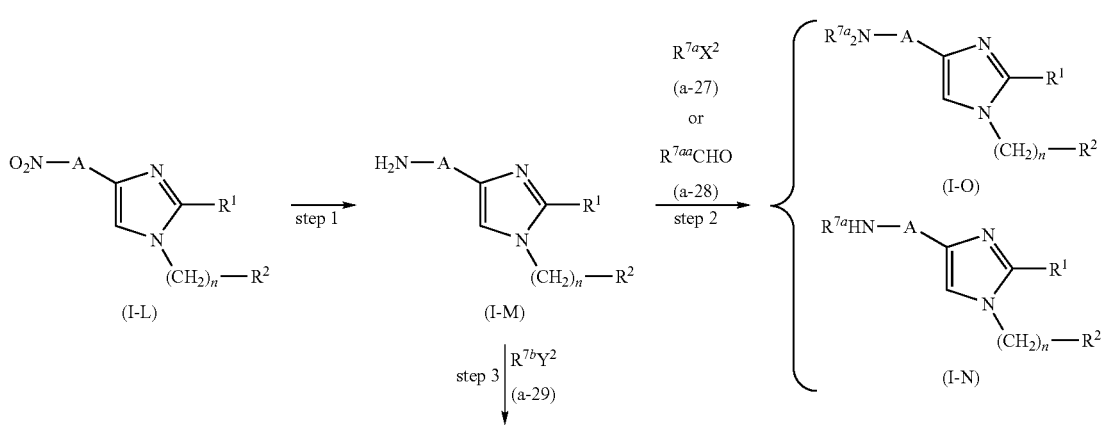

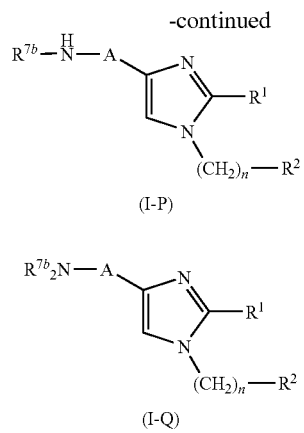

(I-P)

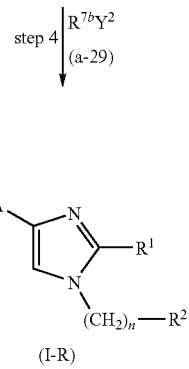

(I-Q)  (I-R)

[In the formulae, $R^1$, $R^2$, $R^{7a}$, $R^{7b}$, n, $X^2$, and A have the same definitions as described above, respectively, $R^{7aa}$ represents lower alkyl or aralkyl lacking one terminal carbon atom as compared with the group in the definition of $R^{7a}$ described above, and $Y^2$ represents a chlorine atom, a bromine atom, or $OR^{7b}$ (wherein $R^{7b}$ has the same definition as described above).]

Step 1

Compound (I-M) can be obtained by reducing a nitro group according to the method described in Shin-Jikken Kagaku Koza, 4th Ed., vol. 14, p. 1522, Maruzen (1978) using Compound (I-L).

Step 2

Compound (I-N) and/or Compound (I-O) can be obtained by reacting Compound (I-M) with preferably 1 to 20 equivalents of Compound (a-27) in a solvent, and if necessary, in the presence of preferably 1 to 20 equivalents of a base at a temperature between −10° C. and the boiling point of the solvent used for 5 minutes to 72 hours.

Compound (a-27) can be obtained as a commercially available product, or by a known method [for example, Shin-Jikken Kagaku Koza, 4th Ed., vol. 14, p. 331, Maruzen (1977), etc.] or a modified method thereof.

Examples of the base include potassium carbonate, potassium hydroxide, sodium hydroxide, sodium methoxide, potassium tert-butoxide, triethylamine, diisopropylethylamine, N-methylmorpholine, pyridine, DBU, DMAP, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, water, and the like. These are used alone or as a mixture thereof.

As an alternative method, Compound (I-N) and/or Compound (I-O) can also be obtained by reacting Compound (I-M) with preferably 1 to 10 equivalents of Compound (a-28) in a solvent in the presence of preferably 1 to 10 equivalents of a reducing agent and preferably 1 to 10 equivalents of an acid at a temperature between −10° C. and the boiling point of the solvent used for 5 minutes to 72 hours.

Compound (a-28) can be obtained as a commercially available product, or by a known method [for example, Shin-Jikken Kagaku Koza, 4th Ed., vol. 14, p. 636, Maruzen (1977), etc.] or a modified method thereof.

Examples of the reducing agent include sodium triacetoxyborohydride, sodium borohydride cyanide, and the like. Examples of the solvent include methanol, ethanol, dichloromethane, chloroform, 1,2-dichloroethane, toluene, acetonitrile, diethyl ether, THF, DME, 1,4-dioxane, DMF, DMA, NMP, water, and the like. These are used alone or as a mixture thereof.

Further, among Compounds (I-N), a compound in which $R^{7a}$ is methyl can also be obtained by reacting Compound (I-M) with preferably 1 to 20 equivalents of methyl chloroformate and then reducing the resulting compound using lithium aluminum hydride or the like.

Step 3

Compound (I-P) and/or Compound (I-Q) can be obtained by reacting Compound (I-M) with preferably 1 to 20 equivalents of Compound (a-29) without solvent or in a solvent, and if necessary, in the presence of preferably 1 to 20 equivalents of a base at a temperature between −10° C. and 150° C. for 5 minutes to 72 hours.

Compound (a-29) can be obtained as a commercially available product, or by a known method [for example, Shin-Jikken Kagaku Koza, 4th Ed., vol. 14, p. 1106, Maruzen (1977), etc.] or a modified method thereof.

Examples of the base include potassium carbonate, potassium hydroxide, sodium hydroxide, sodium methoxide, potassium tert-butoxide, triethylamine, diisopropylethylamine, N-methylmorpholine, pyridine, DBU, DMAP, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, water, and the like. These are used alone or as a mixture thereof.

Step 4

Compound (I-R) can be obtained in the same manner as in the above-mentioned step 3, using Compound (I-N).

Production Method 9

Compound (I) can also be produced according to the following steps.

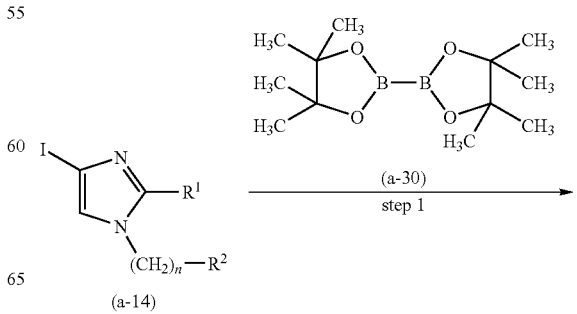

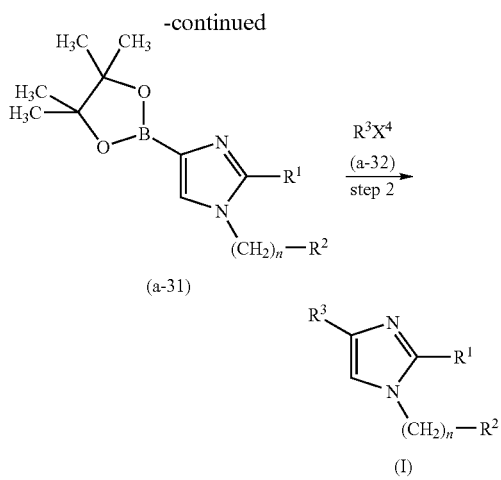

(a-31)

(I)

(In the formulae, $R^1$, $R^2$, $R^3$, $X^4$, and n have the same definitions as described above, respectively.)

Step 1

Compound (a-31) can be obtained by reacting Compound (a-14) obtained in Step 4 of Production method 3 with preferably 1 to 10 equivalents of bis(pinacolate)diborane (Compound (a-30)) in the presence of preferably 0.1 to 10 equivalents of a base and preferably 0.001 to 1 equivalent of a palladium catalyst in a solvent at a temperature between −10° C. and the boiling point of the solvent used for 5 minutes to 72 hours.

Examples of the base include potassium acetate, sodium acetate, potassium carbonate, cesium carbonate, sodium carbonate, sodium hydrogen carbonate, sodium hydroxide, lithium hydroxide, potassium hydroxide, potassium phosphate, pyridine, triethylamine, N-methylmorpholine, N-methylpiperidine, piperidine, piperazine, diisopropylethylamine, DBU, and the like. Examples of the palladium catalyst include a compound in which phosphine ligands are coordinated to palladium atoms, and examples of the palladium source include palladium acetate, palladium trifluoroacetate, tris(dibenzylideneacetone) dipalladium, chloroform adduct thereof, and the like. Examples of the phosphine ligands include triphenylphosphine, 1,1′-bis(diphenylphosphino)ferrocene, o-tolylphosphine, and the like. Any of these compounds is preferably used in an amount of 1 to 10 equivalents based on the palladium source described above. Incidentally, a commercially available reagent such as tetrakis(triphenylphosphine)palladium or 1,1′-bis (diphenylphosphino)ferrocene dichloropalladium can also be used. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, pyridine, water, and the like. These are used alone or as a mixture thereof.

Step 2

Compound (I) can be obtained by reacting Compound (a-31) with preferably 1 to 10 equivalents of Compound (a-32) in the presence of preferably 0.1 to 10 equivalents of a base and preferably 0.001 to 1 equivalent of a palladium catalyst in a solvent at a temperature between −10° C. and the boiling point of the solvent used for 5 minutes to 72 hours.

Compound (a-32) can be obtained as a commercially available product, or by a known method [for example, Shin-Jikken Kagaku Koza, 4th Ed., vol. 14, pp. 335 and 369, Maruzen (1977), etc.] or a modified method thereof.

Examples of the base include potassium acetate, sodium acetate, potassium carbonate, cesium carbonate, sodium carbonate, sodium hydrogen carbonate, sodium hydroxide, lithium hydroxide, potassium hydroxide, potassium phosphate, pyridine, triethylamine, N-methylmorpholine, N-methylpiperidine, piperidine, piperazine, diisopropylethylamine, DBU, and the like. Examples of the palladium catalyst include a compound in which phosphine ligands are coordinated to palladium atoms, and examples of the palladium source include palladium acetate, palladium trifluoroacetate, tris(dibenzylideneacetone) dipalladium, chloroform adduct thereof, and the like. Examples of the phosphine ligands include triphenylphosphine, 1,1′-bis(diphenylphosphino)ferrocene, o-tolylphosphine, and the like. Any of these compounds is preferably used in an amount of 1 to 10 equivalents based on the palladium source described above.

Incidentally, a commercially available reagent such as tetrakis(triphenylphosphine)palladium, 1,1′-bis (diphenylphosphino)ferrocene dichloropalladium can also be used. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, pyridine, water, and the like. These are used alone or as a mixture thereof.

Production Method 10

Compound (I) can also be produced according to the following steps.

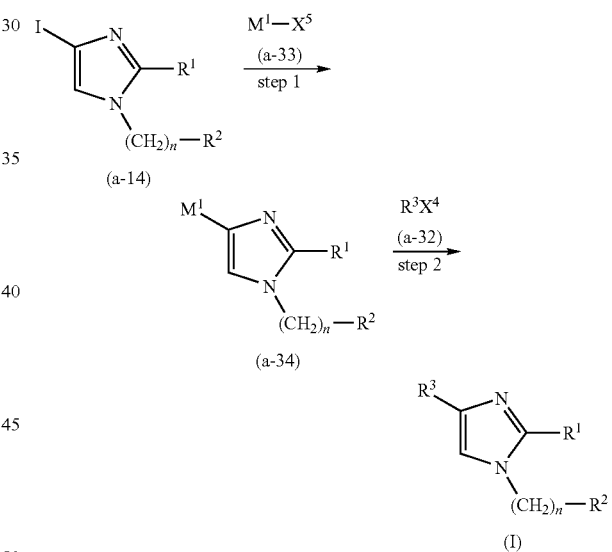

(In the formulae, $R^1$, $R^2$, $R^3$, $M^1$, $X^4$, and n have the same definitions as described above, respectively, and $X^5$ represents a leaving group such as a chlorine atom, a bromine atom, an iodine atom, methoxy, ethoxy, or the like)

Step 1

Compound (a-34) can be obtained by reacting Compound (a-14) obtained in step 4 of Production method 3 with preferably 0.1 to 10 equivalents of a Grignard reagent or an organic lithium reagent in a solvent at a temperature between −78° C. and the boiling point of the solvent used for 5 minutes to 72 hours, and then, reacting the resulting product with preferably 1 to 10 equivalents of Compound (a-33) at a temperature between −78° C. and the boiling point of the solvent used for 5 minutes to 72 hours.

The organic lithium reagent and the Grignard reagent can be obtained as commercially available products, or by a known method [for example, Shin-Jikken Kagaku Koza, 4th Ed., vol. 12, pp. 43 and 62, Maruzen (1976), etc.] or a modified method thereof. Examples of the solvent include benzene, toluene, xylene, diethyl ether, THF, DME, hexanedimethoxyethane, diisopropyl ether, 1,4-dioxane, hexane, and the like. These are used alone or as a mixture thereof.

Step 2

Compound (I) can be obtained in the same manner as in step 5 of Production method 3, using Compound (a-34).

Production Method 11

Compound (I) can also be produced according to the following steps.

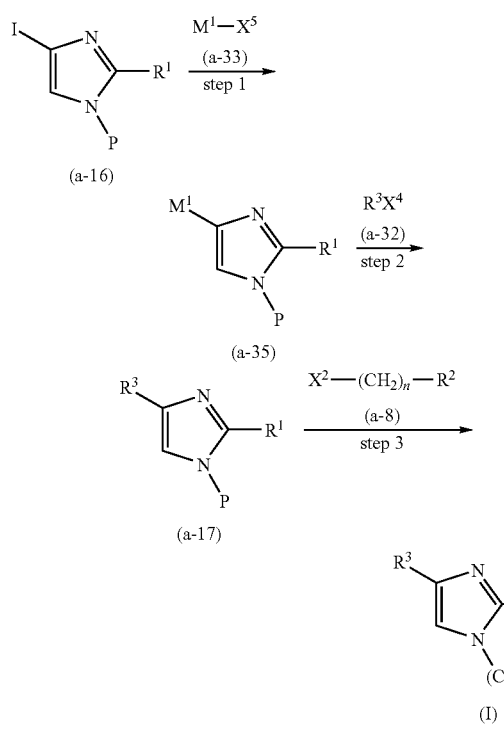

(In the formulae, $R^1$, $R^2$, $R^3$, $M^1$, $X^4$, $X^5$, P, and n have the same definitions as described above, respectively)

Step 1

Compound (a-35) can be obtained in the same manner as in step 1 of Production method 10, using Compound (a-16) obtained in step 6 of Production method 3.

Step 2

Compound (a-17) can be obtained in the same manner as in step 2 of Production method 10, using Compound (a-35).

Step 3

Compound (I) can be obtained in the same manner as in step 8 of Production method 3, using Compound (a-17).

Transformation of a functional group contained in $R^1$, $R^2$, or $R^3$ of Compound (I) can also be carried out by a known method [for example, the method described in Comprehensive Organic Transformations 2nd edition, R. C. Larock, Vch Verlagsgesellschaft Mbh (1999), etc.] or a modified method thereof.

The intermediates and the desired compounds in the above-mentioned respective production methods can be isolated and purified through a separation and purification method generally employed in organic synthetic chemistry, for example, filtration, extraction, washing, drying, concentration, recrystallization, various types of chromatography, and the like.

Further, the intermediate can be subjected to the subsequent reaction without particularly undergoing purification.

Among Compounds (I) and (IA), some may include geometric isomers, stereoisomers such as optical isomers, tautomers, and the like. All possible isomers including these and mixtures thereof are included in the present invention.

To obtain a salt of Compound (I), when Compound (I) is obtained in the form of a salt, it may be purified as it is. Further, when Compound (I) is obtained in a free form, Compound (I) may be dissolved or suspended in a suitable solvent, followed by addition of an acid or a base to form a salt, and then, the resulting salt may be isolated and purified.

Further, Compounds (I) and (IA), and pharmaceutically acceptable salts thereof may exist in the form of adducts with water or any of various solvents in some cases, and these adducts are also included in the present invention.

Specific examples of Compounds (I) and (IA) obtained according to the invention are shown in Tables 1 to 25. However, the compounds of the invention are not limited to these.

TABLE 1

| Ex. No. | Compound No. | $R^{3A}$ |
|---|---|---|
| 1 | 1 | 3-NC-C$_6$H$_4$- |
| 2 | 2 | 3-(H$_3$CH$_2$C-NH-C(O)-)-C$_6$H$_4$- |
| 3 | 3 | 3-H$_3$C-C$_6$H$_4$- |
| 4 | 4 | 2-pyridyl |
| 5 | 5 | 2-OCH$_3$-C$_6$H$_4$- |
| 6 | 6 | 3-H$_3$CO-C$_6$H$_4$- |

TABLE 1-continued (IA) 2-tert-butyl-1-(cyclohexylmethyl)-4-R³ᴬ-imidazole

| Ex. No. | Compound No. | R³ᴬ |
|---|---|---|
| 7 | 7 | 4-methoxyphenyl |
| 8 | 8 | 4-bromophenyl |
| 9 | 9 | 4-(N,N-diethylcarbamoyl)phenyl |
| 10 | 10 | 4-(piperidine-1-carbonyl)phenyl |
| 11 | 11 | 4-(morpholine-4-carbonyl)phenyl |
| 12 | 12 | 4-(4-methylpiperazine-1-carbonyl)phenyl |
| 13 | 13 | 4-(piperazine-1-carbonyl)phenyl |
| 14 | 14 | 4-(4-phenylpiperazine-1-carbonyl)phenyl |
| 15 | 15 | 4-(hydroxymethyl)phenyl |

TABLE 1-continued (IA) 2-tert-butyl-1-(cyclohexylmethyl)-4-R³ᴬ-imidazole

| Ex. No. | Compound No. | R³ᴬ |
|---|---|---|
| 16 | 16 | 4-(chloromethyl)phenyl |
| 17 | 17 | 4-((diethylamino)methyl)phenyl |
| 18 | 18 | 2-bromophenyl |

TABLE 2

(IA) 2-tert-butyl-1-(cyclohexylmethyl)-4-R³ᴬ-imidazole

| Ex. No. | Compound No. | R³ᴬ |
|---|---|---|
| 19 | 19 | 2-(hydroxymethyl)phenyl |
| 20 | 20 | 2-(N,N-diethylcarbamoyl)phenyl |

TABLE 2-continued
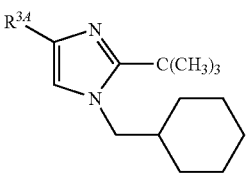
(IA)
| Ex. No. | Compound No. | R³ᴬ |
|---|---|---|
| 21 | 21 | 2-(N,N-dimethylcarbamoyl)phenyl |
| 22 | 22 | 2-(N,N-diethylaminomethyl)phenyl |
| 23 | 23 | 2-nitrophenyl |
| 24 | 24 | 2-methylphenyl |
| 25 | 25 | 2-fluorophenyl |
| 26 | 26 | 2-chlorophenyl |
| 27 | 27 | 2-acetylphenyl |
| 28 | 28 | 3-nitrophenyl |
| 29 | 29 | 3-bromophenyl |
| 30 | 30 | 3-(hydroxymethyl)phenyl |
| 31 | 31 | pyridin-3-yl |
| 32 | 32 | 3-(N,N-diethylcarbamoyl)phenyl |
TABLE 3
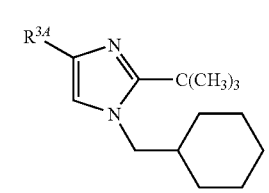
(IA)
| Ex. No. | Compound No. | R³ᴬ |
|---|---|---|
| 33 | 33 | 3-(benzoyloxy)phenyl |
| 34 | 34 | 3-hydroxyphenyl |

TABLE 3-continued
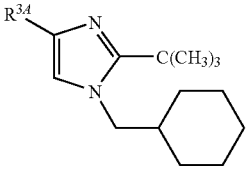
(IA)
| Ex. No. | Compound No. | R³ᴬ |
|---|---|---|
| 35 | 35 |  |
TABLE 4
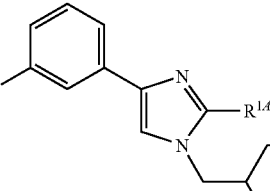
(IA)
| Ex. No. | Compound No. | R¹ᴬ |
|---|---|---|
| 36 | 36 | 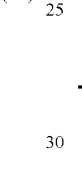 |
| 37 | 37 | 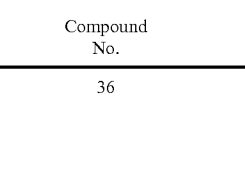 |
| 38 | 38 | 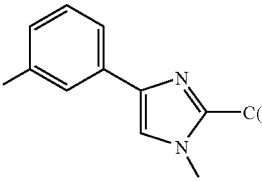 |
TABLE 5
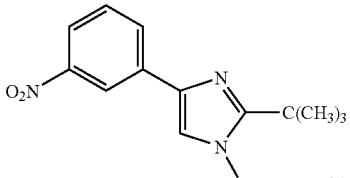
(IA)
| Ex. No. | Compound No. | nA | R²ᴬ |
|---|---|---|---|
| 39 | 39 | 1 | 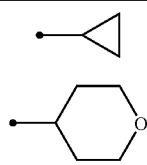 |
TABLE 5-continued
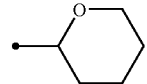
(IA)
| Ex. No. | Compound No. | nA | R²ᴬ |
|---|---|---|---|
| 40 | 40 | 1 | 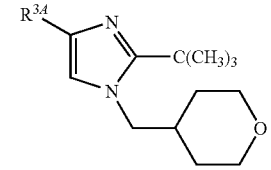 |
| 41 | 41 | 2 | 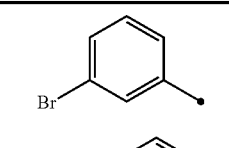 |
| 42 | 42 | 1 | 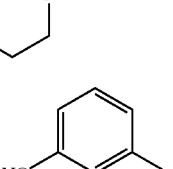 |
TABLE 6
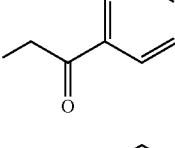
(IA)
| Ex. No. | Compound No. | R³ᴬ |
|---|---|---|
| 43 | 43 | 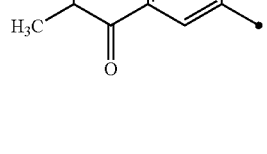 |
| 44 | 44 | |
| 45 | 45 | |
| 46 | 46 | |
| 47 | 47 | |

TABLE 6-continued
(IA)
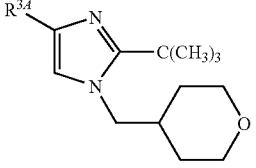
| Ex. No. | Compound No. | R³ᴬ |
|---|---|---|
| 48 | 48 | 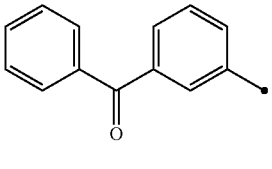 |
| 49 | 49 | 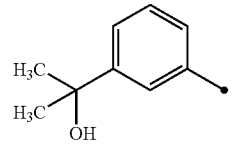 |
| 50 | 50 | 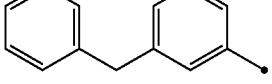 |
| 51 | 51 | 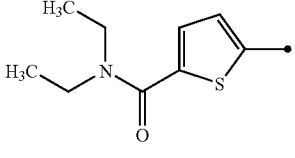 |
| 52 | 52 | 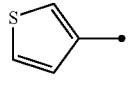 |
| 53 | 53 | 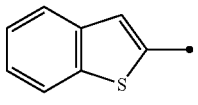 |
| 54 | 54 | 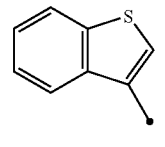 |
| 55 | 55 | 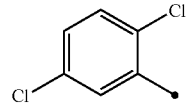 |
| 56 | 56 | 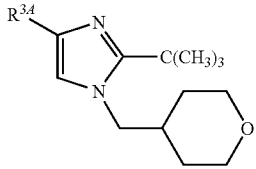 |
TABLE 6-continued
(IA)
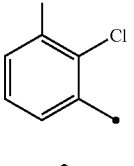
| Ex. No. | Compound No. | R³ᴬ |
|---|---|---|
| 57 | 57 | 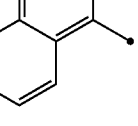 |
| 58 | 58 | 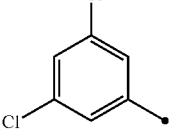 |
| 59 | 59 | 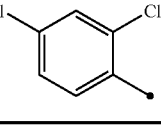 |
| 60 | 60 | 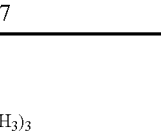 |
TABLE 7
(IA)
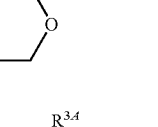
| Ex. No. | Compound No. | R³ᴬ |
|---|---|---|
| 61 | 61 | 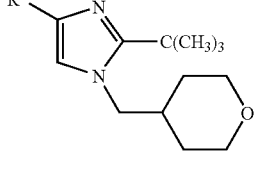 |
| 62 | 62 | 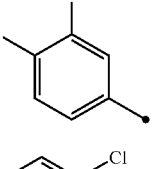 |

TABLE 7-continued (IA)

| Ex. No. | Compound No. | R$^{3A}$ |
|---|---|---|
| 63 | 63 | 3-methyl-2-nitrophenyl |
| 64 | 64 | 3-(N,N-diethylcarbamoyl)-2-methylphenyl |
| 65 | 65 | 3-(N,N-diethylcarbamoyl)-4-chlorophenyl |
| 66 | 66 | 3-(N,N-diethylcarbamoyl)-4-fluorophenyl |
| 67 | 67 | 3-bromo-5-(N,N-diethylcarbamoyl)phenyl |
| 68 | 68 | pyridin-3-yl |
| 69 | 69 | 3-methoxyphenyl |
| 70 | 70 | 3-nitrophenyl |
| 71 | 71 | 3-(N-methyl-N-phenylcarbamoyl)phenyl |
| 72 | 72 | 3-(N-ethylcarbamoyl)phenyl |
| 73 | 73 | 3-(methylamino)phenyl |
| 74 | 74 | 3-(N-methyl-3-methylbutanamido)phenyl |
| 75 | 75 | 3-(N-methyl-N',N'-dimethylsulfamoyl)phenyl |
| 76 | 76 | 3-(N,N-diethylcarbamoyl)phenyl |

TABLE 8

(IA) Structure: R^34 on imidazole with C(CH3)3 and N-CH2-tetrahydropyran

| Ex. No. | Compound No. | R^3.4 |
|---|---|---|
| 77 | 77 | 3-(N,N-diethylamino)phenyl |
| 78 | 78 | 3-(ethylamino)phenyl |
| 79 | 79 | 3-[N-methyl-N-(phenylsulfonyl)amino]phenyl |
| 80 | 80 | 3-[N-methyl-N-(4-acetamidophenylsulfonyl)amino]phenyl |
| 81 | 81 | 5-methylfuran-2-yl |
| 82 | 82 | 3-[N,N-bis(2,2,2-trifluoroethyl)carbamoyl]phenyl |
| 83 | 83 | 3-(N-ethyl-N-methylcarbamoyl)phenyl |
| 84 | 84 | 5-bromopyridin-3-yl |
| 85 | 85 | 5-(N,N-diethylcarbamoyl)pyridin-3-yl |
| 86 | 86 | 3-(piperidine-1-carbonyl)phenyl |
| 87 | 87 | 3-aminophenyl |
| 88 | 88 | 3-[N-methyl-N-(methylsulfonyl)amino]phenyl |
| 89 | 89 | (E)-N,N-diethylacrylamide |
| 90 | 90 | (E)-N,N-bis(2,2,2-trifluoroethyl)acrylamide |
| 91 | 91 | (E)-N,N-diethylthioacrylamide |
| 92 | 92 | (E)-N,N-dipropylacrylamide |

TABLE 8-continued and TABLE 9 content omitted - chemical structure table

TABLE 9-continued

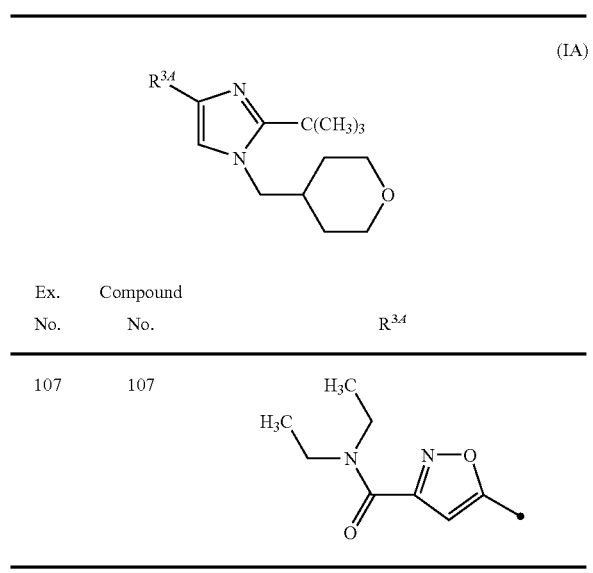

| Ex. No. | Compound No. | $R^{3A}$ |
|---|---|---|
| 107 | 107 | (N-ethyl-N-ethyl-5-methylisoxazole-3-carboxamide) |

TABLE 10

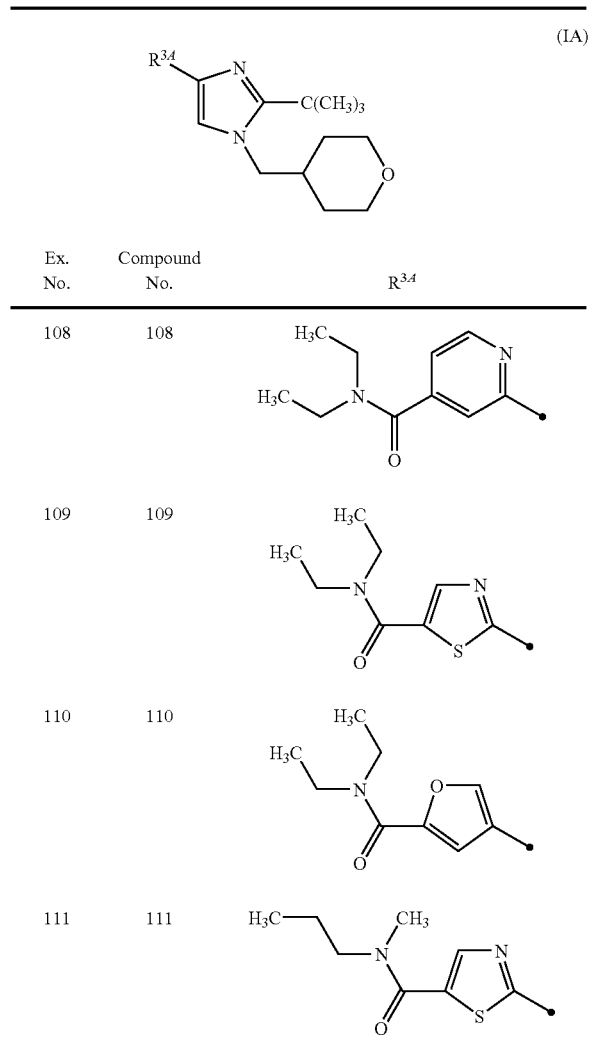

| Ex. No. | Compound No. | $R^{3A}$ |
|---|---|---|
| 108 | 108 | (N,N-diethyl-2-pyridinyl-4-carboxamide) |
| 109 | 109 | (N,N-diethyl-2-methylthiazole-5-carboxamide) |
| 110 | 110 | (N,N-diethyl-4-furan-2-carboxamide) |
| 111 | 111 | (N-propyl-N-methyl-2-methylthiazole-5-carboxamide) |
| 112 | 112 | (N,N-diethyl-5-methylfuran-3-carboxamide) |
| 113 | 113 | (N-(2,2-difluoroethyl)-N-methyl-thiophene-2-carboxamide) |
| 114 | 114 | (N,N-diethyl-1-methylpyrrole-2-carboxamide) |
| 115 | 115 | (N-(2-methoxyethyl)-N-methyl-thiophene-2-carboxamide) |
| 116 | 116 | (N-(2-hydroxyethyl)-N-ethyl-thiophene-2-carboxamide) |
| 117 | 117 | (N-(2,2,2-trifluoroethyl)-N-ethyl-isoxazole-3-carboxamide) |
| 118 | 118 | (N-(cyanomethyl)-N-methyl-thiophene-2-carboxamide) |

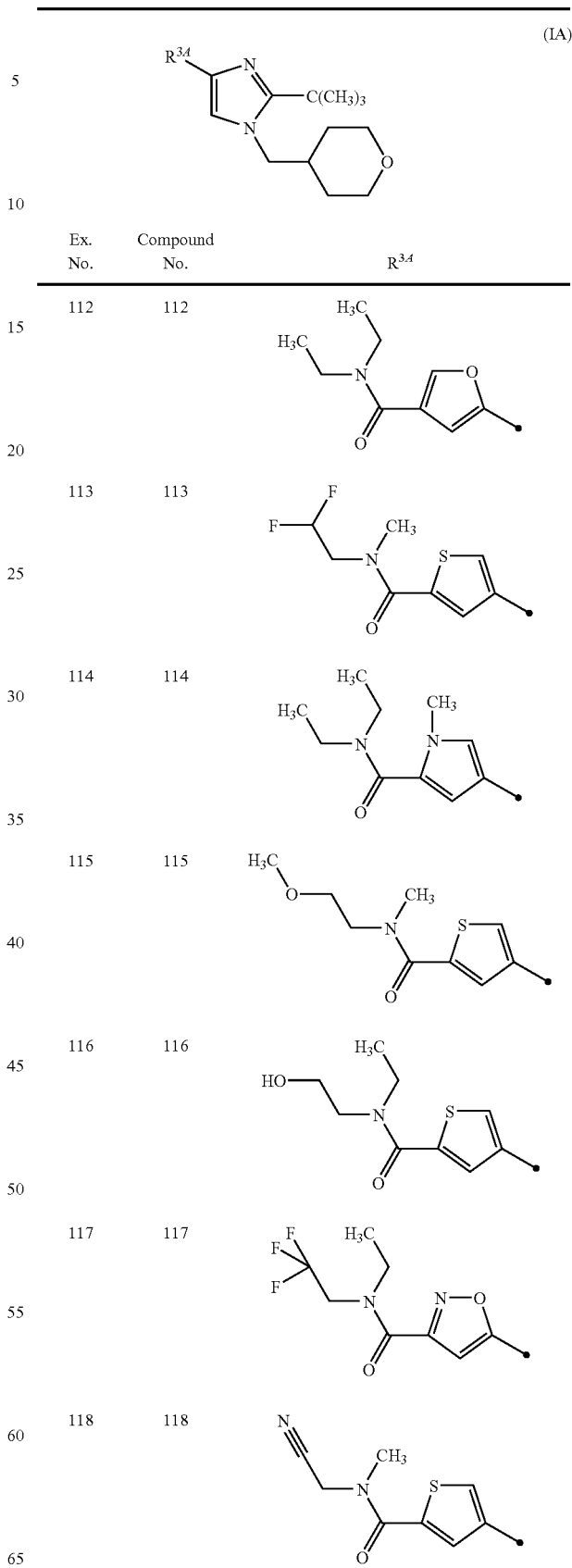

TABLE 10-continued
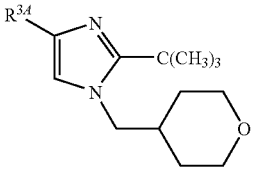
| Ex. No. | Compound No. | R³ᴬ |
|---|---|---|
| 119 | 119 | 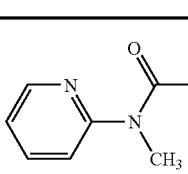 |
| 120 | 120 | 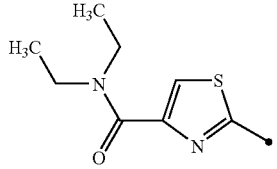 |
| 121 | 121 | 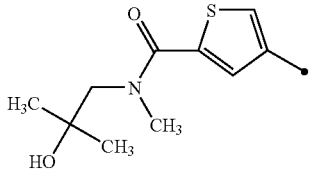 |
TABLE 11
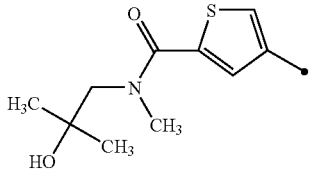
| Ex. No. | Compound No. | R³ᴬ |
|---|---|---|
| 122 | 122 | 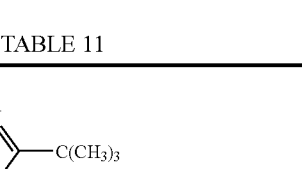 |
| 123 | 123 | 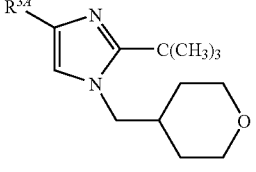 |
| 124 | 124 | 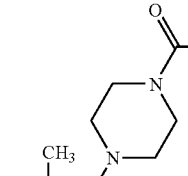 |
| 125 | 125 | 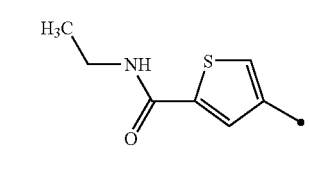 |
| 126 | 126 | 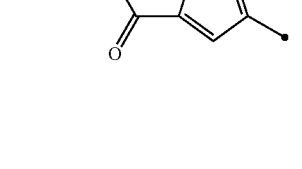 |
| 127 | 127 | 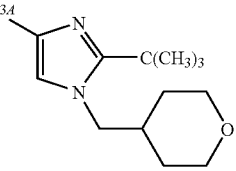 |
| 128 | 128 | 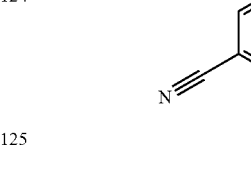 |
| 129 | 129 | 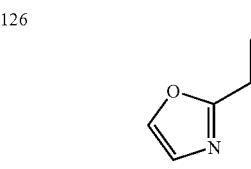 |
| 130 | 130 | 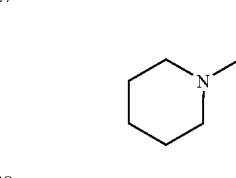 |
| 131 | 131 | 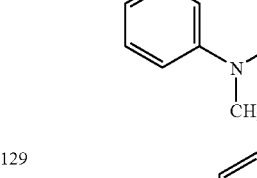 |

TABLE 11-continued (IA)

[Structure: imidazole with R^3A, C(CH3)3, and N-CH2-tetrahydropyran substituents]

| Ex. No. | Compound No. | R^3A |
|---|---|---|
| 132 | 132 | N-methyl-N-(6-pyrazinyl)benzamide group |
| 133 | 133 | N,N-dimethyl thiophene-2-carboxamide group |

TABLE 12

(IA)

[Structure: imidazole with R^3A, C(CH3)3, and N-CH2-tetrahydropyran substituents]

| Ex. No. | Compound No. | R^3A |
|---|---|---|
| 134 | 134 | 6-methoxypyridin-3-yl |
| 135 | 135 | 6-oxo-1,6-dihydropyridin-3-yl |
| 136 | 136 | 6-chloropyrazin-2-yl |
| 137 | 137 | 6-acetylpyrazin-2-yl |

TABLE 12-continued (IA)

[Structure: imidazole with R^3A, C(CH3)3, and N-CH2-tetrahydropyran substituents]

| Ex. No. | Compound No. | R^3A |
|---|---|---|
| 138 | 138 | 1-benzyl-6-oxo-1,6-dihydropyridin-3-yl |
| 139 | 139 | 1-isopropyl-6-oxo-1,6-dihydropyridin-3-yl |
| 140 | 140 | 3-(N,N-dimethylsulfamoyl)phenyl |
| 141 | 141 | 3-(N-acetyl-N-ethylcarbamoyl)phenyl |
| 142 | 142 | 6-(1-methoxyiminoethyl)pyrazin-2-yl |
| 143 | 143 | 6-(N,N-diethylcarbamoyl)pyrazin-2-yl |
| 144 | 144 | 6-(N-methyl-N-propylcarbamoyl)pyrazin-2-yl |
| 145 | 145 | 6-(N-ethyl-N-(2,2,2-trifluoroethyl)carbamoyl)pyrazin-2-yl |

TABLE 13
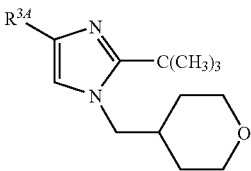
(IA)
| Ex. No. | Compound No. | R³ᴬ |
|---|---|---|
| 146 | 146 | 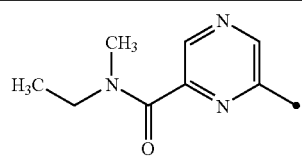 |
| 147 | 147 | 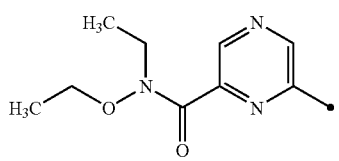 |
| 148 | 148 | 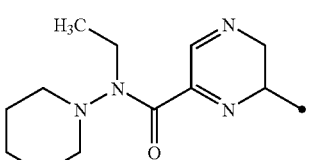 |
| 149 | 149 | 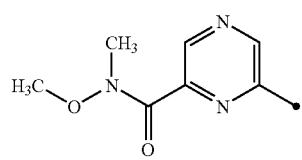 |
| 150 | 150 | 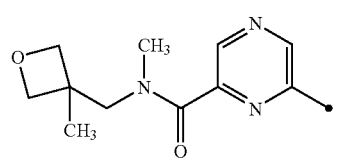 |
| 151 | 151 | 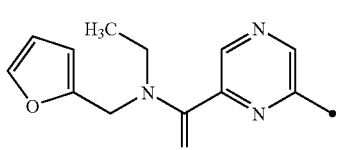 |
| 152 | 152 | 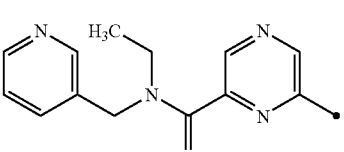 |
| 153 | 153 | 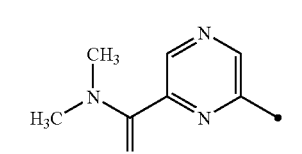 |
TABLE 13-continued
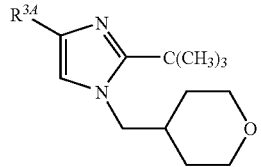
(IA)
| Ex. No. | Compound No. | R³ᴬ |
|---|---|---|
| 154 | 154 | 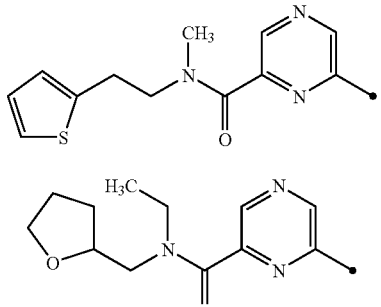 |
| 155 | 155 | |
| 156 | 156 | 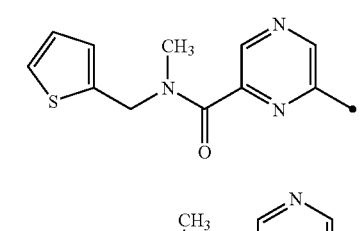 |
| 157 | 157 | |
TABLE 14
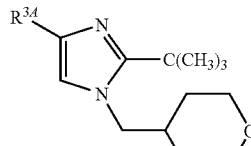
(IA)
| Compound No. | R³ᴬ |
|---|---|
| 158 | 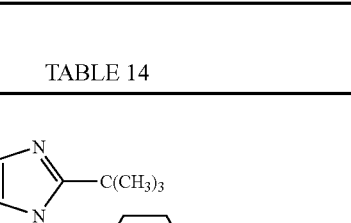 |
| | 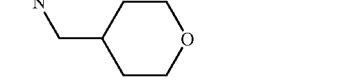 |
| 160 | 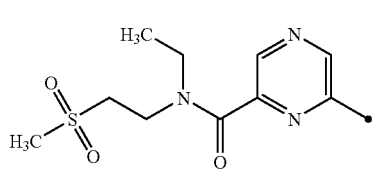 |

TABLE 14-continued
(IA)
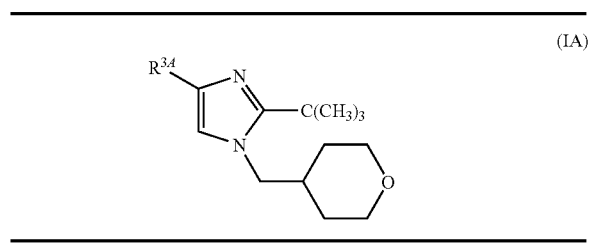
| | | |
|---|---|---|
| 162 | | 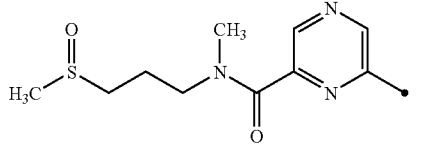 |
| 164 | | 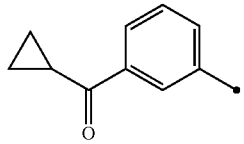 |
| 166 | | 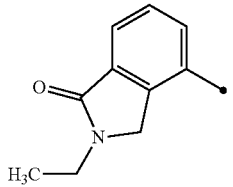 |
| 168 | | 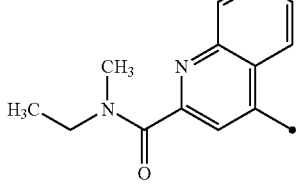 |
| Ex. No. | Compound No. | $R^{3A}$ |
|---|---|---|
| 159 | 159 | 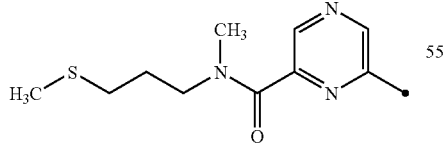 |
| 161 | 161 | 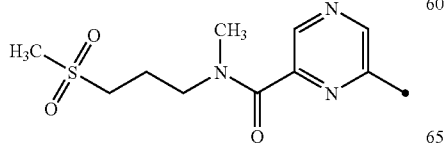 |
| 163 | 163 | |
TABLE 14-continued
(IA)
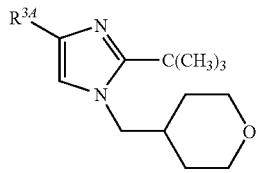
| | | |
|---|---|---|
| 165 | 165 | 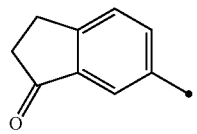 |
| 167 | 167 | 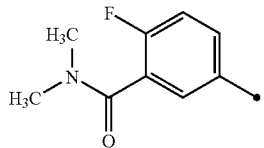 |
| 169 | 169 | 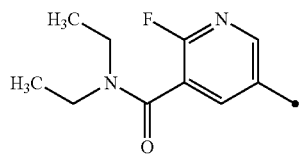 |
TABLE 15
(IA)
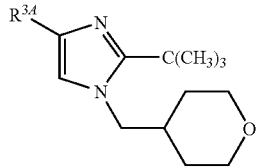
| Ex. No. | Compound No. | $R^{3A}$ |
|---|---|---|
| 170 | 170 | 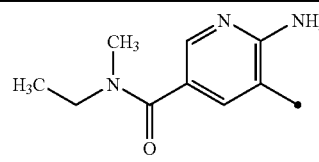 |
| 171 | 171 | 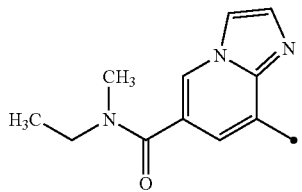 |
| 172 | 172 | 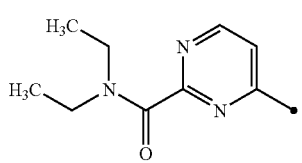 |

TABLE 15-continued
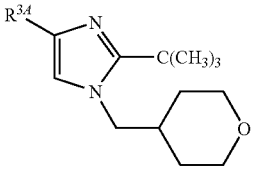
(IA)
| Ex. No. | Compound No. | R³ᴬ |
|---|---|---|
| 173 | 173 | 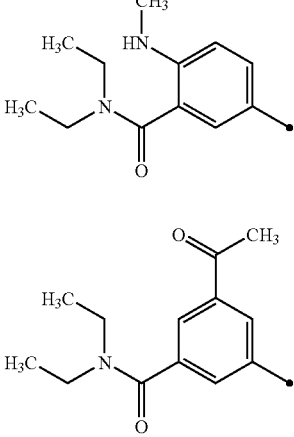 |
| 174 | 174 | 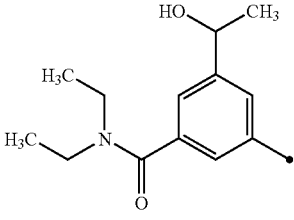 |
| 175 | 175 | 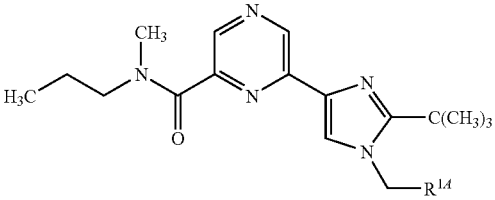 |
TABLE 16
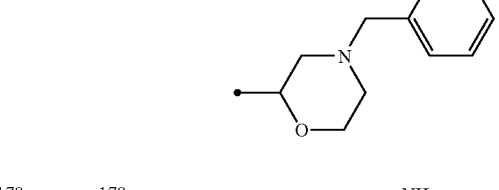
(I)
| Ex. No. | Compound No. | R¹ᴬ |
|---|---|---|
| 176 | 176 | 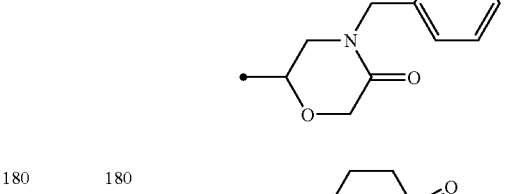 |
TABLE 16-continued
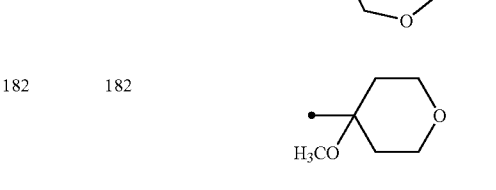
(I)
| Ex. No. | Compound No. | R¹ᴬ |
|---|---|---|
| 177 | 177 | 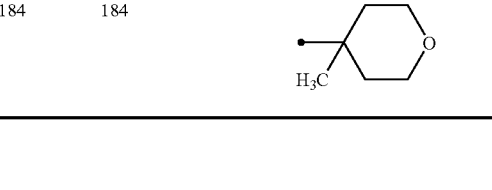 |
| 178 | 178 | 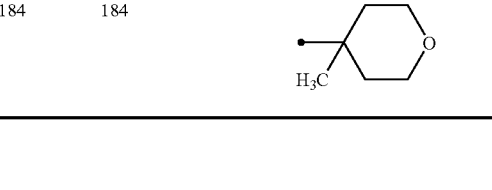 |
| 179 | 179 | 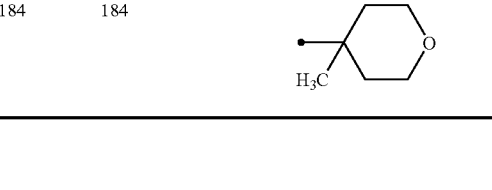 |
| 180 | 180 | 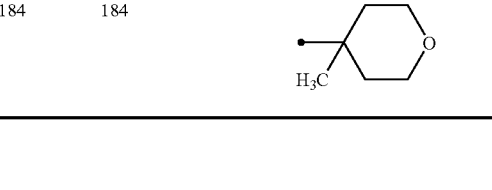 |
| 181 | 181 | 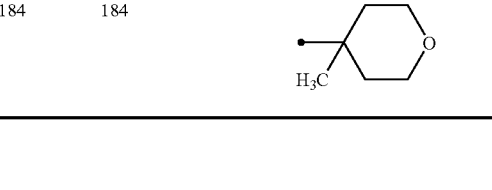 |
| 182 | 182 | 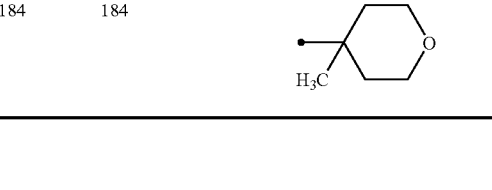 |
| 183 | 183 | 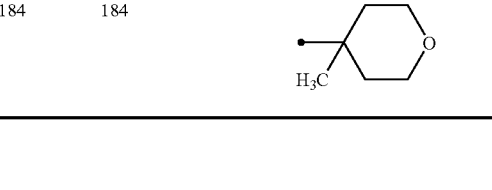 |
| 184 | 184 | 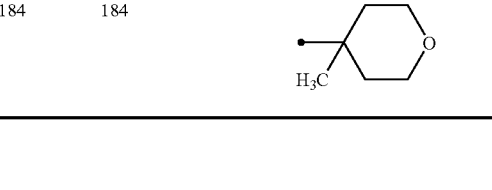 |

TABLE 17

(IA) Structure: R³ᴬ-substituted imidazole with C(CH₃)₃ group, N-linked to CH₂-tetrahydropyran bearing F substituent.

| Ex. No. | Compound No. | R³ᴬ |
|---------|--------------|-----|
| 185 | 185 | N-ethyl-N-methyl pyrazine-2-carboxamide (6-yl) |
| 186 | 186 | N,N-dimethyl pyrazine-2-carboxamide (6-yl) |
| 187 | 187 | N,N-dimethyl benzamide (3-yl) |
| 188 | 188 | N,N-dimethyl thiophene-2-carboxamide (4-yl) |
| 189 | 189 | N-ethyl-N-methyl benzamide (3-yl) |
| 190 | 190 | N,N-dimethyl pyridine-3-carboxamide (5-yl) |
| 191 | 191 | N-ethyl-N-methyl pyridine-2-carboxamide (6-yl) |
| 192 | 192 | N,N-dimethyl pyridine-2-carboxamide (6-yl) |

TABLE 17-continued

| Ex. No. | Compound No. | R³ᴬ |
|---------|--------------|-----|
| 193 | 193 | N-ethyl-N-methyl pyridine-3-carboxamide (5-yl) |
| 194 | 194 | N-methyl-N-propyl pyrazine-2-carboxamide (6-yl) |
| 195 | 195 | N,N-diethyl pyrazine-2-carboxamide (6-yl) |
| 196 | 196 | 2-fluoro-N,N-dimethyl benzamide (5-yl) |
| 197 | 197 | 6-chloropyrazin-2-yl |

TABLE 18

(IA) Structure: R³ᴬ-substituted imidazole with C(CH₃)₃ group, N-linked to CH₂-tetrahydropyran.

| Ex. No. | Compound No. | R³ᴬ |
|---------|--------------|-----|
| 198 | 198 | 2-(3-yl-phenyl)-1-methyl-ethylidene-malononitrile |

TABLE 18-continued (IA)

| Ex. No. | Compound No. | R³ᴬ |
|---|---|---|
| 199 | 199 | 3-[N-methyl-N'-methylthiourea]phenyl |
| 200 | 200 | 6-(2-fluoro-6-methoxyphenyl)pyrazin-2-yl |
| 201 | 201 | 3-(methylthio)phenyl |
| 202 | 202 | 3-(methylsulfinyl)phenyl |
| 203 | 203 | 3-(methylsulfonyl)phenyl |
| 204 | 204 | 5-[N-methyl-N-(2,2,2-trifluoroethyl)carbamoyl]isoxazol-3-yl |
| 205 | 205 | 6-[N-cyclopropyl-N-methylcarbamoyl]pyrazin-2-yl |
| 206 | 206 | 6-[N-(cyclopropylmethyl)-N-methylcarbamoyl]pyrazin-2-yl |

TABLE 18-continued (IA)

| Ex. No. | Compound No. | R³ᴬ |
|---|---|---|
| 207 | 207 | 6-[N-(cyanomethyl)-N-methylcarbamoyl]pyrazin-2-yl |
| 208 | 208 | 6-[N-(2-hydroxyethyl)-N-propylcarbamoyl]pyrazin-2-yl |

TABLE 19

(IA)

| Ex. No. | Compound No. | R³ᴬ |
|---|---|---|
| 209 | 209 | 3-[N-(2,2,2-trifluoroethyl)carbamoyl]phenyl |
| 210 | 210 | 3-[N-(2-fluoroethyl)carbamoyl]phenyl |
| 211 | 211 | 6-[N-(2,2,2-trifluoroethyl)carbamoyl]pyridin-2-yl |
| 212 | 212 | 4-[N-(2,2-difluoroethyl)carbamoyl]thiophen-2-yl |

TABLE 19-continued (IA structure: R³ᴬ-imidazole-C(CH₃)₃ with N-CH₂-tetrahydropyran)

| Ex. No. | Compound No. | R³ᴬ |
|---|---|---|
| 213 | 213 | N-(2,2,2-trifluoroethyl)-5-methylisoxazole-3-carboxamide |
| 214 | 214 | 6-(phenylamino)pyrazin-2-yl |
| 215 | 215 | 6-(methylamino)pyrazin-2-yl |
| 216 | 216 | 6-[N-(2,2,2-trifluoroethyl)carboxamide]pyrazin-2-yl |
| 217 | 217 | 3-oxo-2,3-dihydro-1H-isoindol-4-yl |
| 218 | 218 | 2-chloropyrimidin-4-yl |

TABLE 20

(I structure: R³ᴮ-imidazole-C(CH₃)₃ with N-CH₂-cyclohexyl)

| Ref. No. | Compound No. | R³ᴮ |
|---|---|---|
| 1 | a | 3-(HO₂C)-phenyl |

TABLE 20-continued

| Ref. No. | Compound No. | R³ᴮ |
|---|---|---|
| 2 | b | 4-(propyl ester)-phenyl |
| 3 | c | 4-(HO₂C)-phenyl |
| 4 | d | 2-(propyl ester)-phenyl |
| 5 | e | 2-(HO₂C)-phenyl |
| 6 | f | 3-(ethyl ester)-phenyl |

TABLE 21

(I structure with 3-methoxyphenyl-imidazole-R¹ᴮ, N-CH₂-cyclohexyl)

| Ref. No. | Compound No. | R¹ᴮ |
|---|---|---|
| 7 | g | 4-ethoxybenzyl |

TABLE 21-continued
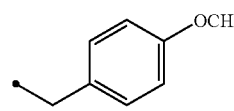
(I)
| Ref. No. | Compound No. | $R^{1B}$ |
|---|---|---|
| 8 | h |  |
| 9 | i | 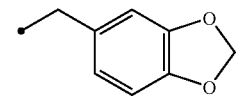 |
| 10 | j | 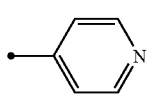 |
TABLE 22
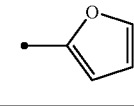
(I)
| Ref. No. | Compound No. | nB | $R^{2B}$ |
|---|---|---|---|
| 11 | k | 1 | 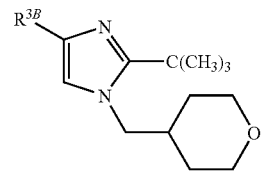 |
| 12 | l | 1 | 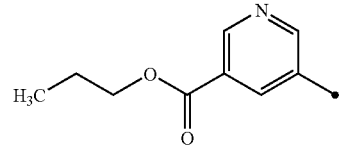 |
TABLE 23
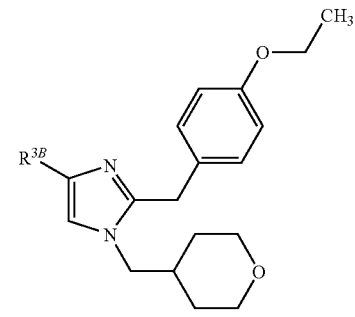
(I)
| Ref. No. | Compound No. | $R^{3B}$ |
|---|---|---|
| 13 | m | 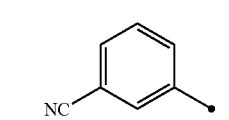 |
| 14 | n | 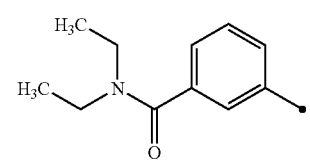 |
TABLE 24
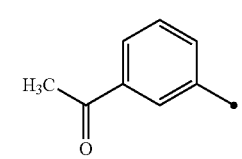
(I)
| Ref. No. | Compound No. | $R^{3B}$ |
|---|---|---|
| 15 | o |  |
| 16 | p |  |
| 17 | q |  |
| 18 | r |  |

TABLE 25

(I) [structure: imidazole with R^3B at 4-position, C(CH3)3 at 2-position, N-CH2-tetrahydropyran]

| Ref. No. | Compound No. | R^3B |
|---|---|---|
| 19 | s | (CH3)2C(-)-O-C(=O)-CH=CH- |
| 20 | t | HO-C(=O)-CH=CH- |
| 25 | y | HOOC-pyrazin-2-yl |

Subsequently, pharmacological activities of some typical Compounds (I) will be specifically described with reference to Test examples.

Test Example 1

Cannabinoid CB1 and CB2 Receptor-Binding Activities ([$^3$H]CP55940 Binding Experiment)

A test was carried out according to the method of Hillard et al. [The Journal of Pharmacology and Experimental Therapeutics, vol. 289, p. 1427 (1999)]. A rat forebrain membrane specimen and a rat spleen membrane specimen were prepared and used in a binding experiment for a CB1 receptor and a binding experiment for a CB2 receptor, respectively. The membrane specimen (forebrain: final concentration of 0.5 mg of protein/mL, spleen: final concentration of 2 mg of protein/mL) was incubated together with a test compound and [$^3$H]CP55940 (manufactured by PerkinElmer) ((−)-cis-3-[2-hydroxy-[3,5-$^3$H]-4-(1,1-dimethylheptyl)phenyl]-trans-4-(3-hydroxypropyl)cyclohexanol)) (final concentration: 0.5 nmol/L) in an assay buffer (50 mmol/L Tris-HCl buffer (pH 7.4), 1 mmol/L EDTA and 3 mmol/L MgCl$_2$) containing 0.1% bovine serum albumin at 25° C. for 1 hour, and the resulting mixture was filtered using a glass filter GF/C (manufactured by Whatman) treated with 1% polyethyleneimine. After the glass filter was washed with the assay buffer containing 0.2% bovine serum albumin, the radioactivity on the glass filter was measured using a liquid scintillation counter (TRI-CARB 2700TR, manufactured by Packard). The binding amount in the presence of 10 μmol/L WIN-55215-2 (manufactured by Tocris) ((R)-(+)-[2,3-dihydro-5-methyl-3-(4-morpholinylmethyl)pyrrolo[1,2,3-de]-1,4-benzoxazin-6-yl]-1-naphthalenylmethanone) was considered to be a non-specific binding amount, and a difference between the total binding amount and the non-specific binding amount was considered to be a specific binding amount. The 50% inhibitory concentration (IC$_{50}$ value) of the test compound against the specific binding was obtained, and the Ki value of the test substance was calculated from the 50% inhibitory concentration and the Kd value of the [$^3$H]CP55940 binding.

As a result, Compounds 28, 32, 42, 47, 48, 49, 65, 66, 70, 72, 76, 77, 82, 83, 84, 85, 90, 92, 102, 133, 143, 144, 146, 153, 185, 186, 187, 188, 204, 205, 206, 207, 208, o, p, and q had a Ki value against the CB2 receptor of less than 1 μmol/L. It was confirmed that Compound (I) or a pharmaceutically acceptable salt thereof has an affinity for the CB2 receptor. Further, the Ki value of Compound (I) or a pharmaceutically acceptable salt thereof against the CB2 receptor showed a value smaller than the Ki value thereof against the CB1 receptor. That is, Compound (I) or a pharmaceutically acceptable salt thereof showed a selective affinity for the CB2 receptor.

Test Example 2

GTPγS Binding Experiment Via Human CB2 Receptor

A test was carried out according to the method of Hillard et al. [The Journal of Pharmacology and Experimental Therapeutics, vol. 289, p. 1427 (1999)]. As for a membrane specimen, a membrane fraction was prepared from CHO-K1 cells in which a human CB2 receptor [Nature, vol. 365, pp. 61-65 (1993)] was stably expressed and used. The membrane specimen (final concentration: 40 μg of protein/mL) was incubated together with a test compound and [$^{35}$S]GTPγS (manufactured by PerkinElmer) (final concentration: 0.05 nmol/L) in an assay buffer (50 mmol/L Tris-HCl buffer (pH 7.4), 100 mmol/L NaCl, 1 mmol/L EDTA, 3 mmol/L MgCl$_2$, and 0.1% bovine serum albumin) containing 20 μmol/L guanosine 5′-diphosphate (GDP) at 30° C. for 1 hour, and the resulting mixture was filtered using a glass filter GF/B (manufactured by Whatman). After the glass filter was washed with the assay buffer, the radioactivity on the glass filter was measured using a liquid scintillation counter (TRI-CARB 2700TR, manufactured by Packard). The binding amount in the presence of 10 μmol/L GTPγS was considered to be a non-specific binding amount, and a difference between the total binding amount and the non-specific binding amount was considered to be a specific binding amount. The ratio of increase in the specific binding amount in the presence of the test compound to the specific binding amount in the absence of the test compound was considered to be an agonistic activity of the test compound. The concentration of the test compound that produces 50% of the maximum effect (EC$_{50}$ value) was calculated by performing a nonlinear regression analysis using the concentration-response data. The percentage of the maximum effect of the test compound (E$_{max}$ value) was calculated by considering the maximum effect of CP55940 (manufactured by Tocris) measured at the same time as 100%.

Compounds 42, 38, 48, 49, 65, 66, 70, 72, 76, 77, 82, 83, 85, 102, 143, 144, 146, 153, 185, 186, 204, 205, 206, and 208 had an EC$_{50}$ value of less than 1 μmol/L and an Emax value of more than 30%. It was confirmed that these compounds have an agonistic activity against the CB2 receptor. That is, it was considered that Compound (I) or a pharmaceutically acceptable salt thereof has an agonistic activity against the CB2 receptor.

From the above results, it was shown that Compound (I) or a pharmaceutically acceptable salt thereof has a high affinity for the CB2 receptor and is useful as a CB2 receptor agonist. Accordingly, it was considered that Compound (I) or a pharmaceutically acceptable salt thereof is useful as a therapeutic and/or preventive agent for a disease associated with a CB2 receptor.

It has been well known that CB2 receptor agonists are effective as anti-inflammatory agents [Nature, vol. 365, p. 61 (1993); British Journal of Pharmacology, vol. 139, p. 775

(2003)] or therapeutic agents for diseases such as pain [Pain, vol. 93, p. 239 (2001); Proceedings of the National Academy of Science of the United States of America, vol. 102, p. 3093 (2005); European Journal of Neuroscience, vol. 17, p. 2750 (2003); European Journal of Neuroscience, vol. 22, p. 371 (2005); European Journal of Neuroscience), vol. 23, p. 1530 (2006)], pruritus (WO2002/065997; WO2003/035109; WO2003/070277; WO2006/046778), or osteoporosis [Proceedings of the National Academy of Science of the United States of America, vol. 103, p. 696 (2006)]. Accordingly, it was considered that Compound (I) or a pharmaceutically acceptable salt thereof is useful as a therapeutic and/or preventive agent for pains (such as neuropathic pain, trigeminal neuralgia, diabetic pain, postherpetic neuralgia, neuropathic low back pain, HIV-related pain, fibromyalgia, cancer pain, inflammatory pain, acute pain, chronic pain, postoperative pain, acute pain after tooth extraction, chronic musculoskeletal pain, noxious pain, psychogenic pain, and menstrual pain), migraine, pruritus, inflammation, allergies, immunodeficiency, autoimmune diseases, chronic rheumatoid arthritis, osteoarthritis, inflammatory bowel disease, irritable bowel syndrome, multiple sclerosis, asthma (such as airway inflammatory cell infiltration, airway hyperresponsiveness, bronchoconstriction, and mucus hypersecretion), chronic obstructive lung disease, emphysema, pulmonary fibrosis, coughing, allergic rhinitis, dermatitis, atopic dermatitis, arteriosclerosis, glaucoma, anorexia, osteoporosis, or the like.

Test example 3

Analgesic Effect of Compounds in Rats with Chronic Constriction Nerve Injury

Rats with chronic constriction nerve injury were produced by partially modifying the method of Mosconi and Kruger et al. (Pain, vol. 64, pp. 37-57 (1996))

Male Crl:CD(SD) rats were used for the experiments. Under pentobarbital anesthesia, the sciatic nerve of the left hind limb of the rat was exfoliated, and the exfoliated region was wrapped with a polyethylene tube (trade name: Intramedic, size: PE-60, manufactured by Becton Dickinson and Company) of 2 mm in length. On days 14 to 21 after the surgery, the rats were placed in an acrylic connected cage with a wire mesh floor (900 mm (length)×210 mm (depth)×140 mm (height)) consisting of 4 cages connected in a row and allowed to acclimate to the environment for at least 20 minutes, and then, the pain was evaluated.

The von Frey filament (trade name: touch test sensory evaluator, Model number: model 58011, manufactured by Muromachi Kikai) was used to evaluate pain, and the results were calculated as a pain threshold. That is, by using a von Frey filament of different stimulus intensity, stimulation was given to the plantar surface of the injured side of rats with chronic constriction nerve injury, and the stimulus intensity to cause paw withdrawal response was obtained. Then, the 50% pain threshold (Paw withdrawal threshold) (g) was calculated by the up down method of Dixon [Annual Review of Pharmacology and Toxicology, vol. 20, pp. 441-462 (1980)]. Incidentally, a normal rat exhibited the 50% pain threshold of from 10 to 12 g on an average.

In the evaluation of the test compound, rats with 50% pain threshold of less than 4 g were used, and the test compound was dissolved in a 0.5% aqueous methyl cellulose solution and orally administered at a dose of 5 mL/kg. One hour after the administration, the pain threshold was measured using von Frey filaments.

As the results, Compounds 65, 66, 70, 76, 83, 85, 102, 133, 143, 144, 146, 153, 185, 186, 187, 188, 204, 205, 206, 207, and 208 significantly increased the pain threshold at a dose of 50 mg/kg or less. That is, it was confirmed that these compounds have a preventive and/or therapeutic effect on pain.

Accordingly, it was confirmed that Compound (I) or a pharmaceutically acceptable salt thereof is useful as a therapeutic and/or preventive agent for pain, and is useful as a therapeutic and/or preventive agent for pain such as neuropathic pain, trigeminal neuralgia, diabetic pain, postherpetic neuralgia, neuropathic low back pain, HIV-related pain, fibromyalgia, cancer pain, or inflammatory pain.

Compound (I) or a pharmaceutically acceptable salt thereof can be administered alone as it is. However, usually, Compound (I) or a pharmaceutically acceptable salt thereof is preferably provided as various pharmaceutical preparations. Further, such pharmaceutical preparations are to be used in animals or humans.

The pharmaceutical preparations according to the present invention can contain Compound (I) or a pharmaceutically acceptable salt thereof alone as an active ingredient or a mixture thereof with an optional active ingredient for another treatment. Further, these pharmaceutical preparations are prepared by mixing the active ingredient with one or more pharmaceutically acceptable carriers (such as a diluent, a solvent and an excipient) and then subjecting the mixture to any method well known in the technical field of pharmaceutics.

As for the administration route, it is preferred to select the most effective route of administration in the treatment. Examples of the administration route include an oral administration and a parenteral administration such as an intravenous administration.

As for the dosage form, for example, tablets, injections, and the like are included.

For example, the tablet suitable for oral administration can be prepared with an excipient such as lactose, a disintegrator such as starch, a lubricant such as magnesium stearate, a binder such as hydroxypropyl cellulose, or the like.

For example, the injection suitable for parenteral administration can be prepared with a diluent or a solvent such as a brine solution, a glucose solution, or a mixture of brine and a glucose solution, or the like.

The doses and the frequencies of administration of Compound (I) or a pharmaceutically acceptable salt thereof may vary depending on dosage form, age and body weight of a patient, nature or seriousness of the symptom to be treated, and the like. However, in the oral administration, in general, a dose of 0.01 to 1000 mg, preferably, 0.05 to 100 mg is administered to an adult patient once or several times a day. In the parenteral administration such as intravenous administration, a dose of 0.001 to 1000 mg, preferably, 0.01 to 100 mg is administered to an adult patient once or several times a day. However, these doses and frequencies of administration vary depending on the various conditions described above.

Hereinafter, the invention will be described more specifically with reference to Examples and Reference examples, however, the scope of the invention is not limited to these examples.

A proton nuclear magnetic resonance spectrum ($^1$H-NMR) used in Examples and Reference examples was measured at 270 MHz or 300 MHz, and exchangeable proton may not be clearly observed in some cases depending on the compounds and measurement conditions. Further, for the descriptions of the multiplicity of signals, those generally applied are used, and the symbol "br" represents an apparent broad signal.

Example 1

3-(2-tert-Butyl-1-cyclohexylmethyl-1H-imidazol-4-yl)benzonitrile (Compound 1)

Under a nitrogen atmosphere, cyclohexanemethylamine (1.04 mL, 8.03 mmol) was dissolved in THF (15 mL), and diisopropylethylamine (2.8 mL, 16.06 mmol) was added thereto at −20° C., and then, a solution obtained by dissolving 3-(2-bromoacetyl)benzonitrile (1.50 g, 6.69 mmol) in THF (5 mL) was slowly added dropwise thereto. After the mixture was stirred for 1 hour under ice-cooling, pivaloyl chloride (2.03 mL, 16.46 mmol) was added thereto, and the mixture was further stirred for 1 hour. Water was added to the mixture, and the mixture was extracted with ethyl acetate. The organic layer was washed with saturated brine and dried over anhydrous magnesium sulfate, and the solvent was evaporated under reduced pressure. To the residue, ammonium trifluoroacetate (2.70 g, 23.7 mmol) was added under an argon atmosphere, and the mixture was stirred at 140° C. for 15 minutes. After the mixture was left to cool to room temperature, water and an aqueous sodium hydrogen carbonate solution were added thereto, and the mixture was extracted with ethyl acetate. The organic layer was washed with saturated brine, and the solvent was evaporated under reduced pressure. The residue was purified by silica gel column chromatography (hexane/ethyl acetate=99/1 to 25/5) to give the title compound 1 (745 mg, 2.31 mmol, yield: 35%).
$^1$H-NMR (δppm, CDCl$_3$): 8.07-8.03 (m, 1H), 7.97 (dt, J=6.7, 2.1 Hz, 1H), 7.46-7.38 (m, 2H), 7.17 (s, 1H), 3.87 (d, J=7.1 Hz, 2H), 1.85-1.70 (m, 6H), 1.47 (s, 9H), 1.28-1.20 (m, 3H), 1.08-1.00 (m, 2H). Mass (m/e): 322 (M+H)$^+$.

Example 2

3-(2-tert-Butyl-1-cyclohexylmethyl-1H-imidazol-4-yl)-N-ethylbenzamide (Compound 2)

Compound a (102 mg, 0.3 mmol) obtained in Reference example 1 was dissolved in DMF (1.0 mL), and a 70% aqueous ethylamine solution (36 μL, 0.45 mmol), 1-(3-dimethylaminopropyl)-3-ethylcarbodiimide hydrochloride (WSC.HCl) (86 mg, 0.45 mmol), and 1-hydroxybenzotriazole hydrate (HOBt.H$_2$O) (69 mg, 0.45 mmol) were added thereto, and then, the mixture was stirred at 60° C. for 2 hours. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50 to 10/90) to give the title compound 2 (67 mg, 0.18 mmol, yield: 60%).
$^1$H-NMR (δppm, CDCl$_3$): 8.13 (s, 1H), 7.88 (d, J=7.7 Hz, 1H), 7.60 (d, J=7.7 Hz, 1H), 7.38 (t, J=7.7 Hz, 1H), 7.19 (s, 1H), 6.39 (brs, 1H), 3.86 (d, J=7.3 Hz, 2H), 3.50 (q, J=7.3 Hz, 2H), 1.84-1.63 (m, 6H), 1.47 (s, 9H), 1.27-1.20 (m, 6H), 1.06-0.96 (m, 2H). Mass (m/e): 368 (M+H)$^+$.

Example 3

2-tert-Butyl-1-cyclohexylmethyl-4-(3-tolyl)-1H-imidazole (Compound 3)

The title compound 3 (67 mg, 0.22 mmol, yield: 10%) was obtained in the same manner as in Example 1, using 2-bromo-3'-methylacetophenone obtained by the method described in Bull. Chem. Soc. Jpn. Vol. 60, p. 1159 (1987) instead of 3-(2-bromoacetyl)benzonitrile.
$^1$H-NMR (δppm, CDCl$_3$): 7.61 (s, 1H), 7.52 (d, J=7.8 Hz, 1H), 7.21 (t, J=7.8 Hz, 1H), 7.10 (s, 1H), 7.00 (d, J=7.8 Hz, 1H), 3.85 (d, J=7.0 Hz, 2H), 2.36 (s, 3H), 1.79-1.70 (m, 6H), 1.47 (s, 9H), 1.26-0.98 (m, 5H). Mass (m/e): 311 (M+H)$^+$.

Example 4

2-(2-tert-Butyl-1-cyclohexylmethyl-1H-imidazol-4-yl)-pyridine (Compound 4)

The title compound 4 (11 mg, 0.04 mmol, yield: 2%) was obtained in the same manner as in Example 1, using 2-(bromoacetyl)pyridine hydrobromide instead of 3-(2-bromoacetyl)benzonitrile.
$^1$H-NMR (δppm, CDCl$_3$): 8.51-8.50 (m, 1H), 7.98 (d, J=7.3 Hz, 1H), 7.69-7.65 (m, 1H), 7.55 (s, 1H), 7.08-7.04 (m, 1H), 3.87 (d, J=6.5 Hz, 2H), 1.92-1.75 (m, 6H), 1.48 (s, 9H), 1.31-0.92 (m, 5H). Mass (m/e): 298 (M+H)$^+$.

Example 5

2-tert-Butyl-1-cyclohexylmethyl-4-(2-methoxyphenyl)-1H-imidazole (Compound 5)

The title compound 5 (35 mg, 0.11 mmol, yield: 4%) was obtained in the same manner as in Example 1, using 2-bromo-2'-methoxyacetophenone instead of 3-(2-bromoacetyl)benzonitrile.
$^1$H-NMR (δppm, CDCl$_3$): 8.25-8.22 (m, 1H), 7.40 (s, 1H), 7.18-7.13 (m, 1H), 7.04-6.99 (m, 1H), 6.92-6.89 (m, 1H), 3.92 (s, 3H), 3.86 (d, J=6.2 Hz, 2H), 1.82-1.67 (m, 6H), 1.47 (s, 9H), 1.31-0.95 (m, 5H). Mass (m/e): 327(M+H)$^+$.

Example 6

2-tert-Butyl-1-cyclohexylmethyl-4-(3-methoxyphenyl)-1H-imidazole (Compound 6)

The title compound 6 (175 mg, 0.54 mmol, yield: 21%) was obtained in the same manner as in Example 1, using 2-bromo-3'-methoxyacetophenone instead of 3-(2-bromoacetyl)benzonitrile.
$^1$H-NMR (δppm, CDCl$_3$): 7.36-7.31 (m, 2H), 7.26-7.21 (m, 1H), 7.11 (m, 1H), 6.75-6.72 (m, 1H), 3.85 (s, 3H), 3.84 (d, J=7.0 Hz, 2H), 1.79-1.71 (m, 6H), 1.47 (s, 9H), 1.26-1.02 (m, 5H). Mass (m/e): 327(M+H)$^+$.

Example 7

2-tert-Butyl-1-cyclohexylmethyl-4-(4-methoxyphenyl)-1H-imidazole (Compound 7)

The title compound 7 (0.14 g, 0.42 mmol, yield: 17%) was obtained in the same manner as in Example 1, using 2-bromo-4'-methoxyacetophenone instead of 3-(2-bromoacetyl)benzonitrile.
$^1$H-NMR (δppm, CDCl$_3$): 7.68 (dt, J=9.4, 2.4 Hz, 2H), 7.01 (s, 1H), 6.88 (dt, J=9.4, 2.4 Hz, 2H), 3.84 (d, J=8.2 Hz, 2H), 3.81 (s, 3H), 1.81-1.72 (m, 6H), 1.47 (s, 9H), 1.29-1.18 (m, 3H), 1.06-0.95 (m, 2H). Mass (m/e): 327 (M+H)$^+$.

Example 8

4-(4-Bromophenyl)-2-tert-butyl-1-cyclohexylmethyl-1H-imidazole (Compound 8)

The title compound 8 (2.71 g, 7.22 mmol, yield: 50%) was obtained in the same manner as in Example 1, using 4-bromophenacyl bromide instead of 3-(2-bromoacetyl)benzonitrile.
$^1$H-NMR (δppm, CDCl$_3$): 7.67-7.66 (m, 2H), 7.47-7.41 (m, 2H), 7.11 (s, 1H), 3.85 (d, J=7.1 Hz, 2H), 1.89-1.68 (m, 6H), 1.46 (s, 9H), 1.31-0.91 (m, 5H). Mass (m/e): 375, 377 (M+H)$^+$.

Example 9

4-(2-tert-Butyl-1-cyclohexylmethyl-1H-imidazol-4-yl)-N,N-diethylbenzamide (Compound 9)

Compound c (51 mg, 0.15 mmol) obtained in Reference example 3 was dissolved in DMF (1.0 mL), and diethylamine (30 μL, 0.29 mmol), WSC.HCl (59 mg, 0.31 mmol), and HOBt.H$_2$O (50 mg, 0.33 mmol) were added thereto, and then, the mixture was stirred at room temperature for 2 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=70/30), and the obtained crude crystals were reslurried in hexane to give the title compound 9 (47 mg, 0.12 mmol, yield: 80%).
$^1$H-NMR (δppm, CDCl$_3$): 7.81-7.75 (m, 2H), 7.37-7.31 (m, 2H), 7.13 (s, 1H), 3.86 (d, J=7.1 Hz, 2H), 3.41 (br, 4H), 1.90-1.66 (m, 6H), 1.47 (s, 9H), 1.34-0.92 (m, 11H). Mass (m/e): 396 (M+H)$^+$.

Example 10

[4-(2-tert-Butyl-1-cyclohexylmethyl-1H-imidazol-4-yl)phenyl]-piperidin-1-ylmethanone (Compound 10)

The title compound 10 (47 mg, 0.12 mmol, yield: 79%) was obtained in the same manner as in Example 9, using piperidine instead of diethylamine.
$^1$H-NMR (δppm, CDCl$_3$): 7.81-7.75 (m, 2H), 7.40-7.34 (m, 2H), 7.15 (s, 1H), 3.86 (d, J=7.1 Hz, 2H), 3.79-3.24 (br, 4H), 1.90-1.48 (m, 12H), 1.47 (s, 9H), 1.30-0.92 (m, 5H). Mass (m/e): 408 (M+H)$^+$.

Example 11

[4-(2-tert-Butyl-1-cyclohexylmethyl-1H-imidazol-4-yl)phenyl]-morpholin-4-yl-methanone (Compound 11)

The title compound 11 (51 mg, 0.12 mmol, yield: 84%) was obtained in the same manner as in Example 9, using morpholine instead of diethylamine.
$^1$H-NMR (δppm, CDCl$_3$): 7.85-7.78 (m, 2H), 7.43-7.36 (m, 2H), 7.17 (s, 1H), 3.86 (d, J=6.9 Hz, 2H), 3.79-3.43 (m, 8H), 1.92-1.68 (m, 6H), 1.47 (s, 9H), 1.35-0.92 (m, 5H). Mass (m/e): 410 (M+H)$^+$.

Example 12

[4-(2-tert-Butyl-1-cyclohexylmethyl-1H-imidazol-4-yl)phenyl]-(4-methylpiperazin-1-yl)methanone (Compound 12)

The title compound 12 (52 mg, 0.12 mmol, yield: 84%) was obtained in the same manner as in Example 9, using 1-methylpiperazine instead of diethylamine.
$^1$H-NMR (δppm, CDCl$_3$): 7.78 (d, J=7.8 Hz, 2H), 7.37 (d, J=7.8 Hz, 2H), 7.13 (s, 1H), 3.86 (d, J=7.1 Hz, 2H), 3.86 (br, 4H), 3.62 (br, 4H), 2.31 (s, 3H), 1.91-1.66 (m, 6H), 1.47 (s, 9H), 1.36-0.90 (m, 5H). Mass (m/e): 423 (M+H)$^+$.

Example 13

[4-(2-tert-Butyl-1-cyclohexylmethyl-1H-imidazol-4-yl)phenyl]-piperazin-1-ylmethanone (Compound 13)

The title compound 13 (21 mg, 0.051 mmol, yield: 54%) was obtained in the same manner as in Example 9, using piperazine instead of diethylamine.
$^1$H-NMR (δppm, CDCl$_3$): 7.82-7.75 (m, 2H), 7.41-7.30 (m, 2H), 7.13 (s, 1H), 3.86 (d, J=6.9 Hz, 2H), 3.57 (br, 4H), 2.91-2.81 (m, 4H), 1.91-1.71 (m, 6H), 1.47 (s, 9H), 1.34-0.93 (m, 5H). Mass (m/e): 409 (M+H)$^+$.

Example 14

[4-(2-tert-Butyl-1-cyclohexylmethyl-1H-imidazol-4-yl)phenyl]-(4-phenylpiperazin-1-yl)methanone (Compound 14)

The title compound 14 (60 mg, 0.13 mmol, yield: 84%) was obtained in the same manner as in Example 9, using 1-phenylpiperazine instead of diethylamine.
$^1$H-NMR (δppm, CDCl$_3$): 7.85-7.79 (m, 2H), 7.46-7.40 (m, 2H), 7.33-7.24 (m, 2H), 7.17 (s, 1H), 6.98-6.86 (m, 3H), 3.87 (d, J=7.2 Hz, 2H), 3.72 (br, 4H), 3.18 (br, 4H), 1.89-1.63 (m, 6H), 1.47 (s, 9H), 1.34-0.91 (m, 5H). Mass (m/e): 485 (M+H)$^+$.

Example 15

[4-(2-tert-Butyl-1-cyclohexylmethyl-1H-imidazol-4-yl)phenyl]methanol (Compound 15)

Compound b (112 mg, 0.293 mmol) obtained in Reference example 2 was dissolved in THF (1.5 mL), and lithium borohydride (20 mg, 0.92 mmol) was added thereto, and then, the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50) to give the title compound 15 (96 mg, 0.29 mmol, yield: quantitative).
$^1$H-NMR (δppm, CDCl$_3$): 7.78-7.72 (m, 2H), 7.35-7.24 (m, 2H), 7.13 (s, 1H), 4.67 (brs, 2H), 3.86 (d, J=6.9 Hz, 2H), 1.87-1.69 (m, 6H), 1.48 (s, 9H), 1.36-0.92 (m, 5H). Mass (m/e): 327 (M+H)$^+$.

Example 16

2-tert-Butyl-4-(4-chloromethylphenyl)-1-cyclohexyl-methyl-1H-imidazole (Compound 16)

Compound 15 (102 mg, 0.31 mmol) obtained in Example 15 was dissolved in concentrated hydrochloric acid (0.5 mL), and the mixture was stirred at 50° C. for 1 hour. After the mixture was left to cool to 0° C., an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10) to give the title compound 16 (35 mg, 0.10 mmol, yield: 33%).

$^1$H-NMR ($\delta$ppm, CDCl$_3$): 7.76-7.72 (m, 2H), 7.36-7.32 (m, 2H), 7.13 (s, 1H), 4.59 (s, 2H), 3.85 (d, J=7.3 Hz, 2H), 1.85-1.68 (m, 6H), 1.47 (s, 9H), 1.28-0.93 (m, 5H).

Example 17

[4-(2-tert-Butyl-1-cyclohexylmethyl-1H-imidazol-4-yl)benzyl]-diethylamine (Compound 17)

Compound 16 (35 mg, 0.10 mmol) obtained in Example 16 was dissolved in acetonitrile (1.0 mL), and diethylamine (53 µL, 0.51 mmol) was added thereto, and then, the mixture was refluxed for 1 hour. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by preparative thin-layer chromatography (chloroform/methanol=80/20) to give the title compound 17 (39 mg, 0.10 mmol, yield: 98%).

$^1$H-NMR ($\delta$ppm, CDCl$_3$): 7.75-7.68 (m, 2H), 7.36-7.29 (m, 2H), 7.10 (s, 1H), 3.85 (d, J=7.4 Hz, 2H), 3.64 (s, 2H), 2.58 (q, J=7.1 Hz, 4H), 1.87-1.69 (m, 6H), 1.47 (s, 9H), 1.36-0.92 (m, 11H). Mass (m/e): 382 (M+H)$^+$.

Example 18

4-(2-Bromophenyl)-2-tert-butyl-1-cyclohexylmethyl-1H-imidazole (Compound 18)

The title compound 18 (1.22 g, 3.25 mmol, yield: 13%) was obtained in the same manner as in Example 8, using 2-bromophenacyl bromide instead of 4-bromophenacyl bromide.

$^1$H-NMR ($\delta$ppm, CDCl$_3$): 8.13 (dd, J=8.0, 1.8 Hz, 1H), 7.61 (s, 1H), 7.56 (dd, J=8.0, 1.2 Hz, 1H), 7.36-7.28 (m, 1H), 7.06-6.98 (m, 1H), 3.88 (d, J=7.1 Hz, 2H), 1.86-1.66 (m, 6H), 1.47 (s, 9H), 1.30-0.93 (m, 5H). Mass (m/e): 375, 377 (M+H)$^+$.

Example 19

[2-(2-tert-Butyl-1-cyclohexylmethyl-1H-imidazol-4-yl)phenyl]methanol (Compound 19)

The title compound 19 (82 mg, 0.25 mmol, yield: 79%) was obtained in the same manner as in Example 15, using Compound d obtained in Reference example 4.

$^1$H-NMR ($\delta$ppm, CDCl$_3$): 7.68 (brs, 1H), 7.46 (dd, J=7.4, 1.7 Hz, 1H), 7.36 (dd, J=7.4, 1.7 Hz, 1H), 7.29-7.19 (m, 2H), 7.08 (s, 1H), 4.57 (s, 2H), 3.90 (d, J=7.3 Hz, 2H), 1.83-1.73 (m, 6H), 1.47 (s, 9H), 1.31-0.94 (m, 5H). Mass (m/e): 327 (M+H)$^+$.

Example 20

2-(2-tert-Butyl-1-cyclohexylmethyl-1H-imidazol-4-yl)-N,N-diethylbenzamide (Compound 20)

The title compound 20 (80 mg, 0.20 mmol, yield: 97%) was obtained in the same manner as in Example 9, using Compound e obtained in Reference example 5.

$^1$H-NMR ($\delta$ppm, CDCl$_3$): 8.02-7.95 (m, 1H), 7.41-7.32 (m, 1H), 7.25-7.13 (m, 2H), 7.11 (s, 1H), 3.81 (d, J=7.3 Hz, 2H), 3.75-3.58 (m, 1H), 3.47-3.32 (m, 1H), 3.17-2.89 (m, 2H), 1.82-1.64 (m, 6H), 1.46 (s, 9H), 1.30-0.89 (m, 8H), 0.81 (t, J=7.2 Hz, 3H). Mass (m/e): 396 (M+H)$^+$.

Example 21

4-(2-tert-Butyl-1-cyclohexylmethyl-1H-imidazol-4-yl)-N,N-dimethylbenzamide (Compound 21)

The title compound 21 (91 mg, 0.25 mmol, yield: quantitative) was obtained in the same manner as in Example 9, using Compound e obtained in Reference example 5 and dimethylamine hydrochloride.

$^1$H-NMR ($\delta$ppm, CDCl$_3$): 7.95-7.90 (m, 1H), 7.40-7.34 (m, 1H), 7.26-7.18 (m, 2H), 7.04 (s, 1H), 3.87 (dd, J=13.9, 7.7 Hz, 1H), 3.77 (dd, J=13.9, 7.7 Hz, 1H), 3.07 (s, 3H), 2.69 (s, 3H), 1.84-1.60 (m, 6H), 1.45 (s, 9H), 1.32-0.91 (m, 5H). Mass (m/e): 368 (M+H)$^+$.

Example 22

[2-(2-tert-Butyl-1-cyclohexylmethyl-1H-imidazol-4-yl)benzyl]-diethylamine (Compound 22)

The title compound 22 (3.0 mg, 0.008 mmol, yield: 4%) was obtained in the same manner as in Example 16 and 17, using Compound 19 obtained in Example 19.

$^1$H-NMR ($\delta$ppm, CDCl$_3$): 7.86-7.78 (m, 1H), 7.60-7.51 (m, 1H), 7.35-7.26 (m, 2H), 7.13 (s, 1H), 4.35 (brs, 2H), 3.88 (d, J=7.3 Hz, 2H), 2.95 (brq, J=6.9 Hz, 4H), 1.89-1.68 (m, 6H), 1.47 (s, 9H), 1.38-0.91 (m, 11H). Mass (m/e): 382 (M+H)$^+$.

Example 23

2-tert-Butyl-1-cyclohexylmethyl-4-(2-nitrophenyl)-1H-imidazole (Compound 23)

The title compound 23 (8.4 mg, 0.025 mmol, yield: 29%) was obtained in the same manner as in Example 1, using 2-nitrophenacyl bromide.

$^1$H-NMR ($\delta$ppm, CDCl$_3$): 8.01-7.92 (m, 1H), 7.60-7.46 (m, 2H), 7.34-7.25 (m, 1H), 7.09 (s, 1H), 3.84 (d, J=7.1 Hz, 2H), 1.84-1.62 (m, 6H), 1.44 (s, 9H), 1.34-0.87 (m, 5H). Mass (m/e): 342 (M+H)$^+$.

Example 24

2-tert-Butyl-1-cyclohexylmethyl-4-(2-toly)-1H-imidazole (Compound 24)

The title compound 24 (76 mg, 0.24 mmol, yield: 21%) was obtained in the same manner as in Example 8, using 2-methylphenacyl bromide instead of 4-bromophenacyl bromide.

¹H-NMR (δppm, CDCl₃): 7.87-7.81 (m, 1H), 7.23-7.08 (m, 3H), 6.94 (s, 1H), 3.87 (d, J=6.9 Hz, 2H), 2.47 (s, 3H), 1.85-1.68 (m, 6H), 1.47 (s, 9H), 1.32-0.92 (m, 5H). Mass (m/e): 311 (M+H)⁺.

Example 25

2-tert-Butyl-1-cyclohexylmethyl-4-(2-fluorophenyl)-1H-imidazole (Compound 25)

The title compound 25 (78 mg, 0.25 mmol, yield: 25%) was obtained in the same manner as in Example 1, using 2-fluorophenacyl bromide.
¹H-NMR (δppm, CDCl₃): 8.23-8.15 (m, 1H), 7.29 (d, J=4.1 Hz, 1H), 7.17-6.99 (m, 3H), 3.86 (d, J=7.1 Hz, 2H), 1.92-1.63 (m, 6H), 1.47 (s, 9H), 1.35-0.92 (m, 5H). Mass (m/e): 315 (M+H)⁺.

Example 26

2-tert-Butyl-4-(2-chlorophenyl)-1-cyclohexylmethyl-1H-imidazole (Compound 26)

Step 1
A mixture of 2-chlorophenacyl bromide (310 mg, 1.33 mmol), tert-butylcarbamidine hydrochloride (210 mg, 1.53 mmol), potassium carbonate (0.420 mg, 3.04 mmol), and acetonitrile (6 mL) was refluxed at 90° C. for 3 hours. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate. Then, the solvent was evaporated under reduced pressure to give 2-tert-butyl-4-(2-chlorophenyl)-1H-imidazole (132 mg, 0.56 mmol, yield: 42%).
¹H-NMR (δppm, CDCl₃): 9.14 (brs, 1H), 8.17 (brs, 1H), 7.64-7.38 (m, 2H), 7.32-7.26 (m, 1H), 7.24-7.09 (m, 1H), 1.43 (s, 9H).
Step 2
To a solution of 2-tert-butyl-4-(2-chlorophenyl)-1H-imidazole (132 mg, 0.563 mmol) obtained in the above in DMF (2.0 mL), sodium hydride (25 mg, 0.63 mmol) was added under ice-cooling in an argon atmosphere, and then, the mixture was stirred at room temperature for 30 minutes. Then, bromomethylcyclohexane (86 μL, 4.47 mmol) and potassium iodide (103 mg, 0.63 mmol) were added thereto, and the mixture was stirred at 80° C. for 4 hours. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10), and the obtained crude crystal was recrystallized from ethanol-water to give the title compound 26 (76 mg, 0.23 mmol, yield: 41%).
¹H-NMR (δppm, CDCl₃): 8.22 (dd, J=7.9, 1.8 Hz, 1H), 7.56 (s, 1H), 7.38-7.25 (m, 2H), 7.09 (dt, J=7.9, 1.8 Hz, 1H), 3.88 (d, J=7.1 Hz, 2H), 1.88-1.68 (m, 6H), 1.47 (s, 9H), 1.36-0.83 (m, 5H). Mass (m/e): 331, 333 (M+H)⁺.

Example 27

1-[2-(2-tert-Butyl-1-cyclohexylmethyl-1H-imidazol-4-yl)phenyl]ethanone (Compound 27)

Compound 18 (100 mg, 0.26 mmol) obtained in Example 18 was dissolved in toluene (1.0 mL), and tributyl(1-ethoxyvinyl)tin (130 μL, 0.39 mmol) and dichlorobis(triphenylphosphine)palladium (21 mg, 0.030 mmol) were added thereto, and then, the mixture was refluxed for 2 hours. After the mixture was left to cool to room temperature, concentrated hydrochloric acid (1 mL) was added thereto, and the mixture was further stirred at room temperature for 1 hour. To the mixture, an aqueous potassium fluoride solution was added, and the mixture was stirred at room temperature for 1 hour, and then, filtered through Celite. To the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by preparative thin-layer chromatography (hexane/ethyl acetate=80/20), and the obtained crude crystals were recrystallized from ethanol-water to give the title compound 27 (35 mg, 0.10 mmol, yield: 39%).
¹H-NMR (δppm, CDCl₃): 7.60 (dd, J=7.8, 0.7 Hz, 1H), 7.41-7.21 (m, 3H), 7.01 (s, 1H), 3.85 (d, J=7.1 Hz, 2H), 2.32 (s, 3H), 1.86-1.66 (m, 6H), 1.43 (s, 9H), 1.34-0.90 (m, 5H). Mass (m/e): 339 (M+H)⁺.

Example 28

2-tert-Butyl-1-cyclohexylmethyl-4-(3-nitrophenyl)-1H-imidazole (Compound 28)

The title compound 28 (12 mg, 0.04 mmol, yield: 1%) was obtained in the same manner as in Example 1, using 2-bromo-3'-nitroacetophenone instead of 3-(2-bromoacetyl)benzonitrile.
¹H-NMR (δppm, CDCl₃): 8.54 (t, J=2.0 Hz, 1H), 8.13 (dt, J=7.8, 1.9 Hz, 1H), 8.00 (dt, J=7.8, 1.9 Hz, 1H), 7.48 (t, J=7.8 Hz, 1H), 7.25 (s, 1H), 3.89 (d, J=7.1 Hz, 2H), 1.90-1.69 (m, 6H), 1.48 (s, 9H), 1.32-1.16 (m, 3H), 1.09-1.01 (m, 2H). Mass (m/e): 342 (M+H)⁺.

Example 29

4-(3-Bromophenyl)-2-tert-butyl-1-cyclohexylmethyl-1H-imidazole (Compound 29)

The title compound 29 (25 mg, 0.07 mmol, yield: 2%) was obtained in the same manner as in Example 1, using 2,3'-dibromoacetophenone instead of 3-(2-bromoacetyl)benzonitrile.
¹H-NMR (δppm, CDCl₃): 7.91 (t, J=1.7 Hz, 1H), 7.67 (dt, J=7.8, 1.3 Hz, 1H), 7.31-7.27 (m, 1H), 7.18 (t, J=7.8 Hz, 1H), 7.12 (s, 1H), 3.85 (d, J=7.2 Hz, 2H), 1.78-1.62 (m, 6H), 1.46 (s, 9H), 1.31-1.19 (m, 3H), 0.98-0.89 (m, 2H). Mass (m/e): 375, 377 (M+H)⁺.

Example 30

[3-(2-tert-Butyl-1-cyclohexylmethyl-1H-imidazol-4-yl)phenyl]methanol (Compound 30)

Under an argon atmosphere, Compound f (123 mg, 0.33 mmol) obtained in Reference example 6 was dissolved in THF (1.5 mL), and lithium borohydride (22 mg, 1.00 mmol) was added thereto, and then, the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=65/35) to give the title compound 30 (82 mg, 0.25 mmol, yield: 75%).

$^1$H-NMR (δppm, CDCl$_3$): 7.77 (s, 1H), 7.67 (d, J=7.7 Hz, 1H), 7.32 (t, J=7.7 Hz, 1H), 7.18 (t, J=7.9 Hz, 1H), 7.13 (s, 1H), 4.70 (s, 2H), 3.86 (d, J=7.2 Hz, 2H), 1.79-1.67 (m, 6H), 1.47 (s, 9H), 1.27-1.19 (m, 3H), 1.07-0.99 (m, 2H). Mass (m/e): 327 (M+H)$^+$.

Example 31

3-(2-tert-Butyl-1-cyclohexylmethyl-1H-imidazol-4-yl)pyridine (Compound 31)

The title compound 31 (134 mg, 0.45 mmol, yield: 18%) was obtained in the same manner as in Example 1, using 3-(bromoacetyl)pyridine monohydrobromate instead of 3-(2-bromoacetyl)benzonitrile.

$^1$H-NMR (δppm, CDCl$_3$): 8.94-8.93 (m, 1H), 8.42-8.40 (m, 1H), 8.12-8.08 (m, 1H), 7.28-7.24 (m, 1H), 7.19 (s, 1H), 3.87 (d, J=7.0 Hz, 2H), 1.82-1.71 (m, 6H), 1.47 (s, 9H), 1.29-1.20 (m, 3H), 1.07-1.00 (m, 2H). Mass (m/e): 298 (M+H)$^+$.

Example 32

3-(2-tert-Butyl-1-cyclohexylmethyl-1H-imidazol-4-yl)-N,N-diethylbenzamide (Compound 32)

The title compound 32 (467 mg, 1.18 mmol, yield: 69%) was obtained in the same manner as in Example 2, using diethylamine instead of ethylamine.

$^1$H-NMR (δppm, CDCl$_3$): 7.83 (dt, J=7.9, 1.3 Hz, 1H), 7.73 (t, J=1.3 Hz, 1H), 7.36 (t, J=7.9 Hz, 1H), 7.17 (dt, J=7.9, 1.3 Hz, 1H), 7.14 (s, 1H), 3.85 (d, J=7.2 Hz, 2H), −3.58-3.51 (m, 2H), 3.32-3.24 (m, 2H), 1.80-1.70 (m, 6H), 1.46 (s, 9H), 1.26-0.98 (m, 11H). Mass (m/e): 396 (M+H)$^+$.

Example 33

Benzoic acid[3-(2-tert-Butyl-1-cyclohexylmethyl-1H-imidazol-4-yl)phenyl]ester (Compound 33)

Step 1

Under an argon atmosphere, 3-hydroxyacetophenone (0.68 g, 5 mmol) was dissolved in dichloromethane (5 mL), and pyridine (2.0 mL, 25 mmol) and benzoyl chloride (0.70 mL, 6.0 mmol) were added thereto, and then, the mixture was stirred at room temperature for 4 hours. To the mixture, an aqueous sodium hydrogen carbonate solution was added, and the mixture was extracted with ethyl acetate. The organic layer was sequentially washed with a 2 mol/L aqueous sodium hydroxide solution, 2 mol/L hydrochloric acid, and saturated brine and dried over anhydrous magnesium sulfate, and the solvent was evaporated under reduced pressure. The residue was purified by silica gel column chromatography (hexane/ethyl acetate=95/5 to 50/50) to give benzoic acid (3-acetylphenyl)ester (1.19 g, 4.96 mmol, yield: 99%).

Step 2

Under an argon atmosphere, benzoic acid (3-acetylphenyl) ester (1.18 g, 4.92 mmol) obtained in the above was dissolved in THF (5 mL), and phenyltrimethylammonium tribromide (1.85 g, 4.92 mmol) was added thereto, and then, the mixture was stirred overnight at room temperature. Water (50 mL) was added to the mixture, and the precipitated solid was collected by filtration. The obtained solid was recrystallized from ethanol to give benzoic acid [3-(2-bromoacetyl)phenyl] ester (0.97 g, 3.03 mmol, yield: 62%).

Step 3

The title compound 33 (0.14 g, 0.33 mmol, yield: 11%) was obtained in the same manner as in Example 1, using benzoic acid [3-(2-bromoacetyl)phenyl]ester obtained in the above instead of 3-(2-bromoacetyl)benzonitrile.

Example 34

3-(2-tert-Butyl-1-cyclohexylmethyl-1H-imidazol-4-yl)phenol (Compound 34)

Compound 33 (0.14 g, 0.32 mmol) obtained in Example 33 was dissolved in ethanol (1.5 mL), and a 2 mol/L aqueous sodium hydroxide solution (1.5 mL, 3.0 mmol) was added thereto, and then, the mixture was stirred at 80° C. for 1 hour. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was recrystallized from ethyl acetate-hexane (1/20) to give the title compound 34 (59 mg, 0.19 mmol, yield: 59%).

$^1$H-NMR (δppm, CDCl$_3$): 7.37 (brs, 1H), 7.21 (brs, 1H), 7.18 (d, J=7.8 Hz, 1H), 7.09 (s, 1H), 6.64 (dt, J=7.8, 2.0 Hz, 1H), 3.85 (d, J=7.1 Hz, 2H), 1.82-1.74 (m, 6H), 1.47 (s, 9H), 1.28-1.19 (m, 3H), 1.07-0.99 (m, 2H). Mass (m/e): 313 (M+H)$^+$.

Example 35

4-[3-(2-tert-Butyl-1-cyclohexylmethyl-1H-imidazol-4-yl)phenyl]morpholine (Compound 35)

The title compound 35 (15 mg, 0.04 mmol, yield: 17%) was obtained in the same manner as in Example 44, using Compound 29 obtained in Example 29.

$^1$H-NMR (δppm, CDCl$_3$): 7.40 (brs, 1H), 7.24-7.22 (m, 2H), 7.10 (s, 1H), 6.78-6.74 (m, 1H), 3.89 (m, 6H), 3.21 (t, J=5.1 Hz, 4H), 1.81-1.71 (m, 6H), 1.47 (s, 9H), 1.24-1.19 (m, 3H), 1.06-0.96 (m, 2H). Mass (m/e): 382 (M+H)$^+$.

Example 36

1-Cyclohexylmethyl-2-isopropenyl-4-(3-methoxyphenyl)-1H-imidazole (Compound 36)

The title compound 36 (5 mg, 0.02 mmol, yield: 0.6%) was obtained in the same manner as in Example 1, using 2-acetoxyisobutyryl chloride instead of pivaloyl chloride.

$^1$H-NMR (δppm, CDCl$_3$): 7.39-7.22 (m, 3H), 7.14 (s, 1H), 6.88-6.76 (m, 1H), 5.43-5.42 (m, 1H), 5.21-5.20 (m, 1H), 3.86 (s, 3H), 3.82 (d, J=6.5 Hz, 2H), 2.23-2.22 (m, 3H), 1.85-1.56 (m, 6H), 1.32-0.85 (m, 5H). Mass (m/e): 311 (M+H)$^+$.

Example 37

1-Cyclohexylmethyl-2-methoxymethyl-4-(3-methoxyphenyl)-1H-imidazole monohydrochloride (Compound 37)

A free base was obtained in the same manner as in Example 1 using methoxyacetyl chloride instead of pivaloyl chloride, and the obtained free base was treated with 4 mol/L hydrogen chloride-ethyl acetate to give the title compound 37 (83 mg, 0.24 mmol, yield: 9%).

$^1$H-NMR (δppm, CDCl$_3$): 7.76 (s, 1H), 7.41-7.32 (m, 2H), 7.26-7.24 (m, 1H), 6.97-6.94 (m, 1H), 5.10 (s, 2H), 4.00 (d, J=7.6 Hz, 2H), 3.97 (s, 3H), 3.50 (s, 3H), 1.78-1.58 (m, 6H), 1.35-0.95 (m, 5H). Mass (m/e): 315 (M+H)$^+$. (as the free base)

Example 38

1-Cyclohexylmethyl-2-(2,2-dimethylpropyl)-4-(3-methoxyphenyl)-1H-imidazole (Compound 38)

The title compound 38 (50 mg, 0.15 mmol, yield: 6%) was obtained in the same manner as in Example 1, using tert-butylacetyl chloride instead of pivaloyl chloride.

$^1$H-NMR (δppm, CDCl$_3$): 7.38-7.22 (m, 3H), 7.07 (s, 1H), 6.77-6.74 (m, 1H), 3.85 (s, 3H), 3.69 (d, J=7.0 Hz, 2H), 2.60 (s, 2H), 1.78-1.62 (m, 6H), 1.28-1.14 (m, 3H), 1.04 (s, 9H), 1.00-0.85 (m, 2H). Mass (m/e): 341 (M+H)$^+$.

Example 39

2-tert-Butyl-4-(3-nitrophenyl)-1-(tetrahydrofuran-2-ylmethyl)-1H-imidazole (Compound 39)

The title compound 39 (32 mg, 0.10 mmol, yield: 20%) was obtained in the same manner as in Example 45, using 2-bromo-3'-nitroacetophenone and tetrahydrofurfuryl bromide.

$^1$H-NMR (δppm, CDCl$_3$): 8.56 (t, J=1.9 Hz, 1H), 8.14-8.11 (m, 1H), 8.03-7.99 (m, 1H), 7.49 (t, J=4.0 Hz, 2H), 4.28-4.06 (m, 3H), 4.00-3.92 (m, 1H), 3.88-3.81 (m, 1H), 2.16-2.07 (m, 1H), 2.02-1.94 (m, 2H), 1.62-1.55 (m, 1H), 1.48 (s, 9H). Mass (m/e): 330 (M+H)$^+$.

Example 40

2-tert-Butyl-1-cyclopropylmethyl-4-(3-nitrophenyl)-1H-imidazole (Compound 40)

The title compound 40 (25 mg, 0.084 mmol, yield: quantitative) was obtained in the same manner as in step 3 of Example 45, using Compound A-1 obtained in Reference example A-1 and cyclopropylmethyl bromide.

$^1$H-NMR (δppm, CDCl$_3$): 8.57 (t, J=1.8 Hz, 1H), 8.16-8.13 (m, 1H), 8.04-8.00 (m, 1H), 7.52-7.47 (m, 2H), 3.95 (d, J=7.2 Hz, 2H), 1.49 (s, 9H), 0.90-0.83 (m, 1H), 0.80-0.73 (m, 2H), 0.47-0.42 (m, 2H). Mass (m/e): 300 (M+H)$^+$.

Example 41

2-tert-Butyl-4-(3-nitrophenyl)-1-[2-(tetrahydro-pyran-4-yl)ethyl]-1H-imidazole (Compound 41)

Step 1

(Tetrahydropyran-4-yl)ethyl-methanesulfonate (264 mg, 1.26 mmol, yield: quantitative) was obtained in the same manner as in step 2 of Example 45, using 2-(tetrahydropyran-4-yl)ethanol instead of (tetrahydropyran-4-yl)methanol.

$^1$H-NMR (δppm, CDCl$_3$): 4.29 (t, J=6.0 Hz, 2H), 3.99-3.94 (m, 2H), 3.39 (td, J=11.7, 1.8 Hz, 2H), 3.02 (s, 3H), 1.73-1.62 (m, 4H), 1.43-1.24 (m, 3H). Mass (m/e): 209 (M+H)$^+$.

Step 2

The title compound 41 (12.4 mg, 0.035 mmol, yield: 28%) was obtained in the same manner as in step 3 of Example 45, using (tetrahydropyran-4-yl)ethyl-methanesulfonate obtained in the above and Compound A-1 obtained in Reference example A-1.

$^1$H-NMR (δppm, CDCl$_3$): 8.54-8.53 (m, 1H), 8.13-8.10 (m, 1H), 8.02 (dd, J=8.1, 1.1 Hz, 1H), 7.49 (t, J=8.1 Hz, 1H), 7.25 (s, 1H), 4.14-4.08 (m, 2H), 4.03-3.97 (m, 2H), 3.46-3.38 (m, 2H), 1.88-1.80 (m, 2H), 1.69-1.61 (m, 5H), 1.49 (s, 9H). Mass (m/e): 358 (M+H)$^+$.

Example 42

2-tert-Butyl-4-(3-nitrophenyl)-1-(tetrahydropyran-2-ylmethyl)-1H-imidazole (Compound 42)

The title compound 42 (5.2 mg, 0.015 mmol, yield: 20%) was obtained in the same manner as in Reference example A-2, using 2-(bromomethyl)tetrahydro-2H-pyran.

$^1$H-NMR (δppm, CDCl$_3$): 8.56-8.55 (m, 1H), 8.13-8.11 (m, 1H), 8.02-7.99 (m, 1H), 7.48 (t, J=8.1 Hz, 1H), 7.42 (s, 1H), 4.09-4.02 (m, 3H), 3.61-3.55 (m, 1H), 3.44-3.35 (m, 1H), 1.93-1.90 (m, 1H), 1.68-1.47 (m, 14H). Mass (m/e): 344 (M+H)$^+$.

Example 43

4-(3-Bromophenyl)-2-tert-butyl-1-(tetrahydropyran-4-ylmethyl)-1H-imidazole (Compound 43)

The title compound 43 (830 mg, 2.20 mmol, yield: 55%) was obtained in the same manner as in Example 45, using 2,3'-dibromoacetophenone.

Example 44

1-{3-[2-tert-Butyl-1-(tetrahydropyran-4-ylmethyl)-1H-imidazol-4-yl]phenyl}piperidine (Compound 44)

Under an argon atmosphere, Compound 43 (70 mg, 0.19 mmol) obtained in Example 43 was dissolved in toluene (1 mL), and piperidine (37 μL, 0.37 mmol), cesium carbonate (121 mg, 0.37 mmol), (±)-2,2'-bis(diphenylphosphino)-1,1'-binaphthalene ((±)-BINAP) (23 mg, 0.04 mmol), and tri(dibenzylideneacetone) dipalladium(0) (17 mg, 0.02 mmol) were added thereto, and then, the mixture was stirred overnight at 100° C. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=65/35) to give the title compound 44 (4 mg, 0.01 mmol, yield: 6%).

$^1$H-NMR (δppm, CDCl$_3$): 7.39 (brs, 1H), 7.22-7.20 (m, 2H), 7.08 (s, 1H), 6.81-6.79 (m, 1H), 4.00 (dd, J=11.1, 4.0 Hz, 2H), 3.92 (d, J=7.3 Hz, 2H), 3.37 (dt, J=11.1, 1.6 Hz, 2H), 3.19 (t, J=5.5 Hz, 4H), 2.08-2.04 (m, 1H), 1.75-1.68 (m, 4H), 1.66-1.60 (m, 4H), 1.47 (s, 9H), 1.44 (td, J=11.1, 4.0 Hz, 2H). Mass (m/e): 382 (M+H)$^+$.

Example 45

3-(2-tert-Butyl-1-(tetrahydropyran-4-ylmethyl)-1H-imidazol-4-yl)benzonitrile (Compound 45)

Step 1

A mixture of 3-(2-bromoacetyl)benzonitrile (500 mg, 2.23 mmol), tert-butylcarbamidine hydrochloride (610 mg, 4.46 mmol), potassium carbonate (770 mg, 5.58 mmol), and acetonitrile (10 mL) was refluxed for 1 hour. After the reaction was completed, the mixture was left to cool to room temperature. Then, water was added thereto, and the mixture was extracted with ethyl acetate. The organic layer was washed with saturated brine and dried over anhydrous magnesium sulfate. Then, the solvent was evaporated under reduced pressure to give 3-(2-tert-butyl-1H-imidazol-4-yl)benzonitrile (500 mg, 2.22 mmol, yield: 99%).

$^1$H-NMR (δppm, CDCl$_3$): 8.95 (brs, 1H), 8.08 (s, 1H), 8.00-7.98 (m, 1H), 7.52-7.38 (m, 2H), 7.24 (s, 1H), 1.43 (s, 9H). Mass (m/e): 226 (M+H)$^+$.

Step 2

Under an argon atmosphere, (tetrahydropyran-4-yl)methanol (14.01 g, 120.6 mmol) was dissolved in dichloromethane (241 mL), and triethylamine (50.44 mL, 361.8 mmol) was added thereto under ice-cooling, and then, methanesulfonyl chloride (11.21 mL, 144.7 mmol) was slowly added dropwise thereto at 10° C. or lower. After the dropwise addition was completed, the mixture was stirred at room temperature for 2 hours. Water was added to the mixture, and the mixture was extracted with ethyl acetate. The organic layer was washed with saturated brine and dried over anhydrous magnesium sulfate, and the solvent was evaporated under reduced pressure. The residue was reslurried in hexane to give (tetrahydropyran-4-yl)methylmethanesulfonate (20.51 g, 105.6 mmol, yield: 87%).

$^1$H-NMR (δppm, CDCl$_3$): 4.07 (d, J=6.6 Hz, 2H), 4.00 (dd, J=11.8, 2.2 Hz, 2H), 3.40 (dt, J=11.8, 2.2 Hz, 2H), 3.02 (s, 3H), 2.10-1.96 (m, 1H), 1.69-1.63 (m, 2H), 1.47-1.32 (m, 2H). Mass (m/e): 195 (M+H)$^+$ Step 3

Under an argon atmosphere, 3-(2-tert-butyl-1H-imidazol-4-yl)benzonitrile (671 mg, 2.98 mmol) obtained in step 1 described above was dissolved in DMF (10 mL), and sodium hydride (286 mg, 7.15 mmol) was added thereto, and then, the mixture was stirred at 50° C. for 30 minutes. Then, (tetrahydropyran-4-yl)methylmethanesulfonate (868 mg, 4.47 mmol) obtained in step 2 described above was added to the mixture, and the mixture was stirred at 80° C. for 2 hours. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10) to give the title compound 45 (235 mg, 0.73 mmol, yield: 25%).

$^1$H-NMR (δppm, CDCl$_3$): 8.06 (s, 1H), 7.97-7.96 (m, 1H), 7.43-7.41 (m, 2H), 7.19 (s, 1H), 4.05-3.99 (m, 2H), 3.95 (d, J=7.0 Hz, 2H), 3.43-3.35 (m, 2H), 2.32-1.98 (m, 1H), 1.72-1.62 (m, 2H), 1.48 (s, 9H), 1.51-1.35 (m, 2H). Mass (m/e): 324 (M+H)$^+$.

Example 46

1-{3-[2-tert-Butyl-1-(tetrahydropyran-4-ylmethyl)-1H-imidazol-4-yl]phenyl}-propan-1-one (Compound 46)

Under an argon atmosphere, Compound 45 (50 mg, 0.15 mmol) obtained in Example 45 was dissolved in THF (1 mL), and an ether solution of ethyl magnesium bromide (3.0 mol/L; 256 μL, 0.77 mmol) was added thereto at −60° C., and then, the mixture was stirred at this temperature for 1 hour. After the mixture was further stirred overnight at room temperature, water was added to the mixture under ice-cooling, and then, 1 mol/L hydrochloric acid was added thereto until the pH of the mixture became acidic. Then, an aqueous sodium hydrogen carbonate solution was added thereto until the pH of the mixture became basic, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=75/25) to give the title compound 46 (19 mg, 0.05 mmol, yield: 35%).

$^1$H-NMR (δppm, CDCl$_3$): 8.30-8.29 (m, 1H), 8.05-7.98 (m, 1H), 7.79-7.76 (m, 1H), 7.46-7.40 (m, 1H), 7.21 (s, 1H), 4.02 (dd, J=11.6, 4.1 Hz, 2H), 3.95 (d, J=7.3 Hz, 2H), 3.39 (t, J=11.6 Hz, 2H), 3.05 (q, J=7.3 Hz, 2H), 2.16-2.02 (m, 1H), 1.70-1.62 (m, 2H), 1.48 (s, 9H), 1.48-1.38 (m, 2H), 1.24 (t, J=7.3 Hz, 3H). Mass (m/e): 355 (M+H)$^+$.

Example 47

1-{3-[2-tert-Butyl-1-(tetrahydropyran-4-ylmethyl)-1H-imidazol-4-yl]phenyl}-2-methylpropan-1-one hydrochloride (Compound 47)

A free base of the title compound (39 mg, 0.11 mmol, yield: 59%) was obtained in the same manner as in Example 46 using a THF solution of isopropyl magnesium chloride (2.0 mol/L) instead of the ether solution of ethyl magnesium bromide. Further, the obtained free base was treated with 4 mol/L hydrogen chloride-ethyl acetate to give the title compound 47 (43 mg, 0.11 mmol, yield: quantitative).

$^1$H-NMR (δppm, CDCl$_3$): 8.28-8.27 (m, 1H), 8.01-7.78 (m, 1H), 7.77-7.74 (m, 1H), 7.43 (t, J=7.8 Hz, 1H), 7.20 (s, 1H), 4.01 (dd, J=11.9, 4.3 Hz, 2H), 3.94 (d, J=7.6 Hz, 2H), 3.62 (m, 1H), 3.38 (t, J=11.9 Hz, 2H), 2.17-2.04 (m, 1H), 1.68-1.42 (m, 4H), 1.49 (s, 9H), 1.24-1.21 (m, 6H). Mass (m/e): 369 (M+H)$^+$. (as the free base)

Example 48

{3-[2-tert-Butyl-1-(tetrahydropyran-4-ylmethyl)-1H-imidazol-4-yl]phenyl}phenylmethanone hydrochloride (Compound 48)

The title compound 48 (60 mg, 0.14 mmol, yield: 73%) was obtained in the same manner as in Example 47 using a THF solution of phenyl magnesium bromide (2.0 mol/L) instead of the ether solution of ethyl magnesium bromide.

$^1$H-NMR (δppm, CDCl$_3$): 8.14-8.05 (m, 2H), 7.84-7.81 (m, 2H), 7.59-7.44 (m, 5H), 7.19 (s, 1H), 4.01 (dd, J=11.3, 3.5 Hz, 2H), 3.93 (d, J=7.3 Hz, 2H), 3.38 (d, J=11.3 Hz, 2H), 2.15-2.02 (m, 1H), 1.68-1.63 (m, 2H), 1.48 (s, 9H), 1.45-1.23 (m, 2H). Mass (m/e): 403 (M+H)$^+$. (as the free base)

Example 49

1-{3-[2-tert-Butyl-1-(tetrahydropyran-4-ylmethyl)-1H-imidazol-4-yl]phenyl}ethanone (Compound 49)

Under an argon atmosphere, Compound 43 (184 mg, 0.49 mmol) obtained in Example 43 was dissolved in toluene (1.5 mL), and tributyl(1-ethoxyvinyl)tin (0.21 mL, 0.62 ml) and bis(triphenylphosphine) palladium(II) dichloride (17 mg, 0.02 mmol) were added thereto, and then, the mixture was refluxed for 8 hours. After the mixture was left to cool to room temperature, 10 mol/L hydrochloric acid (1 mL) was added thereto, and then, the mixture was stirred at room temperature for 5 minutes. The mixture was neutralized with an aqueous potassium carbonate solution and extracted with ethyl acetate. The organic layer was washed with a 10% aqueous ammonium fluoride solution and saturated brine and dried over anhydrous magnesium sulfate, and the solvent was evaporated under reduced pressure. The residue was purified by silica gel column chromatography (hexane/ethyl acetate=95/5→1/99) to give the title compound 49 (85 mg, 0.25 mmol, yield: 51%).

$^1$H-NMR (δppm, CDCl$_3$): 8.29 (t, J=1.4 Hz, 1H), 8.01 (td, J=7.7, 1.4 Hz, 1H), 7.77 (td, J=7.7, 1.4 Hz, 1H), 7.44 (t, J=7.7 Hz, 1H), 7.21 (s, 1H), 4.01 (dd, J=11.4, 3.6 Hz, 2H), 3.95 (d, J=7.4 Hz, 2H), 3.39 (dt, J=11.4, 1.9 Hz, 2H), 2.65 (s, 3H), 2.14-2.05 (m, 1H), 1.69-1.64 (m, 2H), 1.50 (s, 9H), 1.46 (dt, J=11.4, 3.3 Hz, 2H). Mass (m/e): 341 (M+H)$^+$.

Example 50

2-{3-[2-tert-Butyl-1-(tetrahydropyran-4-ylmethyl)-1H-imidazol-4-yl]phenyl}propan-2-ol (Compound 50)

Under an argon atmosphere, Compound 49 (63 mg, 0.19 mmol) obtained in Example 49 was dissolved in THF (1 mL), and a THF solution of methyl magnesium bromide (0.93 mol/L; 0.9 mL, 0.84 mmol) was added thereto at −60° C. Then, the mixture was stirred at this temperature for 1 hour, and thereafter the mixture was stirred at room temperature for 2 hours. Under ice-cooling, an aqueous ammonium chloride solution was added to the mixture, and then, an aqueous sodium hydrogen carbonate solution was added thereto to return the pH of the mixture to basic. Then, the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=75/25) to give the title compound 50 (32 mg, 0.09 mmol, yield: 48%).

$^1$H-NMR (δppm, CDCl$_3$): 7.92-7.88 (m, 1H), 7.65-7.61 (m, 1H), 7.32-7.26 (m, 2H), 7.13 (s, 1H), 4.03-3.97 (m, 2H), 3.91 (d, J=7.6 Hz, 2H), 3.37 (t, J=11.6 Hz, 2H), 2.18-2.00 (m, 2H), 1.60 (s, 6H), 1.48 (s, 9H), 1.51-1.42 (m, 3H). Mass (m/e): 357 (M+H)$^+$.

Example 51

4-(3-Benzylphenyl)-2-tert-butyl-1-(tetrahydropyran-4-ylmethyl)-1H-imidazole monohydrochloride (Compound 51)

Under an argon atmosphere, a free base of Compound 48 (57 mg, 0.14 mmol) obtained in Example 48 was dissolved in trifluoroacetic acid (1 mL), and triethylsilane (91 μL, 0.57 mmol) was added thereto, and then, the mixture was stirred overnight at room temperature. Under ice-cooling, an aqueous sodium hydrogen carbonate solution was added to the mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=80/20) to give a free base of the title compound (35 mg, 0.09 mmol, yield: 64%). Then, the obtained free base was treated with 4 mol/L hydrogen chloride-ethyl acetate to give the title compound 51 (30 mg, 0.07 mmol, yield: 78%).

$^1$H-NMR (δppm, CDCl$_3$): 7.63-7.57 (m, 2H), 7.29-7.18 (m, 6H), 7.08 (s, 1H), 7.00-6.97 (m, 1H), 4.02-3.96 (m, 2H), 4.00 (s, 2H), 3.90 (d, J=7.3 Hz, 2H), 3.36 (t, J=11.6 Hz, 2H), 2.08-2.00 (m, 1H), 1.64-1.62 (m, 2H), 1.47 (s, 9H), 1.46-1.23 (m, 2H). Mass (m/e): 389 (M+H)$^+$. (as the free base)

Example 52

5-[2-tert-Butyl-1-(tetrahydropyran-4-ylmethyl)-1H-imidazol-4-yl]-N,N-diethylthiophene-2-carboxamide (Compound 52)

Step 1
5-Diethylcarbamoylthiophene-2-boronic acid was obtained in the same manner as in Example 2, using 2-carboxythiophene-5-boronic acid and diethylamine.
Step 2
5-(2-tert-Butyl-1H-imidazol-4-yl)-N,N-diethylthiophene-2-carboxamide (63 mg, 0.20 mmol, yield: 36% (2 steps)) was obtained in the same manner as in step 4 of Example 81, using 5-diethylcarbamoylthiophene-2-boronic acid (132 mg, 0.58 mmol) obtained in the above.
Step 3
The title compound 52 (14 mg, 0.03 mmol, yield: 17%) was obtained in the same manner as in step 3 of Example 45, using 5-(2-tert-butyl-1H-imidazol-4-yl)-N,N-diethylthiophene-2-carboxamide obtained in the above.

$^1$H-NMR (δppm, CDCl$_3$): 7.25 (d, J=2.7 Hz, 1H), 7.16 (d, J=2.7 Hz, 1H), 7.06 (s, 1H), 4.04-3.99 (m, 2H), 3.91 (d, J=7.3 Hz, 2H), 3.56 (q, J=7.0 Hz, 4H), 3.39 (t, J=10.0 Hz, 2H), 2.12-2.00 (m, 1H), 1.79-1.61 (m, 2H), 1.46 (s, 9H), 1.43-1.23 (m, 8H). Mass (m/e): 404 (M+H)$^+$.

Example 53

2-tert-Butyl-1-(tetrahydropyran-4-ylmethyl)-4-thiophen-3-yl-1H-imidazole (Compound 53)

The title compound (39 mg, 0.13 mmol, yield: 32%) was obtained in the same manner as in step 4 of Example 81, using 3-thiopheneboronic acid (77 mg, 0.60 mmol).

$^1$H-NMR (δppm, CDCl$_3$): 7.52-7.51 (m, 1H), 7.33-7.26 (m, 2H), 6.98 (s, 1H), 4.00 (dd, J=11.6, 4.1 Hz, 2H), 3.90 (d, J=7.3 Hz, 2H), 3.37 (t, J=11.6 Hz, 2H), 2.12-2.01 (m, 1H), 1.66-1.62 (m, 2H), 1.47 (s, 9H), 1.44-1.35 (m, 2H). Mass (m/e): 305 (M+H)$^+$.

Example 54

4-Benzo[b]thiophen-2-yl-2-tert-butyl-1-(tetrahydropyran-4-ylmethyl)-1H-imidazole (Compound 54)

The title compound 54 (45 mg, 0.13 mmol, yield: 32%) was obtained in the same manner as in step 4 of Example 81, using benzothiophene-2-boronic acid (107 mg, 0.60 mmol).

$^1$H-NMR (δppm, CDCl$_3$): 7.76 (d, J=7.8 Hz, 1H), 7.69 (d, J=7.8 Hz, 1H), 7.49 (s, 1H), 7.32-7.21 (m, 2H), 7.12 (s, 1H), 4.02-3.93 (m, 2H), 3.91 (d, J=7.6 Hz, 2H), 3.38 (t, J=11.6 Hz, 2H), 2.12-2.02 (m, 1H), 1.69-1.62 (m, 2H), 1.48 (s, 9H), 1.44-1.26 (m, 2H). Mass (m/e): 355 (M+H)$^+$.

Example 55

4-Benzo[b]thiophen-3-yl-2-tert-butyl-1-(tetrahydropyran-4-ylmethyl)-1H-imidazole (Compound 55)

The title compound 55 (58 mg, 0.16 mmol, yield: 41%) was obtained in the same manner as in step 4 of Example 81, using 1-benzothiophen-3-ylboronic acid (107 mg, 0.60 mmol).

¹H-NMR (δppm, CDCl₃): 8.31 (d, J=6.5 Hz, 1H), 7.86 (d, J=6.5 Hz, 1H), 7.66 (s, 1H), 7.45-7.32 (m, 2H), 7.17 (s, 1H), 4.04-3.99 (m, 2H), 3.96 (d, J=6.8 Hz, 2H), 3.38 (t, J=10.8 Hz, 2H), 2.16-2.04 (m, 1H), 1.72-1.60 (m, 2H), 1.47 (s, 9H), 1.47-1.27 (m, 2H). Mass (m/e): 355 (M+H)⁺.

Example 56

2-tert-Butyl-4-(2,5-dichlorophenyl)-1-(tetrahydropyran-4-ylmethyl)-1H-imidazole (Compound 56)

Step 1
2-tert-Butyl-4-(2,5-dichlorobenzene)-1H-imidazole (186 mg, 0.69 mmol, yield: 61%) was obtained in the same manner as in step 1 of Example 45, using 2-bromo-1-(2,5-dichlorophenyl)ethanone.
¹H-NMR (δppm, CDCl₃): 8.87 (br, 1H), 8.23 (d, J=2.6 Hz, 1H), 7.66 (d, J=2.0 Hz, 1H), 7.37-7.26 (m, 1H), 7.09 (dd, J=8.6, 2.6 Hz, 1H), 1.43 (s, 9H).
Step 2
The title compound 56 (56 mg, 0.15 mmol, yield: 22%) was obtained in the same manner as in step 3 of Example 45, using 2-tert-butyl-4-(2,5-dichlorobenzene)-1H-imidazole obtained in the above.
¹H-NMR (δppm, CDCl₃): 8.23 (d, J=2.6 Hz, 1H), 7.59 (s, 1H), 7.31-7.25 (m, 1H), 7.07 (dd, J=8.4, 2.6 Hz, 1H), 4.05-3.96 (m, 2H), 3.96 (d, J=7.4 Hz, 2H), 3.44-3.30 (m, 2H), 2.12-2.03 (m, 1H), 1.71-1.63 (m, 2H), 1.47 (s, 9H), 1.47-1.34 (m, 2H). Mass (m/e): 367, 369 (M+H)⁺.

Example 57

2-tert-Butyl-4-(2,3-dichlorophenyl)-1-(tetrahydropyran-4-ylmethyl)-1H-imidazole (Compound 57)

Step 1
2-tert-Butyl-4-(2,3-dichlorobenzene)-1H-imidazole (334 mg, 1.24 mmol, yield: 49%) was obtained in the same manner as in step 1 of Example 45, using 2-bromo-1-(2,3-dichlorophenyl)ethanone.
¹H-NMR (δppm, CDCl₃): 8.98 (br, 1H), 8.12 (dd, J=7.7, 1.5 Hz, 1H), 7.64 (d, J=1.5 Hz, 1H), 7.45-7.22 (m, 2H), 1.43 (s, 9H). Mass (m/e): 269, 271 (M+H)⁺.
Step 2
The title compound 57 (271 mg, 0.74 mmol, yield: 60%) was obtained in the same manner as in step 3 of Example 45, using 2-tert-butyl-4-(2,3-dichlorobenzene)-1H-imidazole obtained in the above.
¹H-NMR (δppm, CDCl₃): 8.15 (dd, J=7.8, 1.9 Hz, 1H), 7.59 (s, 1H), 7.31 (dd, J=7.8, 1.9 Hz, 1H), 7.22 (t, J=7.8 Hz, 1H), 4.05-3.96 (m, 2H), 3.96 (d, J=7.4 Hz, 2H), 3.44-3.32 (m, 2H), 2.16-2.03 (m, 1H), 1.73-1.60 (m, 2H), 1.48 (s, 9H), 1.48-1.34 (m, 2H). Mass (m/e): 367, 369 (M+H)⁺.

Example 58

4-(1-Naphtyl)-2-tert-butyl-1-(tetrahydropyran-4-ylmethyl)-1H-imidazole (Compound 58)

Step 1
4-(1-Naphtyl)-2-tert-butyl-1H-imidazole (670 mg, 2.68 mmol, yield: 92%) was obtained in the same manner as in step 1 of Example 45, using 2-bromo-1-naphtalen-1-ylethanone.
H-NMR (δppm, DMSO-d₆): 11.7 (br, 1H), 8.81-8.78 (m, 1H), 7.92-7.86 (m, 1H), 7.81-7.68 (m, 2H), 7.55-7.44 (m, 3H), 7.35-7.31 (m, 1H), 1.40 (s, 9H). Mass (m/e): 251 (M+H)⁺.

Step 2
The title compound 58 (101 mg, 0.29 mmol, yield: 24%) was obtained in the same manner as in step 3 of Example 45, using 4-(1-naphtyl)-2-tert-butyl-1H-imidazole obtained in step 1 described above.
¹H-NMR (δppm, CDCl₃): 8.67-8.60 (m, 1H), 7.85-7.69 (m, 3H), 7.51-7.43 (m, 3H), 7.11 (s, 1H), 4.07-3.98 (m, 4H), 3.45-3.33 (m, 2H), 2.18-2.06 (m, 1H), 1.76-1.66 (m, 2H), 1.54 (s, 9H), 1.54-1.45 (m, 2H). Mass (m/e): 349 (M+H)⁺.

Example 59

2-tert-Butyl-4-(3,5-dichlorophenyl)-1-(tetrahydropyran-4-ylmethyl)-1H-imidazole (Compound 59)

Step 1
2-tert-Butyl-4-(3,5-dichlorophenyl)-1H-imidazole (187 mg, 0.69 mmol, yield: 88%) was obtained in the same manner as in step 1 of Example 45, using 2-bromo-1-(3,5-dichlorophenyl)ethanone.
¹H-NMR (δppm, CDCl₃): 8.81 (br, 1H), 7.71-7.60 (m, 2H), 7.22-7.14 (m, 2H), 1.42 (s, 9H). Mass (m/e): 269, 271 (M+H)⁺.
Step 2
The title compound 59 (77 mg, 0.21 mmol, yield: 64%) was obtained in the same manner as in step 3 of Example 45, using 2-tert-butyl-4-(3,5-dichlorophenyl)-1H-imidazole obtained in the above.
¹H-NMR (δppm, CDCl₃): 7.62 (d, J=1.6 Hz, 2H), 7.15 (t, J=1.6 Hz, 1H), 7.13 (s, 1H), 4.06-3.96 (m, 2H), 3.93 (d, J=7.4 Hz, 2H), 3.90-3.32 (m, 2H), 2.13-1.99 (m, 1H), 1.69-1.58 (m, 2H), 1.47 (s, 9H), 1.47-1.23 (m, 2H). Mass (m/e): 367, 369 (M+H)⁺.

Example 60

2-tert-Butyl-4-(2,4-dichlorophenyl)-1-(tetrahydropyran-4-ylmethyl)-1H-imidazole (Compound 60)

Step 1
2-tert-Butyl-4-(2,4-dichlorophenyl)-1H-imidazole (289 mg, 1.07 mmol, yield: 61%) was obtained in the same manner as in step 1 of Example 45, using 2-bromo-1-(2,4-dichlorophenyl)ethanone.
H-NMR (δppm, DMSO-d₆): 11.76 (brs 1H), 8.15 (d, J=8.4 Hz, 1H), 7.60 (s, 1H), 7.51 (d, J=2.0 Hz, 1H), 7.39 (dd, J=8.4, 2.0 Hz, 1H), 1.35 (s, 9H). Mass (m/e): 269, 271 (M+H)⁺.
Step 2
The title compound 60 (169 mg, 0.46 mmol, yield: 83%) was obtained in the same manner as in step 3 of Example 45, using 2-tert-butyl-4-(2,4-dichlorophenyl)-1H-imidazole obtained in the above.
¹H-NMR (δppm, CDCl₃): 8.19 (d, J=8.6 Hz, 1H), 7.55 (s, 1H), 7.38 (d, J=2.2 Hz, 1H), 7.28-7.25 (m, 1H), 4.06-3.97 (m, 2H), 3.95 (d, J=7.1 Hz, 2H), 3.44-3.33 (m, 2H), 2.12-2.04 (m, 1H), 1.71-1.60 (m, 2H), 1.47 (s, 9H), 1.47-1.33 (m, 2H). Mass (m/e): 367, 369 (M+H)⁺.

Example 61

2-tert-Butyl-4-(3,4-dichlorophenyl)-1-(tetrahydropyran-4-ylmethyl)-1H-imidazole (Compound 61)

Step 1
2-tert-Butyl-4-(3,4-dichlorophenyl)-1H-imidazole (219 mg, 0.81 mmol, yield: 68%) was obtained in the same manner as in step 1 of Example 45, using 2-bromo-1-(3,4-dichlorophenyl)ethanone.

¹H-NMR (δppm, CDCl₃): 8.82 (br, 1H), 7.89 (s, 1H), 7.60 (d, J=8.2 Hz, 1H), 7.40 (d, J=8.2 Hz, 1H), 7.19 (s, 1H), 1.42 (s, 9H). Mass (m/e): 269, 271 (M+H)⁺.

Step 2

The title compound 61 (82 mg, 0.22 mmol, yield: 54%) was obtained in the same manner as in step 3 of Example 45, using 2-tert-butyl-4-(3,4-dichlorophenyl)-1H-imidazole obtained in the above.

¹H-NMR (δppm, CDCl₃): 7.84 (d, J=2.0 Hz, 1H), 7.56 (dd, J=8.4, 2.0 Hz, 1H), 7.37 (d, J=8.4 Hz, 1H), 7.11 (s, 1H), 4.05-3.97 (m, 2H), 3.92 (d, J=7.4 Hz, 2H), 3.43-3.33 (m, 2H), 2.12-1.99 (m, 1H), 1.68-1.62 (m, 2H), 1.47 (s, 9H), 1.47-1.35 (m, 2H). Mass (m/e): 367, 369 (M+H)⁺.

Example 62

2-tert-Butyl-4-(2,6-dichlorophenyl)-1-(tetrahydropyran-4-ylmethyl)-1H-imidazole (Compound 62)

Step 1

2-tert-Butyl-4-(2,6-dichlorophenyl)-1H-imidazole (200 mg, 0.74 mmol, yield: 40%) was obtained in the same manner as in step 1 of Example 45, using 2-bromo-1-(2,6-dichlorophenyl)ethanone.

¹H-NMR (δppm, CDCl₃): 9.22 (br, 1H), 7.42-7.31 (m, 2H), 7.23-6.91 (m, 2H), 1.43 (s, 9H).

Step 2

The title compound 62 (108 mg, 0.29 mmol, yield: 78%) was obtained in the same manner as in step 3 of Example 45, using 2-tert-butyl-4-(2,6-dichlorophenyl)-1H-imidazole obtained in the above.

¹H-NMR (δppm, CDCl₃): 7.35-7.31 (m, 2H), 7.15-7.09 (m, 1H), 6.88 (s, 1H), 4.06-3.95 (m, 4H), 3.45-3.32 (m, 2H), 2.15-2.00 (m, 1H), 1.71-1.62 (m, 2H), 1.48 (s, 9H), 1.47-1.43 (m, 2H). Mass (m/e): 367, 369 (M+H)⁺.

Example 63

2-tert-Butyl-4-(3-methyl-2-nitrophenyl)-1-(tetrahydropyran-4-ylmethyl)-1H-imidazole (Compound 63)

Step 1

2-Bromo-1-(2-methyl-1-nitrophenyl)ethanone (305 mg, 1.18 mmol, yield: 67%) was obtained in the same manner as in step 2 of Example 33, using 1-(3-methyl-2-nitrophenyl)ethanone.

¹H-NMR (δppm, CDCl₃): 7.62-7.47 (m, 3H), 4.34 (s, 2H), 2.44 (s, 3H).

Step 2

2-tert-Butyl-4-(2-methyl-1-nitrophenyl)-1H-imidazole (154 mg, 0.59 mmol, yield: 63%) was obtained in the same manner as in step 1 of Example 45, using 2-bromo-1-(2-methyl-1-nitrophenyl)ethanone obtained in the above.

¹H-NMR (δppm, CDCl₃): 8.82 (br, 1H), 7.79 (d, J=8.1 Hz, 1H), 7.36 (dd, J=8.1, 7.8 Hz, 1H), 7.15 (d, J=7.8 Hz, 1H), 7.06 (d, J=2.1 Hz, 1H), 2.32 (s, 3H), 1.40 (s, 9H).

Step 3

The title compound 63 (56 mg, 0.16 mmol, yield: 27%) was obtained in the same manner as in step 3 of Example 45, using 2-tert-butyl-4-(2-methyl-1-nitrophenyl)-1H-imidazole obtained in the above.

¹H-NMR (δppm, CDCl₃): 7.78 (d, J=7.9 Hz, 1H), 7.34 (d, J=7.9, 7.6 Hz, 1H), 7.12 (d, J=7.6 Hz, 1H), 6.97 (s, 1H), 4.05-3.95 (m, 2H), 3.90 (d, J=7.3 Hz, 2H), 3.42-3.33 (m, 2H), 2.30 (s, 3H), 2.05-1.95 (m, 1H), 1.66-1.55 (m, 2H), 1.47 (s, 9H), 1.47-1.37 (m, 2H). Mass (m/e): 358 (M+H)⁺.

Example 64

3-(2-tert-Butyl-1-(tetrahydropyran-4-ylmethyl)-1H-imidazol-4-yl)-N,N-diethyl-2-methylbenzamide (Compound 64)

Step 1

3-Bromo-N,N-diethyl-2-methylbenzamide (1.26 g, 4.65 mmol, yield: quantitative) was obtained in the same manner as in Example 2, using 3-bromo-2-methylbenzoic acid.

¹H-NMR (δppm, CDCl₃): 7.53 (dd, J=7.3, 1.7 Hz, 1H), 7.11-7.02 (m, 2H), 3.84-3.27 (m, 2H), 3.10 (brq, 2H), 2.34 (s, 3H), 1.26 (t, J=7.1 Hz, 3H), 1.03 (t, J=7.1 Hz, 3H).

Step 2

3-Acetyl-N,N-diethyl-2-methylbenzamide (238 mg, 1.02 mmol, yield: 91%) was obtained in the same manner as in Example 49, using 3-bromo-N,N-diethyl-2-methylbenzamide obtained in the above.

¹H-NMR (δppm, CDCl₃): 7.63-7.57 (m, 1H), 7.34-7.25 (m, 2H), 3.86-3.72 (m, 1H), 3.45-3.30 (m, 1H), 3.16-3.05 (m, 2H), 2.57 (s, 3H), 2.40 (s, 3H), 1.27 (t, J=7.1 Hz, 3H), 1.03 (t, J=7.1 Hz, 3H). Mass (m/e): 234 (M+H)⁺.

Step 3

3-(2-Bromoacetyl)-N,N-diethyl-2-methylbenzamide (253 mg, 0.81 mmol, yield: 96%) was obtained in the same manner as in step 2 of Example 33, using 3-acetyl-N,N-diethyl-2-methylbenzamide obtained in the above.

¹H-NMR (δppm, CDCl₃): 7.64-7.55 (m, 1H), 7.36-7.25 (m, 2H), 4.40-4.35 (m, 2H), 3.83-3.35 (m, 2H), 3.16-3.06 (m, 2H), 2.39 (s, J=3.0 Hz, 3H), 1.27 (t, J=7.1 Hz, 3H), 1.04 (t, J=7.2 Hz, 3H). Mass (m/e): 312, 314 (M+H)⁺.

Step 4

3-(2-tert-Butyl-1H-imidazol-4-yl)-N,N-diethyl-2-methylbenzamide (176 mg, 0.56 mmol, yield: 69%) was obtained in the same manner as in step 1 of Example 45, using 3-(2-bromoacetyl)-N,N-diethyl-2-methylbenzamide obtained in the above.

¹H-NMR (δppm, CDCl₃): 7.76-7.70 (m, 1H), 7.12-7.00 (m, 2H), 6.94-6.87 (m, 1H), 3.90-3.36 (m, 2H), 3.16 (m, 2H), 2.33 (s, 3H), 1.42 (s, 9H), 1.30-0.95 (m, 6H). Mass (m/e): 314 (M+H)⁺.

Step 5

The title compound 64 (158 mg, 0.38 mmol, yield: 69%) was obtained in the same manner as in step 3 of Example 45, using 3-(2-tert-butyl-1H-imidazol-4-yl)-N,N-diethyl-2-methylbenzamide obtained in the above.

¹H-NMR (δppm, CDCl₃): 7.80 (d, J=7.6 Hz, 1H), 7.26-7.19 (m, 1H), 7.04 (d, J=7.4 Hz, 1H), 6.91 (s, 1H), 4.05-3.97 (m, 2H), 3.95 (d, J=7.4 Hz, 2H), 3.86-3.70 (m, 1H), 3.47-3.30 (m, 3H), 3.14 (q, J=7.1 Hz, 2H), 2.37 (s, 3H), 2.15-1.98 (m, 1H), 1.73-1.59 (m, 2H), 1.47 (s, 9H), 1.47-1.34 (m, 2H), 1.27 (t, J=7.1 Hz, 3H), 1.00 (t, J=7.1 Hz, 3H). Mass (m/e): 412 (M+H)⁺.

Example 65

2-Chloro-5-(2-tert-butyl-1-(tetrahydropyran-4-ylmethyl)-1H-imidazol-4-yl)-N,N-diethylbenzamide (Compound 65)

The title compound 65 [140 mg, 3.24 mmol, yield: 25% (5 steps)] was obtained in the same manner as in Example 64, using 2-chloro-5-bromobenzoic acid.

¹H-NMR (δppm, CDCl₃): 7.77-7.70 (m, 1H), 7.60-7.57 (m, 1H), 7.36-7.30 (m, 1H), 7.09 (s, 1H), 4.05-3.95 (m, 2H), 3.92 (d, J=7.1 Hz, 2H), 3.85-3.67 (br, 2H), 3.43-3.30 (m, 2H), 3.19 (q, J=7.1 Hz, 2H), 214-2.00 (m, 1H), 1.71-1.58 (m, 2H), 1.49 (s, 9H), 1.46-1.36 (m, 2H), 1.28 (t, J=7.1 Hz, 3H), 1.06 (t, J=7.1 Hz, 3H). Mass (m/e): 432, 434 (M+H)⁺.

Example 66

5-(2-tert-Butyl-1-(tetrahydropyran-4-ylmethyl)-1H-imidazol-4-yl)-N,N-diethyl-2-fluorobenzamide hydrochloride (Compound 66)

A free base of Compound 66 (225 mg, 0.54 mmol, yield: 28% (5 steps)) was obtained in the same manner as in Example 64 using 5-bromo-2-fluorobenzoic acid. The obtained free base was treated with 4 mol/L hydrogen chloride-ethyl acetate to give the title compound 66.

¹H-NMR (δppm, CDCl₃): 7.82-7.75 (m, 1H), 7.63 (dd, J=6.4, 2.1 Hz, 1H), 7.05 (s, 1H), 7.08-7.00 (m, 1H), 4.05-3.96 (m, 2H), 3.92 (d, J=7.3 Hz, 2H), 3.58 (q, J=7.1 Hz, 2H), 3.43-3.31 (m, 2H), 3.25 (q, J=7.1 Hz, 2H), 2.14-1.98 (m, 1H), 1.70-1.57 (m, 2H), 1.46 (s, 9H), 1.47-1.34 (m, 2H), 1.29 (t, J=7.1 Hz, 3H), 1.08 (t, J=7.1 Hz, 3H). Mass (m/e): 416 (M+H)⁺. (as the free base)

Example 67

3-Bromo-5-(2-tert-butyl-1-(tetrahydropyran-4-ylmethyl)-1H-imidazol-4-yl)-N,N-diethylbenzamide (Compound 67)

The title compound 67 [36 mg, 0.076 mmol, yield: 5% (5 steps)] was obtained in the same manner as in Example 64, using 3,5-dibromobenzoic acid.

¹H-NMR (δppm, CDCl₃): 7.98-7.95 (m, 1H), 7.66-7.64 (m, 1H), 7.32-7.29 (m, 1H), 7.14 (s, 1H), 4.06-3.98 (m, 2H), 3.93 (d, J=7.4 Hz, 2H), 3.53 (br, 2H), 3.45-3.33 (m, 2H), 3.29 (br, 2H), 2.14-1.97 (m, 1H), 1.70-1.57 (m, 2H), 1.47 (s, 9H), 1.47-1.35 (m, 2H), 1.31-1.06 (m, 6H). Mass (m/e): 476, 478 (M+H)⁺.

Example 68

3-(2-tert-Butyl-1-(tetrahydropyran-4-ylmethyl)-1H-imidazol-4-yl)-pyridine (Compound 68)

The title compound 68 (76 mg, 0.26 mmol, yield: 9%) was obtained in the same manner as in Example 1, using 3-(bromoacetyl)pyridine monohydrobromate and 4-aminomethyltetrahydropyran.

¹H-NMR (δppm, CDCl₃): 8.92 (dd, J=1.9, 0.7 Hz, 1H), 8.43 (dd, J=4.8, 1.9 Hz, 1H), 8.10 (td, J=8.0, 1.9 Hz, 1H), 7.26 (ddd, J=8.0, 4.8, 0.7 Hz, 1H), 7.19 (s, 1H), 4.01 (dd, J=11.8, 3.8 Hz, 2H), 3.95 (d, J=7.3 Hz, 2H), 3.40 (td, J=11.8, 2.0 Hz, 2H), 2.15-2.05 (m, 1H), 1.66 (brd, J=10.1 Hz, 2H), 1.48 (s, 9H), 1.51-1.41 (m, 2H). Mass (m/e): 300 (M+H)⁺.

Example 69

2-tert-Butyl-4-(3-methoxyphenyl)-1-(tetrahydropyran-4-ylmethyl)-1H-imidazole (Compound 69)

The title compound 69 (290 mg, 0.88 mmol, yield: 14%) was obtained in the same manner as in Example 1, using 2-bromo-3'-methoxyacetophenone and 4-aminomethyltetrahydropyran.

¹H-NMR (δppm, CDCl₃): 7.37-7.34 (m, 1H), 7.30 (t, J=1.3 Hz, 1H), 7.24 (t, J=7.9 Hz, 1H), 7.10 (s, 1H), 6.75 (ddd, J=7.9, 2.3, 1.3 Hz, 1H), 4.01 (dd, J=11.4, 4.0 Hz, 2H), 3.93 (d, J=7.4 Hz, 2H), 3.85 (s, 3H), 3.37 (td, J=11.4, 1.9 Hz, 2H), 2.12-2.01 (m, 1H), 1.70-1.61 (m, 2H), 1.48 (s, 9H), 1.42 (dd, J=13.0, 4.5 Hz, 2H). Mass (m/e): 329 (M+H)⁺.

Example 70

2-tert-Butyl-4-(3-nitrophenyl)-1-(tetrahydropyran-4-ylmethyl)-1H-imidazole (Compound 70)

The title compound 70 (918 mg, 2.69 mmol, yield: 27%) was obtained in the same manner as in Example 45, using 2-bromo-3'-nitroacetophenone.

¹H-NMR (δppm, CDCl₃): 8.54 (t, J=2.0 Hz, 1H), 8.12 (td, J=7.9, 2.0 Hz, 1H), 8.02 (dt, J=7.9, 2.0 Hz, 1H), 7.49 (t, J=7.9 Hz, 1H), 7.24 (s, 1H), 4.03 (dd, J=11.4, 4.0 Hz, 2H), 3.96 (d, J=7.4 Hz, 2H), 3.40 (dt, J=11.4, 1.9 Hz, 2H), 2.17-2.03 (m, 1H), 1.67 (brd, J=12.7 Hz, 2H), 1.49 (s, 9H), 1.52-1.42 (m, 2H). Mass (m/e): 344 (M+H)⁺.

Example 71

3-(2-tert-Butyl-1-(tetrahydropyran-4-ylmethyl)-1H-imidazol-4-yl)-N-methyl-N-phenylbenzamide (Compound 71)

The title compound 71 (30 mg, 0.07 mmol, yield: 50%) was obtained in the same manner as in Example 72, using N-methylaniline.

¹H-NMR (δppm, CDCl₃): 7.75-7.73 (m, 2H), 7.23-6.96 (m, 8H), 4.01 (brd, J=8.5 Hz, 2H), 3.90 (d, J=7.3 Hz, 2H), 3.51 (s, 3H), 3.38 (t, J=11.7 Hz, 2H), 2.07-1.99 (m, 1H), 1.67-1.59 (m, 2H), 1.45 (s, 9H), 1.47-1.40 (m, 2H). Mass (m/e): 432 (M+H)⁺.

Example 72

3-(2-tert-Butyl-1-(tetrahydropyran-4-ylmethyl)-1H-imidazol-4-yl)-N-ethylbenzamide (Compound 72)

Compound m (102 mg, 0.3 mmol) obtained in Reference example 13 was dissolved in DMF (1.0 mL), and ethylamine (36 μL, 0.45 mmol), WSC.HCl (86 mg, 0.45 mmol), and HOBt.H₂O (69 mg, 0.45 mmol) were added thereto, and then, the mixture was stirred at 60° for 2 hours. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50 to 10/90) to give the title compound 72 (67 mg, 0.18 mmol, yield: 60%).

¹H-NMR (δppm, CDCl₃): 8.13 (s, 1H), 7.88 (d, J=6.7 Hz, 1H), 7.60 (t, J=7.7 Hz, 1H), 7.38 (t, J=7.7 Hz, 1H), 7.19 (s, 1H), 6.39 (brs, 1H), 3.86 (d, J=7.3 Hz, 2H), 3.50 (q, J=7.3 Hz, 2H), 1.84-1.63 (m, 6H), 1.47 (s, 9H), 1.27-1.20 (m, 6H), 1.06-0.96 (m, 2H). Mass (m/e): 368 (M+H)⁺.

Example 73

N-{3-[2-tert-Butyl-1-(tetrahydropyran-4-ylmethyl)-1H-imidazol-4-yl]phenyl}-N-methylamine (Compound 73)

Under a nitrogen atmosphere, Compound 87 (201 mg, 0.58 mmol) obtained in Example 87 was dissolved in dichloromethane (3 mL), and diisopropylethylamine (0.14 mL, 0.79 mmol) and methyl chloroformate (0.05 mL, 0.67 mmol) were added thereto at 0° C., and then, the mixture was stirred overnight at room temperature. To the mixture, a saturated aqueous ammonium chloride solution was added, and the mixture was extracted with chloroform. The organic layer was washed with saturated brine and dried over anhydrous magnesium sulfate, and the solvent was evaporated under reduced pressure. Under a nitrogen atmosphere, THF (3 mL) was cooled to 0° C., and lithium aluminum hydride (55 mg, 1.45 mmol), and the obtained residue (242 mg) were added thereto, and then, the mixture was stirred overnight at room temperature. The mixture was cooled to 0° C., and water (0.6 mL), a 2 mol/L aqueous sodium hydroxide solution (0.6 mL), and water (1.8 mL) were added thereto in this order, and then, the mixture was stirred for 2 hours. After the mixture was filtered through Celite, the filtrate was concentrated. The residue was purified by silica gel column chromatography (hexane/ethyl acetate=99/1 to 1/99) to give the title compound 73 (131 mg, 0.40 mmol, yield: 69%).

Example 74

N-{3-[2-tert-Butyl-1-(tetrahydropyran-4-ylmethyl)-1H-imidazol-4-yl]phenyl}-3,N-dimethyl-butylamide (Compound 74)

Under a nitrogen atmosphere, Compound 73 (42 mg, 0.13 mmol) obtained in Example 73 was dissolved in dichloroethane (1 mL), and triethylamine (0.09 mL, 0.65 mmol) and isovaleryl chloride (0.05 mL, 0.39 mmol) were added thereto, and then, the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=99/1 to 1/99) to give the title compound 74 (35 mg, 0.09 mmol, yield: 66%).
$^1$H-NMR (δppm, CDCl$_3$): 7.71 (d, J=7.9 Hz, 1H), 7.56 (brs, 1H), 7.37 (t, J=7.8 Hz, 1H), 7.14 (s, 1H), 6.96 (brd, J=8.2 Hz, 1H), 4.02 (dd, J=11.6, 3.7 Hz, 2H), 3.95 (d, J=7.5 Hz, 2H), 3.39 (t, J=11.9 Hz, 2H), 3.28 (s, 3H), 2.18-2.10 (m, 1H), 2.01 (d, J=6.9 Hz, 2H), 1.67 (brd, J=12.8 Hz, 3H), 1.48 (s, 9H), 1.42 (dd, J=12.5, 4.6, 2H), 0.84 (d, J=6.6 Hz, 6H). Mass (m/e): 412 (M+H)$^+$.

Example 75

N-{3-[2-tert-Butyl-1-(tetrahydropyran-4-ylmethyl)-1H-imidazol-4-yl]phenyl}-N,N',N'-trimethylsulfamide (Compound 75)

Under a nitrogen atmosphere, Compound 73 (42 mg, 0.13 mmol) obtained in Example 73 was dissolved in acetonitrile (1 mL), and triethylamine (0.04 mL, 0.26 mmol) and dimethylsulfamoyl chloride (0.02 mL, 0.17 mmol) were added thereto, and then, the mixture was stirred overnight at room temperature. To the mixture, triethylamine (0.04 mL, 0.26 mmol) and dimethylsulfamoyl chloride (0.02 mL, 0.17 mmol) were further added, and the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=99/1 to 1/99) to give the title compound 75 (28 mg, 0.06 mmol, yield: 50%).
$^1$H-NMR (δppm, CDCl$_3$): 7.78 (s, 1H), 7.68 (d, J=7.7 Hz, 1H), 7.34 (t, J=7.4 Hz, 1H), 7.25-7.22 (m, 1H), 7.14 (s, 1H), 4.02 (dd, J=11.6, 3.7 Hz, 2H), 3.94 (d, J=7.5 Hz, 2H), 3.42 (dt, J=11.8, 1.7 Hz, 2H), 3.29 (s, 3H), 2.17 (s, 6H), 2.09-2.02 (m, 1H), 1.66 (brd, J=12.2 Hz, 2H), 1.48 (s, 9H), 1.47-1.38 (m, 2H). Mass (m/e): 435 (M+H)$^+$.

Example 76

3-(2-tert-Butyl-1-(tetrahydropyran-4-ylmethyl)-1H-imidazol-4-yl)-N,N-diethylbenzamide hydrochloride (Compound 76)

A free base of Compound 76 (530 mg, 1.34 mmol, yield: 86%) was obtained in the same manner as in Example 72, using diethylamine. The obtained free base was treated with 4 mol/L hydrogen chloride-ethyl acetate to give the title compound 76.
$^1$H-NMR (δppm, CDCl$_3$): 7.83 (dt, J=7.7, 1.5 Hz, 1H), 7.73 (t, J=1.5 Hz, 1H), 7.36 (t, J=7.7 Hz, 1H), 7.18 (dt, J=7.7, 1.5 Hz, 1H), 7.14 (s, 1H), 4.01 (dd, J=11.4, 4.0 Hz, 2H), 3.93 (d, J=7.3 Hz, 2H), 3.59-3.51 (m, 2H), 3.38 (td, J=11.4, 1.8 Hz, 2H), 3.32-3.25 (m, 2H), 2.11-2.02 (m, 1H), 1.68-1.61 (m, 2H), 1.48 (s, 9H), 1.47-1.36 (m, 2H), 1.25-1.13 (m, 6H). Mass (m/e): 398 (M+H)$^+$. (as the free base)

Example 77

{3-[2-tert-Butyl-1-(tetrahydropyran-4-ylmethyl)-1H-imidazol-4-yl]phenyl}-diethylamine (Compound 77)

Under an argon atmosphere, Compound 87 (115 mg, 0.37 mmol) obtained in Example 87 was dissolved in DMSO (1.5 mL), and ethyl bromide (83 μL, 1.11 mmol) and potassium carbonate (102 mg, 0.74 mmol) were added thereto, and then, the mixture was stirred overnight at 50° C. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=65/35) to give the title compound 77 (53 mg, 0.14 mmol, yield: 39%).
$^1$H-NMR (δppm, CDCl$_3$): 7.17 (t, J=7.9 Hz, 2H), 7.06 (brs, 1H), 7.00 (d, J=7.9 Hz, 1H), 6.57 (dd, J=7.9, 2.5 Hz, 1H), 4.01 (dd, J=11.2, 3.7 Hz, 2H), 3.91 (d, J=7.5 Hz, 2H), 3.42-3.33 (m, 6H), 2.09-2.03 (m, 1H), 1.68-1.62 (m, 2H), 1.47 (s, 9H), 1.44 (dt, J=12.9, 4.5 Hz, 2H), 1.16 (t, J=7.5 Hz, 6H). Mass (m/e): 370 (M+H)$^+$.

Example 78

{3-[2-tert-Butyl-1-(tetrahydropyran-4-ylmethyl)-1H-imidazol-4-yl]phenyl}ethylamine (Compound 78)

In the purification by silica gel column chromatography in Example 77, the title compound 78 (29 mg, 0.09 mmol, yield: 23%) was obtained from another fraction.
$^1$H-NMR (δppm, CDCl$_3$): 7.22-7.03 (m, 4H), 6.49-6.46 (m, 1H), 4.00 (dd, J=11.8, 3.6 Hz, 2H), 3.92 (d, J=7.5 Hz, 2H), 3.38 (dt, J=11.8, 2.0 Hz, 2H), 3.20 (q, J=7.1 Hz, 2H), 2.17-2.02 (m, 1H), 1.67-1.59 (m, 2H), 1.47 (s, 9H), 1.48-1.43 (m, 2H), 1.26 (t, J=7.1 Hz, 3H). Mass (m/e): 342 (M+H)$^+$.

Example 79

N-{3-[2-tert-Butyl-1-(tetrahydropyran-4-ylmethyl)-1H-imidazol-4-yl]phenyl}-N-methylbenzenesulfonamide (Compound 79)

The title compound 79 (29 mg, 0.06 mmol, yield: 52%) was obtained in the same manner as in Example 75, using benzenesulfonyl chloride instead of dimethylsulfamoyl chloride.

$^1$H-NMR (δppm, CDCl$_3$): 7.72 (td, J=7.9, 1.1 Hz, 1H), 7.62-7.51 (m, 4H), 7.47-7.41 (m, 2H), 7.23 (t, J=7.9 Hz, 1H), 7.08 (s, 1H), 6.78 (ddd, J=7.9, 2.2, 1.1 Hz, 1H), 4.02 (dd, J=11.8, 3.8 Hz, 2H), 3.92 (d, J=7.4 Hz, 2H), 3.39 (dt, J=11.8, 1.7 Hz, 2H), 3.20 (s, 3H), 2.10-2.03 (m, 1H), 1.74-1.63 (m, 2H), 1.46 (s, 9H), 1.44 (dt, J=13.0, 4.3 Hz, 2H). Mass (m/e): 468 (M+H)$^+$.

Example 80

N-[4-(N-{3-[2-tert-Butyl-1-(tetrahydropyran-4-ylmethyl)-1H-imidazol-4-yl]phenyl}-N-methylsulfamoyl)phenyl]acetamide (Compound 80)

The title compound 80 (18 mg, 0.03 mmol, yield: 26%) was obtained in the same manner as in Example 75, using 4-acetaminobenzenesulfonyl chloride instead of dimethylsulfamoyl chloride.

$^1$H-NMR (δppm, CDCl$_3$): 7.71 (d, J=7.7 Hz, 1H), 7.61-7.52 (m, 4H), 7.34 (brs, 1H), 7.23 (t, J=7.7 Hz, 1H), 7.10 (s, 1H), 6.79-6.74 (m, 1H), 4.01 (dd, J=11.9, 2.8 Hz, 2H), 3.92 (d, J=7.6 Hz, 2H), 3.39 (dt, J=11.9, 2.0 Hz, 2H), 3.19 (s, 3H), 2.21 (s, 3H), 2.12-2.04 (m, 1H), 1.68-1.63 (m, 2H), 1.46 (s, 9H), 1.48-1.44 (m, 2H). Mass (m/e): 525 (M+H)$^+$.

Example 81

2-tert-Butyl-4-(5-methylfuran-2-yl)-1-(tetrahydrofuran-4-ylmethyl)-1H-imidazole (Compound 81)

Step 1

Trimethylacetonitrile (18.3 g, 0.22 mol) was dissolved in ethanol (12.8 mL, 0.22 mol), and hydrochloric acid gas was blown into the mixture at −20° C. until the mixture was saturated with hydrochloric acid gas, and then, the mixture was stirred overnight at room temperature. The mixture was concentrated, and the obtained crude crystals were washed with isopropyl ether to give ethyl-tert-butyl-imidate (16.24 g, 98 mmol, yield: 45%). The thus obtained ethyl-tert-butyl imidate (16.24 g, 98 mmol) was dissolved in methanol (17.5 mL), and aminoacetaldehyde=dimethyl acetal (11.7 mL, 0.11 mol) was added thereto, and then, the mixture was stirred overnight at room temperature. The mixture was concentrated, and to the residue, concentrated hydrochloric acid (26.2 mL) and water (17.5 mL) were added. The solvent was evaporated under reduced pressure, and the residue was dissolved in water (9 mL), and the pH of the mixture was adjusted to 10 with potassium carbonate, and then, the solvent was evaporated under reduced pressure. The residue was dissolved in ethanol (175 mL), and the solvent was evaporated under reduced pressure. The obtained residue was washed with diisopropyl ether to give 2-tert-butyl-1H-imidazole (9.7 g, 78.2 mmol, yield: 36%).

Step 2

2-tert-Butyl-1H-imidazole (1.0 g, 8.06 mmol) obtained in the above was dissolved in 1,4-dioxane-water (1/1) (38 mL), and sodium carbonate (2.56 g, 24.2 mmol) and iodine (4.5 g, 17.7 mmol) were added thereto, and then, the mixture was stirred overnight at room temperature under shading. To the mixture, acetic acid (70 mL) was added, and the mixture was washed with a saturated aqueous sodium thiosulfate solution with stirring. Thereafter, the mixture was extracted with ethyl acetate, and the organic layer was washed with saturated brine and dried over anhydrous magnesium sulfate, and then, the solvent was evaporated under reduced pressure. The obtained residue was washed with diisopropyl ether to give 4,5-diiodo-2-tert-butylimidazole (2.87 g, 7.65 mmol, yield: 95%).

Step 3

4,5-Diiodo-2-tert-butylimidazole (1.0 g, 2.66 mmol) obtained in the above was dissolved in a 30% aqueous ethanol solution (44 mL), and sodium thiosulfate (2.68 g, 21.3 mmol) was added thereto, and then, the mixture was refluxed for 2 days. The mixture was left to cool to room temperature, and then concentrated. The residue was washed with water to give 4-iodo-2-tert-butylimidazole (532 mg, 2.13 mmol, yield: 80%).

Step 4

4-Iodo-2-tert-butylimidazole (337 mg, 1.35 mmol) obtained in the above was dissolved in 1,4-dioxane-water (2/1) (6 mL), and 5-methylfuran-2-boronic acid (255 mg, 2.02 mmol), sodium carbonate (429 mg, 4.05 mmol), and [1,1'-bis(diphenylphosphino)-ferrocene]dichloropalladium (II) (55 mg, 0.07 mmol) were added thereto, and then, the mixture was stirred at 100° C. for 3.5 hours. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was dissolved in DMF (5 mL) under an argon atmosphere, and sodium hydride (139 mg, 3.47 mmol) was added thereto under ice-cooling, and then, the mixture was stirred at 60° C. for 30 minutes. (Tetrahydropyran-4-yl)methylmethanesulfonate (270 mg, 1.39 mmol) obtained in Step 2 of Example 45 was added thereto, and the mixture was stirred overnight at 60° C. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=95/5 to 50/50) to give the title compound 81 (153 mg, 0.51 mmol, yield: 38%).

$^1$H-NMR (δppm, CDCl$_3$): 7.01 (s, 1H), 6.43 (d, J=3.1 Hz, 1H), 5.98-5.96 (m, 1H), 4.00 (dd, J=11.9, 3.8 Hz, 2H), 3.91 (d, J=7.4 Hz, 2H), 3.37 (dt, J=11.9, 2.0 Hz, 2H), 2.32 (s, 3H), 2.09-2.01 (m, 1H), 1.65-1.62 (m, 2H), 1.46 (s, 9H), 1.46-1.37 (m, 2H). Mass (m/e): 303 (M+H)$^+$.

Example 82

3-(2-tert-Butyl-1-(tetrahydropyran-4-ylmethyl)-1H-imidazol-4-yl)-N,N-bis(2,2,2-trifluoroethyl)benzamide (Compound 82)

Under an argon atmosphere, Compound m (118 mg, 0.35 mmol) obtained in Reference example 13 was dissolved in a thionylchloride/dichloromethane (1/2) solution (3.9 mL), and the mixture was refluxed for 6 hours. After the mixture was left to cool to room temperature, the mixture was concentrated. The residue was dissolved in dichloromethane (1.3 mL), and a solution of N,N-bis(2,2,2-trifluoroethyl)amine (0.11 mL, 0.69 mmol) in dichloromethane (1.3 mL) was slowly added dropwise thereto under ice-cooling. After the dropwise addition was completed, the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (ethyl acetate) to give the title compound 82 (2.5 mg, 0.005 mmol, yield: 1%).

$^1$H-NMR (δppm, CDCl$_3$): 7.92 (td, J=7.9, 1.4 Hz, 1H), 7.72 (t, J=1.4 Hz, 1H), 7.43 (t, J=7.9 Hz, 1H), 7.20 (td, J=7.9, 1.4 Hz, 1H), 7.15 (s, 1H), 4.32-4.18 (m, 4H), 4.02 (dd, J=11.4, 3.5 Hz, 2H), 3.94 (d, J=7.6 Hz, 2H), 3.38 (dt, J=11.4, 2.0 Hz, 2H), 2.12-2.04 (m, 1H), 1.66 (brd, J=12.3 Hz, 2H), 1.49 (s, 9H), 1.48-1.40 (m, 2H). Mass (m/e): 506 (M+H)$^+$.

Example 83

3-(2-tert-Butyl-1-(tetrahydropyran-4-ylmethyl)-1H-imidazol-4-yl)-N-ethyl-N-methylbenzamide hydrochloride (Compound 83)

A free base of Compound 83 (83 mg, 0.22 mmol, yield: 76%) was obtained in the same manner as in Example 72, using N-ethylmethylamine instead of ethylamine. The obtained free base was treated with 4 mol/L hydrogen chloride-ethyl acetate to give the title compound 83.

$^1$H-NMR (δppm, CDCl$_3$): 7.83 (d, J=7.6 Hz, 1H), 7.75 (s, 1H), 7.35 (t, J=7.6 Hz, 1H), 7.19 (d, J=7.6 Hz, 1H), 7.13 (s, 1H), 4.01 (dd, J=11.6, 3.7 Hz, 2H), 3.93 (d, J=7.2 Hz, 2H), 3.60-3.53 (m, 1H), 3.37 (dt, J=11.6, 1.3 Hz, 2H), 3.39-3.26 (m, 1H), 3.07-2.94 (m, 3H), 2.09-2.02 (m, 1H), 1.65 (brd, J=12.5 Hz, 2H), 1.47 (s, 9H), 1.44 (dt, J=12.5, 4.3 Hz, 2H), 1.26-1.12 (m, 3H). Mass (m/e): 384 (M+H)$^+$. (as the free base)

Example 84

3-Bromo-5-[2-tert-Butyl-1-(tetrahydropyran-4-ylmethyl)-1H-imidazol-4-yl]pyridine (Compound 84)

The title compound 84 (89 mg, 0.24 mmol, yield: 24%) was obtained in the same manner as in step 4 of Example 81, using 3-bromopyridine-5-boronic acid instead of 5-methyl-furan-2-boronic acid.

$^1$H-NMR (δppm, CDCl$_3$): 8.81 (d, J=2.0 Hz, 1H), 8.47 (d, J=2.0 Hz, 1H), 8.25 (d, J=2.0 Hz, 1H), 7.20 (s, 1H), 4.02 (dd, J=11.4, 3.2 Hz, 2H), 3.95 (d, J=7.4 Hz, 2H), 3.39 (td, J=11.8, 1.9 Hz, 2H), 2.12-2.02 (m, 1H), 1.65 (brd, J=10.7 Hz, 2H), 1.48 (s, 9H), 1.42 (dt, J=11.8, 3.8 Hz, 2H). Mass (m/e): 378, 380 (M+H)$^+$.

Example 85

5-(2-tert-Butyl-1-(tetrahydropyran-4-ylmethyl)-1H-imidazol-4-yl)-N,N-diethylnicotinamide (Compound 85)

Step 1

Compound n (110 mg, 0.29 mmol) obtained in Reference example 14 was dissolved in a 70% aqueous ethanol solution (1.0 mL), and lithium hydroxide monohydrate (14 mg, 0.34 mmol) was added thereto, and then, the mixture was refluxed for 1 hour. The mixture was left to cool to room temperature, and then concentrated. To the residue, 1 mol/L hydrochloric acid was added, and the pH of the mixture was adjusted to 7. The mixture was extracted with chloroform/isopropyl alcohol (6/1), and the organic layer was dried over anhydrous magnesium sulfate, and the solvent was evaporated under reduced pressure. The residue was washed with acetone/hexane (1/3) to give 5-(2-tert-butyl-1-(tetrahydropyran-4-ylmethyl)-1H-imidazol-4-yl)nicotinic acid (95 mg, 0.277 mmol, yield: 97%).

Step 2

The title compound 85 (53 mg, 0.13 mmol, yield: 48%) was obtained in the same manner as in Example 72, using 5-(2-tert-butyl-1-(tetrahydropyran-4-ylmethyl)-1H-imidazol-4-yl)nicotinic acid obtained in the above.

$^1$H-NMR (δppm, CDCl$_3$): 8.98 (brs, 1H), 8.45 (brs, 1H), 8.11 (br, 1H), 7.21 (s, 1H), 4.02 (dd, J=11.5, 2.9 Hz, 2H), 3.95 (d, J=7.4 Hz, 2H), 3.63-3.52 (m, 2H), 3.39 (t, J=10.7 Hz, 2H), 3.37-3.26 (m, 2H), 2.13-2.03 (m, 1H), 1.68-1.63 (m, 2H), 1.48 (s, 9H), 1.42-1.36 (m, 2H), 1.18-1.12 (m, 6H). Mass (m/e): 399 (M+H)$^+$.

Example 86

{3-[2-tert-Butyl-1-(tetrahydropyran-4-ylmethyl)-1H-imidazol-4-yl]phenyl}-piperidin-1-ylmethanone (Compound 86)

The title compound 86 (41 mg, 0.10 mmol, yield: 73%) was obtained in the same manner as in Example 72, using piperidine instead of ethylamine.

$^1$H-NMR (δppm, CDCl$_3$): 7.82 (dt, J=7.9, 1.3 Hz, 1H), 7.76 (d, J=1.3 Hz, 1H), 7.36 (t, J=7.9 Hz, 1H), 7.18 (dt, J=7.9, 1.3 Hz, 1H), 7.14 (s, 1H), 4.01 (dd, J=11.4, 3.6 Hz, 2H), 3.93 (d, J=7.4 Hz, 2H), 3.72 (brs, 2H), 3.38 (td, J=10.9, 1.8 Hz, 4H), 2.12-2.02 (m, 1H), 1.74-1.63 (m, 8H), 1.47 (s, 9H), 1.43-1.36 (m, 2H). Mass (m/e): 410 (M+H)$^+$.

Example 87

3-[2-tert-Butyl-1-(tetrahydropyran-4-ylmethyl)-1H-imidazol-4-yl]phenylamine (Compound 87)

Compound 70 (198 mg, 0.58 mmol) obtained in Example 70 was dissolved in methanol/THF (2/1) (3 mL), and palladium/carbon (20 mg, 10 wt %) was added thereto, and then, the mixture was stirred at room temperature for 2.5 hours under a hydrogen atmosphere. The mixture was filtered through Celite, and the filtrate was concentrated to give the title compound 87 (201 mg, 0.64 mmol, yield: quantitative).

$^1$H-NMR (δppm, CDCl$_3$): 7.19-7.17 (m, 1H), 7.15-7.09 (m, 2H), 7.07 (s, 1H), 6.53 (dt, J=6.4, 2.5 Hz, 1H), 4.00 (dd, J=11.2, 3.9 Hz, 2H), 3.91 (d, J=7.4 Hz, 2H), 3.37 (td, J=11.8, 2.0 Hz, 2H), 2.09-2.00 (m, 1H), 1.68-1.62 (m, 2H), 1.47 (s, 9H), 1.45-1.38 (m, 2H). Mass (m/e): 314 (M+H)$^+$.

Example 88

N-{3-[2-tert-Butyl-1-(tetrahydropyran-4-ylmethyl)-1H-imidazol-4-yl]phenyl}-N-methyl-methanesulfonamide (Compound 88)

The title compound 88 (22 mg, 0.04 mmol, yield: 14%) was obtained in the same manner as in Example 75, using methanesulfonyl chloride instead of dimethylsulfamoyl chloride.

$^1$H-NMR (δppm, CDCl$_3$): 7.76 (s, 1H), 7.67 (d, J=7.9 Hz, 1H), 7.35 (t, J=7.9 Hz, 1H), 7.22 (d, J=7.9 Hz, 1H), 7.15 (s, 1H), 4.02 (dd, J=11.5, 3.9 Hz, 2H), 3.94 (d, J=7.5 Hz, 2H), 3.39 (t, J=11.5 Hz, 2H), 3.36 (s, 3H), 2.87 (s, 3H), 2.10-2.05 (m, 1H), 1.69-1.62 (m, 2H), 1.48 (s, 9H), 1.43-1.38 (m, 2H). Mass (m/e): 406 (M+H)$^+$.

Example 89

3-(2-tert-Butyl-1-(tetrahydropyran-4-ylmethyl)-1H-imidazol-4-yl)-N,N-diethylacrylamide (Compound 89)

The title compound 89 (60 mg, 0.17 mmol, yield: 84%) was obtained in the same manner as in Example 72, using Compound t obtained in Reference example 20.
$^1$H-NMR (δppm, CDCl$_3$): 7.51 (d, J=14.9 Hz, 1H), 6.97 (d, J=14.9 Hz, 1H), 6.95 (s, 1H), 4.02-3.95 (m, 2H), 3.89 (d, J=7.3 Hz, 2H), 3.48 (q, J=7.2 Hz, 4H), 3.42-3.30 (m, 2H), 2.10-1.94 (m, 1H), 1.66-1.51 (m, 2H), 1.45 (s, 9H), 1.45-1.33 (m, 2H), 1.25-1.09 (m, 6H). Mass (m/e): 348 (M+H)$^+$.

Example 90

3-(2-tert-Butyl-1-(tetrahydropyran-4-ylmethyl)-1H-imidazol-4-yl)-N,N-bis(2,2,2-trifluoroethyl)acrylamide (Compound 90)

Compound t (50 mg, 0.17 mmol) obtained in Reference example 20 was dissolved in thionyl chloride (1.0 mL), and the mixture was stirred under reflux for 1 hour. Thionyl chloride was evaporated under reduced pressure, and the residue was dissolved in dichloromethane (2 mL). Then, diisopropylethylamine (45 μL, 0.26 mmol) and bis(2,2,2-trifluoro)ethylamine (56 μL, 0.34 mmol) were added thereto, and the mixture was stirred under reflux for 1 hour. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by preparative thin-layer chromatography (chloroform/methanol=90/10). The obtained crude crystals were reslurried in hexane to give the title compound 90 (16 mg, 0.034 mmol, yield: 20%).
$^1$H-NMR (δppm, CDCl$_3$): 7.62 (d, J=14.5 Hz, 1H), 7.01 (s, 1H), 6.96 (d, J=14.5 Hz, 1H), 4.24 (q, J=8.5 Hz, 4H), 4.02-3.95 (m, 2H), 3.90 (d, J=7.4 Hz, 2H), 3.42-3.30 (m, 2H), 2.09-1.91 (m, 1H), 1.65-1.50 (m, 2H), 1.45 (s, 9H), 1.45-1.31 (m, 2H). Mass (m/e): 456 (M+H)$^+$.

Example 91

3-(2-tert-Butyl-1-(tetrahydropyran-4-ylmethyl)-1H-imidazol-4-yl)-N,N-diethylthioacrylamide (Compound 91)

Compound 89 obtained in Example 89 was dissolved in DME (1.0 mL), and Lawesson's reagent (103 mg, 0.25 mmol) was added thereto, and then, the mixture was stirred overnight under reflux. The solvent was evaporated under reduced pressure, and the residue was purified by preparative thin-layer chromatography (hexane/ethyl acetate=70/30) to give the title compound 91 (11 mg, 0.030 mmol, yield: 17%).
$^1$H-NMR (δppm, CDCl$_3$): 7.84 (d, J=14.4 Hz, 1H), 7.31 (d, J=14.4 Hz, 1H), 7.01 (s, 1H), 4.16-4.06 (m, 2H), 4.05-3.95 (m, 2H), 3.89 (d, J=7.4 Hz, 2H), 3.74 (q, J=7.2 Hz, 2H), 3.42-3.30 (m, 2H), 2.06-1.95 (m, 1H), 1.66-1.55 (m, 2H), 1.44 (s, 9H), 1.44-1.20 (m, 8H). Mass (m/e): 364 (M+H)$^+$.

Example 92

3-(2-tert-Butyl-1-(tetrahydropyran-4-ylmethyl)-1H-imidazol-4-yl)-N,N-dipropylacrylamide (Compound 92)

The title compound 92 (11 mg, 0.029 mmol, yield: 35%) was obtained in the same manner as in Example 72, using Compound t obtained in Reference example 20 and dipropylamine.
$^1$H-NMR (δppm, CDCl$_3$): 7.49 (d, J=14.9 Hz, 1H), 6.99 (d, J=14.9 Hz, 1H), 6.93 (s, 1H), 4.05-3.95 (m, 2H), 3.88 (d, J=7.3 Hz, 2H), 3.42-3.30 (m, 6H), 2.06-1.97 (m, 1H), 1.66-1.55 (m, 6H), 1.45 (s, 9H), 1.45-1.35 (m, 2H), 1.00-0.87 (m, 6H). Mass (m/e): 376 (M+H)$^+$.

Example 93

3-(2-tert-Butyl-1-(tetrahydropyran-4-ylmethyl)-1H-imidazol-4-yl)-N-methyl-N-(1-methylethyl)acrylamide (Compound 93)

The title compound 93 (97 mg, yield: 82%) was obtained in the same manner as in Example 89, using isopropylmethylamine instead of diethylamine.
$^1$H-NMR (δppm, CDCl$_3$): 7.49 (d, J=15.0 Hz, 1H), 7.01 (d, J=15.0 Hz, 1H), 6.94 (s, 1H), 4.50-4.35 (m, 1H), 4.03-3.94 (m, 2H), 3.88 (d, J=7.4 Hz, 2H), 3.41-3.29 (m, 2H), 2.92 (brs, 3H), 2.08-1.95 (m, 1H), 1.65-1.54 (m, 2H), 1.48-1.30 (m, 2H), 1.45 (s, 9H), 1.16 (brs, 6H). Mass (m/e): 348 (M+H)$^+$.

Example 94

3-[2-tert-Butyl-1-(tetrahydropyran-4-ylmethyl)-1H-imidazol-4-yl]-N-(2-methoxyethyl)-N-methylbenzamide (Compound 94)

The title compound 94 (77 mg, yield: 92%) was obtained in the same manner as in Example 72, using N-(2-methoxyethyl)methylamine instead of ethylamine.
$^1$H-NMR (δppm, CDCl$_3$): 7.83 (d, J=8.1 Hz, 1H), 7.77 (s, 1H), 7.36 (t, J=8.1 Hz, 1H), 7.21 (d, J=8.1 Hz, 1H), 7.14 (s, 1H), 4.03-3.98 (m, 2H), 3.93 (d, J=8.1 Hz, 2H), 3.75-3.65 (m, 2H), 3.50-3.25 (m, 6H), 3.15-2.95 (m, 3H), 2.11-1.98 (m, 1H), 1.68-1.63 (m, 2H), 1.47 (s, 9H), 1.45-1.39 (m, 3H). Mass (m/e): 414 (M+H)$^+$.

Example 95

6-[2-tert-Butyl-1-(tetrahydropyran-4-ylmethyl)-1H-imidazol-4-yl]pyridine-2-carboxylic acid diethylamide (Compound 95)

Step 1
2-Bromo-6-[2-tert-butyl-1-(tetrahydropyran-4-ylmethyl)-1H-imidazol-4-yl]-pyridine (679 mg, 1.79 mmol, yield: 61%) was obtained in the same manner as in step 4 of Example 81, using 6-bromopyridine-2-boronic acid instead of 5-methylfuran-2-boronic acid.
Step 2
6-[2-tert-Butyl-1-(tetrahydropyran-4-ylmethyl)-1H-imidazol-4-yl]-pyridine-2-carboxylic acid propyl ester (380 mg, 0.99 mmol, yield: 75%) was obtained in the same manner as in Reference example 14, using 2-bromo-6-[2-tert-butyl-1-(tetrahydropyran-4-ylmethyl)-1H-imidazol-4-yl]-pyridine obtained in the above instead of Compound 84.

Step 3

The title compound 95 (16 mg, yield: 28%) was obtained in the same manner as in Example 85, using 6-[2-tert-butyl-1-(tetrahydropyran-4-ylmethyl)-1H-imidazol-4-yl]-pyridine-2-carboxylic acid propyl ester obtained in the above instead of Compound n.

$^1$H-NMR (δppm, CDCl$_3$): 8.00 (d, J=8.1 Hz, 1H), 7.74 (t, J=8.1 Hz, 1H), 7.52 (s, 1H), 7.35 (t, J=8.1 Hz, 1H), 4.03-3.94 (m, 4H), 3.57 (q, J=8.1 Hz, 2H), 3.41-3.33 (m, 4H), 2.20-1.85 (m, 2H), 1.72-1.60 (m, 2H), 1.48 (s, 9H), 1.31-1.19 (m, 7H). Mass (m/e): 399 (M+H)$^+$.

Example 96

4-[2-tert-Butyl-1-(tetrahydropyran-4-ylmethyl)-1H-imidazol-4-yl]-N,N-diethylpyridine-2-carboxamide (Compound 96)

Step 1

4-[2-tert-Butyl-1-(tetrahydropyran-4-ylmethyl)-1H-imidazol-4-yl]-2-chloropyridine (435 mg, 1.30 mmol, yield: 62%) was obtained in the same manner as in step 4 of Example 81, using 2-chloropyridine-4-boronic acid instead of 5-methylfuran-2-boronic acid.

Step 2

4-[2-tert-Butyl-1-(tetrahydropyran-4-ylmethyl)-1H-imidazol-4-yl]-pyridine-2-carboxylic acid propyl ester (290 mg, 0.75 mmol, yield: 63%) was obtained in the same manner as in Reference example 14, using 4-[2-tert-butyl-1-(tetrahydropyran-4-ylmethyl)-1H-imidazol-4-yl]-2-chloropyridine obtained in the above instead of Compound 84.

Step 3

The title compound 96 (20 mg, 0.05 mmol, yield: 42%) was obtained in the same manner as in Example 85, using 4-[2-tert-butyl-1-(tetrahydropyran-4-ylmethyl)-1H-imidazol-4-yl]-pyridine-2-carboxylic acid propyl ester obtained in the above instead of Compound n.

$^1$H-NMR (δppm, CDCl$_3$): 8.49 (d, J=8.1 Hz, 1H), 7.83 (s, 1H), 7.72 (d, J=8.1 Hz, 1H), 7.31 (s, 1H), 4.04-3.95 (m, 4H), 3.55 (q, J=5.4 Hz, 2H), 3.43-3.33 (m, 4H), 2.15-1.08 (m, 1H), 1.70-1.62 (m, 2H), 1.49-1.43 (m, 11H), 1.28 (t, J=5.4 Hz, 3H), 1.15 (t, J=5.4 Hz, 3H). Mass (m/e): 399 (M+H)$^+$.

Example 97

5-[2-tert-Butyl-1-(tetrahydropyran-4-ylmethyl)-1H-imidazol-4-yl]-N-cyclobutyl-N-methylnicotinamide (Compound 97)

The title compound 97 (12 mg, 0.03 mmol, yield: 27%) was obtained in the same manner as in Example 85, using N-cyclobutyl-N-methylamine.

$^1$H-NMR (δppm, CDCl$_3$): 8.98 (s, 1H), 8.42 (s, 1H), 8.10 (s, 1H), 7.20 (s, 1H), 4.43-4.15 (m, 1H), 4.04-3.94 (m, 4H), 3.38 (t, J=10.8 Hz, 2H), 3.15-3.08 (m, 3H), 2.35-2.00 (m, 5H), 1.80-1.62 (m, 3H), 1.51-1.40 (m, 12H). Mass (m/e): 411 (M+H)$^+$.

Example 98

4-[2-tert-Butyl-1-(tetrahydropyran-4-ylmethyl)-1H-imidazol-4-yl]-N,N-diethylthiophene-2-carboxamide (Compound 98)

The title compound 98 (45 mg, 0.11 mmol, yield: 56%) was obtained in the same manner as in Example 102 mentioned below, using N,N-diethylamine.

$^1$H-NMR (δppm, CDCl$_3$): 7.57 (s, 1H), 7.56 (s, 1H), 6.97 (s, 1H), 4.03-3.90 (m, 4H), 3.56 (q, J=8.1 Hz, 4H), 3.37 (t, J=10.8 Hz, 2H), 2.16-1.95 (m, 1H), 1.66-1.61 (m, 2H), 1.50-1.43 (m, 11H), 1.27-1.22 (m, 6H). Mass (m/e): 404 (M+H)$^+$.

Example 99

3-[2-tert-Butyl-1-(tetrahydropyran-4-ylmethyl)-1H-imidazol-4-yl]-N-methyl-N-(2,2,2-trifluoroethyl)benzamide (Compound 99)

Compound 209 (42 mg, 0.10 mmol) obtained in Example 209 mentioned below was dissolved in DMF (1 mL), and the mixture was stirred at room temperature for 10 minutes. Thereafter, sodium hydride (20 mg, 0.50 mmol) and methyl iodide (31 μL, 0.50 mmol) were added thereto, and the mixture was stirred at room temperature for 5 hours. Water was added to the mixture under ice-cooling, and the mixture was extracted with ethyl acetate. The organic layer was washed with saturated brine and dried over anhydrous magnesium sulfate, and the solvent was evaporated under reduced pressure. The residue was purified by preparative thin-layer chromatography (ethyl acetate/hexane=70/30) to give the title compound 99 (35 mg, 0.08 mmol, yield: 80%).

$^1$H-NMR (δppm, CDCl$_3$): 7.87 (d, J=8.1 Hz, 1H), 7.78 (s, 1H), 7.38 (t, J=8.1 Hz, 1H), 7.20 (t, J=8.1 Hz, 1H), 7.14 (m, 1H), 4.15-3.92 (m, 6H), 3.37 (t, J=10.8 Hz, 2H), 3.13 (s, 3H), 2.15-1.99 (m, 1H), 1.74-1.62 (m, 2H), 1.53-1.33 (m, 11H). Mass (m/e): 438 (M+H)$^+$.

Example 100

N-sec-Butyl-3-[2-tert-butyl-1-(tetrahydropyran-4-ylmethyl)-1H-imidazol-4-yl]-N-methylbenzamide benzenesulfonate (Compound 100)

Step 1

N-sec-Butyl-3-[2-tert-butyl-1-(tetrahydropyran-4-ylmethyl)-1H-imidazol-4-yl]benzamide (170 mg, 0.43 mmol, yield: 85%) was obtained in the same manner as in Example 72, using sec-butylamine instead of ethylamine.

Step 2

A free base of the title Compound (110 mg, 0.27 mmol, yield: 70%) was obtained in the same manner as in Example 99 using N-sec-butyl-3-[2-tert-butyl-1-(tetrahydropyran-4-ylmethyl)-1H-imidazol-4-yl]benzamide obtained in the above. Further, the obtained free base was dissolved in tert-butylmethyl ether and treated with benzenesulfonic acid (43 mg, 0.27 mmol) to give the title Compound 100 (130 mg, 0.23 mmol, yield: 85%).

$^1$H-NMR (δppm, CDCl$_3$): 7.82 (d, J=8.1 Hz, 1H), 7.72 (s, 1H), 7.35 (t, J=8.1 Hz, 1H), 7.16 (t, J=8.1 Hz, 1H), 7.12 (s, 1H), 4.03-3.90 (m, 4H), 3.83-3.72 (m, 1H), 3.37 (t, J=10.8 Hz, 2H), 2.91-2.75 (m, 3H), 2.07-2.02 (m, 1H), 1.67-1.60 (m, 4H), 1.49-1.45 (m, 11H), 1.22-1.12 (m, 3H), 0.98-0.79 (m, 3H). (as the free base) Mass (m/e): 412 (M+H)$^+$.

Example 101

5-[2-tert-Butyl-1-(tetrahydropyran-4-ylmethyl)-1H-imidazol-4-yl]-N,N-diethylfuran-2-carboxamide (Compound 101)

Step 1

5-Bromofuran-2-carboxylic acid diethylamide (3.29 g, 13.35 mmol, yield: 85%) was obtained in the same manner as in Example 9, using 5-bromofuran-2-carboxylic acid instead of Compound c.

Step 2

Under an argon atmosphere, 5-bromofuran-2-carboxylic acid diethylamide (245 mg, 1.00 mmol) obtained in the above was dissolved in THF, and a solution of n-butyl lithium in n-hexane (1.60 mol/L; 750 μL, 1.20 mmol) was added thereto at −78° C., and then, the mixture was stirred at the same temperature for 1 hour. To the mixture, tributyltin chloride (272 μL, 1.00 mmol) was added, and the mixture was stirred at −50° C. for 3 hours. To the mixture, 1.0 mol/L hydrochloric acid (3.0 mL) was added under ice-cooling, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=80/20) to give N,N-diethyl-5-tributylstannylfuran-2-carboxamide (150 mg, 0.33 mmol, yield: 33%).

Step 3

Compound u (70 mg, 0.20 mmol) obtained in Reference example 21 was dissolved in DMF, and N,N-diethyl-5-tributylstannylfuran-2-carboxamide (145 mg, 0.32 mmol) obtained in the above, tetrakis(triphenylphosphine)palladium (12 mg, 0.01 mmol), and lithium chloride (42 mg, 1.00 mmol) were added thereto, and then, the mixture was stirred at 110° C. for 2 hours. After the mixture was left to cool to room temperature, a saturated aqueous ammonium fluoride solution (5 mL) was added thereto, and the mixture was stirred for 10 minutes. The precipitated solid was removed by Celite filtration, and water was added to the filtrate, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50) to give the title compound 101 (70 mg, 0.18 mmol, yield: 90%).

$^1$H-NMR (δppm, CDCl$_3$): 7.26 (s, 1H), 6.99 (d, J=5.4 Hz, 1H), 6.65 (t, J=5.4 Hz, 1H), 4.03-3.91 (m, 4H), 3.58 (q, J=5.4 Hz, 4H), 3.37 (t, J=8.1 Hz, 2H), 2.09-2.00 (m, 1H), 1.68-1.60 (m, 2H), 1.46-1.43 (m, 11H), 1.28 (t, J=5.4 Hz, 6H). Mass (m/e): 388 (M+H)$^+$.

Example 102

4-[2-tert-Butyl-1-(tetrahydropyran-4-ylmethyl)-1H-imidazol-4-yl]-N-ethyl-N-methylthiophene-2-carboxamide (Compound 102)

Step 1

Compound u (70 mg, 0.20 mmol) obtained in Reference example 21 was dissolved in dioxane (2 mL) and water (1 mL), and 2-carboxythiophene-4-boronic acid pinacol ester (91 mg, 0.36 mmol), 1,1'-bis(diphenylphosphino)ferrocenedichloropalladium/dichloromethane 1:1 adduct (12 mg, 0.01 mmol), and sodium carbonate (64 mg, 0.60 mmol) were added thereto, and then, the mixture was stirred at 110° C. for 8 hours. After the mixture was left to cool to room temperature, water (5 mL) was added thereto, and the pH of the mixture was adjusted to 7.0 with 1 mol/L hydrochloric acid. The mixture was purified by HP-20 resin column chromatography (eluted with water and then with methanol) to give 4-[2-tert-butyl-1-(tetrahydropyran-4-ylmethyl)-1H-imidazol-4-yl]-thiophene-2-carboxylic acid (120 mg, 0.18 mmol, yield: quantitative).

Step 2

The title compound 102 (14 mg, 0.04 mmol, yield: 12%) was obtained in the same manner as in Example 72, using 4-[2-tert-butyl-1-(tetrahydropyran-4-ylmethyl)-1H-imidazol-4-yl]-thiophene-2-carboxylic acid obtained in the above and N-ethyl-N-methylamine.

$^1$H-NMR (δppm, CDCl$_3$): 7.59 (s, 1H), 7.58 (s, 1H), 6.97 (s, 1H), 4.03-3.90 (m, 4H), 3.59 (q, J=8.1 Hz, 2H), 3.37 (t, J=10.8 Hz, 2H), 3.16 (s, 3H), 2.11-2.00 (m, 1H), 1.74-1.62 (m, 2H), 1.46-1.43 (m, 11H), 1.24 (t, J=8.1 Hz, 3H). Mass (m/e): 390 (M+H)$^+$.

Example 103

3-[2-tert-Butyl-1-(tetrahydropyran-4-ylmethyl)-1H-imidazol-4-yl]-N-(2-dimethylaminoethyl)-N-methylbenzamide (Compound 103)

The title compound 103 (34 mg, 0.08 mmol, yield: 53%) was obtained in the same manner as in Example 72, using N,N,N'-trimethylethylenediamine instead of ethylamine.

$^1$H-NMR (δppm, CDCl$_3$): 7.84 (d, J=8.1 Hz, 1H), 7.77 (s, 1H), 7.36 (d, J=8.1 Hz, 1H), 7.20 (d, J=8.1 Hz, 1H), 7.14 (s, 1H), 4.04-3.92 (m, 4H), 3.68-3.60 (m, 2H), 3.39 (q, J=10.8 Hz, 2H), 3.12-2.88 (m, 3H), 2.64-2.48 (m, 2H), 2.36-1.99 (m, 7H), 1.68-1.60 (m, 2H), 1.48-1.45 (m, 11H). Mass (m/e): 427 (M+H)$^+$.

Example 104

3-[2-tert-Butyl-1-(tetrahydropyran-4-ylmethyl)-1H-imidazol-4-yl]-N-ethyl-N-(2-fluoroethyl)benzamide (Compound 104)

The title compound 104 (30 mg, 0.07 mmol, yield: 72%) was obtained in the same manner as in Example 99, using iodoethane instead of iodomethane, and Compound 210 obtained in Example 210 mentioned below.

$^1$H-NMR (δppm, CDCl$_3$): 7.83 (d, J=8.1 Hz, 1H), 7.75 (s, 1H), 7.36 (t, J=8.1 Hz, 1H), 7.19 (d, J=8.1 Hz, 1H), 7.12 (s, 1H), 4.80-4.52 (m, 2H), 4.03-3.91 (m, 4H), 3.82-3.62 (m, 2H), 3.52-3.33 (m, 4H), 2.11-1.95 (m, 1H), 1.67-1.63 (m, 2H), 1.47-1.40 (m, 11H), 1.20-1.12 (m, 3H). Mass (m/e): 416 (M+H)$^+$.

Example 105

6-[2-tert-Butyl-1-(tetrahydropyran-4-ylmethyl)-1H-imidazol-4-yl]-N-ethyl-N-(2,2,2-trifluoroethyl)pyridine-2-carboxamide (Compound 105)

The title compound 105 (27 mg, 0.06 mmol, yield: 60%) was obtained in the same manner as in Example 99, using iodoethane instead of iodomethane, and Compound 211 obtained in Example 211 mentioned below.

$^1$H-NMR (δppm, CDCl$_3$): 8.05 (d, J=8.1 Hz, 1H), 7.79 (t, J=8.1 Hz, 1H), 7.59-7.39 (m, 2H), 4.53 (q, J=8.1 Hz, 1H), 4.21 (q, J=8.1 Hz, 1H), 4.04-3.95 (m, 4H), 3.74-3.57 (m, 2H), 3.38 (t, J=10.8 Hz, 2H), 2.13-2.06 (m, 1H), 1.68-1.64 (m, 1H), 1.49-1.45 (m, 11H), 1.32-1.18 (m, 4H). Mass (m/e): 453 (M+H)$^+$.

Example 106

5-[2-tert-Butyl-1-(tetrahydropyran-4-ylmethyl)-1H-imidazol-4-yl]-N-ethyl-N-methylfuran-2-carboxamide (Compound 106)

The title compound 106 (40 mg, 0.11 mmol, yield: 3%) was obtained in the same manner as in Example 72, using N-ethylmethylamine instead of diethylamine.

$^1$H-NMR (δppm, CDCl$_3$): 7.27 (s, 1H), 6.97 (d, J=2.7 Hz, 1H), 6.64 (d, J=2.7 Hz, 1H), 4.02-3.91 (m, 4H), 3.61 (q, J=5.4 Hz, 2H), 3.36 (t, J=8.1 Hz, 2H), 3.16 (s, 3H), 2.07-1.94 (m, 2H), 1.66-1.61 (m, 1H), 1.46-1.42 (m, 11H), 1.27 (t, J=5.4 Hz, 3H). Mass (m/e): 374 (M+H)$^+$.

Example 107

5-[2-tert-Butyl-1-(tetrahydropyran-4-ylmethyl)-1H-imidazol-4-yl]-N,N-diethylisoxazole-3-carboxamide (Compound 107)

Step 1
5-[2-tert-Butyl-1-(tetrahydropyran-4-ylmethyl)-1H-imidazol-4-yl]isoxazole-3-carboxylic acid ethyl ester (70 mg, 0.19 mmol, yield: 32%) was obtained in the same manner as in step 3 of Example 101, using 5-tributylstannylisoxazole-3-carboxylic acid ethylester obtained by the method described in Tetrahedron, vol. 47, p. 5111 (1991).
Step 2
The title compound 107 (25 mg, 0.06 mmol, yield: 36%) was obtained in the same manner as in Example 85, using 5-[2-tert-butyl-1-(tetrahydropyran-4-ylmethyl)-1H-imidazol-4-yl]isoxazole-3-carboxylic acid ethyl ester obtained in the above.
$^1$H-NMR (δppm, CDCl$_3$): 7.33 (s, 1H), 6.70 (s, 1H), 4.03-3.95 (m, 4H), 3.58-3.54 (m, 4H), 3.38 (t, J=10.8 Hz, 2H), 2.10-2.03 (m, 1H), 1.77-1.61 (m, 2H), 1.46-1.41 (m, 11H), 1.24-1.19 (m, 6H). Mass (m/e): 389 (M+H)$^+$.

Example 108

2-[2-tert-Butyl-1-(tetrahydropyran-4-ylmethyl)-1H-imidazol-4-yl]-N,N-diethylisonicotinamide (Compound 108)

Step 1
A roughly purified product of 2-tert-butyl-1-(tetrahydropyran-4-yl)methyl-4-tributylstannyl-1H-imidazole was obtained in the same manner as in Step 2 of Example 101, using Compound u instead of 5-bromofuran-2-carboxylic acid diethylamide, and the resulting roughly purified product was used in the subsequent step without purification.
Step 2
2-[2-tert-Butyl-1-(tetrahydropyran-4-ylmethyl)-1H-imidazol-4-yl]isonicotinonitrile (60 mg, 0.19 mmol, yield: 12%) was obtained in the same manner as in step 3 of Example 101, using 2-tert-butyl-1-(tetrahydropyran-4-yl)methyl-4-tributylstannyl-1H-imidazole obtained in the above and 2-chloroisonicotinonitrile.
Step 3
2-[2-tert-Butyl-1-(tetrahydropyran-4-ylmethyl)-1H-imidazol-4-yl]isonicotinic acid (100 mg, 0.29 mmol, yield: quantitative) was obtained in the same manner as in Reference example 1, using 2-[2-tert-butyl-1-(tetrahydropyran-4-ylmethyl)-1H-imidazol-4-yl]isonicotinonitrile obtained in the above.
Step 4
The title compound 108 (35 mg, 0.09 mmol, yield: 88%) was obtained in the same manner as in Example 72, using 2-[2-tert-butyl-1-(tetrahydropyran-4-ylmethyl)-1H-imidazol-4-yl]isonicotinic acid obtained in the above and diethylamine.
$^1$H-NMR (δppm, CDCl$_3$): 8.53 (d, J=5.4 Hz, 1H), 7.96 (s, 1H), 7.55 (s, 1H), 7.03 (d, J=5.4 Hz, 1H), 4.01-3.93 (m, 4H), 3.60-3.52 (m, 2H), 3.36 (t, J=10.8 Hz, 2H), 3.33-3.27 (m, 2H), 2.19-2.05 (m, 1H), 1.68-1.64 (m, 2H), 1.47-1.39 (m, 11H), 1.30-1.12 (m, 6H). Mass (m/e): 399 (M+H)$^+$.

Example 109

2-[2-tert-Butyl-1-(tetrahydropyran-4-ylmethyl)-1H-imidazol-4-yl]-N,N-diethylthiazole-5-carboxamide (Compound 109)

Step 1
2-Bromothiazole-5-carboxylic acid diethylamide (131 mg, 0.50 mmol, 34%) was obtained in the same manner as in Example 72, using 2-bromo-5-thiazole carboxylic acid and diethylamine.
Step 2
The title compound 109 (33 mg, 0.08 mmol, yield: 33%) was obtained in the same manner as in step 2 to 3 of Example 101, using 2-bromothiazole-5-carboxylic acid diethylamide obtained in the above.
$^1$H-NMR (δppm, CDCl$_3$): 7.95 (s, 1H), 7.48 (s, 1H), 4.02-3.93 (m, 4H), 3.54 (q, J=8.1 Hz, 4H), 3.36 (t, J=10.8 Hz, 2H), 2.11-2.04 (m, 1H), 1.68-1.60 (m, 2H), 1.47-1.40 (m, 11H), 1.25 (t, J=8.1 Hz, 6H). Mass (m/e): 405 (M+H)$^+$.

Example 110

4-[2-tert-Butyl-1-(tetrahydropyran-4-ylmethyl)-1H-imidazol-4-yl]-N,N-diethylfuran-2-carboxamide (Compound 110)

Step 1
4-Bromofuran-2-carboxylic acid diethylamide (25 mg, 0.10 mmol, yield: 70%) was obtained in the same manner as in step 1 of Example 101, using 4-bromofuran-2-carboxylic acid obtained by the method described in J. Org. Chem., vol. 41, p. 2840 (1976) instead of 5-bromofuran-2-carboxylic acid.
Step 2
The title compound 110 (20 mg, 0.05 mmol, yield: 52%) was obtained in the same manner as in step 3 of Example 101, using 4-bromofuran-2-carboxylic acid diethylamide obtained in the above and 2-tert-butyl-1-(tetrahydropyran-4-yl)methyl-4-tributylstannyl-1H-imidazole obtained in step 1 of Example 108.
$^1$H-NMR (δppm, CDCl$_3$): 7.78 (s, 1H), 7.16 (s, 1H), 6.91 (s, 1H), 4.03-3.89 (m, 4H), 3.57 (q, J=5.4 Hz, 4H), 3.37 (t, J=10.8 Hz, 2H), 2.09-2.00 (m, 1H), 1.68-1.61 (m, 2H), 1.45-1.38 (m, 11H), 1.24 (t, J=5.4 Hz, 6H). Mass (m/e): 388 (M+H)$^+$.

Example 111

2-[2-tert-Butyl-1-(tetrahydropyran-4-ylmethyl)-1H-imidazol-4-yl]-N-methyl-N-propylthiazole-5-carboxamide (Compound III)

Step 1
2-Bromo-N-methyl-N-propylthiazole-5-carboxamide (130 mg, 0.49 mmol, yield: 68%) was obtained in the same manner as in Example 72, using N-methylpropylamine and 2-bromo-5-thiazole carboxylic acid.
Step 2
The title compound III (60 mg, 0.15 mmol, yield: 49%) was obtained in the same manner as in step 3 of Example 101, using 2-bromo-N-methyl-N-propylthiazole-5-carboxamide obtained in the above and 2-tert-butyl-1-(tetrahydropyran-4-yl)methyl-4-tributylstannyl-1H-imidazole obtained in step 1 of Example 108.

¹H-NMR (δppm, CDCl₃): 7.94 (s, 1H), 7.49 (s, 1H), 4.02-3.89 (m, 4H), 3.52-3.46 (m, 2H), 3.36 (q, J=10.8 Hz, 2H), 3.13 (s, 3H), 2.12-2.02 (m, 1H), 1.72-1.60 (m, 4H), 1.47-1.36 (m, 11H), 0.93 (t, J=8.1 Hz, 3H). Mass (m/e): 405 (M+H)⁺.

Example 112

5-[2-tert-Butyl-1-(tetrahydropyran-4-ylmethyl)-1H-imidazol-4-yl]-N,N-diethylfuran-3-carboxamide (Compound 112)

Step 1

5-Bromo-N,N-diethylfuran-3-carboxamide (200 mg, 0.81 mmol, yield: 81%) was obtained in the same manner as in step 1 of Example 101, using 5-bromofuran-3-carboxylic acid instead of 5-bromofuran-2-carboxylic acid.

Step 2

The title compound 112 (35 mg, 0.09 mmol, yield: 36%) was obtained in the same manner as in step 3 of Example 101, using 5-bromo-N,N-diethylfuran-3-carboxamide obtained in the above and 2-tert-butyl-1-(tetrahydropyran-4-yl)methyl-4-tributylstannyl-1H-imidazole obtained in step 1 of Example 108.

¹H-NMR (δppm, CDCl₃): 7.63 (s, 1H), 7.07 (s, 1H), 6.67 (s, 1H), 4.03-3.91 (m, 4H), 3.50 (q, J=8.1 Hz, 4H), 3.37 (t, J=10.8 Hz, 2H), 2.10-2.02 (m, 1H), 1.69-1.60 (m, 2H), 1.46-1.38 (m, 11H), 1.21 (t, J=8.1 Hz, 6H). Mass (m/e): 388 (M+H)⁺.

Example 113

4-[2-tert-Butyl-1-(tetrahydropyran-4-ylmethyl)-1H-imidazol-4-yl]-N-(2,2-difluoroethyl)-N-methylthiophene-2-carboxamide (Compound 113)

The title compound 113 (50 mg, 0.12 mmol, yield: 59%) was obtained in the same manner as in Example 99, using Compound 212 obtained in Example 212 mentioned below.

¹H-NMR (δppm, CDCl₃): 7.68 (s, 1H), 7.63 (s, 1H), 6.99 (s, 1H), 6.28-5.83 (m, 1H), 3.99-3.84 (m, 6H), 3.42-3.32 (m, 5H), 2.10-2.01 (m, 1H), 1.69-1.58 (m, 2H), 1.49-1.40 (m, 11H). Mass (m/e): 426 (M+H)⁺.

Example 114

4-[2-tert-Butyl-1-(tetrahydropyran-4-ylmethyl)-1H-imidazol-4-yl]-N,N-diethyl-1-methyl-1H-pyrrole-2-carboxamide (Compound 114)

Step 1

4-Bromo-N,N-diethyl-1-methyl-1H-pyrrole-2-carboxamide (669 mg, 2.59 mmol, yield: 41%) was obtained in the same manner as in Example 72, using 4-bromo-1-methyl-1H-pyrrole-2-carboxylic acid and diethylamine.

Step 2

The title compound 114 (55 mg, 0.14 mmol, yield: 12%) was obtained in the same manner as in step 3 of Example 101, using 4-bromo-N,N-diethyl-1-methyl-1H-pyrrole-2-carboxamide obtained in the above and 2-tert-butyl-1-(tetrahydropyran-4-yl)methyl-4-tributylstannyl-1H-imidazole obtained in step 1 of Example 108.

¹H-NMR (δppm, CDCl₃): 6.99 (s, 1H), 6.79 (s, 1H), 6.47 (s, 1H), 4.02-3.87 (m, 4H), 3.72 (s, 3H), 3.55 (q, J=8.1 Hz, 4H), 3.36 (t, J=10.8 Hz, 2H), 2.08-2.00 (m, 1H), 1.67-1.62 (m, 2H), 1.45-1.37 (m, 11H), 1.21 (t, J=8.1 Hz, 6H). Mass (m/e): 401 (M+H)⁺.

Example 115

4-[2-tert-Butyl-1-(tetrahydropyran-4-ylmethyl)-1H-imidazol-4-yl]-N-(2-methoxyethyl)-N-methylthiophene-2-carboxamide (Compound 115)

The title compound 115 (25 mg, 0.06 mmol, yield: 40%) was obtained in the same manner as in step 2 of Example 102, using N-(2-methoxyethyl)methylamine instead of N-ethylmethylamine.

¹H-NMR (δppm, CDCl₃): 7.65 (s, 1H), 7.58 (s, 1H), 6.97 (s, 1H), 4.03-3.90 (m, 4H), 3.75-3.72 (m, 2H), 3.65-3.61 (m, 2H), 3.41-3.33 (m, 5H), 3.27 (s, 3H), 2.09-2.00 (m, 1H), 1.67-1.57 (m, 2H), 1.45-1.39 (m, 11H). Mass (m/e): 420 (M+H)⁺.

Example 116

4-[2-tert-Butyl-1-(tetrahydropyran-4-ylmethyl)-1H-imidazol-4-yl]-N-ethyl-N-(2-hydroxyethyl)thiophene-2-carboxamide (Compound 116)

The title compound 116 (25 mg, 0.06 mmol, yield: 40%) was obtained in the same manner as in step 2 of Example 102, using 2-(ethylamino)ethanol instead of N-ethylmethylamine.

¹H-NMR (δppm, CDCl₃): 7.66 (d, J=2.7 Hz, 1H), 7.60 (d, J=2.7 Hz, 1H), 6.98 (s, 1H), 4.03-3.97 (m, 2H), 3.93-3.85 (m, 4H), 3.71-3.62 (m, 4H), 3.36 (t, J=10.8 Hz, 2H), 2.14-1.97 (m, 1H), 1.67-1.62 (m, 2H), 1.49-1.37 (m, 11H), 1.21 (t, J=8.1 Hz, 3H). Mass (m/e): 420 (M+H)⁺.

Example 117

5-[2-tert-Butyl-1-(tetrahydropyran-4-ylmethyl)-1H-imidazol-4-yl]-N-ethyl-N-(2,2,2-trifluoroethyl)isoxazole-3-carboxamide (Compound 117)

The title compound (16 mg, 0.04 mmol, yield: 36%) was obtained in the same manner as in Example 105, using Compound 213 obtained in Example 213 mentioned below.

¹H-NMR (δppm, CDCl₃): 7.34 (s, 1H), 6.77 (s, 1H), 4.60-4.11 (m, 2H), 4.08-3.90 (m, 4H), 3.87-3.63 (m, 2H), 3.37 (t, J=11.6 Hz, 2H), 2.15-1.98 (m, 1H), 1.69-1.57 (m, 2H), 1.51-1.39 (m, 11H), 1.31-1.18 (m, 3H). Mass (m/e): 443 (M+H)⁺.

Example 118

4-[2-tert-Butyl-1-(tetrahydropyran-4-ylmethyl)-1H-imidazol-4-yl]-N-cyanomethyl-N-methylthiophene-2-carboxamide (Compound 118)

Step 1

4-Bromo-N-cyanomethyl-N-methylthiophene-2-carboxamide (325 mg, 1.25 mmol, yield: 84%) was obtained in the same manner as in Example 72, using 4-bromothiophene-2-carboxylic acid and methylaminoacetonitrile hydrochloride.

Step 2

The title compound 118 (150 mg, 0.37 mmol, yield: 47%) was obtained in the same manner as in step 3 of Example 101, using 4-bromo-N-cyanomethyl-N-methylthiophene-2-carboxamide obtained in the above and 2-tert-butyl-1-(tetrahydropyran-4-yl)methyl-4-tributylstannyl-1H-imidazole obtained in step 1 of Example 108.

$^1$H-NMR (δppm, CDCl$_3$): 7.71 (s, 1H), 7.67 (s, 1H), 7.00 (s, 1H), 4.47 (s, 2H), 4.06-3.89 (m, 4H), 3.44-3.31 (m, 5H), 2.13-1.99 (m, 1H), 1.71-1.56 (m, 2H), 1.51-1.37 (m, 11H). Mass (m/e): 401 (M+H)$^+$.

Example 119

4-[2-tert-Butyl-1-(tetrahydropyran-4-ylmethyl)-1H-imidazol-4-yl]-N-methyl-N-(pyridin-2-yl)thiophene-2-carboxamide (Compound 119)

Step 1
4-Bromo-N-methyl-N-(pyridin-2-yl)thiophene-2-carboxamide (100 mg, 0.34 mmol, yield: 67%) was obtained in the same manner as in Example 72, using 4-bromothiophene-2-carboxylic acid and 2-methylaminopyridine.
Step 2
The title compound 119 (40 mg, 0.09 mmol, yield: 46%) was obtained in the same manner as in step 3 of Example 101, using 4-bromo-N-methyl-N-(pyridin-2-yl)thiophene-2-carboxamide obtained in the above and 2-tert-butyl-1-(tetrahydropyran-4-yl)methyl-4-tributylstannyl-1H-imidazole obtained in step 1 of Example 108.
$^1$H-NMR (δppm, CDCl$_3$): 8.52 (d, J=4.8 Hz, 1H), 7.75-7.39 (m, 2H), 7.29-7.22 (m, 1H), 7.20-7.07 (m, 2H), 6.81 (s, 1H), 4.05-3.81 (m, 4H), 3.56 (s, 3H), 3.35 (t, J=10.8 Hz, 2H), 2.07-1.93 (m, 1H), 1.67-1.54 (m, 2H), 1.48-1.34 (m, 11H). Mass (m/e): 439 (M+H)$^+$.

Example 120

2-[2-tert-Butyl-1-(tetrahydropyran-4-ylmethyl)-1H-imidazol-4-yl]-N,N-diethylthiazole-4-carboxamide (Compound 120)

Step 1
2-[2-tert-Butyl-1-(tetrahydropyran-4-ylmethyl)-1H-imidazol-4-yl]thiazole-4-carboxylic acid ethyl ester (220 mg, 0.58 mmol, yield: 58%) was obtained in the same manner as in step 3 of Example 101, using 2-bromothiazole-4-carboxylic acid ethyl ester and 2-tert-butyl-1-(tetrahydropyran-4-yl)methyl-4-tributylstannyl-1H-imidazole obtained in step 1 of Example 108.
Step 2
The title compound 120 (18 mg, 0.04 mmol, yield: 44%) was obtained in the same manner as in step 3 of Example 95, using 2-[2-tert-butyl-1-(tetrahydropyran-4-ylmethyl)-1H-imidazol-4-yl]thiazole-4-carboxylic acid ethyl ester obtained in the above.
$^1$H-NMR (δppm, CDCl$_3$): 7.62 (s, 1H), 7.41 (s, 1H), 4.06-3.90 (m, 4H), 3.57 (q, J=7.1 Hz, 4H), 3.44-3.30 (m, 2H), 2.16-1.99 (m, 1H), 1.72-1.59 (m, 2H), 1.52-1.37 (m, 11H), 1.23 (t, J=7.1 Hz, 6H). Mass (m/e): 405 (M+H)$^+$.

Example 121

4-[2-tert-Butyl-1-(tetrahydropyran-4-ylmethyl)-1H-imidazol-4-yl]-N-(2-hydroxy-2-methylpropyl)-N-methylthiophene-2-carboxamide (Compound 121)

Step 1
1-Chloro-2-methyl-2-propanol (103 μL, 1.00 mmol) was dissolved in a 40% methylamine methanol solution (0.5 mL), and the mixture was stirred at 100° C. for 15 minutes at 100 W in a microwave-assisted chemical synthesis instrument (CEM Discover). After the mixture was left to cool to room temperature, the solvent was evaporated under reduced pressure. Then, acetonitrile (3 mL) was added to the residue, and the precipitated solid was removed by filtration. After an aqueous sodium hydrogen carbonate solution (10 drops) was added to the filtrate, the solvent was evaporated under reduced pressure to give a roughly purified product of 2-methyl-1-(methylamino)propan-2-ol. The roughly purified product was used in the subsequent step as such without purification.
Step 2
The title compound 121 (60 mg, 0.14 mmol, yield: 69%) was obtained in the same manner as in step 2 of Example 102, using 2-methyl-1-(methylamino)propan-2-ol obtained in the above.
$^1$H-NMR (δppm, CDCl$_3$): 7.72 (s, 1H), 7.63 (s, 1H), 6.99 (s, 1H), 4.07-3.85 (m, 4H), 3.64-3.57 (s, 2H), 3.46-3.31 (m, 5H), 2.15-1.97 (m, 1H), 1.71-1.55 (m, 2H), 1.51-1.37 (m, 11H), 1.34-1.23 (m, 6H). Mass (m/e): 434 (M+H)$^+$.

Example 122

{4-[2-tert-Butyl-1-(tetrahydropyran-4-ylmethyl)-1H-imidazol-4-yl]thiophen-2-yl}-[4-(2-hydroxy-2-methylpropyl)piperazin-1-yl]methanone (Compound 122)

Step 1
piperazine (6.88 g, 80.0 mmol) was dissolved in ethanol (40 mL), and 1-chloro-2-methyl-2-propanol (2.18 g, 20.0 mmol) was added thereto, and then, the mixture was stirred at 110° C. for 6 hours. After the mixture was left to cool to room temperature, the solvent was evaporated. Then, ethyl acetate was added to the residue, and the precipitated solid was removed by filtration. The solvent of the filtrate was removed under reduced pressure, and the residue was purified by silica gel column chromatography (ethyl acetate/methanol=90/10) to give 2-methyl-1-(piperazin-1-yl)propan-2-ol (1.89 g, 11.96 mmol, 60%).
Step 2
The title compound 122 (40 mg, 0.08 mmol, yield: 55%) was obtained in the same manner as in step 2 of Example 102, using 2-methyl-1-(piperazin-1-yl)propan-2-ol obtained in the above.
$^1$H-NMR (δppm, CDCl$_3$): 7.57 (d, J=1.3 Hz, 1H), 7.52 (d, J=1.3 Hz, 1H), 6.97 (s, 1H), 4.06-3.88 (m, 4H), 3.82-3.73 (m, 4H), 3.37 (t, J=10.8 Hz, 2H), 2.78-2.55 (m, 4H), 2.37 (s, 2H), 2.14-1.97 (m, 1H), 1.71-1.55 (m, 2H), 1.50-1.39 (m, 11H), 1.19 (s, 6H). Mass (m/e): 489 (M+H)$^+$.

Example 123

4-[2-tert-Butyl-1-(tetrahydropyran-4-ylmethyl)-1H-imidazol-4-yl]-N-ethylthiophene-2-carboxamide (Compound 123)

The title compound 123 (43 mg, 0.11 mmol, yield: 78%) was obtained in the same manner as in step 2 of Example 102, using an aqueous ethylamine solution (12 mol/L).
$^1$H-NMR (δppm, CDCl$_3$): 7.76 (s, 1H), 7.57 (s, 1H), 7.01 (s, 1H), 6.05 (br s, 1H), 4.07-3.87 (m, 4H), 3.56-3.30 (m, 4H), 2.16-1.96 (m, 1H), 1.71-1.57 (m, 2H), 1.51-1.38 (m, 11H), 1.24 (t, J=6.9 Hz, 3H). Mass (m/e): 376 (M+H)$^+$.

Example 124

2-[2-tert-Butyl-1-(tetrahydropyran-4-ylmethyl)-1H-imidazol-4-yl]isonicotinonitrile (Compound 124)

The title compound 124 (70 mg, 0.22 mmol, yield: 68%) was obtained in the same manner as in step 3 of Example 101, using 2-chloro-4-cyanopyridine and 2-tert-butyl-1-(tetrahydropyran-4-yl)methyl-4-tributylstannyl-1H-imidazole obtained in step 1 of Example 108.

$^1$H-NMR (δppm, CDCl$_3$): 8.62 (d, J=4.9 Hz, 1H), 8.21 (s, 1H), 7.28-7.22 (m, 2H), 4.05-3.92 (m, 4H), 3.44-3.30 (m, 2H), 2.19-2.01 (m, 1H), 1.72-1.61 (m, 2H), 1.52-1.42 (m, 11H). Mass (m/e):325 (M+H)$^+$.

Example 125

1-{4-[2-tert-Butyl-1-(tetrahydropyran-4-ylmethyl)-1H-imidazol-4-yl]-2-chloro-7,8-dihydro-5H-pyrido[4,3-d]pyrimidin-6-yl}ethanone (Compound 125)

Step 1

2,4-Dichloro-5,6,7,8-tetrahydropyrido[4,3-d]pyrimidine (1.00 g, 4.16 mmol) obtained by the method described in WO2003/104230 was dissolved in dichloromethane (20 mL), and acetyl chloride (445 μL, 6.26 mmol) and triethylamine (2.17 mL, 15.57 mmol) were added thereto under ice-cooling, and then, the mixture was stirred overnight at room temperature. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give 1-(2,4-dichloro-7,8-dihydro-5H-pyrido[4,3-d]pyrimidin-6-yl)ethanone (884 mg, 3.61 mmol, yield: 87%).

Step 2

The title compound 125 (220 mg, 0.51 mmol, yield: 58%) was obtained in the same manner as in step 3 of Example 101, using 1-(2,4-dichloro-7,8-dihydro-5H-pyrido[4,3-d]pyrimidin-6-yl)ethanone obtained in the above and 2-tert-butyl-1-(tetrahydropyran-4-yl)methyl-4-tributylstannyl-1H-imidazole obtained in step 1 of Example 108.

$^1$H-NMR (δppm, CDCl$_3$): 7.97-7.73 (m, 1H), 5.32 (s, 2H), 4.08-3.71 (m, 6H), 3.39 (t, J=10.8 Hz, 2H), 3.13-2.87 (m, 2H), 2.31-2.01 (m, 4H), 1.74-1.57 (m, 2H), 1.55-1.36 (m, 11H). Mass (m/e):432 (M+H)$^+$.

Example 126

2-[2-tert-Butyl-1-(tetrahydropyran-4-ylmethyl)-1H-imidazol-4-yl]-6-(oxazol-2-yl)pyrazine (Compound 126)

Step 1

2-Chloro-6-(oxazol-2-yl)pyrazine (110 mg, 0.60 mmol, yield: 30%) was obtained in the same manner as in step 3 of Example 101, using 2,6-dichloropyrazine and 2-(tri-N-butylstannyl) oxazole.

Step 2

The title compound 126 (35 mg, 0.91 mmol, yield: 38%) was obtained in the same manner as in step 3 of Example 101, using 2-chloro-6-(oxazol-2-yl)pyrazine obtained in the above and 2-tert-butyl-1-(tetrahydropyran-4-yl)methyl-4-tributylstannyl-1H-imidazole obtained in step 3 of Example 101.

$^1$H-NMR (δppm, CDCl$_3$): 9.31 (s, 1H), 9.11 (s, 1H), 7.85 (s, 1H), 7.76 (s, 1H), 7.36 (s, 1H), 4.07-3.92 (m, 4H), 3.39 (t, J=10.8 Hz, 2H), 2.25-2.08 (m, 1H), 1.72-1.60 (m, 2H), 1.54-1.42 (m, 11H). Mass (m/e):368 (M+H)$^+$.

Example 127

2-[2-tert-Butyl-1-(tetrahydropyran-4-ylmethyl)-1H-imidazol-4-yl]-6-(piperidin-1-yl)pyrazine (Compound 127)

Compound 136 (50 mg, 0.15 mmol) obtained in Example 136 mentioned below was added to piperidine (1.0 mL), and the mixture was stirred at 110° C. for 2 hours at 200 W in a microwave-assisted chemical synthesis instrument (CEM Discover). After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. To the residue, heptane was added, and the precipitated crystal was filtered to give the title compound 127 (40 mg, 0.10 mmol, yield: 69%).

$^1$H-NMR (δppm, CDCl$_3$): 8.45 (s, 1H), 7.94 (s, 1H), 7.43 (s, 1H), 4.07-3.89 (m, 4H), 3.65-3.54 (m, 4H), 3.38 (t, J=10.8 Hz, 2H), 2.19-2.02 (m, 1H), 1.73-1.57 (m, 8H), 1.51-1.42 (m, 11H). Mass (m/e):384 (M+H)$^+$.

Example 128

N-{6-[2-tert-Butyl-1-(tetrahydropyran-4-ylmethyl)-1H-imidazol-4-yl]pyrazin-2-yl}-N-methyl-N-phenylamine (Compound 128)

The title compound 128 (30 mg, 0.07 mmol, yield: 49%) was obtained in the same manner as in Example 99, using Compound 214 obtained in Example 214 mentioned below.

$^1$H-NMR (δppm, CDCl$_3$): 8.49 (s, 1H), 7.78 (s, 1H), 7.47 (s, 1H), 7.45-7.36 (m, 2H), 7.32-7.20 (m, 3H), 4.07-3.92 (m, 4H), 3.52 (s, 3H), 3.39 (t, J=10.8 Hz, 2H), 2.18-2.03 (m, 1H), 1.73-1.62 (m, 2H), 1.54-1.42 (m, 11H). Mass (m/e):406 (M+H)$^+$.

Example 129

3-[2-tert-Butyl-1-(tetrahydropyran-4-ylmethyl)-1H-imidazol-4-yl]benzaldehyde (Compound 129)

The title compound 129 (491 mg, 1.51 mmol, yield: 87%) was obtained in the same manner as in step 4 of Example 81, using 3-formylphenylboronic acid and Compound u obtained in Reference example 21.

$^1$H-NMR (δppm, CDCl$_3$): 10.05 (s, 1H), 8.22 (s, 1H), 8.06 (d, J=7.7 Hz, 1H), 7.70 (d, J=22.5 Hz, 1H), 7.51 (t, J=27.1 Hz, 1H), 7.22 (s, 1H), 4.09-3.85 (m, 4H), 3.37 (t, J=10.8 Hz, 2H), 2.20-2.03 (m, 1H), 1.76-1.58 (m, 2H), 1.54-1.42 (m, 11H). Mass (m/e):327 (M+H)$^+$.

Example 130

1-{3-[2-tert-Butyl-1-(tetrahydropyran-4-ylmethyl)-1H-imidazol-4-yl]phenyl}pyrrolidin-2-one (Compound 130)

The hydrochloride of Compound 87 (70 mg, 0.20 mmol) was dissolved in DMF (1.0 mL), and potassium carbonate (138 mg, 5.00 mmol) and 4-bromobutyryl chloride were added thereto, and then the mixture was stirred at 60° C. for 3 hours. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The obtained residue was dissolved in DMF (1 mL), and sodium hydride (40 mg, 1.00 mmol) was added thereto, and the mixture was stirred at room temperature for 2 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (ethyl acetate/hexane=70/30) to give the title compound 130 (27 mg, 0.07 mmol, yield: 35%).

$^1$H-NMR ($\delta$ppm, CDCl$_3$): 7.95 (s, 1H), 7.55 (d, J=7.7 Hz, 1H), 7.47 (d, J=7.7 Hz, 1H), 7.32 (t, J=7.7 Hz, 1H), 7.13 (s, 1H), 4.06-3.87 (m, 6H), 3.37 (t, J=10.8 Hz, 2H), 2.61 (t, J=7.9 Hz, 2H), 2.24-2.01 (m, 3H), 1.72-1.57 (m, 2H), 1.51-1.34 (m, 11H). Mass (m/e):382 (M+H)$^+$.

Example 131

2-[2-tert-Butyl-1-(tetrahydropyran-4-ylmethyl)-1H-imidazol-4-yl]-6-phenoxy-pyrazine (Compound 131)

Compound 136 (50 mg, 0.15 mmol) obtained in Example 136 mentioned below and phenol (28 mg, 0.30 mmol) were dissolved in DMF (1 mL), and sodium hydride (12 mg, 0.30 mmol) was added thereto, and then, the mixture was stirred at 90° C. for 4 hours. After the mixture was left to cool to room temperature, a saturated aqueous ammonium chloride solution and an aqueous sodium hydrogen carbonate solution were added thereto, and the mixture was extracted with ethyl acetate. The organic layer was washed with saturated brine and dried over anhydrous magnesium sulfate, and the solvent was evaporated under reduced pressure. The residue was purified by preparative thin-layer chromatography (hexane/ethyl acetate=75/25) to give the title compound 131 (20 mg, 0.05 mmol, yield: 34%).

$^1$H-NMR ($\delta$ppm, CDCl$_3$): 8.94 (s, 1H), 8.04 (s, 1H), 7.47-7.34 (m, 3H), 7.29-7.13 (m, 3H), 4.05-3.82 (m, 4H), 3.35 (t, J=10.8 Hz, 2H), 2.18-1.92 (m, 1H), 1.75-1.55 (m, 2H), 1.52-1.34 (m, 11H). Mass (m/e):393 (M+H)$^+$.

Example 132

N-{6-[2-tert-Butyl-1-(tetrahydropyran-4-ylmethyl)-1H-imidazol-4-yl]pyrazin-2-yl}-N-methylbenzamide (Compound 132)

Compound 215 (42 mg, 0.13 mmol) obtained in Example 215 mentioned below was dissolved in acetonitrile (1 mL), and under ice-cooling, triethylamine (71 μL) and benzoyl chloride (30 μL) were added thereto, and then, the mixture was stirred at room temperature for 2 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by preparative thin-layer chromatography (hexane/ethyl acetate=50/50) to give the title compound 132 (10 mg, 0.02 mmol, yield: 18%).

$^1$H-NMR ($\delta$ppm, CDCl$_3$): 8.84 (s, 1H), 7.87 (s, 1H), 7.50-7.14 (m, 6H), 4.11-3.92 (m, 4H), 3.61 (s, 3H), 3.41 (t, J=10.8 Hz, 2H), 2.21-1.99 (m, 1H), 1.73-1.58 (m, 2H), 1.55-1.40 (m, 11H). Mass (m/e):434 (M+H)$^+$.

Example 133

4-[2-tert-Butyl-1-(tetrahydropyran-4-ylmethyl)-1H-imidazol-4-yl]thiophene-2-carboxylic acid dimethylamide (Compound 133)

The title compound 133 (32 mg, 0.09 mmol, yield: 75%) was obtained in the same manner as in step 2 of Example 102, using N,N-dimethylamine.

$^1$H-NMR ($\delta$ppm, CDCl$_3$): 7.62-7.59 (m, 2H), 6.99 (s, 1H), 4.11-3.82 (m, 4H), 3.39 (t, J=10.8 Hz, 2H), 3.19 (br s, 6H), 2.14-1.96 (m, 1H), 1.68-1.58 (m, 2H), 1.46-1.39 (m, 11H). Mass (m/e): 376 (M+H)$^+$.

Example 134

5-[2-tert-Butyl-1-(tetrahydropyran-4-ylmethyl)-1H-imidazol-4-yl]-2-methoxypyridine (Compound 134)

Compound u (1.00 g, 2.87 mmol) obtained in Reference example 21 was dissolved in 1,4-dioxane-water (5/1) (24 mL), and 2-methoxy-5-pyridineboronic acid (917 mg, 6.00 mmol), sodium carbonate (848 mg, 8.00 mmol), and [1,1'-bis(diphenylphosphino)ferrocene]dichloropalladium(II) (183 mg, 0.200 mmol) were added thereto, and then, the mixture was stirred at 100° C. for 1 hour. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 134 (624 mg, 1.89 mmol, yield: 66%).

$^1$H-NMR ($\delta$ppm, CDCl$_3$): 8.49 (dd, J=2.3, 0.7 Hz, 1H), 7.98 (dd, J=8.6, 2.3 Hz, 1H), 7.04 (s, 1H), 6.73 (dd, J=8.6, 0.76 Hz, 1H), 4.13-3.91 (m, 7H), 3.43-3.33 (m, 2H), 2.06-2.02 (m, 1H), 1.68-1.64 (m, 2H), 1.53-1.28 (m, 11H). Mass (m/e): 330 (M+H)$^+$.

Example 135

5-[2-tert-Butyl-1-(tetrahydropyran-4-ylmethyl)-1H-imidazol-4-yl]-1H-pyridin-2-one (Compound 135)

5-[2-tert-Butyl-1-(tetrahydropyran-4-ylmethyl)-1H-imidazol-4-yl]-2-methoxypyridine obtained in Example 134 was dissolved in hydrobromic acid (5 mL), and the mixture was stirred at 110° C. for 30 minutes. After the mixture was left to cool to room temperature, an aqueous sodium hydrogen carbonate solution was added thereto, and the mixture was extracted with chloroform-2-propanol (4/1). The organic layer was washed with saturated brine and dried over anhydrous magnesium sulfate, and the solvent was evaporated under reduced pressure. The residue was purified by silica gel column chromatography to give the title compound 135 (624 mg, 1.89 mmol, yield: 47%).

$^1$H-NMR ($\delta$ppm, CDCl$_3$): 12.0 (brs, 1H), 7.86 (d, J=2.5 Hz, 1H), 7.77 (dd, J=9.4, 2.5 Hz, 1H), 6.91 (s, 1H), 6.60 (d, J=9.4 Hz, 1H), 4.03-3.99 (m, 2H), 3.91 (d, J=7.4 Hz, 2H), 3.42-3.34 (m, 2H), 2.09-2.00 (m, 1H), 1.49-1.26 (m, 13H).

Example 136

2-[2-tert-Butyl-1-(tetrahydropyran-4-ylmethyl)-1H-imidazol-4-yl]-6-chloropyrazine (Compound 136)

Compound u (1.50 g, 4.31 mmol) obtained in Reference example 21 was dissolved in toluene, and 2-chloro-6-tributylstannylpyrazine (2.26 g, 5.60 mmol) obtained by the method described in J. Org. Chem., p. 2616 (2005) and tetrakis(triphenylphosphine)palladium (498 mg, 0.431 mmol) were added thereto, and then, the mixture was heated under reflux for 5 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 136 (448 mg, 1.34 mmol, yield: 31%).

$^1$H-NMR (δppm, CDCl$_3$): 9.11 (s, 1H), 8.34 (s, 1H), 7.63 (s, 1H), 4.01 (dd, J=11.1, 3.8 Hz, 2H), 3.96 (d, J=7.4 Hz, 2H), 3.38 (dt, J=11.1, 2.0 Hz, 2H), 2.17-2.04 (m, 1H), 1.67-1.62 (m, 2H), 1.51-1.37 (m, 11H). Mass (m/e): 335, 337 (M+H)$^+$.

Example 137

1-{6-[2-tert-Butyl-1-(tetrahydropyran-4-ylmethyl)-1H-imidazol-4-yl]pyrazin-2-yl}ethanone
(Compound 137)

Compound 149 (250 mg, 0.645 mmol) obtained in Example 149 mentioned below was dissolved in THF (5 mL), and under an argon atmosphere, a THF solution of methyl magnesium bromide (0.87 mol/L; 2.23 mL, 1.29 mmol) was added thereto at 0° C., and then, the mixture was stirred at room temperature for 1.5 hours. To the mixture, a saturated aqueous ammonium chloride solution was added, and the mixture was extracted with ethyl acetate. The organic layer was dried over anhydrous magnesium sulfate, and the solvent was evaporated under reduced pressure. The residue was purified by silica gel column chromatography to give the title compound 137 (41.0 mg, 0.12 mmol, yield: 91%).

$^1$H-NMR (δppm, CDCl$_3$): 9.37 (s, 1H), 8.99 (s, 1H), 7.62 (s, 1H), 4.13-3.99 (m, 4H), 3.40 (dt, J=12.0, 2.1 Hz, 2H), 2.75 (s, 3H), 2.14-2.05 (m, 1H), 1.74-1.65 (m, 2H), 1.54-1.43 (m, 11H). Mass (m/e): 343 (M+H)$^+$.

Example 138

1-Benzyl-5-[2-tert-butyl-1-(tetrahydropyran-4-ylmethyl)-1H-imidazol-4-yl]-1H-pyridin-2-one
(Compound 138)

Compound 135 (106 mg, 0.34 mmol) obtained in Example 135 was dissolved in methanol (5 mL), and benzyl bromide (105 μL, 0.67 mmol) and sodium methoxide (47.9 mg, 0.67 mmol) were added thereto, and the mixture was stirred overnight at 50° C. To the reaction mixture, a saturated aqueous sodium hydrogen carbonate solution was added, and the mixture was extracted with ethyl acetate. The organic layer was dried over anhydrous magnesium sulfate, and the solvent was evaporated under reduced pressure. The residue was purified by silica gel column chromatography to give the title compound 138 (56.0 mg, 0.14 mmol, yield: 41%).

$^1$H-NMR (δppm, CDCl$_3$): 7.82 (d, J=2.5 Hz, 1H), 7.60 (dd, J=9.4, 2.5 Hz, 1H), 7.33-7.26 (m, 5H), 6.88 (s, 1H), 6.64 (d, J=9.4 Hz, 1H), 5.20 (s, 2H), 4.03-3.97 (m, 2H), 3.99 (d, J=7.3 Hz, 2H), 3.40-3.32 (m, 2H), 2.06-1.99 (m, 1H), 1.65-1.60 (m, 2H), 1.48-1.37 (m, 11H). Mass (m/e): 406 (M+H)$^+$.

Example 139

5-[2-tert-Butyl-1-(tetrahydropyran-4-ylmethyl)-1H-imidazol-4-yl]-1-(1-methylethyl)-1H-pyridin-2-one
(Compound 139)

The title compound 139 (7.8 mg, 0.02 mmol, yield: 6%) was obtained in the same manner as in Example 138, using 2-iodopropane instead of benzyl bromide.

$^1$H-NMR (δppm, CDCl$_3$): 7.88 (, J=2.5 Hz, 1H), 7.54 (dd, J=9.2, 2.5 Hz, 1H), 6.91 (s, 1H), 6.58 (d, J=9.2 Hz, 1H), 5.32-5.27 (m, 1H), 4.04-3.99 (m, 2H), 3.92 (d, J=7.4 Hz, 2H), 3.42-3.33 (m, 2H), 2.07-2.02 (m, 1H), 1.66-1.62 (m, 2H), 1.5-1.26 (m, 17H). Mass (m/e): 358 (M+H)$^+$.

Example 140

3-[2-tert-Butyl-1-(tetrahydropyran-4-ylmethyl)-1H-imidazol-4-yl]-N,N-dimethylbenzenesulfonamide
(Compound 140)

Step 1
In THF (10 mL), dimethylamine hydrochloride (2.04 g, 25.0 mmol) and triethylamine (3.48 mL, 25.0 mmol) were dissolved, and 3-bromobenzenesulfonyl chloride (0.721 mL, 5.00 mmol) was added thereto at 0° C., and then, the mixture was stirred at room temperature for 1 hour. To the mixture, a saturated aqueous sodium hydrogen carbonate solution was added, and the mixture was extracted with ethyl acetate. The organic layer was dried over anhydrous magnesium sulfate, and the solvent was evaporated under reduced pressure. The residue was purified by silica gel column chromatography to give 3-bromo-N,N-dimethylbenzenesulfonamide (1.23 g, 4.66 mmol, yield: 93%).

$^1$H-NMR (δppm, CDCl$_3$): 7.93-7.92 (m, 1H), 7.76-7.70 (m, 2H), 7.44 (t, J=7.9 Hz, 1H), 2.74 (s, 6H).

Step 2
3-Bromo-N,N-dimethylbenzenesulfonamide (396 mg, 1.50 mmol) obtained in the above was dissolved in THF (5 mL), and under an argon atmosphere, a solution of n-butyl lithium in n-hexane (1.60 mol/L; 1.03 mL, 1.65 mmol) was added thereto at −78° C., and then, the mixture was stirred at −78° C. for 10 minutes. To the mixture, tributyltin chloride (0.45 mL, 1.65 mmol) was added, and the mixture was stirred at 0° C. for 30 minutes. Then, a saturated aqueous sodium hydrogen carbonate solution was added thereto, and the mixture was extracted with ethyl acetate. The organic layer was dried over anhydrous magnesium sulfate, and the solvent was evaporated under reduced pressure. The residue was purified by silica gel column chromatography to give N,N-dimethyl-3-tributylstannylbenzenesulfonamide (503 mg, 1.06 mmol, yield: 71%).

$^1$H-NMR (δppm, CDCl$_3$): 7.84-7.67 (m, 2H), 7.54-7.45 (m, 2H), 2.70 (s, 6H), 1.58-1.50 (m, 6H), 1.38-1.26 (m, 6H), 1.15-1.08 (m, 6H), 0.92-0.85 (m, 9H).

Step 3
Compound u (235 mg, 0.68 mmol) obtained in Reference example 21 was dissolved in toluene (10 mL), and N,N-dimethyl-3-tributylstannylbenzenesulfonamide (416 mg, 0.88 mmol) obtained in the above, lithium chloride (42.9 mg, 1.01 mmol), and tetrakis(triphenylphosphine)palladium (78.0 mg, 0.07 mmol) were added thereto, and then, the mixture was stirred under reflux for 3 hours. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 140 (49.0 mg, 0.12 mmol, yield: 18%).

$^1$H-NMR (δppm, CDCl$_3$): 8.10-8.04 (m, 2H), 7.59-7.48 (m, 2H), 7.22 (s, 1H), 4.03 (dd, J=11.4, 3.5 Hz, 2H), 3.95 (d, J=7.4 Hz, 2H), 3.40 (dt, J=11.4, 2.0 Hz, 2H), 2.72 (s, 6H), 2.16-2.07 (m, 1H), 1.69-1.59 (m, 2H), 1.48-1.42 (m, 11H). Mass (m/e): 406 (M+H)⁺.H) ss Example 141

N-Acetyl-3-[2-tert-butyl-1-(tetrahydropyran-4-ylmethyl)-1H-imidazol-4-yl]-N-ethylbenzamide (Compound 141)

Compound 72 (237 mg, 0.64 mmol) obtained in Example 72 was dissolved in DMF (5 mL), and sodium hydride (46.2 mg, 0.96 mmol) and acetyl chloride (68 µL, 0.96 mmol) were added thereto, and then, the mixture was stirred overnight at 50° C. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 141 (32.0 mg, 0.08 mmol, yield: 13%).

$^1$H-NMR (δppm, CDCl$_3$): 8.00-7.97 (m, 2H), 7.44-7.42 (m, 2H), 7.19 (s, 1H), 4.03 (dd, J=11.4, 3.5 Hz, 2H), 3.95 (d, J=7.3 Hz, 2H), 3.84 (q, J=7.1 Hz, 2H), 3.39 (dt, J=11.4, 1.7 Hz, 2H), 2.19 (s, 3H), 2.13-2.05 (m, 1H), 1.68-1.64 (m, 2H), 1.48-1.36 (m, 11H), 1.20 (t, J=7.1 Hz, 3H). Mass (m/e): 412 (M+H)⁺.

Example 142

1-{6-[2-tert-Butyl-1-(tetrahydropyran-4-ylmethyl)-1H-imidazol-4-yl]pyrazin-2-yl}ethanone-O-methyloxime (Compound 142)

Compound 137 (42.0 mg, 0.12 mmol) obtained in Example 137 was dissolved in ethanol (1 mL), and O-methylhydroxylamine hydrochloride (20.5 mg, 0.25 mmol) and potassium carbonate (33.9 mg, 0.25 mmol) were added thereto, and then, the mixture was heated under reflux for 30 minutes. Water was added to the mixture, and the mixture was extracted with ethyl acetate. The organic layer was dried over anhydrous magnesium sulfate, and the solvent was evaporated under reduced pressure. The residue was purified by silica gel column chromatography to give the title compound 142 (39.8 mg, 0.11 mmol, yield: 92%).

$^1$H-NMR (δppm, CDCl$_3$): 9.12 (s, 1H), 8.93 (s, 1H), 7.26 (s, 1H), 4.06 (s, 3H), 4.05-3.93 (m, 4H), 3.44-3.35 (m, 2H), 2.33 (s, 3H), 2.17-2.09 (m, 1H), 1.68-1.65 (m, 2H), 1.59-1.42 (m, 11H). Mass (m/e): 372 (M+H)⁺.

Example 143

6-[2-tert-Butyl-1-(tetrahydropyran-4-ylmethyl)-1H-imidazol-4-yl]-N,N-diethylpyrazine-2-carboxamide (Compound 143)

Compound y (98.0 mg, 0.29 mmol) obtained in Reference example 25 was dissolved in DMF (2 mL), and WSC.HCl (109 mg, 0.57 mmol), HOBt.H$_2$O (87.3 mg, 0.57 mmol), and diethylamine (59 µL, 0.57 mmol) were added thereto, and then, the mixture was stirred at 80° C. for 2 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 143 (60.0 mg, 0.15 mmol, yield: 52%).

$^1$H-NMR (δppm, CDCl$_3$): 9.23 (s, 1H), 8.62 (s, 1H), 7.55 (s, 1H), 4.04-3.69 (m, 4H), 3.59 (q, J=7.1 Hz, 2H), 3.41-3.33 (m, 4H), 2.13-2.05 (m, 1H), 1.67-1.63 (m, 2H), 1.49-1.37 (m, 11H), 1.32-1.22 (m, 6H). Mass (m/e): 400 (M+H)⁺.

Example 144

6-[2-tert-Butyl-1-(tetrahydropyran-4-ylmethyl)-1H-imidazol-4-yl]-N-methyl-N-propylpyrazine-2-carboxamide (Compound 144)

The title compound 144 (188 mg, 0.47 mmol, yield: 65%) was obtained in the same manner as in Example 143, using methylpropylamine instead of diethylamine.

$^1$H-NMR (δppm, CDCl$_3$): 9.24-9.23 (m, 1H), 8.61-8.60 (m, 1H), 7.56-7.53 (m, 1H), 4.04-3.95 (m, 4H), 3.54-3.27 (m, 4H), 3.13-3.05 (m, 3H), 2.17-2.06 (m, 1H), 1.79-1.63 (m, 4H), 1.49-1.36 (m, 11H), 1.04-0.77 (m, 3H). Mass (m/e): 400 (M+H)⁺.

Example 145

6-[2-tert-Butyl-1-(tetrahydropyran-4-ylmethyl)-1H-imidazol-4-yl]-N-ethyl-N-(2,2,2-trifluoroethyl)pyrazine-2-carboxamide (Compound 145)

Compound 216 (70.0 mg, 0.17 mmol) obtained in Example 216 mentioned below was dissolved in DMF (2 mL), and sodium hydride (32.9 mg, 0.83 mmol) and iodoethane (67 µL, 0.83 mmol) were added thereto, and then, the mixture was stirred at room temperature for 1 hour. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography to give the title compound 145 (35.0 mg, 0.08 mmol, yield: 47%).

$^1$H-NMR (δppm, CDCl$_3$): 9.29-9.27 (m, 1H), 8.83-8.66 (m, 1H), 7.54-7.51 (m, 1H), 4.47-4.17 (m, 2H), 4.04-3.96 (m, 4H), 3.76-3.58 (m, 2H), 3.39 (dt, J=11.7, 2.0 Hz, 2H), 2.17-2.00 (m, 1H), 1.67-1.63 (m, 2H), 1.49-1.38 (m, 11H), 1.35-1.20 (m, 3H). Mass (m/e): 454 (M+H)⁺.

Example 146

6-[2-tert-Butyl-1-(tetrahydropyran-4-ylmethyl)-1H-imidazol-4-yl]-N-ethyl-N-methylpyrazine-2-carboxamide (Compound 146)

The title compound 146 (934 mg, 2.42 mmol, yield: 83%) was obtained in the same manner as in Example 143, using N-ethyl-N-methylamine instead of diethylamine.

$^1$H-NMR (δppm, CDCl$_3$): 9.29 (s, 1H), 8.63 (s, 1H), 7.59-7.56 (m, 1H), 4.04-3.97 (m, 4H), 3.66-3.36 (m, 4H), 3.14-3.07 (m, 3H), 2.17-2.04 (m, 1H), 1.68-1.64 (m, 2H), 1.51 (s, 9H), 1.47-1.42 (m, 2H), 1.33-1.24 (m, 3H). Mass (m/e): 386 (M+H)⁺.

Example 147

6-[2-tert-Butyl-1-(tetrahydropyran-4-ylmethyl)-1H-imidazol-4-yl]-N-ethoxy-N-ethylpyrazine-2-carboxamide (Compound 147)

The title compound 147 (7.0 mg, 0.02 mmol, yield: 4%) was obtained in the same manner as in Example 216 mentioned below, and then in Example 145, using O-ethylhydroxylamine instead of 2,2,2-trifluoroethylamine.
¹H-NMR (δppm, CDCl₃): 9.21 (s, 1H), 8.73 (s, 1H), 7.61 (s, 1H), 4.38 (q, J=7.0 Hz, 2H), 4.23 (q, J=7.0 Hz, 2H), 4.02 (dd, J=11.9, 3.8 Hz, 2H), 3.97 (d, J=7.3 Hz, 2H), 3.39 (dt, J=11.9, 2.0 Hz, 2H), 2.18-2.09 (m, 1H), 1.68-1.63 (m, 2H), 1.53-1.41 (m, 11H), 1.39-1.34 (m, 6H). Mass (m/e): 416 (M+H)⁺.

Example 148

6-[2-tert-Butyl-1-(tetrahydropyran-4-ylmethyl)-1H-imidazol-4-yl]-N-ethyl-N-(piperidin-1-yl)pyrazine-2-carboxamide (Compound 148)

The title compound 148 (29.0 mg, 0.06 mmol, yield: 41%) was obtained in the same manner as in Example 216 mentioned below, and then in Example 145, using 1-aminopiperidine instead of 2,2,2-trifluoroethylamine.
¹H-NMR (δppm, CDCl₃): 9.12 (s, 1H), 9.05 (s, 1H), 7.77 (s, 1H), 4.43 (d, J=11.2 Hz, 2H), 4.07-3.93 (m, 6H), 3.38 (dt, J=11.9, 2.0 Hz, 2H), 2.96 (dt, J=11.9, 2.6 Hz, 2H), 2.32-2.11 (m, 5H), 1.79-1.62 (m, 4H), 1.49-1.38 (m, 11H), 1.34-1.23 (m, 3H). Mass (m/e): 455 (M+H)⁺.

Example 149

6-[2-tert-Butyl-1-(tetrahydropyran-4-ylmethyl)-1H-imidazol-4-yl]-N-methoxy-N-methylpyrazine-2-carboxamide (Compound 149)

The title compound 149 (41.0 mg, 0.11 mmol, yield: 91%) was obtained in the same manner as in Example 143, using N,O-dimethylhydroxylamine hydrochloride instead of diethylamine.
¹H-NMR (δppm, CDCl₃): 9.27 (s, 1H), 8.63 (s, 1H), 7.58 (s, 1H), 4.04-3.95 (m, 4H), 3.74 (s, 3H), 3.41 (s, 3H), 3.38 (dt, J=11.7, 1.7 Hz, 2H), 2.14-2.05 (m, 1H), 1.72-1.69 (m, 2H), 1.49-1.35 (m, 11H). Mass (m/e): 388 (M+H)⁺.

Example 150

6-[2-tert-Butyl-1-(tetrahydropyran-4-ylmethyl)-1H-imidazol-4-yl]-N-methyl-N-(3-methyloxetan-3-ylmethyl)pyrazine-2-carboxamide (Compound 150)

The title compound 150 (23.0 mg, 0.05 mmol, yield: 27%) was obtained in the same manner as in Example 216 mentioned below, and then in Example 145, using methylamine hydrochloride and 3-(chloromethyl)-3-methyloxetane.
¹H-NMR (δppm, CDCl₃): 9.25-9.23 (m, 1H), 8.61-8.59 (m, 1H), 7.55-7.54 (m, 1H), 4.74-4.54 (m, 2H), 4.43-4.28 (m, 2H), 4.02 (dd, J=11.7, 3.5 Hz, 2H), 3.98 (d, J=7.6 Hz, 2H), 3.82-3.74 (m, 2H), 3.43-3.32 (m, 2H), 3.05 (s, 3H), 2.08-2.04 (m, 1H), 1.67-1.62 (m, 2H), 1.49-1.38 (m, 11H) 1.29-1.26 (m, 3H). Mass (m/e): 442 (M+H)⁺.

Example 151

6-[2-tert-Butyl-1-(tetrahydropyran-4-ylmethyl)-1H-imidazol-4-yl]-N-ethyl-N-(furan-2-ylmethyl)pyrazine-2-carboxamide (Compound 151)

The title compound 151 (50 mg, 0.11 mmol, yield: 69%) was obtained in the same manner as in Example 216 mentioned below, and then in Example 145, using furfurylamine instead of 2,2,2-trifluoroethylamine.
¹H-NMR (δppm, CDCl₃): 9.24-9.23 (m, 1H), 8.73-8.66 (m, 1H), 7.54-7.41 (m, 1H), 7.40-7.36 (m, 1H), 6.39-6.22 (m, 2H), 4.76-4.69 (m, 2H), 4.04-3.92 (m, 4H), 3.65-3.33 (m, 4H), 2.17-2.15 (m, 1H), 1.68-1.61 (m, 2H), 1.49-1.36 (m, 11H), 1.26-1.19 (m, 3H). Mass (m/e): 452 (M+H)⁺.

Example 152

6-[2-tert-Butyl-1-(tetrahydropyran-4-ylmethyl)-1H-imidazol-4-yl]-N-ethyl-N-(pyridin-3-ylmethyl)pyrazine-2-carboxamide (Compound 152)

The title compound 152 (36.0 mg, 0.08 mmol, yield: 61%) was obtained in the same manner as in Example 216 mentioned below, and then in Example 143, using 3-pyridylmethylamine instead of diethylamine.
¹H-NMR (δppm, CDCl₃): 9.27-9.25 (m, 1H), 8.83-8.57 (m, 3H), 7.82-7.79 (m, 1H), 7.54-6.89 (m, 2H), 4.79-4.74 (m, 2H), 4.04-3.80 (m, 4H), 3.54-3.32 (m, 4H), 2.17-2.08 (m, 1H), 1.69-1.62 (m, 2H), 1.49-1.35 (m, 11H), 1.27-1.22 (m, 3H). Mass (m/e): 463 (M+H)⁺.

Example 153

6-[2-tert-Butyl-1-(tetrahydropyran-4-ylmethyl)-1H-imidazol-4-yl]-N,N-dimethylpyrazine-2-carboxamide (Compound 153)

The title compound 153 (918 mg, 2.47 mmol, yield: 71%) was obtained in the same manner as in Example 143, using dimethylamine hydrochloride instead of diethylamine.
¹H-NMR (δppm, CDCl₃): 9.25 (s, 1H), 8.62 (s, 1H), 7.57 (s, 1H), 4.02 (dd, J=11.7, 3.5 Hz, 2H), 3.97 (d, J=7.4 Hz, 2H), 3.38 (dt, J=11.7, 2.1 Hz, 2H), 3.17 (s, 3H), 3.10 (s, 3H), 2.17-2.06 (m, 1H), 1.68-1.62 (m, 2H), 1.52-1.42 (m, 11H). Mass (m/e): 372 (M+H)⁺.

Example 154

6-[2-tert-Butyl-1-(tetrahydropyran-4-ylmethyl)-1H-imidazol-4-yl]-N-methyl-N-[2-(thiophen-2-yl)ethyl]pyrazine-2-carboxamide (Compound 154)

The title compound 154 (8.0 mg, 0.02 mmol, yield: 12%) was obtained in the same manner as in Example 216 mentioned below, and then in Example 145, using 2-(2-aminoethyl)thiophene and iodoethane.
¹H-NMR (δppm, CDCl₃): 9.24-9.23 (m, 1H), 8.59-8.43 (m, 1H), 7.56-7.46 (m, 1H), 7.11-7.08 (m, 1H), 6.95-6.67 (m, 2H), 3.98-3.68 (m, 6H), 3.39-3.24 (m, 4H), 3.18-3.00 (m, 3H), 2.18-1.90 (m, 1H), 1.64-1.55 (m, 2H), 1.49-1.29 (m, 11H). Mass (m/e): 468 (M+H)⁺.

Example 155

6-[2-tert-Butyl-1-(tetrahydropyran-4-ylmethyl)-1H-imidazol-4-yl]-N-ethyl-N-(tetrahydrofuran-2-ylmethyl)pyrazine-2-carboxamide (Compound 155)

The title compound 155 (56 mg, 0.12 mmol, yield: 70%) was obtained in the same manner as in Example 216 mentioned below, and then in Example 145, using tetrahydrofurylamine instead of 2,2,2-trifluoroethylamine.
¹H-NMR (δppm, CDCl₃): 9.24-9.21 (m, 1H), 8.64-8.61 (m, 1H), 7.56 (s, 1H), 4.33-4.12 (m, 1H), 4.04-3.31 (m, 13H), 2.18-2.08 (m, 1H), 1.99-1.90 (m, 1H), 1.71-1.62 (m, 4H), 1.49-1.40 (m, 11H), 1.33-1.18 (m, 3H). Mass (m/e): 456 (M+H)$^+$.

Example 156

6-[2-tert-Butyl-1-(tetrahydropyran-4-ylmethyl)-1H-imidazol-4-yl]-N-methyl-N-(thiophen-2-ylmethyl) pyrazine-2-carboxamide (Compound 156)

The title compound 156 (43 mg, 0.09 mmol, yield: 61%) was obtained in the same manner as in Example 216 mentioned below, and then in Example 145, using 2-thiophenemethylamine instead of 2,2,2-trifluoroethylamine, and iodomethane instead of iodoethane.
$^1$H-NMR (δppm, CDCl$_3$): 9.27-9.25 (m, 1H), 8.80-8.67 (m, 1H), 7.56-7.33 (m, 1H), 7.31-7.26 (m, 1H), 7.11-6.99 (m, 2H), 4.91 (s, 2H), 4.02-3.95 (m, 2H), 3.89 (d, J=7.2 Hz, 2H), 3.36 (dq, J=11.8, 2.5 Hz, 2H), 3.12-3.09 (m, 3H), 2.18-1.94 (m, 1H), 1.62-1.56 (m, 2H), 1.49-1.26 (m, 11H). Mass (m/e): 454 (M+H)$^+$.

Example 157

6-[2-tert-Butyl-1-(tetrahydropyran-4-ylmethyl)-1H-imidazol-4-yl]-N-methyl-N-[2-(methylsulphanyl) ethyl]pyrazine-2-carboxamide (Compound 157)

The title compound 157 (43 mg, 0.09 mmol, yield: 61%) was obtained in the same manner as in Example 216 mentioned below, and then in Example 145, using 2-(methylsulphanyl)ethylamine instead of 2,2,2-trifluoroethylamine, and iodomethane instead of iodoethane.
$^1$H-NMR (δppm, CDCl$_3$): 9.25 (s, 1H), 8.74-8.63 (m, 1H), 7.57 (s, 1H), 4.02 (dd, J=11.7, 7.4 Hz, 2H), 3.99 (d, J=7.4 Hz, 2H), 3.78-3.61 (m, 2H), 3.38 (dt, J=11.7, 1.5 Hz, 2H), 3.17-3.15 (m, 3H), 2.92-2.81 (m, 2H), 2.18-1.98 (m, 4H), 1.68-1.63 (m, 2H), 1.49-1.36 (m, 11H). Mass (m/e): 432 (M+H)$^+$.

Example 158

6-[2-tert-Butyl-1-(tetrahydropyran-4-ylmethyl)-1H-imidazol-4-yl]-N-methyl-N-(oxetan-3-yl)pyrazine-2-carboxamide (Compound 158)

The title compound 158 (26 mg, 0.06 mmol, yield: 14%) was obtained in the same manner as in Example 216 mentioned below, and then in Example 145, using 3-aminooxetane instead of 2,2,2-trifluoroethylamine, and iodomethane instead of iodoethane.
$^1$H-NMR (δppm, CDCl$_3$): 9.27-9.24 (m, 1H), 8.66-8.65 (m, 1H), 7.57-7.46 (m, 1H), 5.60-5.15 (m, 1H), 4.98-4.74 (m, 4H), 4.04-3.96 (m, 4H), 3.41-3.24 (m, 5H), 2.16-2.04 (m, 1H), 1.67-1.63 (m, 2H), 1.52-1.45 (m, 11H). Mass (m/e): 414 (M+H)$^+$.

Example 159

6-[2-tert-Butyl-1-(tetrahydropyran-4-ylmethyl)-1H-imidazol-4-yl]-N-ethyl-N-[2-(methylsulphanyl) ethyl]pyrazine-2-carboxamide (Compound 159)

The title compound 159 (45 mg, 0.10 mmol, yield: 37%) was obtained in the same manner as in Example 216 mentioned below, and then in Example 145, using 2-(methylsulphanyl)ethylamine instead of 2,2,2-trifluoroethylamine.
$^1$H-NMR (δppm, CDCl$_3$): 9.25 (s, 1H), 8.74-8.64 (m, 1H), 7.57-7.53 (m, 1H), 4.05-3.96 (m, 4H), 3.74-3.37 (m, 6H), 2.96-2.82 (m, 2H), 2.24-1.95 (m, 4H), 1.67-1.62 (m, 2H), 1.52-1.41 (m, 11H), 1.33-1.23 (m, 3H). Mass (m/e): 446 (M+H)$^+$.

Example 160

6-[2-tert-Butyl-1-(tetrahydropyran-4-ylmethyl)-1H-imidazol-4-yl]-N-ethyl-N-(2-methanesulfonylethyl) pyrazine-2-carboxamide (Compound 160)

Compound 159 (39.2 mg, 0.09 mmol) obtained in Example 159 was dissolved in chloroform (1 mL), and m-chloroperbenzoic acid (45.6 mg, 0.26 mmol) was added thereto, and then, the mixture was stirred at room temperature for 3 hours. The mixture was washed with saturated brine and dried over anhydrous magnesium sulfate, and the solvent was evaporated under reduced pressure. The residue was purified by silica gel column chromatography to give the title compound 160 (18 mg, 0.04 mmol, yield: 42%).
$^1$H-NMR (δppm, CDCl$_3$): 9.29-9.24 (m, 1H), 8.86-8.66 (m, 1H), 7.63-7.50 (m, 1H), 4.05-3.91 (m, 6H), 3.62-3.33 (m, 6H), 3.09-2.76 (m, 3H), 2.18-2.07 (m, 1H), 1.67-1.62 (m, 2H), 1.49-1.41 (m, 11H), 1.30-1.26 (m, 3H). Mass (m/e): 478 (M+H)$^+$.

Example 161

6-[2-tert-Butyl-1-(tetrahydropyran-4-ylmethyl)-1H-imidazol-4-yl]-N-methyl-N-(3-methylsulphanylpropyl)pyrazine-2-carboxamide (Compound 161)

The title compound 161 (68 mg, 0.15 mmol, yield: 38%) was obtained in the same manner as in Example 216 mentioned below, and then in Example 145, using 3-methylsulphanylpropylamine instead of 2,2,2-trifluoroethylamine, and iodomethane instead of iodoethane.
$^1$H-NMR (δppm, CDCl$_3$): 9.26-9.24 (m, 1H), 8.64-8.62 (m, 1H), 7.57 (s, 1H), 4.02 (dd, J=10.9, 3.9 Hz, 2H), 3.99 (d, J=7.6 Hz, 2H), 3.70-3.34 (m, 4H), 3.15-3.09 (m, 3H), 2.65-2.37 (m, 2H), 2.18-1.90 (m, 6H), 1.67-1.63 (m, 2H), 1.52-1.41 (m, 11H). Mass (m/e): 446 (M+H)$^+$.

Example 162

6-[2-tert-Butyl-1-(tetrahydropyran-4-ylmethyl)-1H-imidazol-4-yl]-N-(3-methanesulfinylpropyl)-N-methylpyrazine-2-carboxamide (Compound 162)

Compound 161 (57.0 mg, 0.13 mmol) obtained in Example 161 was dissolved in chloroform (1 mL), and m-chloroperbenzoic acid (45.7 mg, 0.26 mmol) was added thereto, and then, the mixture was stirred at room temperature for 3 hours. The mixture was washed with saturated brine and dried over anhydrous magnesium sulfate, and the solvent was evaporated under reduced pressure. The residue was purified by silica gel column chromatography to give the title compound 162 (18.0 mg, 0.04 mmol, 31%).
$^1$H-NMR (δppm, CDCl$_3$): 9.26 (s, 1H), 8.67-8.63 (m, 1H), 7.65-7.59 (m, 1H), 4.03-3.97 (m, 4H), 3.86-3.55 (m, 2H), 3.4-3.35 (m, 2H), 3.17-3.14 (m, 3H), 2.87-2.53 (m, 5H), 2.34-2.07 (m, 3H), 1.67-1.63 (m, 2H), 1.49-1.37 (m, 11H). Mass (m/e): 462 (M+H)$^+$

Example 163

6-[2-tert-Butyl-1-(tetrahydropyran-4-ylmethyl)-1H-imidazol-4-yl]-N-(3-methanesulfonylpropyl)-N-methylpyrazine-2-carboxamide (Compound 163)

Compound 163 (20 mg, 0.04 mmol, 31%) was obtained in the purification by silica gel column chromatography in Example 162.

$^1$H-NMR (δppm, CDCl$_3$): 9.30-9.27 (m, 1H), 8.70-8.63 (m, 1H), 7.69-7.58 (m, 1H), 4.04-3.97 (m, 4H), 3.77-3.35 (m, 4H), 3.22-3.05 (m, 5H), 2.98-2.90 (m, 3H), 2.42-2.10 (m, 3H), 1.64-1.59 (m, 2H), 1.52-1.37 (m, 11H). Mass (m/e): 478 (M+H)$^+$.

Example 164

{3-[2-tert-Butyl-1-(tetrahydropyran-4-ylmethyl)-1H-imidazol-4-yl]phenyl}cyclopropylethanone (Compound 164)

Step 1

3-Iodobenzoic acid (3.01 g, 12.1 mmol) was dissolved in DMF (30 mL), and HOBt.H$_2$O (2.45 g, 18.1 mmol), WSC.HCl (3.02 g, 15.8 mmol), N,O-dimethylhydroxylamine hydrochloride (1.30 g, 13.3 mmol), and triethylamine (1.86 mL, 14.6 mmol) were added thereto, and then, the mixture was stirred at room temperature for 4 hours. Water (60 mL) was added to the mixture, and the mixture was extracted with ethyl acetate. The organic layer was washed with saturated brine, a saturated aqueous sodium hydrogen carbonate solution, and saturated brine, and then, dried over anhydrous sodium sulfate. Then, the solvent was evaporated under reduced pressure, and the obtained residue was purified by silica gel flash column chromatography (ethyl acetate/n-heptane=100/0 to 50/50) to give 3-iodo-N-methoxy-N-methylbenzamide (3.23 g, yield: 82%).

$^1$H-NMR (δppm, CDCl$_3$): 8.02 (dd, J=1.3, 1.3 Hz, 1H), 7.79 (ddd, J=7.9, 1.3, 1.0 Hz, 1H), 7.64 (ddd, J=7.9, 1.3, 1.0 Hz, 1H), 7.14 (dd, J=7.9, 7.9 Hz, 1H), 3.55 (s, 3H), 3.35 (s, 3H).

Step 2

Compound u (0.191 g, 0.548 mmol) obtained in Reference example 21 was dissolved in THF (4.0 mL) and the solution was cooled to −78° C. Then, a solution of n-butyl lithium in n-hexane (1.6 mol/L; 0.51 mL, 0.82 mmol) was added thereto, and the mixture was stirred at the same temperature for 0.5 hours. To the mixture, trimethoxyborane (0.19 mL, 1.70 mmol) was added, and the mixture was stirred at 0° C. for 1 hour. To the reaction mixture, 3-iodo-N-methoxy-N-methylbenzamide (189 mg, 0.58 mmol) obtained in the above, diphenylphosphinoferrocene palladium dichloride-dichloromethane complex (36 mg, 0.04 mmol), and sodium tert-butoxide (158 mg, 1.64 mmol) were added, and the mixture was stirred at 50° C. for 3 hours. To the mixture, water (10 mL) was added, and the mixture was extracted with ethyl acetate. The organic layer was washed with saturated brine and dried over anhydrous sodium sulfate, and the solvent was evaporated under reduced pressure. The obtained residue was purified by NH silica gel flash column chromatography (ethyl acetate/n-heptane=100/0 to 40/60) to give 3-[2-tert-butyl-(1-tetrahydropyran-4-ylmethyl)-1H-imidazol-4-yl]-N-methoxy-N-methylbenzamide (174 mg, yield: 83%).

$^1$H-NMR (δppm, CDCl$_3$): 7.99 (dd, J=1.5, 1.5 Hz, 1H), 7.91 (ddd, J=7.6, 1.5, 1.5 Hz, 1H), 7.48 (ddd, J=7.6, 1.5, 1.5 Hz, 1H), 7.37 (dd, J=7.7, 7.7 Hz, 1H), 7.16 (s, 1H), 4.06-3.97 (m, 2H), 3.93 (d, J=7.3 Hz, 2H), 3.58 (s, 3H), 3.44-3.32 (m, 2H), 3.36 (s, 3H), 2.14-1.99 (m, 1H), 1.71-1.16 (m, 2H), 1.54-1.42 (m, 2H), 1.40 (s, 9H).

Step 3

3-[2-tert-Butyl-(1-tetrahydropyran-4-ylmethyl)-1H-imidazol-4-yl]-N-methoxy-N-methylbenzamide (56 mg, 0.15 mmol) obtained in the above was dissolved in THF (2.0 mL) and the solution was cooled to 0° C. Then, a THF solution of cyclopropyl magnesium bromide (0.5 mol/L; 435 μL, 0.22 mmol) was added to the solution, and the mixture was stirred at the same temperature for 1 hour and further stirred at room temperature for 1 hour. To the mixture, a THF solution of cyclopropyl magnesium bromide (0.5 mol/L; 435 μL, 0.22 mmol) was further added, and the mixture was stirred at room temperature for 2 hours. To the mixture, methanol (5 mL) and water (5 mL) were added, and the mixture was extracted with ethyl acetate. The organic layer was washed with saturated brine and dried over anhydrous sodium sulfate, and the solvent was evaporated under reduced pressure. The obtained residue was purified by silica gel flash column chromatography (chloroform/methanol=100/0 to 90/10) to give the title compound 164 (4 mg, 0.01 mmol, yield: 7%).

$^1$H-NMR (δppm, CDCl$_3$): 8.33 (dd, J=1.5, 1.5 Hz, 1H), 8.01 (ddd, J=7.7, 1.5, 1.5 Hz, 1H), 7.84 (ddd, J=7.7, 1.5, 1.5 Hz, 1H), 7.45 (dd, J=7.7, 7.7 Hz, 1H), 7.21 (s, 1H), 4.08-3.97 (m, 2H), 3.94 (d, J=7.5 Hz, 2H), 3.46-3.33 (m, 2H), 2.84-2.67 (m, 1H), 2.17-2.01 (m, 1H), 1.76-1.61 (m, 2H), 1.74 (s, 9H), 1.53-1.44 (m, 2H), 1.31-1.21 (m, 2H), 1.13-1.01 (m, 2H). Mass (m/e): 367 (M+H)$^+$.

Example 165

6-[2-tert-Butyl-1-(tetrahydropyran-4-ylmethyl)-1H-imidazol-4-yl]indan-1-one (Compound 165)

Step 1

6-Bromoindan-1-one (300 mg, 1.42 mmol), bis(pinacolate) diboron (433 mg, 1.70 mmol), [1,1'-bis(diphenylphosphino) ferrocene]dichloropalladium-methylene chloride complex (116 mg, 0.142 mmol), and potassium acetate (417 mg, 4.26 mmol) were dissolved in DMF (3.0 mL), and the mixture was stirred at 80° C. for 3 hours. After the mixture was left to cool to room temperature, water was added thereto, and the mixture was filtered through Celite. To the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=10/1 to 2/1) to give 6-(4,4,5,5-tetramethyl[1,3,2]dioxaboran-2-yl)indan-1-one (286 mg, 1.11 mmol, yield: 78%).

$^1$H-NMR (δppm, CDCl$_3$): 8.24 (s, 1H), 7.99 (d, J=7.3 Hz, 1H), 7.47 (d, J=7.6 Hz, 1H), 3.19-3.12 (m, 2H), 2.71-2.67 (m, 2H), 1.34 (s, 12H). Mass (m/e): 259 (M+H)$^+$.

Step 2

Compound u (316 mg, 0.91 mmol) obtained in Reference example 21 was dissolved in 1,4-dioxane-water (2/1) (6 mL), and 6-(4,4,5,5-tetramethyl[1,3,2]dioxaboran-2-yl)indan-1-one (281 mg, 1.09 mmol) obtained in the above, sodium carbonate (289 mg, 2.73 mmol), and [1,1'-bis(diphenylphosphino)ferrocene]dichloropalladium-methylene chloride complex (74 mg, 0.09 mmol) were added thereto, and the mixture was stirred at 80° C. for 1 hour. After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give the title compound 165 (191 mg, 0.54 mmol, yield: 60%).

$^1$H-NMR (δppm, CDCl$_3$): 8.13 (dd, J=8.0, 1.6 Hz, 1H), 8.04 (d, J=1.6 Hz, 1H), 7.46 (d, J=8.0 Hz, 1H), 7.18 (s, 1H), 4.06-3.97 (m, 2H), 3.94 (d, J=7.3 Hz, 2H), 3.43-3.32 (m, 2H), 3.18-3.09 (m, 2H), 2.76-2.68 (m, 2H), 2.14-2.00 (m, 1H), 1.72-1.61 (m, 2H), 1.53-1.33 (m, 2H), 1.48 (s, 9H). Mass (m/e): 353 (M+H)$^+$.

Example 166

4-[2-tert-Butyl-1-(tetrahydropyran-4-ylmethyl)-1H-imidazol-4-yl]-2-ethyl-2,3-dihydroisoindol-1-one (Compound 166)

To a solution of Compound 217 (100 mg, 0.28 mmol) obtained in Example 217 mentioned below in DMF (2.0 mL), sodium hydride (14 mg, 0.35 mmol) was added under ice-cooling in an argon atmosphere, and the mixture was stirred at room temperature for 30 minutes. Then, ethyl iodide (90 μL, 1.13 mmol) was added thereto, and the mixture was stirred at room temperature for 1 hour. Water was added to the mixture, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5), and the obtained crude crystals were reslurried in heptane to give the title compound 166 (80 mg, 0.21 mmol, yield: 74%).

$^1$H-NMR (δppm, CDCl$_3$): 7.74 (dd, J=7.4, 1.0 Hz, 1H), 7.68 (dd, J=7.3, 1.0 Hz, 1H), 7.40 (dd, J=7.4, 7.3 Hz, 1H), 7.17 (s, 1H), 4.75 (s, 2H), 4.04-3.94 (m, 2H), 3.96 (d, J=7.1 Hz, 2H), 3.71 (q, J=7.2 Hz, 2H), 3.44-3.31 (m, 2H), 2.16-1.98 (m, 1H), 1.72-1.59 (m, 2H), 1.53-1.35 (m, 2H), 1.48 (s, 9H), 1.29 (t, J=7.2 Hz, 3H). Mass (m/e): 382 (M+H)$^+$.

Example 167

5-[2-tert-Butyl-1-(tetrahydropyran-4-ylmethyl)-1H-imidazol-4-yl]-2-fluoro-N,N-dimethylbenzamide (Compound 167)

Step 1
5-Bromo-2-fluorobenzoic acid (500 mg, 2.23 mmol) was dissolved in DMF (5.0 mL), and dimethylamine hydrochloride (223 mg, 2.72 mmol), WSC.HCl (511 mg, 2.66 mmol), HOBt.H$_2$O (410 mg, 2.68 mmol), and potassium carbonate (367 mg, 2.66 mmol) were added thereto, and the mixture was stirred at room temperature for 3 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50) to give 5-bromo-2-fluoro-N,N-dimethylbenzamide (550 mg, 2.23 mmol, yield: 99%).

$^1$H-NMR (δppm, CDCl$_3$): 7.55-7.45 (m, 2H), 7.03-6.95 (m, 1H), 3.12 (s, 3H), 2.94 (d, J=1.3 Hz, 3H).
Step 2
2-Fluoro-N,N-dimethyl-5-(4,4,5,5-tetramethyl[1,3,2]dioxaboran-2-yl)benzamide (654 mg, 2.23 mmol, yield: 99%) was obtained in the same manner as in step 1 of Example 165, using 5-bromo-2-fluoro-N,N-dimethylbenzamide obtained in the above instead of 6-bromoindan-1-one.

$^1$H-NMR (δppm, CDCl$_3$): 7.87-7.77 (m, 2H), 7.11-7.04 (m, 1H), 3.12 (s, 3H), 2.92 (d, J=1.3 Hz, 3H), 1.33 (s, 12H). Mass (m/e): 294 (M+H)$^+$.
Step 3
The title compound 167 (730 mg, 1.89 mmol, yield: 66%) was obtained in the same manner as in step 2 of Example 165, using 2-fluoro-N,N-dimethyl-5-(4,4,5,5-tetramethyl[1,3,2]dioxaboran-2-yl)benzamide obtained in the above instead of 6-(4,4,5,5-tetramethyl[1,3,2]dioxaboran-2-yl)indan-1-one.

$^1$H-NMR (δppm, CDCl$_3$): 7.85-7.82 (m, 1H), 7.72 (dd, J=6.2, 2.0 Hz, 1H), 7.11-7.02 (m, 2H), 4.06-3.96 (m, 2H), 3.92 (d, J=7.3 Hz, 2H), 3.45-3.30 (m, 2H), 3.14 (s, 3H), 2.94 (d, J=1.5 Hz, 3H), 2.13-1.98 (m, 1H), 1.72-1.57 (m, 2H), 1.50-1.32 (m, 2H), 1.46 (s, 9H). Mass (m/e): 388 (M+H)$^+$.

Example 168

4-[2-tert-Butyl-1-(tetrahydropyran-4-ylmethyl)-1H-imidazol-4-yl]-N-ethyl-N-methylquinoline-2-carboxamide (Compound 168)

Step 1
4-Hydroxyquinoline-2-carboxylic acid (1.00 g, 5.29 mmol) was dissolved in DMF (10 mL), and N-ethylmethylamine (91 μL, 10.6 mmol), WSC.HCl (2.03 g, 10.6 mmol), and HOBt.H$_2$O (1.62 g, 10.6 mmol), were added thereto, and the mixture was stirred at room temperature for 3 hours. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give N-ethyl-4-hydroxy-N-methyl-quinoline-2-carboxamide (615 mg, 2.67 mmol, yield: 50%). Mass (m/e): 231 (M+H)$^+$.
Step 2
N-Ethyl-4-hydroxy-N-methylquinoline-2-carboxamide (615 mg, 2.67 mmol) obtained in the above was dissolved in pyridine (8.0 mL), and trifluoromethanesulfonic anhydride (1.0 mL, 5.92 mmol) was added thereto under ice-cooling in an argon atmosphere, and then, the mixture was stirred at room temperature for 30 minutes. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=98/2) to give N-ethyl-N-methyl-4-trifluoromethanesulfonyloxyquinoline-2-carboxamide (914 mg, 2.52 mmol, yield: 94%).

$^1$H-NMR (δppm, CDCl$_3$): 8.19 (dd, J=8.3, 3.6 Hz, 1H), 8.10 (d, J=8.3 Hz, 1H), 7.92-7.84 (m, 1H), 7.82-7.72 (m, 2H), 3.78-3.46 (m, 2H), 3.23-3.15 (m, 3H), 1.37-1.27 (m, 3H). Mass (m/e): 363 (M+H)$^+$.
Step 3
2-tert-Butyl-1-(tetrahydropyran-4-yl)methyl-4-tributylstannyl-1H-imidazole (99 mg, 0.19 mmol) obtained in Step 1 of Example 108, was dissolved in DMF (1.0 mL), and N-ethyl-4-trifluoromethanesulfonyloxy-N-methylquinoline-2-carboxamide (96 mg, 0.39 mmol) obtained in the above, tetrakis(triphenylphosphine)palladium(0) (23 mg, 0.02 mmol), and lithium chloride (41 mg, 0.98 mmol) were added thereto, and then, the mixture was stirred at 100° C. for 1 hour. After the mixture was left to cool to room temperature, an aqueous potassium fluoride solution was added thereto, and the mixture was stirred at room temperature for 1 hour, and then, the mixture was filtered through Celite. To the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give the title compound 168 (14 mg, 0.03 mmol, yield: 17%).

$^1$H-NMR (δppm, CDCl$_3$): 9.03-8.94 (m, 1H), 8.12-8.02 (m, 1H) 7.87 (s, 1H), 7.74-7.63 (m, 1H), 7.61-7.53 (m, 1H), 7.36 (s, 1H), 4.06-3.95 (m, 4H), 3.78-3.46 (m, 2H), 3.46-3.30 (m, 2H), 3.18-3.07 (m, 3H), 2.17-2.04 (m, 1H), 1.74-1.60 (m, 2H), 1.55-1.35 (m, 2H), 1.53 (s, 9H), 1.35-1.18 (m, 3H). Mass (m/e): 435 (M+H)$^+$.

Example 169

5-[2-tert-Butyl-1-(tetrahydropyran-4-ylmethyl)-1H-imidazol-4-yl]-N,N-diethyl-2-fluoronicotinamide (Compound 169)

Step 1

5-Bromo-N,N-diethyl-2-fluoronicotinamide (31 mg, 0.11 mmol, yield: 75%) was obtained in the same manner as in Example 9, using 5-bromo-2-fluoronicotinic acid instead of Compound c.

$^1$H-NMR (δppm, CDCl$_3$): 8.32-8.28 (m, 1H), 7.90 (dd, J=7.8, 2.5 Hz, 1H), 3.57 (q, J=7.1 Hz, 2H), 3.22 (q, J=7.1 Hz, 2H), 1.26 (t, J=7.1 Hz, 3H), 1.14 (t, J=7.1 Hz, 3H). Mass (m/e): 275, 277 (M+H)$^+$.

Step 2

The title compound 169 (8.0 mg, 0.02 mmol, yield: 17%) was obtained in the same manner as in step 3 of Example 168, using 5-bromo-N,N-diethyl-2-fluoronicotinamide obtained in the above instead of N-ethyl-N-methyl-4-trifluoromethanesulfonyloxyquinoline-2-carboxamide.

$^1$H-NMR (δppm, CDCl$_3$): 8.57 (dd, J=2.3, 1.2 Hz, 1H), 8.14 (dd, J=8.8, 2.3 Hz, 1H), 7.14 (s, 1H), 4.06-3.98 (m, 2H), 3.94 (d, J=7.4 Hz, 2H), 3.58 (q, J=7.1 Hz, 2H), 3.45-3.33 (m, 2H), 3.24 (q, J=7.1 Hz, 2H), 2.14-2.00 (m, 1H), 1.71-1.59 (m, 2H), 1.51-1.35 (m, 2H), 1.47 (s, 9H), 1.27 (t, J=7.1 Hz, 3H), 1.12 (t, J=7.1 Hz, 3H). Mass (m/e): 417 (M+H)$^+$.

Example 170

6-Amino-5-[2-tert-butyl-1-(tetrahydropyran-4-ylmethyl)-1H-imidazol-4-yl]-N-ethyl-N-methylnicotinamide (Compound 170)

Step 1

6-Amino-5-bromo-N-ethyl-N-methylnicotinamide (501 mg, 1.94 mmol, yield: 84%) was obtained in the same manner as in step 1 of Example 168, using 6-amino-5-bromonicotinic acid instead of 4-hydroxyquinoline-2-carboxylic acid.

$^1$H-NMR (δppm, CDCl$_3$): 8.13 (d, J=2.0 Hz, 1H), 7.80 (d, J=2.0 Hz, 1H), 5.11 (s, 2H), 3.46 (brs, 2H), 3.04 (s, 3H), 1.21 (t, J=7.2 Hz, 3H). Mass (m/e): 258, 260 (M+H)$^+$.

Step 2

The title compound 170 (52 mg, 0.13 mmol, yield: 60%) was obtained in the same manner as in step 3 of Example 168, using 6-amino-5-bromo-N-ethyl-N-methylnicotinamide obtained in the above instead of N-ethyl-N-methyl-4-trifluoromethanesulfonyloxyquinoline-2-carboxamide.

$^1$H-NMR (δppm, CDCl$_3$): 8.03 (d, J=1.5 Hz, 1H), 7.76 (d, J=1.5 Hz, 1H), 7.19 (s, 1H), 6.92 (brs, 2H), 4.07-3.97 (m, 2H), 3.94 (d, J=7.4 Hz, 2H), 3.57-3.30 (m, 4H), 3.05 (s, 3H), 2.06-1.96 (m, 1H), 1.72-1.54 (m, 2H), 1.54-1.32 (m, 2H), 1.48 (s, 9H), 1.33-1.14 (m, 3H). Mass (m/e): 400 (M+H)$^+$.

Example 171

8-[2-tert-Butyl-1-(tetrahydropyran-4-ylmethyl)-1H-imidazol-4-yl]-N-ethyl-N-methylimidazo[1,2-a]pyridine-6-carboxamide (Compound 171)

Step 1

6-Amino-5-bromo-N-ethyl-N-methylnicotinamide (250 mg, 0.97 mmol) obtained in Step 1 of Example 170 was dissolved in ethanol (2.5 mL), and a 50% aqueous chloroacetaldehyde solution was added thereto, and the mixture was stirred overnight under reflux. After the mixture was left to cool to room temperature, an aqueous sodium hydrogen carbonate solution was added thereto, and the mixture was extracted with a chloroform/isopropanol (6/1) mixed solution. The organic layer was washed with saturated brine and dried over anhydrous magnesium sulfate, and the solvent was evaporated under reduced pressure. The residue was purified by silica gel column chromatography (chloroform/methanol=98/2) to give 8-bromo-N-ethyl-N-methylimidazo[1,2-a]pyridine-6-carboxamide (65 mg, 0.23 mmol, yield: 24%).

$^1$H-NMR (δppm, CDCl$_3$): 8.31 (d, J=1.3 Hz, 1H), 7.75 (d, J=1.2 Hz, 1H), 7.71 (d, J=1.2 Hz, 1H), 7.49 (d, J=1.3 Hz, 1H), 3.49 (brs, 2H), 3.07 (s, 3H), 1.24 (t, J=7.1 Hz, 3H). Mass (m/e): 282, 284 (M+H)$^+$.

Step 2

The title compound 171 (15 mg, 0.04 mmol, yield: 22%) was obtained in the same manner as in step 3 of Example 168, using 8-bromo-N-ethyl-N-methylimidazo[1,2-a]pyridine-6-carboxamide obtained in the above instead of N-ethyl-N-methyl-4-trifluoromethanesulfonyloxyquinoline-2-carboxamide.

$^1$H-NMR (δppm, CDCl$_3$): 8.26 (s, 1H), 8.22 (d, J=1.5 Hz, 1H), 8.06 (d, J=1.5 Hz, 1H), 7.70 (d, J=1.2 Hz, 1H), 7.62 (d, J=1.2 Hz, 1H), 4.04-3.96 (m, 4H), 3.59-3.33 (m, 4H), 3.10 (s, 3H), 2.28-2.17 (m, 1H), 1.71-1.57 (m, 2H), 1.52-1.38 (m, 2H), 1.50 (s, 9H), 1.32-1.23 (m, 3H). Mass (m/e): 424 (M+H)$^+$.

Example 172

4-[2-tert-Butyl-1-(tetrahydropyran-4-ylmethyl)-1H-imidazol-4-yl]-N,N-diethylpyrimidine-2-carboxamide (Compound 172)

Step 1 n-Propyl 4-[2-tert-butyl-1-(tetrahydropyran-4-ylmethyl)-1H-imidazol-4-yl]pyrimidine-2-carboxylate (27 mg, 0.08 mmol, yield: 44%) was obtained in the same manner as in Reference example 2, using Compound 218 obtained in Example 218 instead of Compound 8.

$^1$H-NMR (δppm, CDCl$_3$): 8.78 (d, J=5.3 Hz, 1H), 8.03 (d, J=5.3 Hz, 1H), 7.88 (s, 1H), 4.42 (t, J=6.9 Hz, 2H), 4.07-3.95 (m, 4H), 3.48-3.33 (m, 2H), 2.21-2.08 (m, 1H), 1.89 (tt, J=7.4, 6.9 Hz, 2H), 1.69-1.56 (m, 2H), 1.53-1.34 (m, 2H), 1.48 (s, 9H), 1.04 (t, J=7.4 Hz, 3H). Mass (m/e): 387 (M+H)$^+$.

Step 2

4-[2-tert-Butyl-1-(tetrahydropyran-4-ylmethyl)-1H-imidazol-4-yl]pyrimidine-2-carboxylic acid (53 mg, 0.15 mmol, yield: 99%) was obtained in the same manner as in Reference example 3, using n-propyl 4-[2-tert-butyl-1-(tetrahydropyran-4-ylmethyl)-1H-imidazol-4-yl]pyrimidine-2-carboxylate obtained in the above instead of Compound b.

¹H-NMR (δppm, CDCl₃): 8.78 (d, J=5.3 Hz, 1H), 8.09 (d, J=5.3 Hz, 1H), 7.92 (s, 1H), 4.09-3.95 (m, 4H), 3.47-3.33 (m, 2H), 2.23-2.07 (m, 1H), 1.72-1.57 (m, 2H), 1.55-1.36 (m, 2H), 1.49 (s, 9H). Mass (m/e): 345 (M+H)⁺.

Step 3

The title compound 172 (45 mg, 0.11 mmol, yield: 75%) was obtained in the same manner as in Example 9, using 4-[2-tert-butyl-1-(tetrahydropyran-4-ylmethyl)-1H-imidazol-4-yl]pyrimidine-2-carboxylic acid obtained in the above instead of Compound c.

¹H-NMR (δppm, CDCl₃): 8.65 (d, J=5.3 Hz, 1H), 7.88 (d, J=5.3 Hz, 1H), 7.75 (s, 1H), 4.04-3.95 (m, 2H), 3.95 (d, J=7.4 Hz, 2H), 3.60 (q, J=7.1 Hz, 2H), 3.43-3.32 (m, 2H), 3.21 (q, J=7.1 Hz, 2H), 2.17-2.07 (m, 1H), 1.68-1.56 (m, 2H), 1.52-1.36 (m, 2H), 1.47 (s, 9H), 1.30 (t, J=7.1 Hz, 3H), 1.14 (t, J=7.1 Hz, 3H). Mass (m/e): 400 (M+H)⁺.

Example 173

5-[2-tert-Butyl-1-(tetrahydropyran-4-ylmethyl)-1H-imidazol-4-yl]-N,N-diethyl-2-(methylamino)benzamide (Compound 173)

Compound 66 (55 mg, 0.13 mmol) obtained in Example 66 was dissolved in a 40% aqueous methylamine solution (0.5 mL), and the mixture was stirred at 180° C. for 1 hour in a microwave-assisted chemical synthesis instrument (CEM Discover). After the mixture was left to cool to room temperature, an aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=97/3) to give the title compound 173 (2.2 mg, 0.01 mmol, yield: 8%).

¹H-NMR (δppm, CDCl₃): 7.64 (dd, J=8.4, 1.8 Hz, 1H), 7.50 (d, J=1.8 Hz, 1H), 6.92 (s, 1H), 6.66 (d, J=8.4 Hz, 1H), 4.04-3.95 (m, 2H), 3.89 (d, J=6.9 Hz, 2H), 3.50-3.30 (m, 6H), 2.82 (s, 3H), 2.12-1.95 (m, 1H), 1.70-1.60 (m, 2H), 1.55-1.33 (m, 2H), 1.46 (s, 9H), 1.20 (t, J=7.3 Hz, 6H). Mass (m/e): 427 (M+H)⁺.

Example 174

3-Acetyl-5-[2-tert-butyl-1-(tetrahydropyran-4-ylmethyl)-1H-imidazol-4-yl]-N,N-diethylbenzamide (Compound 174)

The title compound 174 (73 mg, 0.17 mmol, yield: 42%) was obtained in the same manner as in Example 49, using Compound 67 obtained in Example 67 instead of Compound 43.

¹H-NMR (δppm, CDCl₃): 8.33 (s, 1H), 8.00 (s, 1H), 7.77 (s, 1H), 7.21 (s, 1H), 4.08-3.89 (m, 4H), 3.63-3.27 (m, 6H), 2.63 (s, 3H), 2.17-2.00 (m, 1H), 1.73-1.56 (m, 2H), 1.55-1.33 (m, 2H), 1.48 (s, 9H), 1.31-1.13 (m, 6H). Mass (m/e): 440 (M+H)⁺.

Example 175

3-[2-tert-Butyl-1-(tetrahydropyran-4-ylmethyl)-1H-imidazol-4-yl]-N,N-diethyl-5-(1-hydroxylethyl)benzamide (Compound 175)

The title compound 175 (64 mg, 0.15 mmol, yield: 80%) was obtained in the same manner as in Example 30, using Compound 174 obtained in Example 174 instead of Compound f.

¹H-NMR (δppm, CDCl₃): 7.83-7.80 (m, 1H), 7.65-7.61 (m, 1H), 7.22-7.19 (m, 1H), 7.13 (s, 1H), 4.93 (q, J=6.1 Hz, 1H), 4.06-3.94 (m, 2H), 3.92 (d, J=7.6 Hz, 2H), 3.62-3.12 (m, 6H), 2.14-2.00 (m, 1H), 1.91 (brs, 1H), 1.70-1.56 (m, 2H), 1.55-1.32 (m, 2H), 1.52 (d, J=6.1 Hz, 3H), 1.47 (s, 9H), 1.27-1.09 (m, 6H). Mass (m/e): 442 (M+H)⁺.

Example 176

6-[2-tert-Butyl-1-(3,6-dihydro-2H-pyran-4-ylmethyl)-1H-imidazol-4-yl]-N-methyl-N-propylpyrazine-2-carboxamide (Compound 176)

Step 1

(3,6-Dihydro-2H-pyran-4-yl)methylmethanesulfonate (19 mg, 0.10 mmol, yield: 57%) was obtained in the same manner as in step 2 of Example 45, using (3,6-dihydro-2-H-pyran-4-yl)methanol obtained by the method described in J. Am. Chem. Soc., vol. 125, p. 4704 (2003) instead of (tetrahydropyran-4-yl)methanol.

¹H-NMR (δppm, CDCl₃): 5.94-5.90 (m, 1H), 4.65-4.63 (m, 2H), 4.20-4.15 (m, 2H), 3.85-3.80 (m, 2H), 3.03 (s, 3H), 2.22-2.16 (m, 2H).

Step 2

The title compound 176 (16 mg, 0.04 mmol, yield: 24%) was obtained in the same manner as in Example 177 mentioned below, using (3,6-dihydro-2H-pyran-4-yl)methylmethanesulfonate obtained in the above instead of 4-benzyl-2-(chloromethyl)morpholine.

¹H-NMR (δppm, CDCl₃): 9.25-9.23 (m, 1H), 8.63-8.61 (m, 1H), 7.52-7.46 (m, 1H), 5.48-5.42 (m, 1H), 4.64 (s, 2H), 4.18-4.12 (m, 2H), 3.84-3.77 (m, 2H), 3.58-3.25 (m, 2H), 3.14-3.04 (m, 3H), 2.12-2.02 (m, 2H), 1.82-1.63 (m, 2H), 1.48 (s, 9H), 1.05-0.76 (m, 3H). Mass (m/e): 398 (M+H)⁺.

Example 177

6-[1-(4-Benzylmorpholin-2-ylmethyl)-2-tert-butyl-1H-imidazol-4-yl]-N-methyl-N-propylpyrazine-2-carboxamide (Compound 177)

Compound v (667 mg, 2.21 mmol) obtained in Reference example 22 was dissolved in DMF (7.0 mL), and 4-benzyl-2-(chloromethyl)morpholine (600 mg, 2.65 mmol) obtained by the method described in J. Med. Chem., vol. 33, p. 1406 (1990) and cesium carbonate (3.59 g, 11.0 mmol) were added thereto, and the mixture was stirred overnight at 90° C. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give the title compound 177 (336 mg, 0.68 mmol, yield: 31%).

¹H-NMR (δppm, CDCl₃): 9.24-9.20 (m, 1H), 8.63-8.61 (m, 1H), 7.68-7.64 (m, 1H), 7.37-7.24 (m, 5H), 4.12-4.07 (m, 2H), 3.92-3.82 (m, 2H), 3.67-3.27 (m, 5H), 3.15-3.06 (m, 3H), 2.85-2.62 (m, 2H), 2.25-2.12 (m, 1H), 2.04-1.93 (m, 1H), 1.79-1.65 (m, 2H), 1.46 (s, 9H), 1.05-0.78 (m, 3H). Mass (m/e): 491 (M+H)⁺.

Example 178

6-[2-tert-Butyl-1-(morpholin-2-ylmethyl)-1H-imidazol-4-yl]-N-methyl-N-propylpyrazine-2-carboxamide (Compound 177)

Step 1

The title compound 178 (111 mg, 0.28 mmol, yield: 47%) was obtained in the same manner as in Example 87, using Compound 177 obtained in Example 177 instead of Compound 70.

¹H-NMR (δppm, CDCl₃): 9.24-9.21 (m, 1H), 8.64-8.61 (m, 1H), 7.69-7.65 (m, 1H), 4.12-4.07 (m, 2H), 3.97-3.71 (m, 2H), 3.64-3.27 (m, 3H), 3.16-3.06 (m, 3H), 3.02-2.79 (m, 3H), 2.72-2.61 (m, 1H), 2.25 (brs, 1H), 1.80-1.67 (m, 2H), 1.48 (s, 9H), 1.06-0.79 (m, 3H). Mass (m/e): 401 (M+H)⁺.

Example 179

6-[1-(4-Benzyl-5-oxomorpholin-2-ylmethyl)-2-tert-butyl-1H-imidazol-4-yl]-N-methyl-N-propylpyrazine-2-carboxamide (Compound 179)

The title compound 179 (120 mg, 0.24 mmol, yield: 13%) was obtained in the same manner as in step 1 of Example 177, using 4-benzyl-2-chloromethylmorpholin-3-one obtained by the method described in U.S. 636218 instead of 4-benzyl-2-(chloromethyl)morpholine.

¹H-NMR (δppm, CDCl₃): 9.24-9.21 (m, 1H), 8.64-8.62 (m, 1H), 7.64-7.60 (m, 1H), 7.41-7.23 (m, 5H), 4.72-4.56 (m, 2H), 4.46-4.35 (m, 1H), 4.24-3.98 (m, 4H), 3.59-3.15 (m, 4H), 3.16-3.03 (m, 3H), 1.79-1.65 (m, 2H), 1.44 (s, 9H), 1.05-0.77 (m, 3H). Mass (m/e): 505 (M+H)⁺.

Example 180

6-[2-tert-Butyl-1-(1,1-dioxotetrahydrothiopyran-4-ylmethyl)-1H-imidazol-4-yl]-N-methyl-N-propylpyrazine-2-carboxamide (Compound 180)

Step 1

(Tetrahydrothiopyran-4-yl)methylmethanesulfonate (870 mg, 4.14 mmol, yield: 59%) was obtained in the same manner as in step 2 of Example 45, using (tetrahydrothiopyran-4-yl)methanol obtained by the method described in US2007/082931 instead of (tetrahydropyran-4-yl)methanol.

¹H-NMR (δppm, CDCl₃): 4.04 (d, J=6.4 Hz, 2H), 3.01 (s, 3H), 2.81-2.56 (m, 4H), 2.15-2.04 (m, 2H), 1.89-1.71 (m, 1H), 1.56-1.38 (m, 2H).

Step 2

(Trahydrothiopyran-4-yl)methylmethanesulfonate (60 mg, 0.29 mmol) obtained in the above was dissolved in chloroform (3.0 mL), and m-chloroperbenzoic acid (150 mg, 0.87 mmol) was added thereto, and then, the mixture was stirred at room temperature for 1 hour. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give (1,1-dioxotetrahydrothiopyran-4-yl)methylmethanesulfonate (41 mg, 0.17 mmol, yield: 60%).

¹H-NMR (δppm, CDCl₃): 4.13 (d, J=5.9 Hz, 2H), 3.16-2.96 (m, 4H), 3.05 (s, 3H), 2.26-2.16 (m, 2H), 2.10-1.92 (m, 3H).

Step 3

The title compound 180 (22 mg, 0.05 mmol, yield: 79%) was obtained in the same manner as in step 1 of Example 177, using (1,1-dioxotetrahydrothiopyran-4-yl)methyl-methanesulfonate obtained in the above instead of 4-benzyl-2-(chloromethyl)morpholine.

¹H-NMR (δppm, CDCl₃): 9.26-9.23 (m, 1H), 8.61 (s, 1H), 7.57-7.51 (m, 1H), 4.05 (d, J=6.6 Hz, 2H), 3.58-3.24 (m, 2H), 3.16-2.90 (m, 7H), 2.19-1.94 (m, 5H), 1.81-1.62 (m, 2H), 1.49 (s, 9H), 1.06-0.74 (m, 3H). Mass (m/e): 448 (M+H)⁺.

Example 181

6-[2-tert-Butyl-1-([1,4]dioxepan-6-ylmethyl)-1H-imidazol-4-yl]-N-methyl-N-propylpyrazine-2-carboxamide (Compound 181)

Step 1

Under an argon atmosphere, 6-methylene-[1,4]-dioxepane (200 mg, 1.75 mmol) obtained by the method described in Liebigs Ann. Chem., vol. 736, p. 75 (1970) was dissolved in THF (5.0 mL), and a THF solution of borane (1.0 mol/L; 1.9 mL, 1.9 mmol) was added thereto under ice-cooling, and then, the mixture was stirred at room temperature for 2 hours. To the mixture, a 37% aqueous hydrogen peroxide solution (0.54 mL, 5.25 mmol) and a 10% aqueous sodium hydroxide solution (1.9 mL, 5.25 mmol) were added under ice-cooling, and the mixture was stirred at room temperature for 1 hour. Water was added to the mixture, and the mixture was extracted with chloroform/isopropanol (6/1). The organic layer was washed with saturated brine and dried over anhydrous magnesium sulfate, and the solvent was evaporated under reduced pressure. The residue was purified by silica gel column chromatography (chloroform/methanol=95/5) to give ([1,4]-dioxepan-6-yl)methanol (81 mg, 0.61 mmol, yield: 70%).

¹H-NMR (δppm, CDCl₃): 4.02-3.93 (m, 2H), 3.83-3.71 (m, 6H), 3.69-3.60 (m, 2H), 2.29-2.17 (m, 1H).

Step 2

([1,4]-dioxepan-6-yl)methylmethanesulfonate (111 mg, 0.53 mmol, yield: 87%) was obtained in the same manner as in step 2 of Example 45, using ([1,4]-dioxepan-6-yl)methanol obtained in the above instead of (tetrahydropyran-4-yl)-methanol.

¹H-NMR (δppm, CDCl₃): 4.26-4.22 (m, 2H), 3.99-3.90 (m, 2H), 3.79-3.70 (m, 6H), 3.03 (s, 3H), 2.53-2.41 (m, 1H).

Step 3

The title compound 181 (150 mg, 0.36 mmol, yield: 84%) was obtained in the same manner as in step 1 of Example 177, using ([1,4]-dioxepan-6-yl)methylmethanesulfonate obtained in the above instead of 4-benzyl-2-(chloromethyl) morpholine.

¹H-NMR (δppm, CDCl₃): 9.24-9.23 (m, 1H), 8.63-8.62 (m, 1H), 7.60-7.57 (m, 1H), 4.14 (dd, J=7.7, 1.8 Hz, 2H), 3.95-3.87 (m, 2H), 3.82-3.79 (m, 4H), 3.71 (dd, J=12.8, 4.8 Hz, 2H), 3.57-3.28 (m, 2H), 3.14-3.05 (m, 3H), 2.57-2.45 (m, 1H), 1.78-1.66 (m, 2H), 1.50 (s, 9H), 1.05-0.77 (m, 3H). Mass (m/e): 416 (M+H)⁺.

Example 182

6-[2-tert-Butyl-1-(4-methoxytetrahydropyran-4-ylmethyl)-1H-imidazol-4-yl]-N-methyl-N-propylpyrazine-2-carboxamide (Compound 182)

Step 1

Under an argon atmosphere, 4,4-dimethoxytetrahydropyran (4.39 g, 30.0 mmol) was dissolved in dichloromethane (60 mL), and tert-butyl isocyanide (3.73 mL, 33.0 mmol) and titanium tetrachloride (3.95 mL, 36.8 mmol) were added thereto at −78° C., and then, the mixture was stirred overnight at room temperature. To the mixture, an aqueous sodium hydrogen carbonate solution was added, and the mixture was filtered through Celite, and then, the filtrate was extracted with chloroform. The organic layer was washed with saturated brine and dried over anhydrous magnesium sulfate, and the solvent was evaporated under reduced pressure. The residue was purified by silica gel column chromatography (hexane/ethyl acetate=80/20) to give 4-methoxytetrahydropyran-4-carbonitrile (3.30 g, 23.4 mmol, yield: 78%).

¹H-NMR (δppm, CDCl₃): 3.98-3.89 (m, 2H), 3.72-3.62 (m, 2H), 3.47 (s, 3H), 2.18-2.08 (m, 2H), 1.92-1.81 (m, 2H).
Step 2
4-Methoxytetrahydropyran-4-carbonitrile (3.30 g, 232.2 mmol) obtained in the above was dissolved in water (30 mL), and potassium hydroxide (9.90 g, 177 mmol) was added thereto, and then, the mixture was stirred under reflux for 4 hours. The mixture was left to cool to room temperature, and then washed with diethyl ether. To the aqueous layer, concentrated hydrochloric acid (20 mL) was added, and the mixture was extracted with chloroform-isopropanol (6/1). The organic layer was dried over anhydrous magnesium sulfate, and the solvent was evaporated under reduced pressure to give a roughly purified product of 4-methoxytetrahydropyran-4-carboxylic acid (3.73 g, 23.2 mmol, yield: 99%). This roughly purified product was used in the subsequent step as such.
Step 3
Under an argon atmosphere, lithium aluminum hydride (240 mg, 6.24 mmol) was suspended in THF (20 mL), and the roughly purified product of 4-methoxytetrahydropyran-4-carboxylic acid (1.00 g, 6.24 mmol) obtained in the above was gently added thereto under ice-cooling, and then, the mixture was stirred at room temperature for 1 hour. To the mixture, water (0.24 mmol), a 15% aqueous sodium hydroxide solution (0.24 mL), and water (0.72 mL) were sequentially added under ice-cooling, and then, the mixture was stirred at room temperature for 30 minutes. The mixture was filtered through Celite, and the solvent was evaporated under reduced pressure. The residue was purified by silica gel column chromatography (hexane/ethyl acetate=1/1) to give (4-methoxytetrahydropyran-4-yl)methanol (428 mg, 2.93 mmol, yield: 47%).
¹H-NMR (δppm, CDCl₃): 3.74-3.69 (m, 4H), 3.54 (d, J=5.9 Hz, 2H), 3.24 (s, 3H), 1.81-1.70 (m, 3H), 1.64-1.53 (m, 2H).
Step 4
(4-Methoxytetrahydropyran-4-yl)methyl trifluoromethylsulfonate (84 mg, 0.17 mmol, yield: 94%) was obtained in the same manner as in step 1 of Reference example 23, using (4-methoxytetrahydropyran-4-yl)methanol obtained in the above instead of (4-fluorotetrahydropyran-4-yl)methanol.
¹H-NMR (δppm, CDCl₃): 4.39 (s, 2H), 3.81-3.65 (m, 4H), 3.29 (s, 3H), 1.84-1.59 (m, 4H).
Step 5
The title compound 182 (5.2 mg, 0.01 mmol, yield: 4%) was obtained in the same manner as in Example 177, using (4-methoxytetrahydropyran-4-yl)methyl trifluoromethanesulfonate obtained in the above instead of 4-benzyl-2-(chloromethyl)morpholine.
¹H-NMR (δppm, CDCl₃): 9.24-9.21 (m, 1H), 8.64-8.61 (m, 1H), 7.88-7.85 (m, 1H), 4.11 (s, 2H), 3.81-3.63 (m, 4H), 3.58-3.25 (m, 5H), 3.14-3.07 (m, 3H), 1.82-1.62 (m, 6H), 1.50 (s, 9H), 1.05-0.79 (m, 3H). Mass (m/e): 430 (M+H)⁺.

Example 183

6-[2-tert-Butyl-1-(4-cyanotetrahydropyran-4-ylmethyl)-1H-imidazol-4-yl]-N-methyl-N-propylpyrazine-2-carboxamide (Compound 183)

Step 1
Methyl 4-cyanotetrahydropyran-4-carboxylate (200 mg, 1.18 mmol) obtained by the method described in US2004/0072082 was dissolved in a mixed solution of THF (5.0 mL), methanol (1.0 mL), and water (0.5 mL), and sodium borohydride (90 mg, 2.4 mmol) was added thereto, and then, the mixture was stirred at room temperature for 1 hour. Under ice-cooling, acetone and saturated brine were added to the mixture, and the mixture was extracted with ethyl acetate. The organic layer was dried over anhydrous magnesium sulfate, and the solvent was evaporated under reduced pressure. The residue was purified by silica gel column chromatography (hexane/ethyl acetate=50/50 to 0/100) to give (4-cyanotetrahydropyran-4-yl)methanol (132 mg, 0.94 mmol, yield: 80%).
¹H-NMR (δppm, CDCl₃): 4.05-3.95 (m, 2H), 3.78-3.60 (m, 4H), 1.95-1.85 (m, 2H), 1.71-1.55 (m, 2H).
Step 2
(4-Cyanotetrahydropyran-4-yl)methylmethanesulfonate (201 mg, 0.94 mmol, 99%) was obtained in the same manner as in step 2 of Example 45, using (4-cyanotetrahydropyran-4-yl)methanol obtained in the above instead of (tetrahydropyran-4-yl)methanol.
¹H-NMR (δppm, CDCl₃): 4.20 (s, 2H), 4.07-3.98 (m, 2H), 3.79-3.66 (m, 2H), 3.13 (s, 3H), 1.99-1.90 (m, 2H), 1.79-1.64 (m, 2H).
Step 3
The title compound 183 (61 mg, 0.14 mmol, yield: 39%) was obtained in the same manner as in Example 177, using (4-cyanotetrahydropyran-4-yl)methylmethanesulfonate obtained in the above instead of 4-benzyl-2-(chloromethyl)morpholine.
¹H-NMR (δppm, CDCl₃): 9.26-9.23 (m, 1H), 8.70-8.67 (m, 1H), 8.00-7.96 (m, 1H), 4.33 (s, 2H), 4.08-3.99 (m, 2H), 3.82-3.69 (m, 2H), 3.59-3.27 (m, 2H), 3.15-3.10 (m, 3H), 1.96-1.88 (m, 2H), 1.84-1.67 (m, 4H), 1.52 (s, 9H), 1.05-0.78 (m, 3H). Mass (m/e): 425 (M+H)⁺.

Example 184

6-[2-tert-Butyl-1-(4-methyltetrahydropyran-4-ylmethyl)-1H-imidazol-4-yl]-N-methyl-N-propylpyrazine-2-carboxamide (Compound 184)

Step 1
(4-Methyltetrahydropyran-4-yl)methylmethanesulfonate (208 mg, 1.00 mmol, yield: 87%) was obtained in the same manner as in step 2 of Example 45, using (4-methyltetrahydropyran-4-yl)methanol obtained by the method described in WO2003/022801 instead of (tetrahydropyran-4-yl)methanol.
¹H-NMR (δppm, CDCl₃): 3.99 (s, 2H), 3.81-3.59 (m, 4H), 3.03 (s, 3H), 1.69-1.57 (m, 2H), 1.42-1.32 (m, 2H), 1.12 (s, 3H).
Step 2
The title compound 184 (80 mg, 0.19 mmol, yield: 34%) was obtained in the same manner as in Example 177, using (4-methyltetrahydropyran-4-yl)methylmethanesulfonate obtained in the above instead of 4-benzyl-2-(chloromethyl)morpholine.
¹H-NMR (δppm, CDCl₃): 9.26-9.23 (m, 1H), 8.63-8.60 (m, 1H), 7.62-7.58 (m, 1H), 3.99 (s, 2H), 3.91-3.82 (m, 2H), 3.69-3.57 (m, 2H), 3.57-3.25 (m, 2H), 3.14-3.04 (m, 3H), 1.85-1.65 (m, 4H), 1.53-1.48 (m, 2H), 1.47 (s, 9H), 1.07 (s, 3H), 1.05-0.77 (m, 3H). Mass (m/e): 414 (M+H)⁺.

Example 185

6-[2-tert-Butyl-1-(4-fluorotetrahydropyran-4-ylmethyl)-1H-imidazol-4-yl]-N-ethyl-N-methylpyrazine-2-carboxamide (Compound 185)

Step 1
N-Ethyl-N-methylpyrazinecarboxamide (37.6 g, 228 mmol, yield: 94%) was obtained in the same manner as in step 1 of Example 168, using pyrazine carboxylic acid instead of 4-hydroxyquinoline-2-carboxylic acid.

$^1$H-NMR (δppm, CDCl$_3$): 8.94-8.90 (m, 1H), 8.63-8.61 (m, 1H), 8.56-8.53 (m, 1H), 3.68-3.38 (m, 2H), 3.14-3.08 (m, 3H), 1.31-1.20 (m, 3H).

Step 2

6-Tributylstannyl-N-ethyl-N-methylpyrazine-2-carboxamide (6.45 g, 14.2 mmol, yield: 33%) was obtained in the same manner as in step 2 of Reference example 22, using N-ethyl-N-methylpyrazinecarboxamide obtained in the above instead of N-methyl-N-propylpyrazinecarboxamide.

$^1$H-NMR (δppm, CDCl$_3$): 8.74-8.70 (m, 1H), 8.57-8.54 (m, 1H), 3.68-3.41 (m, 2H), 3.13-3.09 (m, 3H), 1.50-1.12 (m, 21H), 0.88 (t, J=7.3 Hz, 9H).

Step 3

The title compound 185 (36 mg, 0.09 mmol, yield: 41%) was obtained in the same manner as in step 3 of Reference example 22, using 6-tributylstannyl-N-ethyl-N-methylpyrazine-2-carboxamide obtained in the above instead of 6-tributylstannyl-N-methyl-N-propylpyrazine-2-carboxamide, and Compound w obtained in step 2 of Reference example 23 instead of 2-tert-butyl-4-iodo-1H-imidazole.

$^1$H-NMR (δppm, CDCl$_3$): 9.25-9.23 (m, 1H), 8.68-8.65 (m, 1H), 7.80-7.77 (m, 1H), 4.30 (d, J=23.5 Hz, 2H), 3.93-3.83 (m, 2H), 3.79-3.67 (m, 2H), 3.67-3.37 (m, 2H), 3.14-3.08 (m, 3H), 1.94-1.64 (m, 4H), 1.49 (s, 9H), 1.28 (t, J=6.9 Hz, 3H). Mass (m/e): 404 (M+H)$^+$.

Example 186

6-[2-tert-Butyl-1-(4-fluorotetrahydropyran-4-ylmethyl)-1H-imidazol-4-yl]-N,N-dimethylpyrazine-2-carboxamide (Compound 186)

Step 1

Propyl 6-[2-tert-butyl-1-(4-fluorotetrahydropyran-4-ylmethyl)-1H-imidazol-4-yl]pyrazine-2-carboxylate (510 mg, 1.26 mmol, yield: 89%) was obtained in the same manner as in Reference example 2, using 6-[2-tert-butyl-1-(4-fluorotetrahydropyran-4-ylmethyl)-1H-imidazol-4-yl]-2-chloropyrazine obtained in Example 197 mentioned below instead of Compound 8.

$^1$H-NMR (δppm, CDCl$_3$): 9.38 (s, 1H), 9.05 (s, 1H), 7.94 (d, J=1.8 Hz, 1H), 4.39 (t, J=6.8 Hz, 2H), 4.30 (d, J=23.4 Hz, 2H), 3.92-3.84 (m, 2H), 3.78-3.67 (m, 2H), 1.92-1.67 (m, 6H), 1.49 (s, 9H), 1.06 (t, J=7.7 Hz, 3H). Mass (m/e): 405 (M+H)$^+$.

Step 3

6-[2-tert-Butyl-1-(4-fluorotetrahydropyran-4-ylmethyl)-1H-imidazol-4-yl]-pyrazine-2-carboxylic acid (370 mg, 1.02 mmol, yield: 82%) was obtained in the same manner as in Reference example 3, using propyl 6-[2-tert-butyl-1-(4-fluorotetrahydropyran-4-ylmethyl)-1H-imidazol-4-yl]pyrazine-2-carboxylate obtained in the above instead of Compound b.

$^1$H-NMR (δppm, CDCl$_3$): 9.37 (s, 1H), 9.21 (s, 1H), 7.85 (d, J=1.5 Hz, 1H), 4.34 (d, J=23.4 Hz, 2H), 3.95-3.87 (m, 2H), 3.80-3.69 (m, 2H), 1.92-1.70 (m, 4H), 1.50 (s, 9H). Mass (m/e): 363 (M+H)$^+$.

Step 4

The title compound 186 (115 mg, 0.30 mmol, yield: 71%) was obtained in the same manner as in step 1 of Example 167, using 6-[2-tert-butyl-1-(4-fluorotetrahydropyran-4-ylmethyl)-1H-imidazol-4-yl]pyrazine-2-carboxylic acid obtained in the above instead of 5-bromo-2-fluorobenzoic acid.

$^1$H-NMR (δppm, CDCl$_3$): 9.24 (s, 1H), 8.67 (s, 1H), 7.79 (d, J=1.8 Hz, 1H), 4.30 (d, J=23.5 Hz, 2H), 3.92-3.84 (m, 2H), 3.78-3.67 (m, 2H), 3.17 (s, 3H), 3.13 (s, 3H), 1.90-1.68 (m, 4H), 1.49 (s, 9H). Mass (m/e): 390 (M+H)$^+$.

Example 187

3-[2-tert-Butyl-1-(4-fluorotetrahydropyran-4-ylmethyl)-1H-imidazol-4-yl]-N,N-dimethylbenzamide (Compound 187)

Step 1

3-[2-tert-Butyl-1-(4-fluorotetrahydropyran-4-ylmethyl)-1H-imidazol-4-yl]benzoic acid (137 mg, 0.380 mmol, yield: 70%) was obtained in the same manner as in step 2 of Example 165, using Compound w obtained in step 2 of Reference example 23 instead of Compound u, and 3-carboxyphenylboronic acid instead of 6-(4,4,5,5-tetramethyl[1,3,2]dioxaboran-2-yl)indan-1-one.

$^1$H-NMR (δppm, CDCl$_3$): 8.52-8.50 (m, 1H), 8.05-8.00 (m, 1H), 7.94-7.90 (m, 1H), 7.48-7.41 (m, 2H), 4.29 (d, J=23.8 Hz, 2H), 3.93-3.85 (m, 2H), 3.80-3.68 (m, 2H), 1.88-1.67 (m, 4H), 1.50 (s, 9H). Mass (m/e): 361 (M+H)$^+$.

Step 2

The title compound 187 (8.0 mg, 0.02 mmol, yield: 12%) was obtained in the same manner as in step 1 of Example 167, using 3-[2-tert-butyl-1-(4-fluorotetrahydropyran-4-ylmethyl)-1H-imidazol-4-yl]benzoic acid obtained in the above instead of 5-bromo-2-fluorobenzoic acid.

$^1$H-NMR (δppm, CDCl$_3$): 7.88-7.82 (m, 1H), 7.82-7.79 (m, 1H), 7.40-7.33 (m, 2H), 7.24-7.19 (m, 1H), 4.26 (d, J=24.1 Hz, 2H), 3.92-3.83 (m, 2H), 3.78-3.66 (m, 2H), 3.12 (s, 3H), 2.99 (s, 3H), 1.89-1.59 (m, 4H), 1.47 (s, 9H).

Mass (m/e): 388 (M+H)$^+$.

Example 188

4-[2-tert-Butyl-1-(4-fluorotetrahydropyran-4-ylmethyl)-1H-imidazol-4-yl]-N,N-dimethylthiophene-2-carboxamide (Compound 189)

Step 1

4-Bromo-N,N-dimethylthiophene-2-carboxamide (214 mg, 0.91 mmol, yield: 95%) was obtained in the same manner as in step 1 of Example 167, using 4-bromothiophene-2-carboxylic acid instead of 5-bromo-2-fluorobenzoic acid.

$^1$H-NMR (δppm, CDCl$_3$): 7.36 (d, J=1.3 Hz, 1H), 7.25 (d, J=1.3 Hz, 1H), 3.20 (brs, 6H).

Step 2

The title compound 188 (24 mg, 0.061 mmol, yield: 33%) was obtained in the same manner as in step 3 of Reference example 22, using Compound x obtained in Reference example 24 instead of 6-tributylstannyl-N-methyl-N-propylpyrazine-2-carboxamide, and 4-bromo-N,N-dimethylthiophene-2-carboxamide obtained in the above instead of 2-tert-butyl-4-iodo-1H-imidazole.

$^1$H-NMR (δppm, CDCl$_3$): 7.63 (d, J=1.3 Hz, 1H), 7.61 (d, J=1.3 Hz, 1H), 7.24 (d, J=1.7 Hz, 1H), 4.25 (d, J=24.1 Hz, 2H), 3.92-3.83 (m, 2H), 3.78-3.66 (m, 2H), 3.20 (brs, 6H), 1.89-1.64 (m, 4H), 1.46 (s, 9H). Mass (m/e): 394 (M+H)$^+$.

Example 189

3-[2-tert-Butyl-1-(4-fluorotetrahydropyran-4-ylmethyl)-1H-imidazol-4-yl]-N-ethyl-N-methylbenzamide (Compound 188)

The title compound 189 (36 mg, 0.90 mmol, yield: 50%) was obtained in the same manner as in step 1 of Example 168, using 3-[2-tert-butyl-1-(4-fluorotetrahydropyran-4-ylmethyl)-1H-imidazol-4-yl]benzoic acid obtained in step 1 of Example 187 instead of 4-hydroxyquinoline-2-carboxylic acid.

$^1$H-NMR (δppm, CDCl$_3$): 7.87-7.82 (m, 1H), 7.80-7.78 (m, 1H), 7.41-7.32 (m, 2H), 7.23-7.17 (m, 1H), 4.26 (d, J=23.8 Hz, 2H), 3.92-3.83 (m, 2H), 3.78-3.66 (m, 2H), 3.66-3.20 (m, 2H), 3.11-2.91 (m, 3H), 1.90-1.58 (m, 4H), 1.47 (s, 9H), 1.29-1.09 (m, 3H). Mass (m/e): 402 (M+H)$^+$.

Example 190

5-[2-tert-Butyl-1-(4-fluorotetrahydropyran-4-ylmethyl)-1H-imidazol-4-yl]-N,N-dimethylnicotinamide (Compound 190)

Step 1

5-Bromo-N,N-dimethylnicotinamide (212 mg, 0.925 mmol, yield: 93%) was obtained in the same manner as in step 1 of Example 167, using 5-bromonicotinic acid instead of 5-bromo-2-fluorobenzoic acid.

$^1$H-NMR (δppm, CDCl$_3$): 8.72 (d, J=2.3 Hz, 1H), 8.59 (d, J=2.3 Hz, 1H), 7.93-7.91 (m, 1H), 3.13 (brs, 3H), 3.03 (brs, 3H).

Step 2

The title compound 190 (15 mg, 0.039 mmol, yield: 20%) was obtained in the same manner as in step 2 of Example 188, using 5-bromo-N,N-dimethylnicotinamide obtained in the above instead of 4-bromo-N,N-dimethylthiophene-2-carboxamide.

$^1$H-NMR (δppm, CDCl$_3$): 9.01 (d, J=2.0 Hz, 1H), 8.47 (d, J=2.0 Hz, 1H), 8.17-8.13 (m, 1H), 7.47 (d, J=1.7 Hz, 1H), 4.28 (d, J=23.8 Hz, 2H), 3.94-3.83 (m, 2H), 3.79-3.67 (m, 2H), 3.14 (brs, 3H), 3.03 (brs, 3H), 1.90-1.64 (m, 4H), 1.47 (s, 9H). Mass (m/e): 389 (M+H)$^+$.

Example 191

6-[2-tert-Butyl-1-(4-fluorotetrahydropyran-4-ylmethyl)-1H-imidazol-4-yl]-N-ethyl-N-methylpicolinamide (Compound 191)

Step 1

6-Bromo-N-ethyl-N-methylpicolinamide (240 mg, 0.990 mmol, yield: 99%) was obtained in the same manner as in step 1 of Example 168, using 6-bromopicolinic acid instead of 4-hydroxyquinoline-2-carboxylic acid.

$^1$H-NMR (δppm, CDCl$_3$): 7.70-7.57 (m, 2H), 7.56-7.51 (m, 1H), 3.64-3.35 (m, 2H), 3.10-3.06 (m, 3H), 1.29-1.20 (m, 3H).

Step 2

The title compound 191 (13 mg, 0.032 mmol, yield: 16%) was obtained in the same manner as in step 2 of Example 188, using 6-bromo-N-ethyl-N-methylpicolinamide obtained in the above instead of 4-bromo-N,N-dimethylthiophene-2-carboxamide.

$^1$H-NMR (δppm, CDCl$_3$): 8.04-7.98 (m, 1H), 7.79-7.72 (m, 2H), 7.44-7.39 (m, 1H), 4.28 (d, J=23.5 Hz, 2H), 3.92-3.83 (m, 2H), 3.79-3.67 (m, 2H), 3.66-3.37 (m, 2H), 3.12-3.08 (m, 3H), 1.89-1.65 (m, 4H), 1.48 (s, 9H), 1.30-1.23 (m, 3H). Mass (m/e): 403 (M+H)$^+$.

Example 192

6-[2-tert-Butyl-1-(4-fluorotetrahydropyran-4-ylmethyl)-1H-imidazol-4-yl]-N,N-dimethylpicolinamide (Compound 192)

Step 1

6-Bromo-N,N-dimethylpicolinamide (120 mg, 0.594 mmol, yield: 39%) was obtained in the same manner as in step 1 of Example 167, using 6-bromopicolinic acid instead of 5-bromo-2-fluorobenzoic acid.

$^1$H-NMR (δppm, CDCl$_3$): 7.69-7.60 (m, 2H), 7.56-7.51 (m, 1H), 3.12 (s, 3H), 3.11 (s, 3H).

Step 2

The title compound 192 (13 mg, 0.033 mmol, yield: 9%) was obtained in the same manner as in step 2 of Example 188, using 6-bromo-N,N-dimethylpicolinamide obtained in the above instead of 4-bromo-N,N-dimethylthiophene-2-carboxamide.

$^1$H-NMR (δppm, CDCl$_3$): 8.01 (dd, J=8.1, 1.1 Hz, 1H), 7.79-7.73 (m, 2H), 7.42 (dd, J=8.1, 1.1 Hz, 1H), 4.28 (d, J=23.5 Hz, 2H), 3.91-3.83 (m, 2H), 3.79-3.67 (m, 2H), 3.15 (brs, 3H), 3.13 (brs, 3H), 1.90-1.68 (m, 4H), 1.48 (s, 9H). Mass (m/e): 389 (M+H)$^+$.

Example 193

5-[2-tert-Butyl-1-(4-fluorotetrahydropyran-4-yl)methyl-1H-imidazol-4-yl]-N-ethyl-N-methylnicotinamide (Compound 193)

Step 1

5-Bromo-N-ethyl-N-methylnicotinamide (223 mg, 0.917 mmol, yield: 93%) was obtained in the same manner as in step 1 of Example 168, using 5-bromonicotinic acid instead of 4-hydroxyquinoline-2-carboxylic acid.

$^1$H-NMR (δppm, CDCl$_3$): 8.73-8.71 (m, 1H), 8.57 (br s, 1H), 7.90 (br s, 1H), 3.67-3.24 (m, 2H), 3.11-2.96 (m, 3H), 1.31-1.13 (m, 3H).

Step 2

The title compound 193 (16 mg, 0.040 mmol, yield: 21%) was obtained in the same manner as in step 2 of Example 188, using 5-bromo-N-ethyl-N-methylnicotinamide obtained in the above instead of 4-bromo-N,N-dimethylthiophene-2-carboxamide.

$^1$H-NMR (δppm, CDCl$_3$): 9.03-9.01 (m, 1H), 8.48-8.46 (m, 1H), 8.15-8.12 (m, 1H), 7.48-7.46 (m, 1H), 4.28 (d, J=24.1 Hz, 2H), 3.94-3.84 (m, 2H), 3.79-3.68 (m, 2H), 3.66-3.22 (m, 2H), 3.11-2.97 (m, 3H), 1.90-1.57 (m, 4H), 1.47 (s, 9H), 1.31-1.09 (m, 3H). Mass (m/e): 403 (M+H)$^+$.

Example 194

6-[2-tert-Butyl-1-(4-fluorotetrahydropyran-4-ylmethyl)-1H-imidazol-4-yl]-N-methyl-N-propylpyrazine-2-carboxamide (Compound 194)

The title compound 194 (78.3 mg, 0.188 mmol, yield: 60%) was obtained in the same manner as in step 2 of Reference example 23, using Compound v obtained in step 3 of Reference example 22 instead of 2-tert-butyl-4-iodo-1H-imidazole.

$^1$H-NMR (δppm, CDCl$_3$): 9.25-9.23 (m, 1H), 8.67-8.64 (m, 1H), 7.79-7.76 (m, 1H), 4.30 (d, J=23.6 Hz, 2H), 3.95-3.83 (m, 2H), 3.78-3.68 (m, 2H), 3.62-3.25 (m, 2H), 3.14-3.08 (m, 3H), 1.86-1.68 (m, 6H), 1.49 (s, 9H), 1.05-0.78 (m, 3H). Mass (m/e): 418(M+H)$^+$.

Example 195

6-[2-tert-Butyl-1-(4-fluorotetrahydropyran-4-ylmethyl)-1H-imidazol-4-yl]-N,N-diethylpyrazine-2-carboxamide (Compound 195)

Step 1

N,N-Diethylpyrazinecarboxamide (12.8 g, 71.4 mmol, yield: 89%) was obtained in the same manner as in step 1 of Reference example 22, using diethylamine instead of methylpropylamine.

$^1$H-NMR (δppm, CDCl$_3$): 8.90 (d, J=1.5 Hz, 1H), 8.61 (d, J=2.5 Hz, 1H), 8.53 (dd, J=2.5, 1.5 Hz, 1H), 3.59 (q, J=7.1 Hz, 2H), 3.40 (q, J=7.1 Hz, 2H), 1.29 (t, J=7.1 Hz, 3H), 1.20 (t, J=7.1 Hz, 3H).

Step 2

6-Tributylstannyl-N,N-diethylpyrazine-2-carboxamide (4.40 g, 9.40 mmol, yield: 22%) was obtained in the same manner as in step 2 of Reference example 22, using N,N-diethylpyrazinecarboxamide obtained in the above instead of N-methyl-N-propylpyrazinecarboxamide.

$^1$H-NMR (δppm, CDCl$_3$): 8.71 (s, 1H), 8.55 (s, 1H), 3.58 (q, J=7.1 Hz, 2H), 3.44 (q, J=7.1 Hz, 2H), 1.67-0.84 (m, 33H).

Step 3

The title compound 195 (43.8 mg, 0.105 mmol, yield: 48%) was obtained in the same manner as in step 3 of Example 185, using 6-tributylstannyl-N,N-diethylpyrazine-2-carboxamide obtained in the above instead of 6-tributylstannyl-N-ethyl-N-methylpyrazine-2-carboxamide.

$^1$H-NMR (δppm, CDCl$_3$): 9.24-9.23 (m, 1H), 8.68-8.67 (m, 1H), 7.79-7.77 (m, 1H), 4.30 (d, J=23.5 Hz, 2H), 3.92-3.84 (m, 2H), 3.78-3.67 (m, 2H), 3.58 (q, J=7.2 Hz, 2H), 3.40 (q, J=7.2 Hz, 2H), 1.93-1.58 (m, 4H), 1.49 (s, 9H), 1.29 (t, J=7.2 Hz, 3H), 1.28 (t, J=7.2 Hz, 3H). Mass (m/e): 418 (M+H)$^+$.

Example 196

5-[2-tert-Butyl-1-(4-fluorotetrahydropyran-4-ylmethyl)-1H-imidazol-4-yl]-2-fluoro-N,N-dimethylbenzamide (Compound 196)

The title compound 196 (99.0 mg, 0.244 mmol, yield: 65%) was obtained in the same manner as in step 3 of Example 167, using Compound w obtained in step 2 of Reference example 23 instead of Compound u.

$^1$H-NMR (δppm, CDCl$_3$): 7.82 (ddd, J=8.6, 5.0, 2.3 Hz, 1H), 7.76 (dd, J=6.3, 2.3 Hz, 1H), 7.33 (d, J=1.7 Hz, 1H), 7.06 (dd, J=8.9, 8.6 Hz, 1H), 4.25 (d, J=23.8 Hz, 2H), 3.92-3.83 (m, 2H), 3.78-3.65 (m, 2H), 3.14 (s, 3H), 2.95 (d, J=1.7 Hz, 3H), 1.89-1.58 (m, 4H), 1.46 (s, 9H). Mass (m/e): 406 (M+H)$^+$.

Example 197

6-[2-tert-Butyl-1-(4-fluorotetrahydropyran-4-ylmethyl)-1H-imidazol-4-yl]-2-chloropyrazine (Compound 197)

The title compound 197 (545 mg, 1.55 mmol, yield: 71%) was obtained in the same manner as in step 3 of Example 185, using 6-tributylstannyl-2-chloropyrazine instead of 6-tributylstannyl-N-ethyl-N-methylpyrazine-2-carboxamide.

$^1$H-NMR (δppm, CDCl$_3$): 9.11 (s, 1H), 8.36 (s, 1H), 7.84 (d, J=1.7 Hz, 1H), 4.29 (d, J=23.1 Hz, 2H), 3.93-3.83 (m, 2H), 3.79-3.67 (m, 2H), 1.92-1.64 (m, 4H), 1.48 (s, 9H). Mass (m/e): 353, 355 (M+H)$^+$.

Example 198

2-(1-{3-[2-tert-Butyl-1-(tetrahydropyran-4-ylmethyl)-1H-imidazol-4-yl]phenyl}ethylidene)malononitrile (Compound 198)

Compound 49 (46 mg, 0.14 mmol) obtained in Example 49 was dissolved in toluene (2.0 mL) under an argon atmosphere, and malononitrile (0.0900 mL, 1.62 mmol) and diethylamine (0.168 mL, 1.62 mmol) were added thereto, and then, the mixture was stirred at 100° C. for 10 hours. After the mixture was left to cool to room temperature, water was added thereto, and the mixture was extracted with ethyl acetate. The organic layer was washed with saturated brine and dried over anhydrous sodium sulfate, and the solvent was evaporated under reduced pressure. The residue was purified by preparative thin-layer chromatography (chloroform/methanol=20/1) to give the title compound 198 (7.6 mg, 0.020 mmol, yield: 14%).

$^1$H-NMR (δppm, CDCl$_3$): 7.94 (dd, J=1.7, 1.7 Hz, 1H), 7.88 (ddd, J=7.7, 1.7, 1.7 Hz, 1H), 7.45 (dd, J=7.7, 7.7 Hz, 1H), 7.35 (ddd, J=7.7, 1.7, 1.7 Hz, 1H), 7.17 (s, 1H), 4.06-3.98 (m, 2H), 3.95 (d, J=7.3 Hz, 2H), 3.44-3.32 (m, 2H), 2.67 (s, 3H), 2.16-2.00 (m, 1H), 1.71-1.60 (m, 2H), 1.51-1.41 (m, 2H), 1.48 (s, 9H). Mass (m/e): 389 (M+H)$^+$.

Example 199

1-{3-[2-tert-Butyl-1-(tetrahydropyran-4-ylmethyl)-1H-imidazol-4-yl]phenyl}-1,3-dimethylthiourea (Compound 199)

Compound 73 (50 mg, 0.15 mmol) obtained in Example 73 was dissolved in 1,4-dioxane (2.0 mL), and methyl isothiocyanate (0.0500 mL, 0.731 mmol) was added thereto, and then, the mixture was stirred at 70° C. for 3 hours. After the mixture was left to cool to room temperature, a saturated aqueous sodium hydrogen carbonate solution was added thereto, and the mixture was extracted with ethyl acetate. The organic layer was washed with saturated brine and dried over anhydrous sodium sulfate, and the solvent was evaporated under reduced pressure to give the title compound 199 (48 mg, 0.12 mmol, yield: 80%).

$^1$H-NMR (δppm, CDCl$_3$): 7.75 (ddd, J=7.9, 1.7, 1.7 Hz, 1H), 7.64 (dd, J=1.7, 1.7 Hz, 1H), 7.43 (dd, J=7.9, 7.9 Hz, 1H), 7.15 (s, 1H), 7.05-7.00 (m, 1H), 5.48-5.38 (m, 1H), 4.06-3.98 (m, 2H), 3.95 (d, J=7.3 Hz, 2H), 3.69 (s, 3H), 3.44-3.33 (m, 2H), 3.02 (d, J=4.6 Hz, 3H), 2.14-2.02 (m, 1H), 1.71-1.60 (m, 2H), 1.53-1.36 (m, 2H), 1.48 (s, 9H). Mass (m/e): 401 (M+H)$^+$.

Example 200

2-[2-tert-Butyl-1-(tetrahydropyran-4-ylmethyl)-1H-imidazol-4-yl]-6-(2-fluoro-6-methoxyphenyl)pyrazine (Compound 200)

Compound 136 (100 mg, 0.299 mmol) obtained in Example 136, palladium acetate (3.4 mg, 0.015 mmol), dicyclohexyl-(2',6'-dimethoxybiphenyl-2-yl)phosphane (18 mg, 0.044 mmol), 2-fluoro-6-methoxyphenylboronic acid (102 mg, 0.600 mmol), and potassium phosphate (190 mg, 0.895 mmol) were dissolved in toluene (1.0 mL) under an argon atmosphere, and the mixture was stirred at 100° C. for 4 hours. After the mixture was left to cool to room temperature, water was added thereto, and the mixture was extracted with ethyl acetate. The organic layer was washed with saturated brine and dried over anhydrous sodium sulfate, and the solvent was evaporated under reduced pressure. After the residue was purified by preparative thin-layer chromatography (heptane/ethyl acetate=1/1), the obtained white solid was reslurried in diisopropyl ether to give the title compound 200 (60 mg, 0.14 mmol, yield: 47%).

$^1$H-NMR (δppm, CDCl$_3$): 9.17 (s, 1H), 8.43 (s, 1H), 7.60 (s, 1H), 7.40-7.30 (m, 1H), 6.87-6.75 (m, 2H), 4.03-3.95 (m, 2H), 3.94 (d, J=7.5 Hz, 2H), 3.78 (s, 3H), 3.41-3.28 (m, 2H), 2.16-2.03 (m, 1H), 1.68-1.58 (m, 2H), 1.49 (s, 9H), 1.49-1.32 (m, 2H). Mass (m/e): 425 (M+H)$^+$.

Example 201

2-tert-Butyl-4-(3-methylsulfanylphenyl)-1-(tetrahydropyran-4-ylmethyl)-1H-imidazole (Compound 201)

Compound u (1.00 g, 2.87 mmol) obtained in Reference example 21 was dissolved in THF (10 mL) under an argon atmosphere, and the solution was cooled to −78° C. To this solution, a solution of n-butyl lithium in n-hexane (1.6 mol/L; 2.70 mL, 4.32 mmol) was added, and the mixture was stirred at the same temperature for 20 minutes. To the mixture, trimethyl borate (1.00 mL, 8.62 mmol) was added, and the mixture was further stirred at 0° C. for 1 hour. To the mixture, a THF solution (10 mL) of 3-bromothioanisole (0.610 g, 3.00 mmol) was added dropwise, and further diphenylphosphinoferrocene palladium dichloride-dichloromethane complex (469 mg, 0.574 mmol), and sodium tert-butoxide (830 mg, 8.64 mmol) were added thereto, and then, the mixture was stirred at 50° C. for 3 hours. After the mixture was left to cool to room temperature, water was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=100/0→70/30) to give the title compound 201 (433 mg, 1.26 mmol, yield: 44%).

$^1$H-NMR (δppm, CDCl$_3$): 7.69 (dd, J=1.7, 1.7 Hz, 1H), 7.52 (ddd, J=7.7, 1.7, 1.7 Hz, 1H), 7.26 (dd, J=7.7, 7.7 Hz, 1H), 7.12-7.07 (m, 1H), 7.11 (s, 1H), 4.05-3.96 (m, 2H), 3.93 (d, J=7.3 Hz, 2H), 3.43-3.32 (m, 2H), 2.51 (s, 3H), 2.16-1.97 (m, 1H), 1.71-1.60 (m, 2H), 1.50-1.35 (m, 2H), 1.48 (s, 9H). Mass (m/e): 345 (M+H)$^+$.

Example 202

2-tert-Butyl-4-(3-methanesulfonylphenyl)-1-(tetrahydropyran-4-ylmethyl)-1H-imidazole (Compound 202)

Compound 201 (160 mg, 0.464 mmol) obtained in Example 201 was dissolved in dichloromethane (2.0 mL) under an argon atmosphere, and the solution was cooled to 0° C. To this solution, 3-chloroperbenzoic acid (94.0 mg, 0.463 mmol) was added, and the mixture was stirred at room temperature for 2 hours. Water was added to the mixture, and the mixture was extracted with ethyl acetate. The organic layer was washed with a saturated aqueous sodium thiosulfate solution and saturated brine and dried over anhydrous magnesium sulfate, and the solvent was evaporated under reduced pressure. The residue was purified by silica gel column chromatography (chloroform/methanol=100/0 to 97/3) to give the title compound 202 (88 mg, 0.24 mmol, yield: 52%).

$^1$H-NMR (δppm, CDCl$_3$): 8.00 (dd, J=1.7, 1.7 Hz, 1H), 7.93 (ddd, J=7.7, 1.7, 1.7 Hz, 1H), 7.49 (dd, J=7.7, 7.7 Hz, 1H), 7.42 (ddd, J=7.7, 1.7, 1.7 Hz, 1H), 7.23 (s, 1H), 4.06-3.98 (m, 2H), 3.95 (d, J=7.3 Hz, 2H), 3.45-3.32 (m, 2H), 2.75 (s, 3H), 2.17-2.01 (m, 1H), 1.70-1.60 (m, 2H), 1.48 (s, 9H), 1.47-1.35 (m, 2H). Mass (m/e): 361 (M+H)$^+$.

Example 203

2-tert-Butyl-4-(3-methanesulfonylphenyl)-1-(tetrahydropyran-4-ylmethyl)-1H-imidazole (Compound 203)

Compound 202 (79 mg, 0.22 mmol) obtained in Example 202 was dissolved in dichloromethane (1.0 mL) under an argon atmosphere, and the solution was cooled to 0° C. To this solution, 3-chloroperbenzoic acid (89 mg, 0.44 mmol) was added, and the mixture was stirred at room temperature for 1 hour. Water was added to the mixture, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=100/0 to 97/3) to give the title compound 203 (40 mg, 0.11 mmol, yield: 50%).

$^1$H-NMR (δppm, CDCl$_3$): 8.25 (dd, J=1.7, 1.7 Hz, 1H), 8.09 (ddd, J=7.7, 1.7, 1.7 Hz, 1H), 7.74 (ddd, J=7.7, 1.7, 1.7 Hz, 1H), 7.53 (dd, J=7.7, 7.7 Hz, 1H), 7.23 (s, 1H), 4.06-3.98 (m, 2H), 3.95 (d, J=7.3 Hz, 2H), 3.45-3.33 (m, 2H), 3.07 (s, 3H), 2.16-2.00 (m, 1H), 1.70-1.61 (m, 2H), 1.51-1.36 (m, 2H), 1.48 (s, 9H). Mass (m/e): 377 (M+H)$^+$.

Example 204

5-[2-tert-Butyl-1-(tetrahydropyran-4-ylmethyl)-1H-imidazol-4-yl]-N-methyl-N-(2,2,2-trifluoroethyl) isoxazole-3-carboxamide (Compound 204)

The title compound 204 (40 mg, 0.09 mmol, yield: 72%) was obtained in the same manner as in Example 99, using 5-[2-tert-butyl-1-(tetrahydropyran-4-ylmethyl)-1H-imidazol-4-yl]-N-(2,2,2-trifluoroethyl)isoxazole-3-carboxamide obtained in Example 213 mentioned below.

$^1$H-NMR (δppm, CDCl$_3$): 7.36-7.32 (m, 1H), 6.79 (d, J=7.5 Hz, 1H), 4.62-4.46 (m, 1H), 4.27-4.13 (m, 1H), 4.08-3.91 (m, 4H), 3.45-3.20 (m, 5H), 2.17-1.96 (m, 1H), 1.69-1.55 (m, 2H), 1.52-1.41 (m, 11H). Mass (m/e): 429 (M+H)$^+$.

Example 205

6-[2-tert-Butyl-1-(tetrahydropyran-4-ylmethyl)-1H-imidazol-4-yl]-N-cyclopropyl-N-methylpyrazine-2-carboxamide (Compound 205)

The title compound 205 (209 mg, 0.53 mmol, yield: 60%) was obtained in the same manner as in Example 216 mentioned below, and then in Example 145, using cyclopropylamine instead of 2,2,2-trifluoroethylamine, and iodomethane instead of iodoethane.

$^1$H-NMR (δppm, CDCl$_3$): 9.24 (s, 1H), 8.56 (s, 1H), 7.57 (s, 1H), 4.03 (dd, J=11.4, 3.6 Hz, 2H), 3.96 (d, J=7.4 Hz, 2H), 3.38 (dt, J=11.4, 1.8 Hz, 2H), 3.16 (s, 3H), 3.00-2.94 (m, 1H), 2.15-2.05 (m, 1H), 1.67-1.63 (m, 2H), 1.49-1.35 (m, 11H), 0.55-0.42 (m, 4H). Mass (m/e): 398 (M+H)$^+$.

Example 206

6-[2-tert-Butyl-1-(tetrahydropyran-4-ylmethyl)-1H-imidazol-4-yl]-N-cyclopropylmethyl-N-methylpyrazine-2-carboxamide (Compound 206)

The title compound 206 (282 mg, 0.69 mmol, yield: 79%) was obtained in the same manner as in Example 216 mentioned below, and then in Example 145, using aminomethylcyclopropane instead of 2,2,2-trifluoroethylamine, and iodomethane instead of iodoethane.

$^1$H-NMR (δppm, CDCl$_3$): 9.24 (s, 1H), 8.61 (s, 1H), 7.58-7.55 (m, 1H), 4.01 (dd, J=11.7, 4.0 Hz, 2H), 3.97 (d, J=7.4 Hz, 2H), 3.39-3.23 (m, 4H), 3.22-3.13 (m, 3H), 2.18-2.04 (m, 1H), 1.67-1.63 (m, 3H), 1.49-1.40 (m, 11H), 0.62-0.49 (m, 2H), 0.37-0.14 (m, 2H). Mass (m/e): 412 (M+H)$^+$.

Example 207

6-[2-tert-Butyl-1-(tetrahydropyran-4-ylmethyl)-1H-imidazol-4-yl]-N-cyanomethyl-N-methylpyrazine-2-carboxamide (Compound 207)

The title compound 207 (387 mg, 0.98 mmol, yield: 84%) was obtained in the same manner as in Example 143, using methylaminoacetonitrile instead of diethylamine.

$^1$H-NMR (δppm, CDCl$_3$): 9.33-9.31 (m, 1H), 8.88-8.72 (m, 1H), 7.91-7.57 (m, 1H), 4.55-4.46 (m, 2H), 4.08-3.97 (m, 4H), 3.43-3.10 (m, 5H), 2.18-2.04 (m, 1H), 1.73-1.64 (m, 2H), 1.49-1.23 (m, 11H). Mass (m/e): 397 (M+H)$^+$.

Example 208

6-[2-tert-Butyl-1-(tetrahydropyran-4-ylmethyl)-1H-imidazol-4-yl]-N-(2-hydroxyethyl)-N-methylpyrazine-2-carboxamide monohydrochloride (Compound 208)

A free base was obtained in the same manner as in Example 143 using 2-(propylamino)ethanol instead of diethylamine, and the obtained free base was treated with 4 mol/L hydrogen chloride-ethyl acetate to give the title compound 208 (171 mg, 0.37 mmol, yield: 42%).

$^1$H-NMR (δppm, DMSO-d$_6$): 9.25-9.23 (m, 1H), 8.67 (s, 1H), 8.12-8.03 (m, 1H), 6.54 (s, 1H), 4.13-3.22 (m, 12H), 2.22-2.07 (m, 1H), 1.65-1.20 (m, 15H), 0.94-0.65 (m, 3H). Mass (m/e): 430 (M+H)$^+$. (as the free base)

Example 209

3-[2-tert-Butyl-1-(tetrahydropyran-4-ylmethyl)-1H-imidazol-4-yl]-N-(2,2,2-trifluoroethyl)benzamide (Compound 209)

The title compound 209 (190 mg, 0.45 mmol, yield: 75%) was obtained in the same manner as in Example 72, using 2,2,2-trifluoroethylamine instead of ethylamine.

Example 210

3-[2-tert-Butyl-1-(tetrahydropyran-4-ylmethyl)-1H-imidazol-4-yl]-N-(2-fluoroethyl)benzamide (Compound 210)

The title compound 210 (140 mg, 0.36 mmol, yield: 72%) was obtained in the same manner as in Example 72, using 2-fluoroethylamine hydrochloride instead of ethylamine.

Example 211

6-[2-tert-Butyl-1-(tetrahydropyran-4-ylmethyl)-1H-imidazol-4-yl]-N-(2,2,2-trifluoroethyl)pyridine-2-carboxamide (Compound 211)

The title compound 211 (85 mg, 0.20 mmol, yield: 80%) was obtained in the same manner as in Example 95.

Example 212

4-[2-tert-Butyl-1-(tetrahydropyran-4-ylmethyl)-1H-imidazol-4-yl]-N-(2,2-difluoroethyl)thiophene-2-carboxamide (Compound 212)

The title compound 212 (125 mg, 0.31 mmol, yield: quantitative) was obtained in the same manner as in Example 102, using 2,2-difluoroethylamine instead of N-ethylmethylamine.

Example 213

5-[2-tert-Butyl-1-(tetrahydropyran-4-ylmethyl)-1H-imidazol-4-yl]isoxazole-3-carboxylic acid (2,2,2-trifluoroethyl)amide (Compound 213)

The title compound 213 was obtained in the same manner as in step 2 of Example 107, using trifluoromethylamine.

Example 214

N-{6-[2-tert-Butyl-1-(tetrahydropyran-4-ylmethyl)-1H-imidazol-4-yl]pyrazin-2-yl}-N-phenylamine (Compound 214)

The title compound 214 (60 mg, 0.15 mmol, yield: 60%) was obtained in the same manner as in step 1 of Example 127, using aniline instead of piperidine.

Example 215

N-{6-[2-tert-Butyl-1-(tetrahydropyran-4-ylmethyl)-1H-imidazol-4-yl]pyrazin-2-yl}-N-methylamine (Compound 215)

The title compound 215 (300 mg, 0.91 mmol, yield: 45%) was obtained in the same manner as in Example 127, using a 40% aqueous solution of N-methylamine.

Example 216

6-[2-tert-Butyl-1-(tetrahydropyran-4-ylmethyl)-1H-imidazol-4-yl]-N-(2,2,2-trifluoroethyl)pyrazine-2-carboxamide (Compound 216)

The title compound 216 (245 mg, 0.58 mmol, yield: 90%) was obtained in the same manner as in Example 143, using 2,2,2-trifluoroethylamine instead of diethylamine.

$^1$H-NMR (δppm, CDCl$_3$): 9.37 (s, 1H), 9.18 (s, 1H), 8.36-32 (m, 1H), 7.58 (s, 1H), 4.20-4.12 (m, 2H), 4.06-4.00 (m, 4H), 3.41 (dt, J=11.7, 1.7 Hz, 2H), 2.18-2.10 (m, 1H), 1.74-1.69 (m, 2H), 1.57-1.39 (m, 11H).

Example 217

4-[2-tert-Butyl-1-(tetrahydropyran-4-ylmethyl)-1H-imidazol-4-yl]-2,3-dihydroisoindol-1-one (Compound 217)

Step 1

4-(4,4,5,5-tetramethyl[1,3,2]dioxaboran-2-yl)-2,3-dihydroisoindol-1-one (381 mg, 1.47 mmol, yield: 31%) was obtained in the same manner as in step 1 of Example 164, using 4-bromo-2,3-dihydroisoindol-1-one obtained by the method described in WO2004/108672 instead of 6-bromoindan-1-one.

$^1$H-NMR (δppm, CDCl$_3$): 8.02-7.93 (m, 2H), 7.49 (dd, J=7.5, 7.2 Hz, 1H), 6.68 (brs, 1H), 4.61 (s, 2H), 1.35 (s, 12H). Mass (m/e): 260 (M+H)$^+$.

Step 2

The title compound 217 (212 mg, 0.60 mmol, yield: 62%) was obtained in the same manner as in step 2 of Example 165, using 4-(4,4,5,5-tetramethyl[1,3,2]dioxaboran-2-yl)-2,3-dihydroisoindol-1-one obtained in the above instead of 6-(4,4,5,5-tetramethyl[1,3,2]dioxaboran-2-yl)indan-1-one.

$^1$H-NMR (δppm, CDCl$_3$): 7.81 (dd, J=7.9, 1.0 Hz, 1H), 7.73 (dd, J=7.6, 1.0 Hz, 1H), 7.45 (dd, J=7.9, 7.6 Hz, 1H), 7.18 (s, 1H), 6.40 (brs, 1H), 4.83 (s, 2H), 4.07-3.97 (m, 2H), 3.96 (d, J=7.6 Hz, 2H), 3.45-3.33 (m, 2H), 2.16-2.00 (m, 1H), 1.73-1.62 (m, 2H), 1.55-1.34 (m, 2H), 1.48 (s, 9H). Mass (m/e): 354 (M+H)$^+$.

Example 218

4-[2-tert-Butyl-1-(tetrahydropyran-4-ylmethyl)-1H-imidazol-4-yl]-2-chloropyrimidine (Compound 218)

The title compound 218 (27 mg, 0.08 mmol, yield: 44%) was obtained in the same manner as in step 3 of Example 168, using 2,4-dichloropyrimidine instead of N-ethyl-N-methyl-4-trifluoromethanesulfonyloxyquinoline-2-carboxamide.

$^1$H-NMR (δppm, CDCl$_3$): 8.50 (d, J=5.3 Hz, 1H), 7.84 (d, J=5.3 Hz, 1H), 7.78 (s, 1H), 4.04-3.95 (m, 2H), 3.96 (d, J=7.4 Hz, 2H), 3.44-3.32 (m, 2H), 2.21-2.06 (m, 1H), 1.68-1.58 (m, 2H), 1.54-1.32 (m, 2H), 1.47 (s, 9H). Mass (m/e): 335 (M+H)$^+$.

Example 219

Tablet (Compound o)

Tablets having the following formulation are prepared according to the conventional method. Compound o (40 g), lactose (286.8 g), and potato starch (60 g) are mixed, and a 10% aqueous solution of hydroxypropyl cellulose (120 g) is added thereto. The resulting mixture is kneaded, granulated, dried, and then subjected to size reduction according to the conventional method to prepare granules for tableting. The granules are mixed with 1.2 g of magnesium stearate, and the mixture is tableted by means of a tableting machine (Model RT-15 manufactured by Kikusui K.K.) having a pestle of 8 mm in diameter to give tablets (containing 20 mg of the active ingredient per tablet).

TABLE 26

| Formulation: | |
| --- | --- |
| Compound o | 20 mg |
| Lactose | 143.4 mg |
| Potato starch | 30 mg |
| Hydroxypropylcellulose | 6 mg |
| Magnesium stearate | 0.6 mg |
| | 200 mg |

Example 220

Injection Preparation (Compound q)

An injection preparation having the following formulation is prepared according to the conventional method. Compound q (1 g) is added to distilled water for injection and mixed therein. Then, hydrochloric acid and an aqueous sodium hydroxide solution are further added thereto to adjust the pH of the mixed liquid to 7, and the total amount is made 1000 mL with distilled water for injection. The resulting mixed liquid is aseptically filled in glass vials in 2 mL portions per vial to obtain an injection preparation (containing 2 mg of the active ingredient per vial).

TABLE 27

| Formulation: | |
| --- | --- |
| Compound q | 2 mg |
| Hydrochloric acid | ad lib. |
| Aqueous sodium hydroxide solution | ad lib. |
| Distilled water for injection | ad lib. |
| | 2.00 mL |

Reference Example A-1

2-tert-Butyl-4-(3-nitrophenyl)-1H-imidazole (Compound A-1)

The title compound A-1 (247 mg, 1.00 mmol, yield: 65%) was obtained in the same manner as in Example 1, using 2-bromo-3'-nitroacetophenone instead of 3-(2-bromoacetyl)benzonitrile.

$^1$H-NMR (δppm, CDCl$_3$): 8.57 (s, 1H), 8.07-8.03 (m, 2H), 7.51 (t, J=8.1 Hz, 1H), 7.31 (s, 1H), 1.43 (s, 9H). Mass (m/e): (M+H)$^+$ 246.

Reference Example A-2

1-Benzyl-2-tert-butyl-4-(3-nitrophenyl)-1H-imidazole (Compound A-2)

Under an argon atmosphere, Compound A-1 (68 mg, 0.28 mmol) was dissolved in DMF (0.7 mL), and sodium hydride (29 mg, 0.67 mmol) was added thereto, and then, the mixture was stirred under ice-cooling for 1 hour. Thereafter, benzyl bromide (40 μg, 0.34 mmol) and potassium iodide (112 mg, 0.67 mmol) were added to the mixture, and the mixture was stirred at room temperature for 4 hours. To the mixture, an aqueous sodium hydrogen carbonate solution was added, and the mixture was extracted with ethyl acetate. The organic layer was washed with water and dried over anhydrous magnesium sulfate, and the solvent was evaporated under reduced pressure. The residue was purified by silica gel column chromatography (hexane/ethyl acetate=90/10) to give the title compound A-2 (90 mg, 0.27 mmol, yield: 95%).

$^1$H-NMR (δppm, CDCl$_3$): 8.53 (t, J=2.0, 1H), 8.11-8.08 (m, 1H), 8.03-7.99 (m, 1H), 7.48 (t, J=8.1 Hz, 1H), 7.37-7.36 (m, 3H), 7.13-7.11 (m, 3H), 5.35 (s, 2H), 1.49 (s, 9H). Mass (m/e): (M+H)$^+$336.

Reference Example 1

3-(2-tert-Butyl-1-cyclohexylmethyl-1H-imidazol-4-yl)benzoic acid (Compound a)

Compound 1 (0.17 g, 0.53 mmol) obtained in Example 1 was dissolved in ethanol (60 mL), and a 2 mol/L aqueous sodium hydroxide solution (60 mL, 120 mmol) was added thereto, and then, the mixture was refluxed overnight. After the mixture was left to cool to room temperature, the solvent was evaporated under reduced pressure. To the residue, 2 mol/L hydrochloric acid was added to adjust the pH of the mixture to 4. Then, the mixture was extracted with chloroform, and the organic layer was washed with saturated brine and dried over anhydrous magnesium sulfate. Then, the solvent was evaporated under reduced pressure to give the title compound a (178 mg, 0.52 mmol, yield: 98%).

$^1$H-NMR (δppm, CDCl$_3$): 8.46-8.35 (m, 1H), 7.89-7.79 (m, 2H), 7.23-7.16 (m, 1H), 7.06-6.98 (m, 1H), 3.80-3.69 (m, 2H), 2.47-2.19 (m, 6H), 1.37 (s, 9H), 1.19-1.11 (m, 3H), 0.95-0.86 (m, 2H). Mass (m/e): 339(M−H)$^−$.

Reference Example 2 n-Propyl 4-(2-tert-butyl-1-cyclohexylmethyl-1H-imidazol-4-yl)benzoate (Compound b)

Compound 8 (2.51 g, 6.69 mmol) obtained in Example 8, palladium acetate (230 mg, 1.01 mmol), 1,3-bis(diphenylphosphino)propane (413 mg, 1.00 mmol), and potassium carbonate (1.14 g, 8.29 mmol) were dissolved in DMF (6.0 mL), and n-propanol (20 mL) was added thereto, and then, the mixture was refluxed for 3 hours under a carbon monoxide atmosphere. The mixture was left to cool to room temperature, and then filtered through Celite. To the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=30/1 to 10/1) to give the title compound b (1.43 g, 3.74 mmol, yield: 56%).

$^1$H-NMR (δppm, CDCl$_3$): 8.04-7.98 (m, 2H), 7.85-7.79 (m, 2H), 7.22 (s, 1H), 4.27 (d, J=7.1 Hz, 2H), 3.87 (d, J=6.8 Hz, 2H), 1.88-1.67 (m, 8H), 1.48 (s, 9H), 1.34-0.92 (m, 8H). Mass (m/e): 383 (M+H)$^+$.

Reference Example 3

4-(2-tert-Butyl-1-cyclohexylmethyl-1H-imidazol-4-yl)benzoic acid (Compound c)

Compound b (1.20 g, 3.13 mmol) obtained in Reference example 2 and lithium hydroxide monohydrate (0.149 g, 3.56 mmol) were dissolved in a 50% aqueous methanol solution (6.0 mL), and the mixture was stirred under reflux for 1 hour. After the mixture was cooled to 0° C., 3 mol/L hydrochloric acid (1.2 mL) was slowly added thereto. The precipitated white solid was collected by filtration to give the title compound c (0.984 g, 2.89 mmol, yield: 93%).

$^1$H-NMR (δppm, DMSO-d$_6$): 7.92-7.86 (m, 2H), 7.85-7.80 (m, 2H), 7.73 (s, 1H), 3.89 (d, J=7.1 Hz, 2H), 1.96-1.59 (m, 6H), 1.40 (s, 9H), 1.29-0.95 (m, 5H). Mass (m/e): 339 (M−H)$^−$.

Reference Example 4 n-Propyl 2-(2-tert-butyl-1-cyclohexylmethyl-1H-imidazol-4-yl)benzoate (Compound d)

The title compound d (1.00 g, 2.61 mmol, yield: 91%) was obtained in the same manner as in Reference example 2, using Compound 18 obtained in Example 18.

$^1$H-NMR (δppm, CDCl$_3$): 7.68 (dd, J=7.8, 1.2 Hz, 1H), 7.52 (dd, J=7.8, 1.2 Hz, 1H), 7.45-7.36 (m, 1H), 7.27-7.21 (m, 1H), 7.06 (s, 1H), 4.17 (t, J=6.7 Hz, 2H), 3.84 (d, J=7.1 Hz, 2H), 1.87-1.53 (m, 8H), 1.44 (s, 9H), 1.33-0.94 (m, 5H), 0.88 (t, J=7.4 Hz, 3H). Mass (m/e): 383 (M+H)$^+$.

Reference Example 5

2-(2-tert-Butyl-1-cyclohexylmethyl-1H-imidazol-4-yl)benzoic acid (Compound e)

The title compound e (562 mg, 1.65 mmol, yield: 72%) was obtained in the same manner as in Reference example 3, using Compound d obtained in Reference example 4.

$^1$H-NMR (δppm, CDCl$_3$): 8.44 (dd, J=7.8, 1.1 Hz, 1H), 7.55 (dd, J=7.8, 1.1 Hz, 1H), 7.49-7.40 (m, 1H), 7.40-7.30 (m, 1H), 7.20 (s, 1H), 3.93 (d, J=7.4 Hz, 2H), 1.88-1.70 (m, 6H), 1.51 (s, 9H), 1.36-0.90 (m, 5H). Mass (m/e): 339 (M−H)$^−$.

Reference Example 6

Ethyl 3-(2-tert-butyl-1-cyclohexylmethyl-1H-imidazol-4-yl)benzoate (Compound f)

Under an argon atmosphere, Compound a (300 mg, 0.94 mmol) obtained in Reference example 1 was dissolved in ethanol (4 mL), and thionyl chloride (0.17 mL, 0.24 mmol) was added thereto at −20° C. Thereafter, the mixture was stirred at room temperature for 3 hours, and then, further refluxed for 1 hour. The mixture was left to cool and concentrated under reduced pressure. To the residue, a 2 mol/L aqueous sodium hydroxide solution was added to adjust the pH of the mixture to 10, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=99/1 to 75/25) to give the title compound f (215 mg, 0.58 mmol, yield: 62%).

$^1$H-NMR (δppm, CDCl$_3$): 8.33 (t, J=1.3 Hz, 1H), 8.04 (dt, J=7.7, 1.3 Hz, 1H), 7.85 (dt, J=7.7, 1.3 Hz, 1H), 7.41 (t, J=7.7 Hz, 1H), 7.20 (s, 1H), 4.39 (q, J=7.1 Hz, 2H), 3.86 (d, J=7.1 Hz, 2H), 1.86-1.71 (m, 6H), 1.48 (s, 9H), 1.41 (t, J=7.1 Hz, 3H), 1.29-1.20 (m, 3H), 1.08-1.00 (m, 2H). Mass (m/e): 369 (M+H)$^+$.

Reference Example 7

1-Cyclohexylmethyl-2-(4-ethoxybenzyl)-4-(3-methoxyphenyl)-1H-imidazole (Compound g)

The title compound g (474 mg, 1.17 mmol, yield: 47%) was obtained in the same manner as in Example 1, using 4-ethoxyphenylacetyl chloride instead of pivaloyl chloride.

¹H-NMR (δppm, CDCl₃): 7.38-7.33 (m, 2H), 7.26 (t, J=7.6 Hz, 1H), 7.11-7.08 (m, 3H), 6.79 (d, J=7.6 Hz, 2H), 6.79-6.76 (m, 1H), 4.10 (s, 2H), 3.98 (q, J=7.0 Hz, 2H), 3.85 (s, 3H), 3.50 (d, J=7.3 Hz, 2H), 1.73-1.54 (m, 6H), 1.38 (t, J=7.0 Hz, 3H), 1.18-0.75 (m, 5H). Mass (m/e): 405 (M+H)⁺.

Reference Example 8

1-Cyclohexylmethyl-2-(4-methoxybenzyl)-4-(3-methoxyphenyl)-1H-imidazole monohydrochloride (Compound h)

A free base of the title compound (357 mg, 0.92 mmol, yield: 36%) was obtained in the same manner as in Example 1 using 4-methoxyphenylacetyl chloride instead of pivaloyl chloride. To the obtained free base, 4 mol/L hydrogen chloride-ethyl acetate was added and the precipitated solid was collected by filtration to give the title compound h (314 mg, 0.74 mmol, yield: 80%).
¹H-NMR (δppm, CDCl₃): 7.82-7.81 (m, 1H), 7.40-7.28 (m, 4H), 6.96-6.75 (m, 4H), 4.63 (s, 2H), 3.99 (s, 3H), 3.78 (s, 3H), 3.70 (d, J=7.0 Hz, 2H), 1.78-1.53 (m, 5H), 1.20-1.10 (m, 4H), 0.93-0.81 (m, 2H). Mass (m/e): 391 (M+H)⁺. (as the free base)

Reference Example 9

2-Cyclobutyl-1-cyclohexylmethyl-4-(3-methoxyphenyl)-1H-imidazole (Compound i)

The title compound i (68 mg, 0.21 mmol, yield: 8%) was obtained in the same manner as in Example 1, using cyclobutanecarbonyl chloride instead of pivaloyl chloride.
¹H-NMR (δppm, CDCl₃): 7.38-7.32 (m, 2H), 7.27-7.21 (m, 1H), 7.04 (s, 1H), 6.77-6.74 (m, 1H), 3.86 (s, 3H), 3.59 (d, J=7.0 Hz, 2H), 2.63-2.55 (m, 2H), 2.38-2.26 (m, 2H), 2.12-1.92 (m, 2H), 1.83-1.72 (m, 6H), 1.59-0.82 (m, 6H). Mass (m/e): 325 (M+H)⁺.

Reference Example 10

2-Benzo[1,3]dioxol-5-ylmethyl-1-cyclohexylmethyl-4-(3-methoxyphenyl)-1H-imidazole (Compound j)

The title compound j (32 mg, 0.08 mmol, yield: 3%) was obtained in the same manner as in Example 1, using benzo[1,3]dioxol-5-ylacetyl chloride instead of pivaloyl chloride.
¹H-NMR (δppm, CDCl₃): 7.36-7.26 (m, 3H), 7.08 (s, 1H), 6.79-6.63 (m, 4H), 5.91 (s, 2H), 4.08 (s, 2H), 3.86 (s, 3H), 3.53 (d, J=7.3 Hz, 2H), 2.11-2.05 (m, 1H), 1.72-1.56 (m, 6H), 1.20-1.12 (m, 2H), 0.94-0.78 (m, 2H). Mass (m/e): 405 (M+H)⁺.

Reference Example 11

4-[2-tert-Butyl-4-(3-nitrophenyl)imidazol-1-ylmethyl]pyridine (Compound k)

The title compound k (149 mg, 0.44 mmol, yield: 36%) was obtained in the same manner as in Example 45, using 4-picolylamine instead of cyclohexanemethylamine, and 2-bromo-3'-nitroacetophenone instead of 3-(2-bromoacetyl)benzonitrile.
¹H-NMR (δppm, CDCl₃): 8.64 (d, J=5.8 Hz, 2H), 8.57-8.56 (m, 1H), 8.18-8.15 (m, 1H), 8.08-8.05 (m, 1H), 7.52 (t, J=8.1 Hz, 1H), 7.19 (s, 1H), 7.09 (d, J=5.8 Hz, 2H), 5.44 (s, 2H), 1.46 (s, 9H). Mass (m/e): 337 (M+H)⁺.

Reference Example 12

2-tert-Butyl-1-(furan-2-ylmethyl)-4-(3-nitrophenyl)-1H-imidazole (Compound l)

The title compound l (8.8 mg, 0.027 mmol, yield: 2%) was obtained in the same manner as in Example 45, using furfurylamine instead of cyclohexanemethylamine, and 2-bromo-3'-nitroacetophenone instead of 3-(2-bromoacetyl)benzonitrile.
¹H-NMR (δppm, CDCl₃): 8.53-8.52 (m, 1H), 8.11-8.09 (m, 1H), 8.02 (dd, J=7.8, 1.8 Hz, 1H), 7.48 (t, J=7.8 Hz, 1H), 7.31-7.29 (m, 1H), 7.22 (s, 1H), 6.40-6.32 (m, 2H), 5.27 (s, 2H), 1.53 (s, 9H). Mass (m/e): 326 (M+H)⁺.

Reference Example 13

3-(2-tert-Butyl-1-(tetrahydropyran-4-ylmethyl)-1H-imidazol-4-yl)benzoic acid (Compound m)

Compound 45 (6.13 g, 19.0 mmol) obtained in Example 45 was dissolved in ethanol (60 mL), and a 2 mol/L aqueous sodium hydroxide solution (60 mL, 120 mmol) was added thereto, and the mixture was refluxed overnight. After the mixture was left to cool to room temperature, the solvent was evaporated under reduced pressure. To the residue, 2 mol/L hydrochloric acid was added to adjust the pH of the mixture to 4. Then, the mixture was extracted with chloroform, and the organic layer was washed with saturated brine and dried over anhydrous magnesium sulfate. Then, the solvent was evaporated under reduced pressure to give the title compound m (4.50 g, 13.2 mmol, yield: 69%).
¹H-NMR (δppm, CDCl₃): 8.53-8.52 (m, 1H), 7.99-7.90 (m, 2H), 7.42 (t, J=7.0 Hz, 1H), 7.19 (s, 1H), 4.02 (dd, J=10.3, 3.0 Hz, 2H), 3.96 (d, J=6.8 Hz, 2H), 3.40 (t, J=10.3 Hz, 2H), 2.32-2.05 (m, 1H), 1.72-1.60 (m, 2H), 1.52 (s, 9H), 1.48-1.40 (m, 2H). Mass (m/e): 343 (M+H)⁺.

Reference Example 14

Propyl 5-(2-tert-butyl-1-(tetrahydropyran-4-ylmethyl)-1H-imidazol-4-yl)nicotinate (Compound n)

Compound 84 (188 mg, 0.50 mmol) obtained in Example 84 was dissolved in DMF (1.0 mL), and 1,3-(diphenylphosphino)propane (21 mg, 0.05 mmol), potassium carbonate (166 mg, 1.2 mmol), palladium(II) acetate (11 mg, 0.05 mmol), and propyl alcohol (2 mL) were added thereto, and then, the mixture was stirred at 90° C. for 2.5 hours under a carbon monoxide atmosphere. The mixture was left to cool to room temperature and filtered through Celite, and the filtrate was concentrated. To the residue, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10 to 1/99) to give the title compound n (116 mg, 0.30 mmol, yield: 60%).
¹H-NMR (δppm, CDCl₃): 9.14 (d, J=2.0 Hz, 1H), 9.03 (d, J=2.0 Hz, 1H), 8.58 (t, J=2.0 Hz, 1H), 7.25 (s, 1H), 4.33 (t, J=6.7 Hz, 2H), 4.02 (dd, J=11.3, 3.1 Hz, 2H), 3.97 (d, J=7.5 Hz, 2H), 3.39 (dt, J=11.3, 2.0 Hz, 2H), 2.12-2.05 (m, 1H), 1.82 (qt, J=7.4, 6.7 Hz, 2H), 1.80-1.72 (m, 2H), 1.49 (s, 9H), 1.47-1.38 (m, 2H), 1.05 (t, J=7.4 Hz, 3H). Mass (m/e): 386 (M+H)$^+$.

Reference Example 15

2-(4-Ethoxybenzyl)-4-(3-methoxyphenyl)-1-(tetrahydro-pyran-4-ylmethyl)-1H-imidazole (Compound o)

The title compound o (160 mg, 0.39 mmol, yield: 31%) was obtained in the same manner as in Example 1, using 4-aminomethyltetrahydropyran hydrochloride, 2-bromo-3'-methoxyacetophenone and 4-ethoxyphenylacetic acid.

$^1$H-NMR (δppm, CDCl$_3$): 7.37-7.32 (m, 2H), 7.27 (t, J=7.9 Hz, 1H), 7.12-7.09 (m, 3H), 6.84-6.77 (m, 3H), 4.12 (s, 2H), 3.99 (q, J=6.9 Hz, 2H), 3.92-3.87 (m, 5H), 3.58 (d, J=7.3 Hz, 2H), 3.24-3.16 (m, 2H), 1.67-1.60 (m, 1H), 1.45-1.37 (m, 5H), 1.26-1.13 (m, 2H). Mass (m/e): 407 (M+H)$^+$.

Reference Example 16

3-[2-(4-Ethoxybenzyl)-1-(tetrahydropyran-4-ylmethyl)-1H-imidazol-4-yl]benzonitrile (Compound p)

The title compound p [40 mg, 0.10 mmol, yield: 4% (2 steps)] was obtained in the same manner as in Example 45, using 2-(4-ethoxyphenyl)-acetoamidine instead of tert-butyl-carbamidine hydrochloride.

$^1$H-NMR (δppm, CDCl$_3$): 8.08-8.05 (m, 1H), 8.01-7.97 (m, 1H), 7.50-7.41 (m, 2H), 7.16 (s, 1H), 7.10 (d, J=8.4 Hz, 2H), 6.82 (d, J=8.4 Hz, 2H), 4.11 (s, 2H), 4.00 (q, J=7.0 Hz, 2H), 3.98-3.88 (m, 2H), 3.61 (d, J=7.3 Hz, 2H), 3.21 (t, J=11.6 Hz, 2H), 1.71-1.55 (m, 1H), 1.46-1.37 (m, 5H), 1.28-1.18 (m, 2H). Mass (m/e): 402 (M+H)$^+$.

Reference Example 17

3-[2-(4-Ethoxybenzyl)-1-(tetrahydropyran-4-ylmethyl)-1H-imidazol-4-yl]-N,N-diethylbenzamide (Compound q)

Step 1

3-Acetyl-N,N-diethylbenzamide (530 mg, 2.42 mmol, yield: 81%) was obtained in the same manner as in Example 2, using 3-acetylbenzoic acid.

Step 2

The title compound q [5 mg, 0.01 mmol, yield: 1% (3 steps)] was obtained in the same manner as in Example 63, using 3-acetyl-N,N-diethylbenzamide obtained in the above and 2-(4-ethoxyphenyl)acetamidine.

$^1$H-NMR (δppm, CDCl$_3$): 7.83 (dt, J=7.7, 1.4 Hz, 1H), 7.76 (t, J=1.4 Hz, 1H), 7.38 (t, J=7.7 Hz, 1H), 7.20 (dt, J=7.7, 1.4 Hz, 1H), 7.12 (s, 1H), 7.10 (d, J=8.1 Hz, 2H), 6.82 (d, J=8.1 Hz, 2H), 4.11 (s, 2H), 4.00 (q, J=7.0 Hz, 2H), 3.90 (dd, J=11.5, 3.5 Hz, 2H), 3.61-3.52 (m, 2H), 3.59 (d, J=7.3 Hz, 2H), 3.34-3.24 (m, 2H), 3.20 (td, J=11.5, 1.8 Hz, 2H), 1.72-1.60 (m, 3H), 1.46-1.41 (m, 2H), 1.42-1.38 (m, 3H), 1.28-1.13 (m, 6H). Mass (m/e): 476 (M+H)$^+$.

Reference Example 18

1-{3-[2-(4-Ethoxybenzyl)-1-(tetrahydropyran-4-ylmethyl)-1H-imidazol-4-yl]phenyl}ethanone (Compound r)

The title compound r (12 mg, 0.03 mmol, yield: 31%) was obtained in the same manner as in Example 46, using Compound p obtained in Reference example 16 and a THF solution of methyl magnesium bromide.

$^1$H-NMR (δppm, CDCl$_3$): 8.32-8.30 (m, 1H), 8.04-8.00 (m, 1H), 7.83-7.79 (m, 1H), 7.47 (t, J=7.0 Hz, 1H), 7.19 (s, 1H), 7.10 (d, J=7.6 Hz, 2H), 6.82 (d, J=7.6 Hz, 2H), 4.13 (s, 2H), 4.00 (q, J=6.2 Hz, 2H), 3.94-3.88 (m, 2H), 3.60 (d, J=6.5 Hz, 2H), 3.22 (t, J=10.5 Hz, 2H), 2.66 (s, 3H), 1.73-1.60 (m, 1H), 1.47-1.32 (m, 4H), 1.30-1.13 (m, 3H). Mass (m/e): 419 (M+H)$^+$.

Reference Example 19 tert-Butyl 3-(2-tert-butyl-1-(tetrahydropyran-4-ylmethyl)-1H-imidazol-4-yl)acrylate (Compound s)

Step 1

A mixture of 4-iodo-2-tert-butylimidazole (200 mg, 0.80 mmol) obtained in Step 3 of Example 81, tert-butyl acrylate (240 μL, 1.63 mmol), palladium acetate (18 mg, 0.080 mmol), triphenylphosphine (42 mg, 0.016 mmol), potassium carbonate (133 mg, 0.962 mmol), and DMF (10 mL) was stirred at 100° C. for 3 hours. The mixture was left to cool to room temperature and filtered through Celite. To the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=80/20) to give 3-(2-tert-butyl-1H-imidazol-4-yl)acrylic acid tert-butyl ester (51 mg, 0.22 mmol, yield: 26%).

$^1$H-NMR (δppm, CDCl$_3$): 9.05-5.80 (m, 3H), 1.54-1.48 (m, 9H), 1.39 (m, 9H). Mass (m/e): 251 (M+H)$^+$.

Step 2

The title compound s (35 mg, 0.10 mmol, yield: 49%) was obtained in the same manner as in step 3 of Example 45, using 3-(2-tert-butyl-1H-imidazol-4-yl)acrylic acid tert-butyl ester obtained in the above.

$^1$H-NMR (δppm, CDCl$_3$): 7.42 (d, J=15.7 Hz, 1H), 7.00 (s, 1H), 6.44 (d, J=15.7 Hz, 1H), 4.04-3.96 (m, 2H), 3.89 (d, J=7.1 Hz, 2H), 3.42-3.30 (m, 2H), 2.06-1.97 (m, 1H), 1.66-1.55 (m, 2H), 1.49 (s, 9H), 1.47 (s, 9H), 1.47-1.31 (m, 2H). Mass (m/e): 349 (M+H)$^+$.

Reference Example 20

3-(2-tert-Butyl-1-(tetrahydropyran-4-ylmethyl)-1H-imidazol-4-yl)acrylic acid (Compound t)

The title compound t (199 mg, 0.68 mmol, yield: 71%) was obtained in the same manner as in Reference example 1, using Compound s obtained in Reference example 19.

$^1$H-NMR (δppm, DMSO-d$_6$): 7.81 (s, 1H), 7.40 (d, J=15.9 Hz, 1H), 6.45 (d, J=15.9 Hz, 1H), 4.02 (d, J=7.1 Hz, 2H), 3.90-3.81 (m, 2H), 3.31-3.20 (m, 2H), 2.18-1.98 (m, 1H), 1.56-1.20 (m, 4H), 1.43 (s, 9H). Mass (m/e): 293 (M+H)$^+$.

Compounds u, v, w, and x shown in the following table were obtained by the methods shown in Reference examples 22 to 24.

TABLE 28

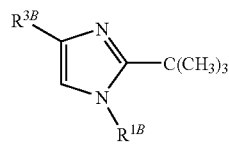

| Ref. No. | Compound No. | R³ᴮ | R¹ᴮ |
|---|---|---|---|
| 21 | u | I | —CH₂—(tetrahydropyran-4-yl) |
| 22 | v | 6-(N-methyl-N-propylcarbamoyl)pyrazin-2-yl (H₃C-CH₂-CH₂-N(CH₃)-C(O)-pyrazine) | H |
| 23 | w | I | —CH₂—(4-fluorotetrahydropyran-4-yl) |
| 24 | x | —Sn(C₄H₉)₃ | —CH₂—(4-fluorotetrahydropyran-4-yl) |

Reference Example 21

2-tert-Butyl-4-iodo-1-(tetrahydropyran-4-ylmethyl)-1H-imidazole (Compound U)

4-Iodo-2-tert-butylimidazole (5.00 g, 0.02 mol) obtained in step 3 of Example 81 was dissolved in DMF (86 mL), and cesium carbonate (32.59 g, 0.10 mol) and (tetrahydropyran-4-yl)methylmethanesulfonate (5.05 g, 0.03 mol) obtained in step 2 of Example 45 were added thereto, and then, the mixture was stirred at 90° C. for 8 hours. After the mixture was left to cool to room temperature, water was added thereto, and the mixture was stirred for 20 minutes under ice-cooling. The precipitated crystal was collected by filtration to give the title compound u (4.30 g, 0.01 mol, yield: 50%).

¹H-NMR (δppm, CDCl₃): 6.91 (s, 1H), 4.06-3.95 (m, 2H), 3.88 (d, J=7.3 Hz, 2H), 3.36 (t, J=10.8 Hz, 2H), 2.09-1.90 (m, 1H), 1.68-1.54 (m, 2H), 1.47-1.38 (m, 11H). Mass (m/e):349 (M+H)⁺.

Reference Example 22

6-(2-tert-Butyl-1H-imidazol-4-yl)-N-ethyl-N-propylpyrazine-2-carboxamide (Compound v)

Step 1

Pyrazine carboxylic acid (1.00 g, 8.06 mmol) was dissolved in DMF (5 mL), and methylpropylamine (99 μL, 9.69 mmol), WSC.HCl (1.85 g, 9.69 mmol), and HOBt.H₂O (1.48 g, 9.69 mmol) were added thereto, and then, the mixture was stirred at room temperature for 1 hour. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50) to give N-methyl-N-propylpyrazinecarboxamide (1.41 g, 7.86 mmol, yield: 98%).

¹H-NMR (δppm, CDCl₃): 8.94-8.88 (m, 1H), 8.63-8.60 (m, 1H), 8.56-8.52 (m, 1H), 3.58-3.30 (m, 2H), 3.16-3.05 (m, 3H), 1.80-1.60 (m, 2H), 1.04-0.76 (m, 3H).

Step 2

2,2,6,6-Tetramethylpiperidine (30.2 mL, 179 mmol) was dissolved in THF (40 mL), and a THF solution of n-butyl lithium (2.6 mol/L; 66.0 mL, 172 mmol) was added thereto at −78° C., and then, the mixture was stirred at 0° C. for 20 minutes. After the mixture was cooled to −78° C. again, N-methyl-N-propylpyrazine carboxamide (7.63 g, 42.6 mmol) obtained in the above and a THF solution (35 mL) of tributyltin chloride (23.1 mL, 85.2 mmol) were added thereto, and the mixture was stirred at the same temperature for 1 hour. To the mixture, a mixed liquid (60 mL) of concentrated hydrochloric acid, ethanol, and THF (1/4/5) was slowly added, and 3 mol/L hydrochloric acid (100 mL) was added thereto at 0° C. The mixture was stirred at room temperature for 1 hour, and then extracted with hexane. The organic layer was washed with saturated brine and dried over anhydrous magnesium sulfate, and the solvent was evaporated under reduced pressure. The residue was purified by silica gel column chromatography (hexane/ethyl acetate=70/30) to give 6-tributylstannyl-N-methyl-N-propylpyrazine-2-carboxamide (6.26 g, 13.4 mmol, yield: 31%).

¹H-NMR (δppm, CDCl₃): 8.73-8.68 (m, 1H), 8.56-8.54 (m, 1H), 3.58-3.34 (m, 2H), 3.15-3.07 (m, 3H), 1.97-0.73 (m, 32H).

Step 3

2-tert-Butyl-4-iodo-1H-imidazole (3.01 g, 12.0 mmol) obtained in step 3 of Example 81 was dissolved in DMF (30 mL), and 6-tributylstannyl-N-methyl-N-propylpyrazine-2-carboxamide (6.20 g, 13.2 mmol) obtained in the above, palladium(II) acetate (270 mg, 1.21 mmol), tri(2-methylphenyl)phosphine (732 mg, 2.41 mmol), and copper(I) iodide (230 mg, 1.20 mmol) were added thereto, and then, the mixture was stirred at 100° C. for 1 hour. After the mixture was left to cool to room temperature, an aqueous potassium fluoride solution was added thereto, and the mixture was stirred at room temperature for 1 hour. Then, the mixture was filtered through Celite, and to the filtrate, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5) to give the title compound v (2.19 g, 7.27 mmol, yield: 61%).

$^1$H-NMR (δppm, CDCl$_3$): 9.72-7.59 (m, 4H), 3.62-2.97 (m, 5H), 1.79-1.63 (m, 2H), 1.44 (s, 9H), 1.10-0.76 (m, 3H). Mass (m/e): 302 (M+H)$^+$.

Reference Example 23

2-tert-Butyl-1-(4-fluorotetrahydropyran-4-ylmethyl)-4-iodo-1H-imidazole (Compound w)

Step 1

(4-Fluorotetrahydropyran-4-yl)methanol (1.40 g, 10.4 mmol) obtained by the method described in WO2006/034093 was dissolved in pyridine (14 mL), and trifluoromethanesulfonic anhydride (3.80 mL, 22.6 mmol) was slowly added thereto at 0° C., and then, the mixture was stirred at room temperature for 1 hour. To the mixture, water was added, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=70/30) to give (4-fluorotetrahydropyran-4-yl)methyl trifluoromethanesulfonate (1.80 g, 6.67 mmol, yield: 65%).

$^1$H-NMR (δppm, CDCl$_3$): 4.45 (d, J=19.1 Hz, 2H), 3.93-3.85 (m, 2H), 3.80-3.69 (m, 2H), 1.92-1.66 (m, 4H).

Step 2

2-tert-Butyl-4-iodo-1H-imidazole (1.50 g, 6.00 mmol) obtained in step 3 of Example 81 was dissolved in DMF (15 mL), and (4-fluorotetrahydropyran-4-yl)methyl trifluoromethanesulfonate (1.75 g, 6.57 mmol) obtained in the above and cesium carbonate (9.78 g, 30.0 mmol) were added thereto, and then, the mixture was stirred at 90° C. for 3 hours. After the mixture was left to cool to room temperature, the water was added thereto, and the mixture was stirred for 1 hour under ice-cooling. The precipitated crystal was collected by filtration and dried under reduced pressure to give the title compound w (2.07 g, 5.65 mmol, yield: 94%).

$^1$H-NMR (δppm, CDCl$_3$): 7.17 (d, J=1.8 Hz, 1H), 4.21 (d, J=23.5 Hz, 2H), 3.92-3.82 (m, 2H), 3.77-3.67 (m, 2H), 1.89-1.56 (m, 4H), 1.41 (s, 9H).

Reference Example 24

2-tert-Butyl-1-(4-fluorotetrahydropyran-4-yl)methyl-4-tributylstannyl-1H-imidazole (Compound x)

Under an argon atmosphere, Compound w (500 mg, 1.64 mmol) obtained in Step 2 of Reference example 23 was dissolved in THF (10 mL), and a solution of n-butyl lithium in n-hexane (1.6 mol/L, 1.10 mL, 1.76 mmol) was added dropwise thereto at −78° C., and then, the mixture was stirred at the same temperature for 30 minutes. To the mixture, tributyltin chloride (420 μL, 1.55 mmol) was added, and the mixture was stirred at −15° C. for 2 hours. To the mixture, 1 mol/L hydrochloric acid was added, and the mixture was extracted with ethyl acetate. The organic layer was washed with a saturated aqueous sodium hydrogen carbonate solution and saturated brine and dried over anhydrous magnesium sulfate. Then, the solvent was evaporated under reduced pressure to give a roughly purified product of the title compound x (445 mg, 0.84 mmol, yield: 63%).

$^1$H-NMR (δppm, CDCl$_3$): 7.01 (d, J=2.3 Hz, 1H), 4.23 (d, J=24.4 Hz, 2H), 3.90-3.81 (m, 2H), 3.77-3.65 (m, 2H), 1.82-1.22 (m, 22H), 1.41 (s, 9H), 0.96-0.82 (m, 9H).

Reference Example 25

2-[2-tert-Butyl-1-(tetrahydropyran-4-ylmethyl)-1H-imidazol-4-yl]pyrazine-2-carboxylic acid (Compound y)

Step 1

Compound 136 (427 mg, 1.28 mmol) obtained in Example 136 was dissolved in DMF-n-propanol (1/3) (12 mL), and palladium acetate (28.6 mg, 0.128), 2,2'-bis(diphenylphosphino)-1,1'-binaphtyl (79.4 mg, 0.128 mmol), and potassium acetate (151 mg, 1.54 mmol) were added thereto, and the mixture was stirred at 80° C. for 3.5 hours under a carbon monoxide atmosphere. To the mixture, an aqueous sodium hydrogen carbonate solution was added, and the mixture was extracted with ethyl acetate. The organic layer was washed with saturated brine and dried over anhydrous magnesium sulfate, and the solvent was evaporated under reduced pressure. The residue was purified by silica gel column chromatography to give 2-[2-tert-butyl-1-(tetrahydropyran-4-ylmethyl)-1H-imidazol-4-yl]pyrazine-2-carboxylic acid n-propyl ester (419 mg, 1.08 mmol, yield: 85%).

$^1$H-NMR (δppm, CDCl$_3$): 9.39 (s, 1H), 9.03 (s, 1H), 7.75 (s, 1H), 4.39 (t, J=6.8 Hz, 2H), 4.04-3.96 (m, 4H), 3.44-3.35 (m, 2H), 2.17-2.05 (m, 1H), 1.90-1.82 (m, 2H), 1.68-1.63 (m, 2H), 1.49-1.41 (m, 11H), 1.06 (t, J=7.4 Hz, 3H).

Step 2

2-[2-tert-Butyl-1-(tetrahydropyran-4-ylmethyl)-1H-imidazol-4-yl]pyrazine-2-carboxylic acid propyl ester (419 mg, 1.08 mmol) obtained in the above was dissolved in ethanol-water (1/1) (10 mL), and lithium hydroxide (91.0 mg, 2.17 mmol) was added thereto, and then, the mixture was stirred at 50° C. for 1 hour. To the mixture, water was added, and the mixture was washed with diethyl ether. After the pH of the aqueous layer was adjusted to 3 with hydrochloric acid, the aqueous layer was extracted with chloroform-2-propanol (4/1). The organic layer was dried over anhydrous magnesium sulfate, and the solvent was evaporated under reduced pressure to give the title compound y (354 mg, 1.03 mmol, yield: 95%).

$^1$H-NMR (δppm, CDCl$_3$): 9.39 (s, 1H), 9.19 (s, 1H), 7.64 (s, 1H), 4.07-4.00 (m, 4H), 3.42 (dt, J=11.9, 2.1 Hz, 2H), 2.19-2.10 (m, 1H), 1.69-1.65 (m, 2H), 1.54-1.39 (m, 11H). Mass (m/e): 345 (M+H)$^+$.

INDUSTRIAL APPLICABILITY

According to the present invention, a novel imidazole derivative or a pharmaceutically acceptable salt thereof which has an effect to modulate a CB2 receptor and is useful as a therapeutic and/or preventive agent for a pain or the like, can be provided.

The invention claimed is:

1. An imidazole derivative selected from the group consisting of:

- 5-(2-tert-Butyl-1-(tetrahydropyran-4-ylmethyl)-1H-imidazol-4-yl)-N,N-diethyl-2-fluorobenzamide;
- 3-(2-tert-Butyl-1-(tetrahydropyran-4-ylmethyl)-1H-imidazol-4-yl)-N,N-diethylbenzamide;
- 3-(2-tert-Butyl-1-(tetrahydropyran-4-ylmethyl)-1H-imidazol-4-yl)-N-ethyl-N-methylbenzamide;
- 5-(2-tert-Butyl-1-(tetrahydropyran-4-ylmethyl)-1H-imidazol-4-yl)-N,N-diethylnicotinamide;
- 4-[2-tert-Butyl-1-(tetrahydropyran-4-ylmethyl)-1H-imidazol-4-yl]-N-ethyl-N-methylthiophene-2-carboxamide;
- 6-[2-tert-Butyl-1-(tetrahydropyran-4-ylmethyl)-1H-imidazol-4-yl]-N,N-diethylpyrazine-2-carboxamide;
- 6-[2-tert-Butyl-1-(tetrahydropyran-4-ylmethyl)-1H-imidazol-4-yl]-N-methyl-N-propylpyrazine-2-carboxamide;
- 6-[2-tert-Butyl-1-(tetrahydropyran-4-ylmethyl)-1H-imidazol-4-yl]-N-ethyl-N-methylpyrazine-2-carboxamide;
- 6-[2-tert-Butyl-1-(tetrahydropyran-4-ylmethyl)-1H-imidazol-4-yl]-N,N-dimethylpyrazine-2-carboxamide;
- 6-[2-tert-Butyl-1-(4-fluorotetrahydropyran-4-ylmethyl)-1H-imidazol-4-yl]-N-ethyl-N-methylpyrazine-2-carboxamide;
- 6-[2-tert-Butyl-1-(4-fluorotetrahydropyran-4-ylmethyl)-1H-imidazol-4-yl]-N,N-dimethylpyrazine-2-carboxamide; and
- 5-[2-tert-Butyl-1-(tetrahydropyran-4-ylmethyl)-1H-imidazol-4-yl]-N-methyl-N-(2,2,2-trifluoroethyl)isoxazole-3-carboxamide;

or a pharmaceutically acceptable salt thereof.

2. A pharmaceutical composition comprising the imidazole derivative or the pharmaceutically acceptable salt thereof according to claim 1, together with a pharmaceutically acceptable carrier.

* * * * *